(12) United States Patent
Huang et al.

(10) Patent No.: US 8,999,983 B2
(45) Date of Patent: *Apr. 7, 2015

(54) MODULATORS OF HEC1 ACTIVITY AND METHODS THEREFOR

(71) Applicants: Taivex Therapeutics Corporation, Taipei (TW); Development Center for Biotechnology, New Taipei (TW)

(72) Inventors: Jiann-Jyh Huang, Luodong Township (TW); Shih-Hsien Chuang, Taoyuan (TW); Ying-Shuan Eda Lee, Taipei (TW); Yu-Ling Huang, Hsinchu (TW); Johnson Lau, Newport Beach, CA (US)

(73) Assignees: Taivex Therapeutics Corporation, Taipei (TW); Development Center of Biotechnology, New Taipei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 13/689,590

(22) Filed: Nov. 29, 2012

(65) Prior Publication Data

US 2013/0190312 A1   Jul. 25, 2013

Related U.S. Application Data

(60) Provisional application No. 61/564,773, filed on Nov. 29, 2011.

(51) Int. Cl.
| | | |
|---|---|---|
| *A61K 31/5377* | (2006.01) | |
| *C07D 417/12* | (2006.01) | |
| *C07D 417/14* | (2006.01) | |
| *A61K 31/4439* | (2006.01) | |
| *A61K 31/497* | (2006.01) | |
| *A61K 31/501* | (2006.01) | |
| *A61K 31/506* | (2006.01) | |
| *A61K 45/06* | (2006.01) | |
| *C07D 277/46* | (2006.01) | |

(52) U.S. Cl.
CPC .......... *A61K 31/5377* (2013.01); *C07D 417/12* (2013.01); *C07D 417/14* (2013.01); *A61K 31/4439* (2013.01); *A61K 31/497* (2013.01); *A61K 31/501* (2013.01); *A61K 31/506* (2013.01); *A61K 45/06* (2013.01); *C07D 277/46* (2013.01)

(58) Field of Classification Search
None
See application file for complete search history.

(56) References Cited

U.S. PATENT DOCUMENTS

| | | |
|---|---|---|
| 2006/0140956 A1 | 6/2006 | Lee et al. |
| 2011/0071032 A1 | 3/2011 | Zeillinger et al. |
| 2011/0230486 A1 | 9/2011 | Lau et al. |
| 2013/0171634 A1* | 7/2013 | Huang et al. ............... 435/6.11 |

FOREIGN PATENT DOCUMENTS

| | | |
|---|---|---|
| WO | 03/105891 | 12/2003 |
| WO | 2004/033666 | 4/2004 |
| WO | 2005/026137 | 3/2005 |
| WO | 2007/004038 | 1/2007 |
| WO | 2007/131071 | 11/2007 |
| WO | 2010/056506 | 5/2010 |

OTHER PUBLICATIONS

Benet (Eur J Respir Dis Suppl. 1984;134:45-61).*
Mukaiyama (Tetrahedron 55 (1999) 8609-8670).*
Chan, Helen S.L. et al., "Multidrug Resistance Protein (MRP) Expression in Retinoblastoma Correlates with the Rare Failure of Chemotherapy despite Cyclosporine for Reversal of P-Glycoprotein", Cancer Research, vol. 57, pp. 2325-2330, 1997.
Ferretti, C. et al, "Expression of the kinetochore protein Hec1 during the cell cycle in normal and cancer cells and its regulation by the pRb pathway", Cell Cycle, vol. 9, No. 20, pp. 4174-4182, 2010.
Patent Cooperation Treaty, "Notification of Transmittal of the International Search Report and the Written Opinion of the International Searching Authority, or the Declaration", PCT/US12/65923, mailed on Feb. 11, 2013.
Qiu, X.L. et al., "Synthesis and Biological Evaluation of a Series of Novel Inhibitor of Nek2/Hec1 Analogues", Journal of Medical Chemistry, vol. 52, No. 6, pp. 1757-1767, 2009.
Wu, G. et al., "Small Molecule Targeting the Hec1/Nek2 Mitotic Pathway Suppresses Tumor Cell Growth in Culture and in Animal", Cancer Research, vol. 68, pp. 8393-8399, 2008.
PubChem, "F5773-1986—Compound Summary", http://pubchem.ncbi.nl.m.nih.goy/summary/summary.cgi?cid=4551765#x304, Feb. 2, 2013.
PubChem, "F5773-1987—Compound Summary", http://pubchem.ncbi.nl.m.nih.gov/summary/summary.cgi?cid=4551766#x304, Feb. 2, 2013.
PubChem, "F5773-1988—Compound Summary", http://pubchem.ncbi.nl.m.nih.gov/summary/summary.cgi?cid=4551767#x304, Feb. 2, 2013.
Sahu, M. et al., "Condensed Heterocycles: Synthesis of 2-Aryl-5-oxo-5-H-pyrido-[3',2': 5,6]pyrimido[2,1-h][1,3,4]- oxadiazoles/thiadiazoles, 9-Aryl-5-oxo-5H-pyrido[3',2': 5,6]pyrimido[2, 14h]-thiadiazoles & 2-Aryl-6-hydroxy[1,3,4]- thiadiazolo/thiazolo[3,2-1]-benzimidazoles", Indiana Journal of Chemistry, Dec. 1986, vol. 25B, pp. 1266-1268.
PubChem, "ZINC00946516—Compound Summary", http://pubchem.ncbi.nl.m.nih.gov/summary/summary.cgi?cid=1185425#x304, Feb. 2, 2013.
PubChem, "ZINC01746105—Compound Summary", http://pubchem.ncbi.nl.m.nih.gov/summary/summary.cgi?cid=155416#x304, Feb. 2, 2013.
PubChem, "ZINC04072672—Compound Summary", http://pubchem.ncbi.nl.m.nih.gov/summary/summary.cgi?cid=4168446#x304, Feb. 2, 2013.

* cited by examiner

*Primary Examiner* — Jeffrey S Lundgren
*Assistant Examiner* — William Lee
(74) *Attorney, Agent, or Firm* — Fish & Tsang, LLP

(57) ABSTRACT

Compounds, compositions, and methods for modulation of Hec1/Nek2 interaction are provided. Such compounds disrupt Nek2/Hec1 binding and may be useful as chemotherapeutic agents for neoplastic diseases.

13 Claims, 10 Drawing Sheets

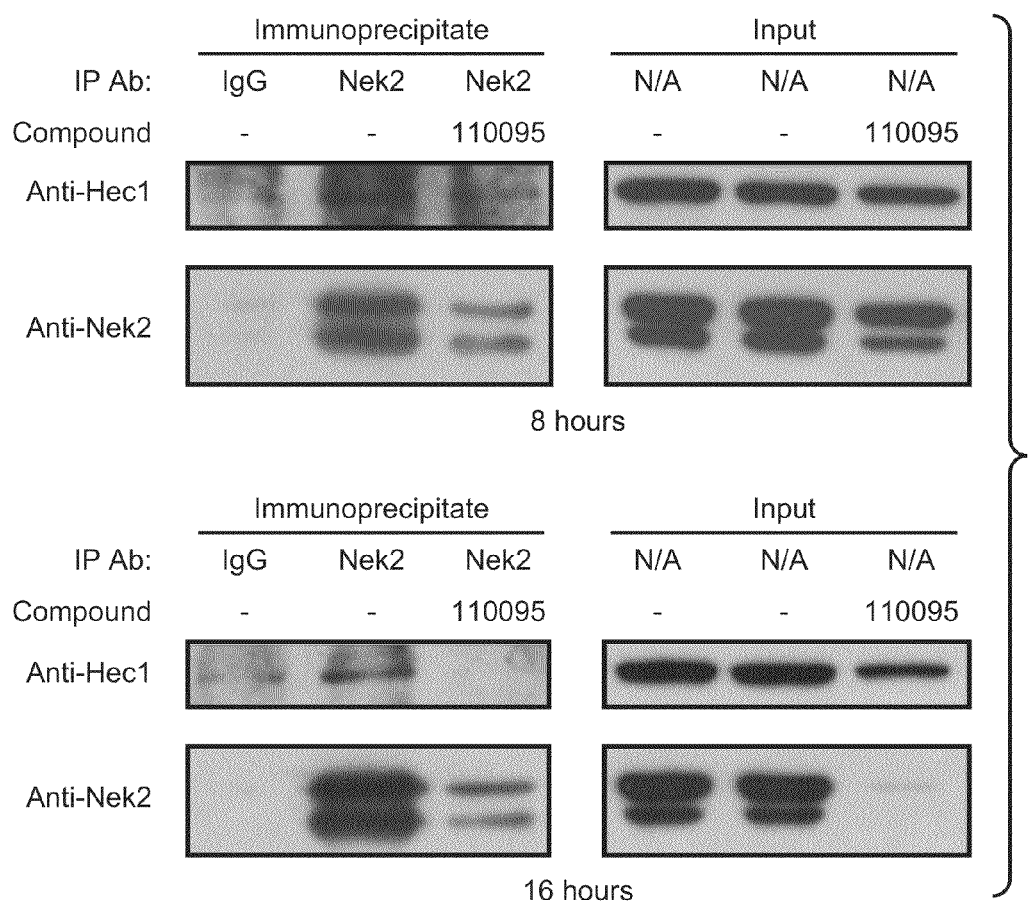
FIG. 1
FIG. 6
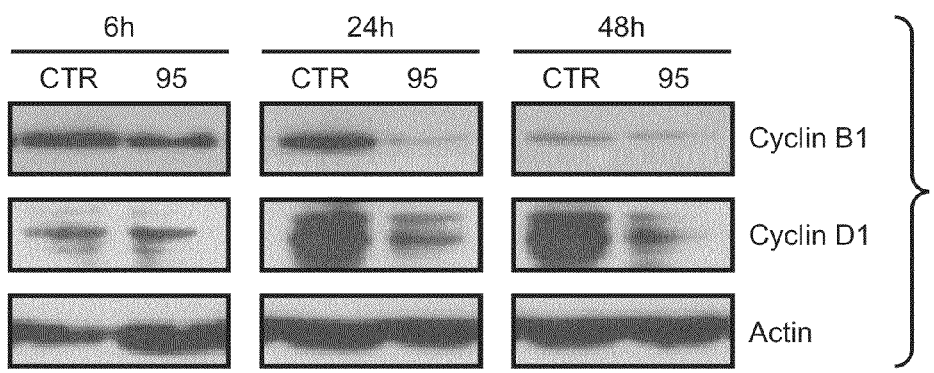

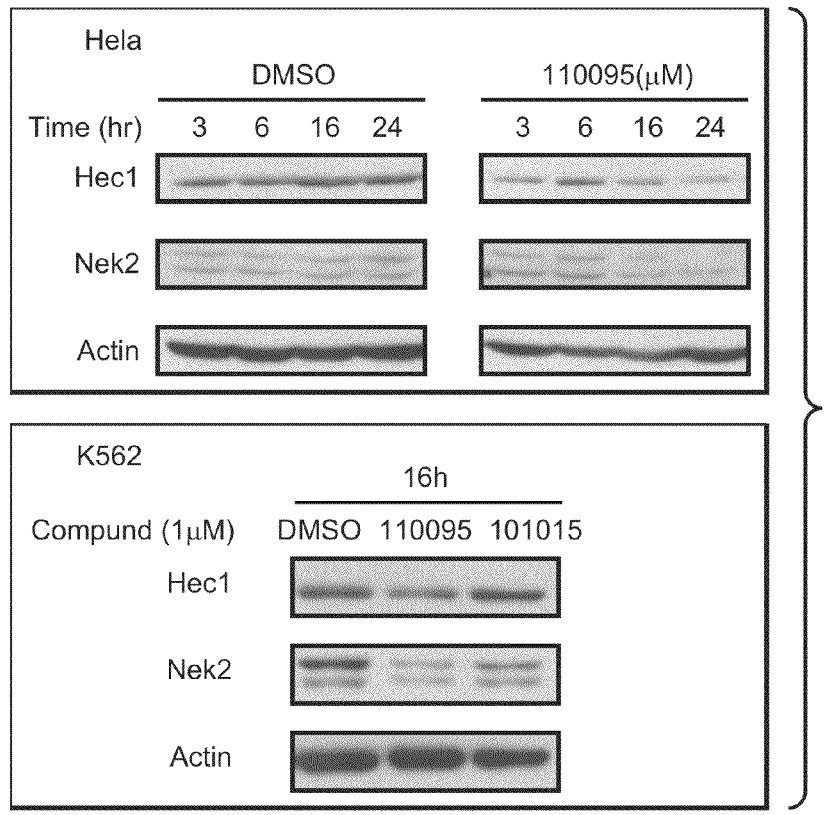
FIG. 2
FIG. 3
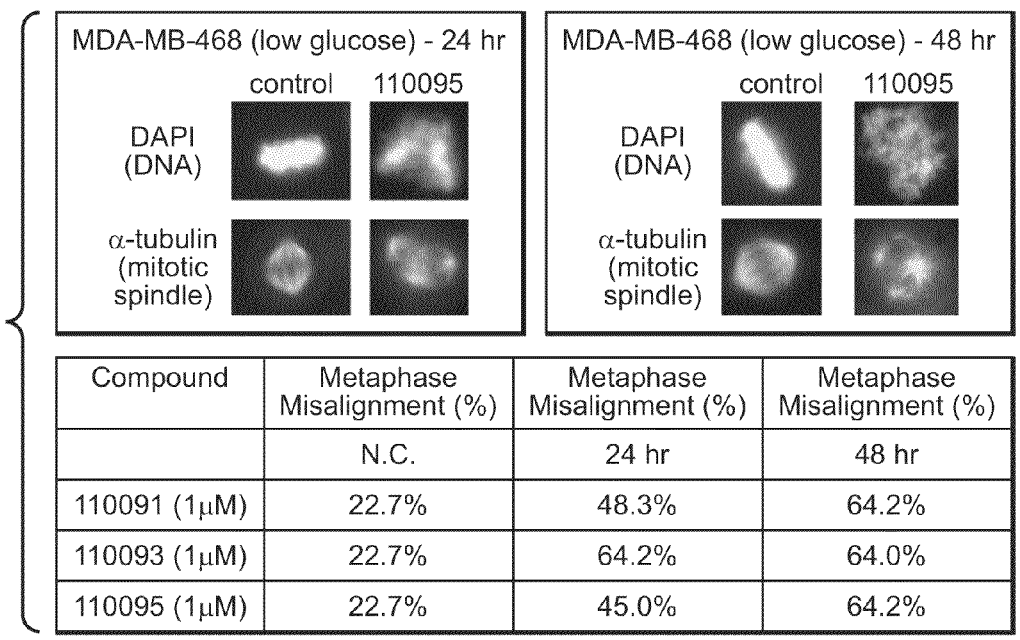

1 µM 110091, 110093, 110095 treatment in Hela cells in DMEM medium (Low glucose)

1 µM 110078 (78), 1 µM 110079 (79) and 100 nM Taxol (Tax) treatment of HeLa cells

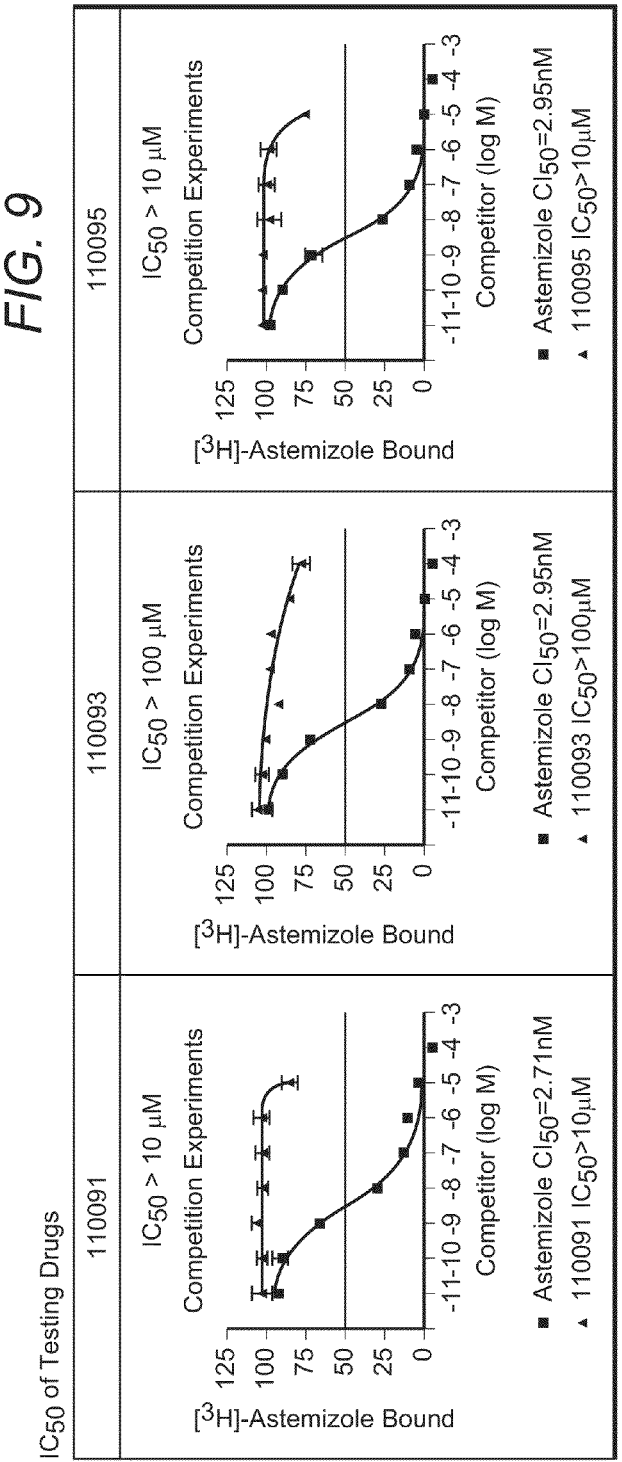

MODULATORS OF HEC1 ACTIVITY AND METHODS THEREFOR

This application claims priority to U.S. Provisional Application with Ser. No. 61/564,773, which was filed on 29 Nov. 2011, and is further related to International application WO 2011/115998, both of which are incorporated by reference herein.

The claimed invention was made as a result of activities undertaken within the scope of a joint research agreement between Taivex Therapeutics Corporation, Taipei, Taiwan, and Development Center for Biotechnology, New Taipei City, Taiwan.

FIELD OF THE INVENTION

The field of the invention is various compounds, compositions, and methods related to modulation of activity of Hec1, particularly as it related to inhibition of tumor cell propagation and growth.

BACKGROUND

While mechanisms associated with mitotic regulation are conceptually an attractive target in attempts to reduce tumor cell growth, compounds with high specific activity and selectivity and desirable pharmacological profile have been elusive. For example, the spindle apparatus can be targeted with spindle toxins (e.g., taxanes, vinca alkaloids, etc.) with relatively high activity, but many spindle toxins are unacceptable for pharmaceutical intervention as such poisons are often non-specific.

To improve specificity of treatment, components for spindle and kinetochore regulation or mitotic checkpoint control may be selected that have been shown to be functionally associated with cancer. For example, Hec1 is a critical component in spindle checkpoint signaling that is highly expressed in cancer and helps assure correct segregation of chromosomes during cell division. Hec1 interacts with various other kinetochore components including Nuf2, Spc 24, Spc25, and Zwint-1, as well as with mitotic kinases Nek2 and Aurora B. Overexpression of Hec1 is a common feature of a large variety of cancers and cancer cell lines, and can often serve as a prognostic marker in primary breast cancer and other cancers. Based on the apparent importance of Hec1 in tumor cell growth, inhibitory MA (siMA) has been used to reduce Hec1 expression and has shown considerable promise, at least in an animal model. However, in vivo delivery of effective amounts of siMA with high specificity to the tumor is often problematic.

More recently, various small molecule inhibitors have been developed that interfere with the Nek2/Hec1 interaction. Since Nek2 is a regulatory component of Hec1 in mitosis, abrogation of the Hec1/Nek2 function was expected to result in chromosome mis-segregation and cell death. Several promising compounds have been reported (see Qiu et al, *J. Med. Chem.*, 2009, 52 (6), pp 1757-1767; Wu et al, *Cancer Res.* 2008 Oct. 15; 68(20):8393-9) that had significant cell killing activity and directly targeted the Hec1/Nek2 pathway. These and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply. However, while the observed activity was in at least some cases promising, problems associated with solubility, toxicity, and the need to use relatively high concentrations in order to be effective nevertheless remained.

Thus, there remains a pressing need for improved compounds, compositions, and methods for Hec1 inhibition, particularly as it relates to use of such compounds in the treatment of cancer and other proliferative diseases.

SUMMARY OF THE INVENTION

The inventors have discovered certain compounds that are capable of selectively disrupting a Hec1/Nek2 complex and/or to selectively preventing Hec1 from binding to Nek2. Consequently, the compounds and compositions presented herein are capable of inducing abnormal mitosis and apoptosis in cancer cells, and of accumulating sub G1 apoptotic cells. Treatment of cells with contemplated compounds may also alter expression of a number of cell cycle and apoptotic regulators. For example, especially contemplated compounds can induce caspase 3 and PARP cleavage, down-regulation of anti-apoptotic regulators (including Mcl-1 and XIAP), and induction of cyclin B1 and cyclin D1 degradation. All the above-mentioned cell-cycle and apoptotic regulators are key players in normal cell growth. Therefore, contemplated compounds can be used to abrogate Hec1/Nek2 function and may be used for anticancer therapy, to inhibit cancer cell proliferation, and/or induce cell death.

In one embodiment of the inventive concept, the inventive subject matter is drawn to various compounds, compositions, and methods for Hec1 inhibition. More particularly, contemplated compounds may include those according to Formula I

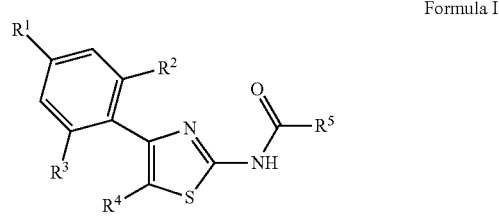

Formula I where $R^1$, $R^2$, $R^3$, $R^4$, and $R^5$ are described as further below. In some embodiments of the inventive concept compounds can have a structure according to Formulae II and/or III (with respective radicals described in more detail below).

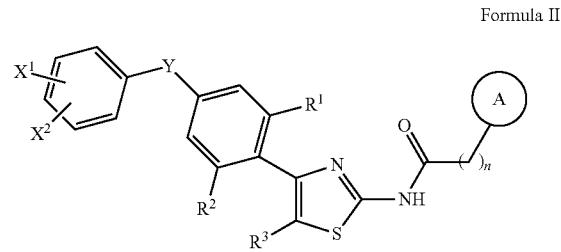

Formula II

Formula III

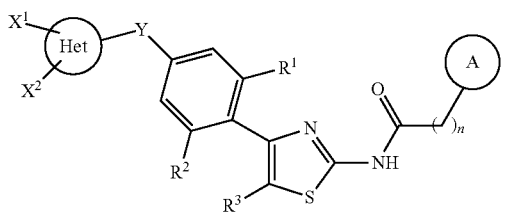

In still other embodiments of the inventive concept, contemplated compounds can have a structure according to Formulae IV, V, and/or VI.

Formula IV

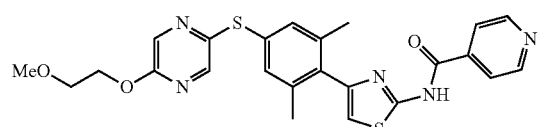

Formula V

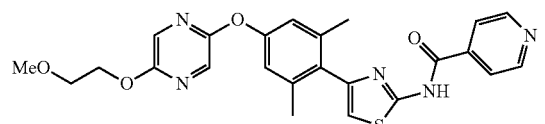

Formula VI

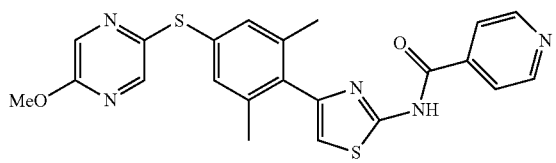

In some embodiments of the inventive concept, $R^1$, $R^2$, and $R^3$ may be, independently, hydrogen, alkyl, alkenyl; alkynyl, alkoxy, aryl, halogen, nitro, cyano, cycloalkyl, heterocycloalkyl, cycloalkenyl, heterocycloalkenyl, $OR_a$, $SR_a$, $NR_aR_b$, —$S(O)_2R_a$, —$S(O)_2NR_aR_b$, —$C(O)R_a$, —$C(O)NR_aR_b$, —$NR_aC(O)R_b$, —$NR_aS(O)_2R_b$, —$N{=}CR_aR_b$, and/or —$NR_aC(O)NHR_b$; where $R_a$ and $R_b$ can be independently hydrogen, alkyl, alkenyl, alkynyl, aryl, aryloxy, alkoxy, hydroxy, heteroaryl, cycloalkyl, heterocycloalkyl, cycloalkenyl, or heterocycloalkenyl, or $R_a$ and $R_b$, together with a nitrogen atom to which they are bonded, are heteroaryl, heterocycloalkyl, or heterocycloalkenyl. In other embodiments of the inventive subject matter, $R^2$, $R^3$, and $R^4$ may independently be hydrogen $C_1$-$C_6$ alkyl, halogen, or $OR_a$. In still other embodiments of the inventive concept, $R^5$ may be alkyl, phenylalkyl, heteroarylalkyl, phenyalkenyl, heteroarylalkenyl, phenyl, heteroaryl, heterocycloalkyl, or heterocycloalkenyl. Such aryl, heteroaryl, and/or pyridinyl groups may be substituted aryl, heteroaryl, and pyridinyl groups, respectively. Each of $R^1$, $R^2$, $R^3$, $R^4$, $R^5$, $R_a$, and $R_b$ may be independently optionally substituted; in addition, n may be 0 or 1.

In other embodiments of the inventive concept, $X^1$ and $X^2$ may be, independently, H, alkyl, alkenyl, alkynyl, halogen, nitro, cyano, cycloalkyl, heterocycloalkyl, cycloalkenyl, heterocycloalkenyl, $OR_a$, $NR_aR_b$, —$S(O)_2R_a$, —$S(O)_2NR_aR_b$, —$C(O)R_a$, —$C(O)NR_aR_b$, —$NR_aC(O)Rb$, —$NR_aS(O)_2R_b$, —$N{=}CR_aR_b$, —$NR_aC(O)NHR_b$, or -$A^1(CH_2)_mA^2(CH_2)_pA^3(CH_2)_qA^4R_c$, where n, m, p, and or q are, independently, 4 or less. In such embodiments $A^1$, $A^2$, $A^3$, and $A^4$ may be independently selected from null, $CH_2$, $CHR_a$, $CR_aR_b$, O, NH, $NR_a$, S, SO, and $SO_2$. Similarly, $R_c$ may be hydrogen, alkyl, alkenyl, alkynyl, alkoxy, aryl, halogen, nitro, cyano, cycloalkyl, heterocycloalkyl, cycloalkenyl, heterocycloalkenyl, $OR_a$, $SR_a$, $NR_aR_b$, —$S(O)_2R_a$, —$S(O)_2NR_aR_b$, —$C(O)R_a$, —$C(O)NR_aR_b$, —$NR_aC(O)R_b$, —$NR_aS(O)_2R_b$, —$N{=}CR_aR_b$, or —$NR_aC(O)NHR_b$. In still other aspects of the inventive subject matter, Y may be $CH_2$, $CHR_a$, $CR_aR_b$, O, NH, S, SO, or $SO_2$. Each of $X^1$ and $X^2$ may be independently optionally substituted.

In some embodiments of the inventive subject matter, where $R^1$ and $R^2$ are methyl and where $R^3$ is hydrogen, $R^5$ may not be thiazolyl, N-methylimidazolyl, pyrazinyl, pyridinyl, morpholinyl, phenyl, or dimethoxyphenyl. In other embodiments of the inventive subject matter, where $R^1$, $R^2$, and $R^3$ are methyl, $R^5$ may not be thiazolyl, N-methylimidazolyl, pyrazinyl, pyridinyl, morpholinyl, phenyl, methoxyphenyl, dihydroxyphenyl, hydroxymethoxyphenyl, trifluoromethylphenyl, or dimethoxyphenyl. In still other embodiments of the inventive concept, where $R^1$ and $R^2$ are methyl and where $R^3$ is hydroxyl or methoxy, $R^5$ may not be phenyl.

In other embodiments of the inventive concept, a thiazole ring may be substituted by a compound from the group

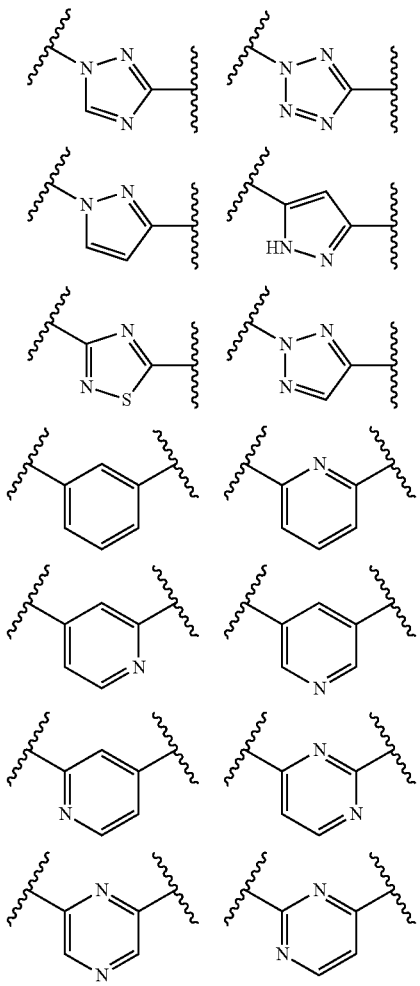

-continued

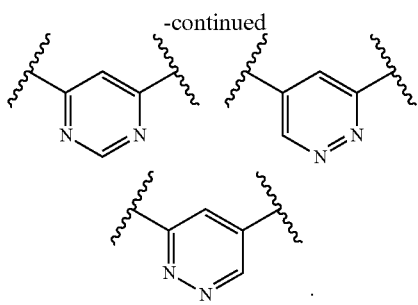

In still other embodiments of the inventive concept,

A may be one or more of:

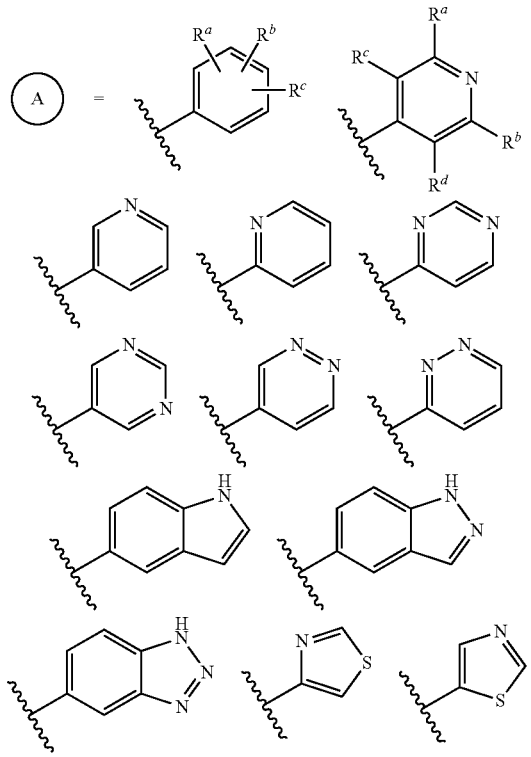

where $R_c$ and/or $R_d$ may be $R_a$.

Compounds of the inventive concept may be in combination with an ion to form a salt, or as a free base. Similarly, compounds of the inventive concept may include metabolites of the compounds described above, for example, where $R^1$ is $SR_a$ and wherein the S is the form of a sulfone or sulphoxide.

In some aspects of the inventive subject matter, contemplated compounds are inhibitors of Hec1, and/or may be characterized as disrupting Hec1/Nek2 interaction. Consequently, the compounds presented herein may be particularly suitable for use as therapeutic agents that disrupt the mitotic pathway. Another embodiment of the inventive concept is a pharmaceutical composition that includes a compound of the inventive concept and a pharmaceutically acceptable carrier.

Such a compound may be formulated for oral administration, injection, and/or topical application. Such a pharmaceutical composition may contain a compound of the inventive concept in a concentration effective at modifying and/or disrupting Hec1/Nek1 interactions in a patient when the pharmaceutical composition is administered to the patient. Such a pharmaceutical composition may, optionally, include a drug that interferes with microtubule formation and/or degradation.

Thus, in another aspect of the inventive subject matter, a method of disrupting Nek2/Hec1 interaction is contemplated that may include a step of contacting a Nek2/Hec1 complex with one or more compounds presented herein in an amount that is effective to disrupt Nek2/Hec1 binding. While all manners of contacting are generally contemplated, in such an embodiment the Hec1/Nek2 complex may be formed in vivo in a mammal, and a compound of the inventive concept may be administered orally, topically, or parenterally. Optionally, a method of the inventive concept may include co-administration of a drug that interferes with microtubule formation and/or degradation.

Another embodiment of the inventive concept is a method for treating neoplastic disease in a mammal, including the step of administering a compound of the inventive concept in an amount effective to disrupt Hec1/Nec2 binding and/or disrupt a Hec1/Nek2 complex. In such an embodiment a compound of the inventive concept may be administered orally, topically, or parenterally. Optionally, a method of the inventive concept may include co-administration of an antineoplastic drug.

Yet another embodiment of the inventive subject matter is a method for altering and/or improving a pharmacokinetic parameter of a compound of the inventive concept that includes the step of forming a tosylate salt of the compound. Such compounds may be selected from:

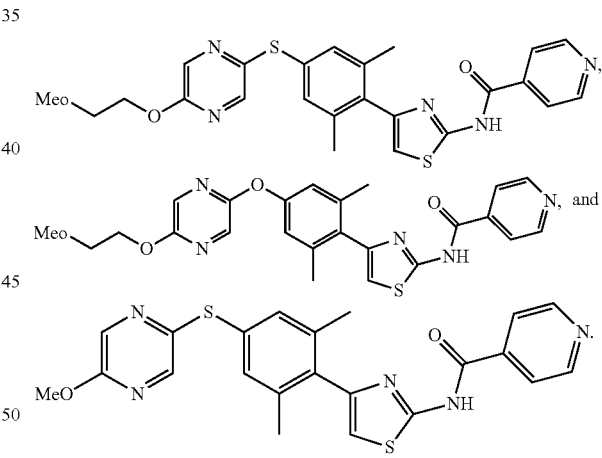

Similarly, another embodiment of the inventive subject matter is a pharmaceutical composition that includes a carrier and a tosylate salt of a compound of the inventive concept.

Various objects, features, aspects and advantages of the inventive subject matter will become more apparent from the following detailed description of preferred embodiments, along with the accompanying drawings and figures in which like numerals represent like components.

BRIEF DESCRIPTION OF THE FIGURES

FIG. 1 shows results of immunoprecipitation studies demonstrating disruption of Hec1-Nek2 interaction using an exemplary compound according to the inventive subject matter.

FIG. 2 shows results of immunoblot analyses demonstrating reduction of Nek2 protein in cancer cells treated with exemplary compounds according to the inventive subject matter.

FIG. 3 shows results of fluorescent microscopy studies demonstrating chromosomal misalignment in cancer cells treated with exemplary compounds according to the inventive subject matter for various time periods.

FIG. 6 shows results of immunblotting studies demonstrating cyclin B1 and cyclin D1 degradation in cancer cells after treatment with an exemplary compound according to the inventive subject matter.

FIG. 7 shows results of tumor outgrowth studies.

FIG. 8 shows results of permeability studies of cells treated with exemplary compounds according to the inventive subject matter, demonstrating moderate Caco-2 permeability in both directions with no indication of significant active efflux.

FIG. 9 shows results of binding studies, demonstrating hERG binding of exemplary compounds with $IC_{50}$ of >10-100 μM.

DETAILED DESCRIPTION

Contemplated Compounds

Figure 4:
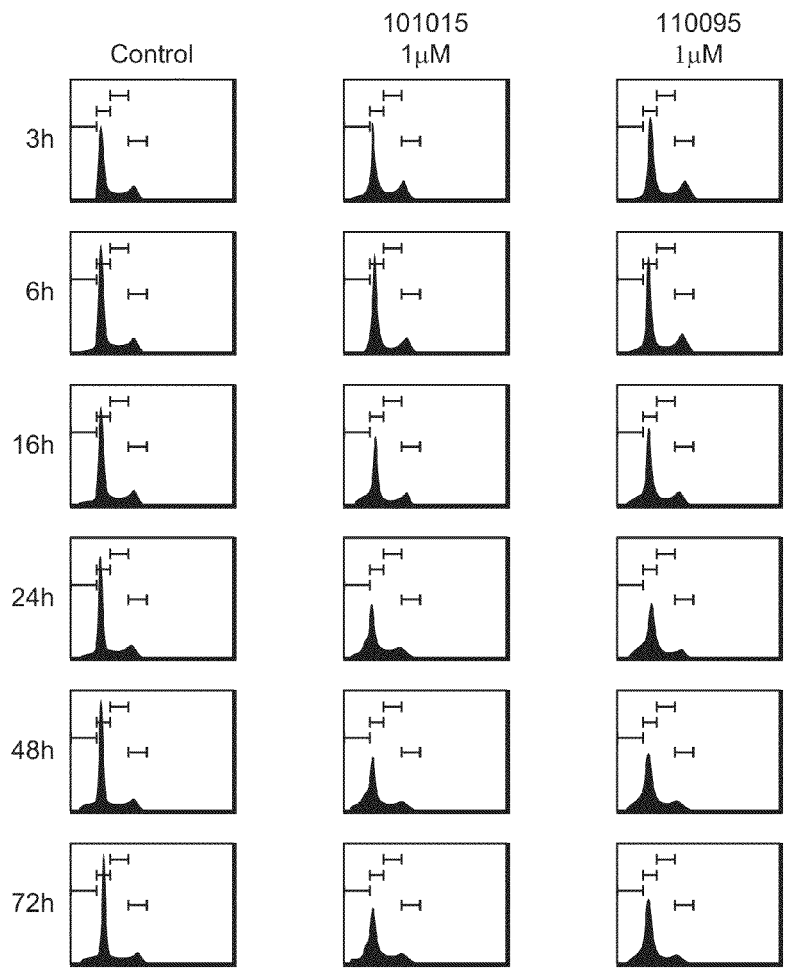
FIG. 4 shows results of fluorescence activated cell sorting (FACS) studies demonstrating the induction of apoptosis in cancer cells by cell cycle analysis after treatment with exemplary compounds according to the inventive subject matter.

The inventors have discovered that certain compounds according to Formula I can be prepared and have advantageous properties as moieties that interfere with Hec1. Particularly preferred compounds will include those according to Formula I

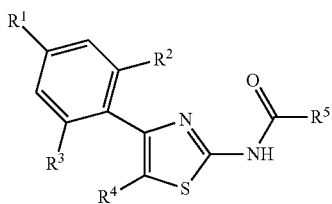

Formula I

In some embodiments of the inventive concept, $R^1$ may be hydrogen, alkyl, alkenyl, alkynyl, alkoxy, aryl, halogen, nitro, cyano, cycloalkyl, heterocycloalkyl, cycloalkenyl, heterocycloalkenyl, $OR_a$, $SR_a$, $NR_aR_b$, —$S(O)_2R_a$, —$S(O)_2NR_aR_b$, —$C(O)R_a$, —$C(O)NR_aR_b$, —$NR_aC(O)R_b$, —$NR_aS(O)_2R_b$, —N=$CR_aR_b$, or —$NR_aC(O)NH$—$R_b$; $R_a$ and $R_b$ are independently hydrogen, alkyl, alkenyl, alkynyl, aryl, aryloxy, alkoxy, hydroxy, heteroaryl, cycloalkyl, heterocycloalkyl, cycloalkenyl, or heterocycloalkenyl, or $R_a$ and $R_b$, together with a nitrogen atom to which they are bonded, are heteroaryl, heterocycloalkyl, or heterocycloalkenyl; $R^2$, $R^3$, and $R^4$ are independently hydrogen, $C_1$-$C_6$ alkyl, halogen, or $OR_a$; and $R^5$ is alkyl, phenylalkyl, heteroarylalkyl, phenyalkenyl, heteroarylalkenyl, phenyl, heteroaryl, heterocycloalkyl, or heterocycloalkenyl; wherein each of $R^1$, $R^2$, $R^3$, $R^4$, $R^5$, $R_a$, and $R_b$ are independently optionally substituted. In other embodiments of the inventive concept compounds include those where (I) $R^1$ and $R^2$ are methyl and where $R^3$ is hydrogen, $R^5$ is not thiazolyl, N-methylimidazolyl, pyrazinyl, pyridinyl, morpholinyl, phenyl, or dimethoxyphenyl, (II) where $R^1$, $R^2$, and $R^3$ are methyl, $R^5$ is not thiazolyl, N-methylimidazolyl, pyrazinyl, pyridinyl, morpholinyl, phenyl, methoxyphenyl, dihydroxyphenyl, hydroxymethoxyphenyl, trifluoromethylphenyl, or dimethoxyphenyl, and/or (1.1) where $R^1$ and $R^2$ are methyl and where $R^3$ is hydroxyl or methoxy, $R^5$ is not phenyl.

In some embodiments of the inventive concept $R^1$ may be alkoxy, $SR_3$, $OR_a$, or, —$S(O)_2R_a$, such that $R_a$ is alkyl or optionally substituted aryl, that $R^2$, $R^3$, and $R^4$ are independently hydrogen or $C_1$-$C_6$ alkyl, and that $R^5$ is optionally substituted heteroaryl. Other compounds of the inventive concept are among those where $R^1$ is alkoxy, $SR_a$, $OR_a$, or, —$S(O)_2R_a$, where $R_a$ is alkyl or an optionally substituted aryl, where $R^2$ and $R^3$ are $C_1$-$C_6$ alkyl, and where $R^5$ is optionally substituted (e.g., halogenated) pyridinyl In some embodiments of the inventive subject matter, $R^1$ can be $OR_a$, wherein $R_a$ is optionally substituted aryl, $R^2$ and $R^3$ are $C_1$-$C_6$ alkyl, and $R^5$ is an optionally substituted pyridinyl.

Consequently, and viewed from a different perspective, compounds of the inventive concept may have a structure according to Formula II

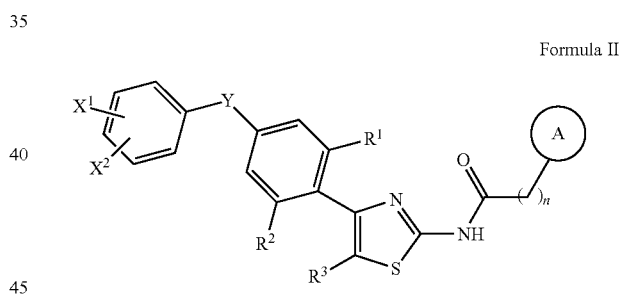

Formula II in which wherein $X^1$ and $X^2$ can be independently H, alkyl, alkenyl, alkynyl, halogen, nitro, cyano, cycloalkyl, heterocycloalkyl, cycloalkenyl, heterocycloalkenyl, $OR_a$, $NR_aR_b$, —$S(O)_2R_a$, —$S(O)_2NR_3R_b$, —$C(O)R_a$, —$C(O)NR_aR_b$, —$NR_aC(O)R_b$, —$NR_aS(O)_2R_b$, —N=$CR_aR_b$, or —$NR_aC(O)NHR_b$; alternatively, $X^1$ and $X^2$ may be independently -$A^1(CH_2)_mA^2(CH_2)_pA^3(CH_2)_qA^4R_c$; where $A^1$, $A^2$, $A^3$, and $A^4$ are independently selected from null, $CH_2$, $CHR_a$, $CR_aR_b$, O, NH, $NR_a$, S, SO, and $SO_2$; where $R_c$ is independently hydrogen, alkyl, alkenyl, alkynyl, alkoxy, aryl, halogen, nitro, cyano, cycloalkyl, heterocycloalkyl, cycloalkenyl, heterocycloalkenyl, $OR_a$, $SR_a$, $NR_aR_b$, —$S(O)_2R_a$, —$S(O)_2NR_aR_b$, —$C(O)R_a$, —$C(O)NR_aR_b$, —$NR_aC(O)R_b$, —$NR_aS(O)_2R_b$, —N=$CR_aR_b$, or —$NR_aC(O)NHR_b$; and where m, p, and q are independently 0, 1, 2, 3, or 4; Y is $CH_2$, $CHR_a$, $CR_aR_b$, O, NH, $NR_a$, S, SO, or $SO_2$; $R^1$, $R^2$, and $R^3$ are independently H, alkyl, alkoxy, or halogen; n is 0, 1, or 2; and in which A is an optionally substituted aryl or an optionally substituted heteroaryl. Embodiments of the inventive concept may include a compound as shown below

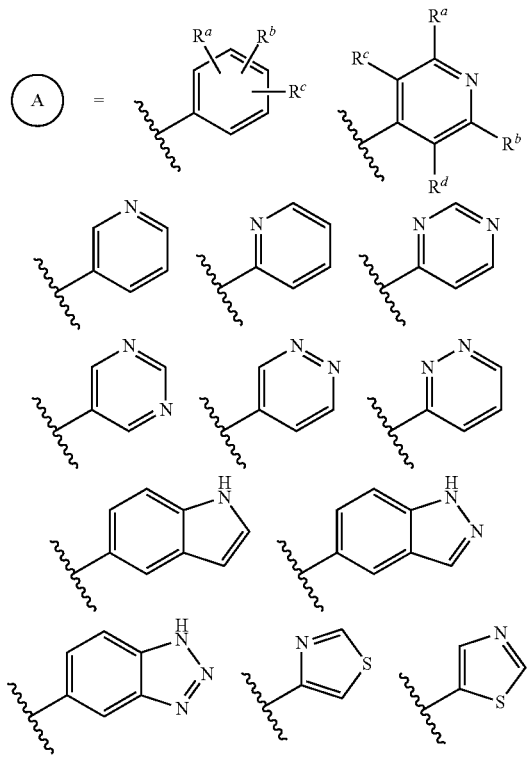

wherein each of $X^1$ and $X^2$ is independently optionally substituted, and wherein $R_c$ and $R_d$ are independently $R_a$. Among such compounds, it is further contemplated that Y may be O, S, or $SO_2$, and/or that A may be an optionally substituted pyridinyl. Most typically, $X^1$ and $X^2$ in such compounds will be independently H, alkyl, and alkoxy, and n is 0 or 1. With respect to remaining radicals, the same considerations as provided for Formula I apply.

Still further compound of the inventive subject matter may have a structure according to Formula III

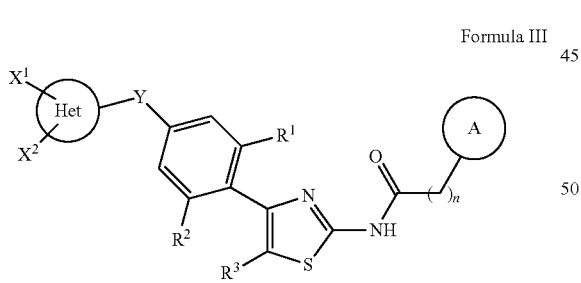

Formula III in which wherein $X^1$ and $X^2$ may be independently H, alkyl, alkenyl, alkynyl, halogen, nitro, cyano, cycloalkyl, heterocycloalkyl, cycloalkenyl, heterocycloalkenyl, $OR_a$, $NR_aR_b$, —$S(O)_2R_a$, —$S(O)_2NR_aR_b$, —$C(O)R_a$, —$C(O)NR_aR_b$, —$NR_aC(O)R_b$, —$NR_aS(O)_2R_b$, —N=$CR_aR_b$, or —$NR_aC(O)NHR_b$. Alternatively, $X^1$ and $X^2$ may be independently -$A^1(CH_2)_mA^2(CH_2)_pA^3(CH_2)_qA^4R_c$; where $A^1$, $A^2$, $A^3$, and $A^4$ are independently selected from null, $CH_2$, $CHR_a$, $CR_aR_b$, O, NH, $NR_a$, S, SO, and $SO_2$; where $R_c$ is independently hydrogen, alkyl, alkenyl, alkynyl, alkoxy, aryl, halogen, nitro, cyano, cycloalkyl, heterocycloalkyl, cycloalkenyl, heterocycloalkenyl, $OR_a$, $SR_a$, $NR_aR_b$, —$S(O)_2R_a$, —$S(O)_2NR_aR_b$, —$C(O)R_a$, —$C(O)NR_aR_b$, —$NR_aC(O)R_b$, —$NR_aS(O)_2R_b$, —N=$CR_aR_b$, or —$NR_aC(O)NHR_b$; and where m, p and q are 0, 1, 2, 3, or 4; Y is $CH_2$, $CHR_a$, $CR_aR_b$, O, NH, $NR_a$, S, SO, or $SO_2$; $R^1$, $R^2$, and $R^3$ are independently H, alkyl, alkoxy, or halogen; n is 0, 1, or 2; wherein each of $X^1$ and $X^2$ is independently optionally substituted; wherein $R_c$, and $R_d$ is independently $R_a$, and in which A and Het are independently an aromatic and optionally substituted aryl or heteroaryl. Among other suitable choices, a compound of the inventive subject matter have a structure as described above, wherein

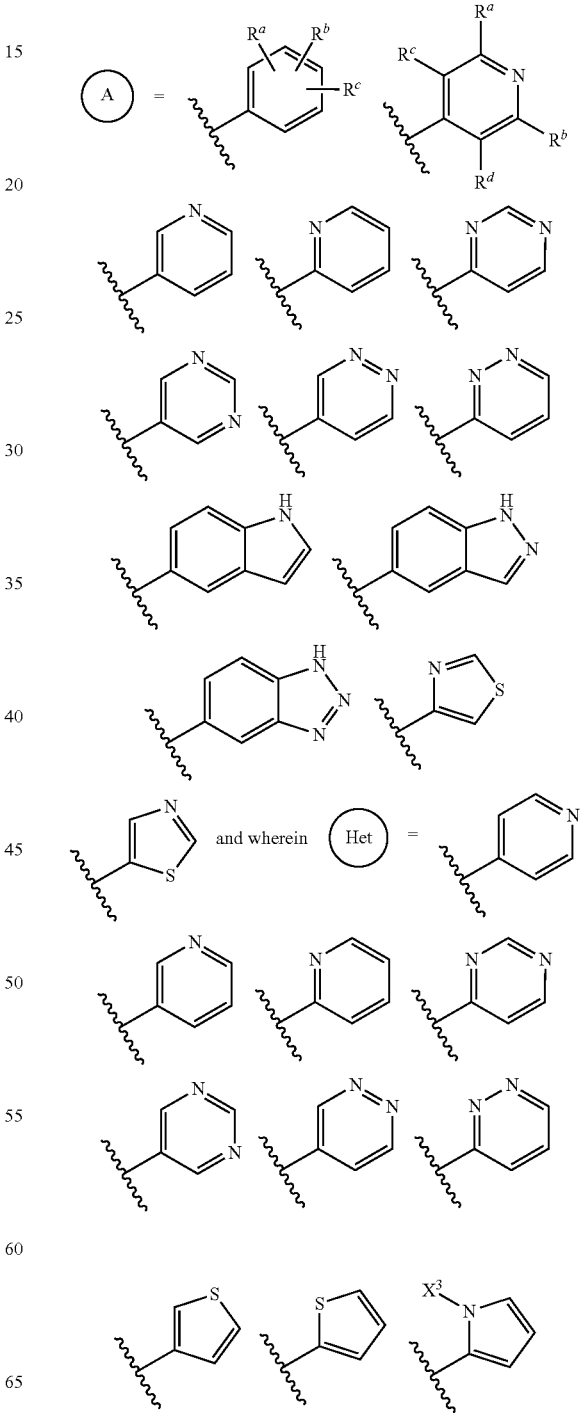

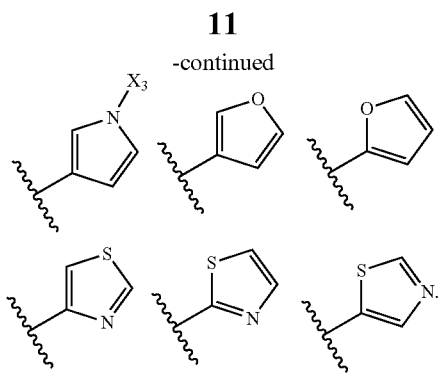

With respect to remaining radicals, the same considerations as noted for Formula I apply. Suitable compounds of the inventive concept according to Formula II may include those in which A is an optionally substituted pyridinyl, and/or wherein Y is O, S, or $SO_2$.

In view of the above and further experimental data (see below), compounds of the inventive concept may have a structure as shown below

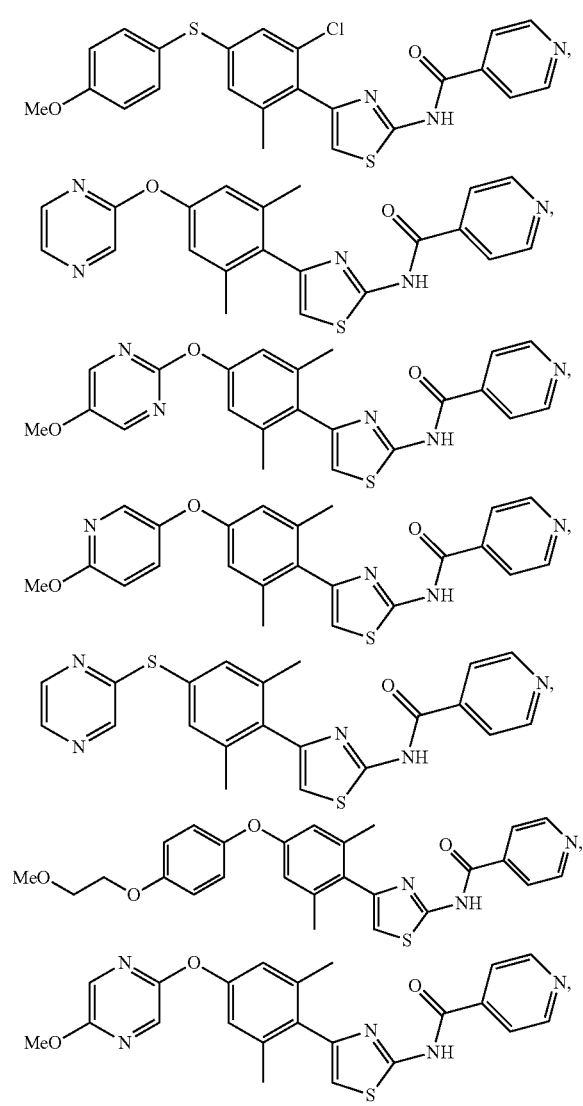

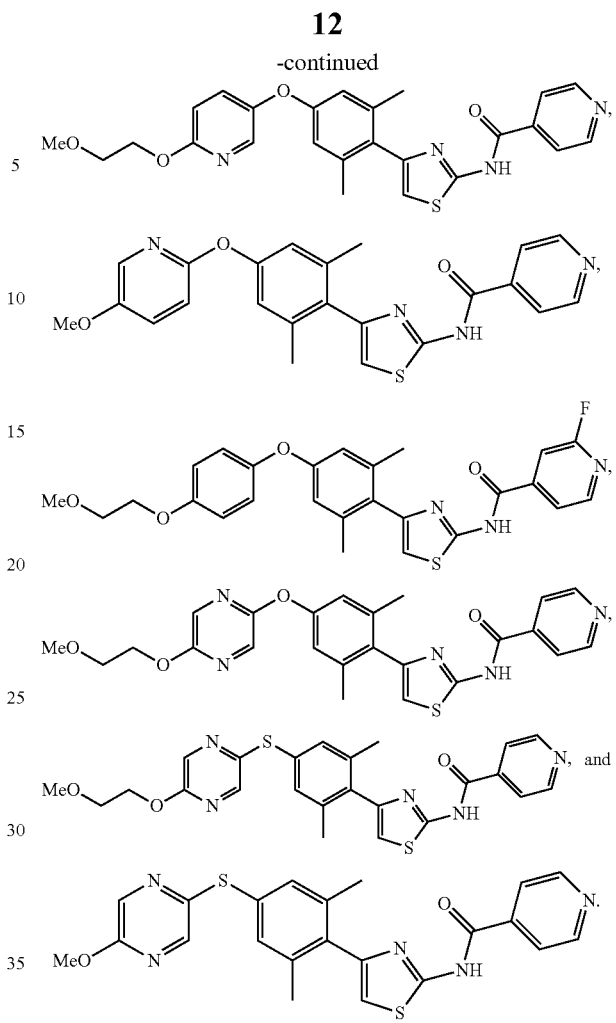

In yet another aspect of the inventive subject matter includes compounds as shown immediately below, their metabolites, prodrugs, and/or salts thereof.

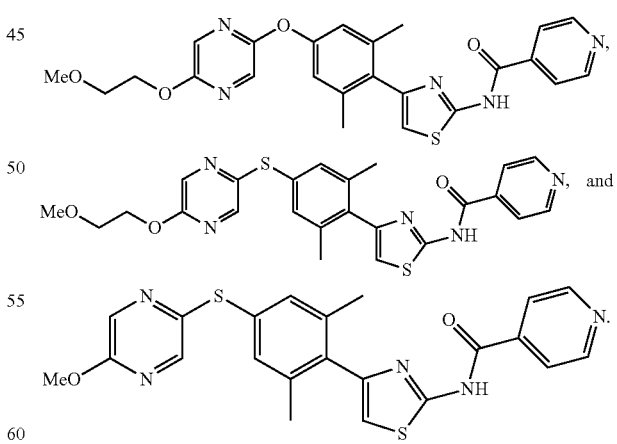

In still further aspects of the inventive concept, it should be appreciated that the central thiazole ring of the compounds having Formula I-III may be replaced with a number of heterocyclic and/or aromatic ring systems as is shown for Formula I*-III* below

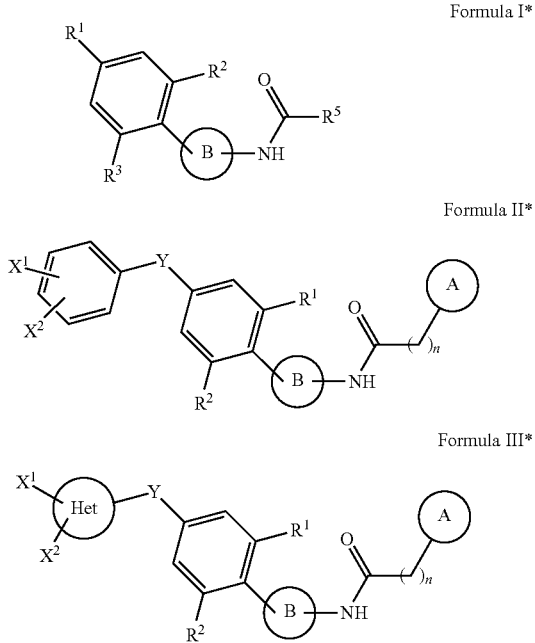

Formula I*

Formula II*

Formula III* in which B is defined as shown below (with respect to remaining radicals, the same considerations as noted for Formula I-III above apply)

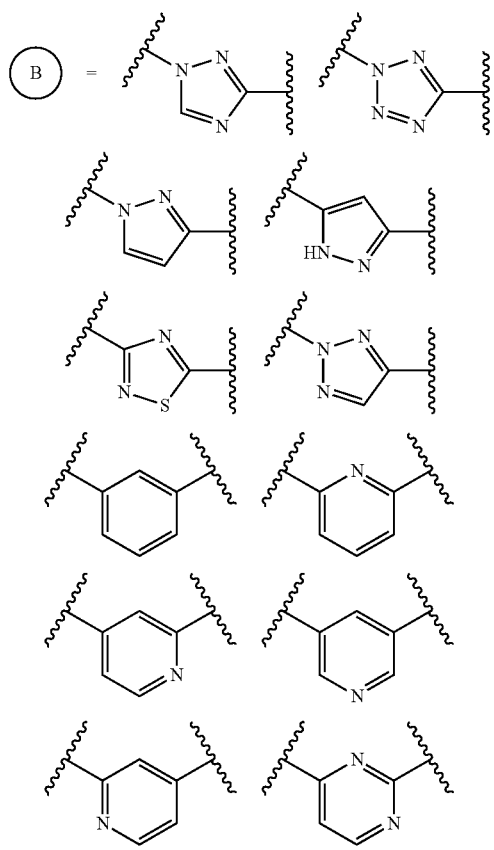

The term "alkyl" as used herein refers to a hydrocarbon radical, which may be straight, cyclic, or branched. The term "alkenyl", refers to an alkyl having at least one double bond. Where more than one double bond is present, it is contemplated that the double bonds may be conjugated or un-conjugated. The term "alkynyl", as used herein refers to an alkyl having at least one triple bond. Contemplated alkynyls may further include another triple bond or double bond, which may or may not be conjugated with the first triple bond. The term "alkoxy", as used herein, refers to an O-alkyl group, wherein the "alkyl" is defined as provided above.

A "cycloalkyl" as used herein refers to a non-aromatic monovalent monocyclic or polycyclic radical having from 3 to 14 carbon atoms, each of which may be saturated or unsaturated, and may be un-substituted or substituted by one or more suitable substituents as defined herein, and to which may be fused one or more aryl groups, heteroaryl groups, cycloalkyl groups, or heterocycloalkyl groups which themselves may be un-substituted or substituted by one or more substituents. Examples of cycloalkyl groups include cyclopropyl, cycloheptyl, cyclooctyl, cyclodecyl, cyclobutyl, adamantyl, norpinanyl, decalinyl, norbornyl, cyclohexyl, and cyclopentyl.

A "heterocycloalkyl" as used herein refers to a non-aromatic monovalent monocyclic or polycyclic radical having 1-5 heteroatoms selected from nitrogen, oxygen, and sulfur, and may be unsubstituted or substituted by one or more suitable substituents as defined herein, and to which may be fused one or more aryl groups, heteroaryl groups, cycloalkyl groups, or heterocycloalkyl groups which themselves may be un-substituted or substituted by one or more substituents. Examples of heterocycloalkyl groups include oxiranyl, pyrrolidinyl, piperidyl, tetrahydropyran, and morpholinyl.

An "aryl" (Ar) as used herein refers to an aromatic monocyclic or polycyclic radical comprising generally between 5 and 18 carbon ring members, which may be un-substituted or substituted by one or more suitable substituents as defined herein, and to which may be fused one or more cycloalkyl groups, heterocycloalkyl groups, or heteroaryl groups, which themselves may be un-substituted or substituted by one or more suitable substituents. Thus, the term "aryl group" includes a benzyl group (Bzl). Examples include phenyl, biphenyl, 1,2,3,4-tetrahydronaphthyl, naphthyl, anthryl, and phenanthryl.

A "heteroaryl" as used herein refers to an aromatic monocyclic or polycyclic radical comprising generally between 4 and 18 ring members, including 1-5 heteroatoms selected from nitrogen, oxygen, and sulfur, which may be un-substituted or substituted by one or more suitable substituents as defined below, and to which may be fused one or more cycloalkyl groups, heterocycloalkyl groups, or aryl groups, which themselves may be unsubstituted or substituted by one or more suitable substituents. Examples include thienyl, furanyl, thiazolyl, triazolyl, imidazolyl, isoxazolyl, oxadiazolyl, tetrazolyl, pyridyl, pyrrolyl, thiadiazolyl, oxadiazolyl, oxathiadiazolyl, thiatriazolyl, pyrimidinyl, isoquinolinyl, quinolinyl, napthyridinyl, phthalimidyl, benzimidazolyl, and benzoxazolyl.

The term "heterocycle" or "heterocyclic" as used herein refers to aromatic and non-aromatic heterocyclic groups, typically with 4 to 10 atoms forming a ring, and containing one or more heteroatoms (typically O, S, or N). Non-aromatic heterocyclic groups include groups having only 4 atoms in their ring system, but aromatic heterocyclic groups typically have at least 5 atoms in their ring system. Examples of non-aromatic heterocyclic groups include pyrrolidinyl, tetrahydrofuranyl, tetrahydrothienyl, tetrahydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo(3.i.0)hexanyl, 3H-indolyl, and quinolizinyl.

Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, is benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, quinazolinyl, benzothiazolyl, benzoxazolyl, quinoxalinyl, naphthyridinyl, and furopyridinyl. Contemplated 4-10 membered heterocycles may be C-attached or N-attached (where appropriate). For instance, a group derived from pyrrole may be pyrrol-1-yl (N-attached) or pyrrol-3-yl (C-attached).

As still further used herein, the term "substituted" as used herein refers to a replacement or modification of an atom (radical) or chemical group (e.g., $NH_2$, or OH) in a molecule with a functional group to produce a substituted molecule, and particularly contemplated functional groups include nucleophilic groups (e.g., —$NH_2$, —OH, —SH, —NC, etc.), electrophilic groups (e.g., C(O)OR, C(O)OH, etc.), polar groups (e.g., —OH), non-polar groups (e.g., aryl, alkyl, alkenyl, alkynyl, etc.), ionic groups (e.g.; —$NH_3$), and halogens (e.g., —F, —Cl), and all chemically reasonable combinations thereof. For example, where the molecule is an alkyl, the replaced radical is a hydrogen radical, and the functional group is a hydroxyl group, the H-atom is substituted by an OH group to form a substituted alkyl. In another example, where the molecule is an amino acid, the modified group is the amino group, and the functional group is an alkyl group, the amino group is alkylated to form an N-substituted amino acid.

For example, suitable substituents include halogen (chloro, iodo, bromo, or fluoro); $C_{1-6}$-alkyl; $C_{1-6}$-alkenyl; $C_{1-6}$-alkynyl, hydroxyl, $C_{1-6}$ alkoxyl; amino; nitro; thiol; thioether; imine; cyano; amido; phosphonato; phosphine; carboxyl; carbonyl; aminocarbonyl; thiocarbonyl; sulfonyl; sulfonamine; sulfonamide; ketone; aldehyde; ester; oxygen (=O); haloalkyl (e.g., trifluoromethyl); carbocyclic cycloalkyl, which may be monocyclic or fused or non-fused polycyclic (e.g., cyclopropyl, cyclobutyl, cyclopentyl, or cyclohexyl), or a heterocycloalkyl, which may be monocyclic or fused or non-fused polycyclic (e.g., pyrrolidinyl, piperidinyl, piperazinyl, morpholinyl, or thiazinyl); carbocyclic or heterocyclic, monocyclic or fused or non-fused polycyclic aryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl, or benzofuranyl); amino (primary, secondary, or tertiary); nitro; thiol; thioether, O-lower alkyl; O-aryl, aryl; aryl-lower alkyl; $CO_2CH_3$; $CONH_2$; $OCH_2CONH_2$; $NH_2$; $SO_2NH_2$; $OCHF_2$; $CF_3$; $OCF_3$; etc. It should be appreciated that all substituents contemplated herein may be further optionally substituted by one or more substituents noted above. Suitable substituents include, but are not limited to, hydroxyl groups, halogens, oxo groups, alkyl groups (and especially lower alkyl), acyl groups, sulfonyl groups, mercapto groups, alkylthio groups, alkyloxyl groups, cycloalkyl groups, heterocycloalkyl groups, aryl groups, heteroaryl groups, carboxyl groups, amino groups, alkylamino groups, dialkylamino groups, carbamoyl groups, aryloxyl groups, heteroaryloxyl groups, arylthio groups, heteroarylthio groups.

Moreover, it should also be appreciated that compounds according to the inventive subject matter may comprise one or more asymmetric centers, and may therefore exist in different enantiomeric forms, and that all enantiomeric forms of contemplated compounds are specifically contemplated herein. Accordingly, where contemplated compounds exhibit optical activity and/or have stereoisomers, all optical activities and/or isomeric forms are contemplated herein. Similarly, where double bonds distinguish a Z-form from an E-form (or cis- from trans-), both isomers are contemplated. Moreover, it is noted that the compounds according to the inventive subject matter may also be isotopically-labeled. Examples of suitable isotopes include, but are not limited to, $^2H$, $^3H$, $^{13}C$, $^{14}C$, $^{15}N$, $^{18}O$ $^{17}O$, $^{18}F$, or $^{36}Cl$. Certain isotopically-labeled compounds of the inventive subject matter, for example those into which $^{14}C$ and/or $^3H$ is/are incorporated, may be useful in drug and/or substrate tissue distribution assays. Alternatively, substitution with non-radioactive isotopes (e.g., $^2H$ or $^{13}C$) can afford certain therapeutic advantages resulting from greater metabolic stability, for example increased in vivo half-life or reduced dosage requirements and, hence, may be preferable in some circumstances.

Contemplated compounds may be prepared as pharmaceutically acceptable salt(s), which especially include salts of acidic or basic groups that may be present in the contemplated compounds. For example, where contemplated compounds are basic in nature it should be noted that such compounds can form a wide variety of salts with various inorganic and organic acids. Suitable acids will provide pharmacologically acceptable anions, including chloride, bromide, iodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate (1,1'-methylene-bis-(2-hydroxy-3-naphthoate)) anions. Similarly, where contemplated compounds are acidic in nature it should be noted that such compounds may form base salts with various pharmacologically acceptable cations, and especially suitable cations include alkali metal or alkaline earth metal ions (e.g., sodium and potassium cations).

In still further contemplated aspects, the compounds presented herein may be prepared as prodrugs, and all known manners and types of prodrugs are considered suitable for use herein, so long as such prodrug will increase the concentration of the drug (or metabolite of the prodrug) at a target organ, target cell, and/or Hec1. For example, where contemplated compounds have a free amino, amido, hydroxy, thio, or carboxylic group, it is contemplated that such groups can be employed to covalently and releasably bind and/or couple to a moiety that converts the drug into a prodrug. Therefore, prodrugs particularly include those in which contemplated compounds form an ester, amide, disulfide bond, or any cleavable bond with a suitable moiety. Such moieties may assist in organ or cell-specific delivery of the drug, and therefore particularly include receptor ligands and their analogs, antibody or antibody fragments, single chain antibodies, peptides, aptamers, or other high-affinity ligands (Kd<$10^6$M).

For example, a carboxyl group can be derived to form an amide or alkyl ester, which may include an ether, amine-, and/or carboxylic acid group. Free hydroxyl groups may be derived using hemisuccinates, phosphate esters, dimethylaminoacetates, and phosphoryloxymethyloxycarbonyls, as outlined by D. Fleisher et al (*Advanced Drug Delivery* 40 Reviews (1996) 19, p. 115). Carbamate prodrugs of hydroxyl and amino groups are also contemplated, as are carbonate prodrugs and sulfate esters of hydroxyl groups. Deriving hydroxyl groups as (acyloxy)methyl and (acyloxy)ethyl-ethers, wherein the acyl group may be an alkyl ester (optionally substituted), or where the acyl group is an amino acid ester are also contemplated (prodrugs of this type are described in R. P. Robinson et al., *J. Medicinal Chemistry* (1996) 39. p. 10).

In still further contemplated aspects, it should be appreciated that the compounds according to the inventive subject matter may also be active as a metabolite (of a prodrug or non-prodrug form) and that all of such metabolites are contemplated herein. For example, suitable metabolites include hydroxylated forms, oxidized forms, glucuronidated forms, sulfated forms, etc. Moreover, it is also noted that the metabolites may be more active than the originally administered form.

Contemplated Compositions and Formulations

Based on the activity of the compounds as Hec1 modulators, the inventors contemplate that the compounds and compositions according to the inventive subject matter may be employed for prophylaxis and/or treatment of various diseases associated with Hec1 dysfunction and/or overexpression in a mammal, and in fact for all diseases that positively respond to administration of contemplated compounds. The term "dysfunction of Hec1" as used herein refers to any abnormality in Hec1, especially as it relates to its association with Nek2 function and spindle checkpoint signaling. Such abnormalities may be due to one or more of a mutation (e.g., increasing or reducing affinity to a binding partner), temporary or permanent overexpression (e.g., activated by inappropriate or mutated promoter), irreversible or tighter binding of an activator, inappropriate activation by non-physiological molecule, etc. Consequently, particularly contemplated diseases include neoplastic diseases, and especially cancerous neoplastic diseases (e.g., breast cancer, squamous cell cancer, bladder cancer, gastric cancer, pancreatic cancer, head cancer, neck cancer, oesophageal cancer, prostate cancer, colorectal cancer, lung cancer, renal cancer, gynecological cancer, or thyroid cancer). Non cancerous neoplastic diseases include benign hyperplasia of the skin (e.g., psoriasis) or prostate (e.g., benign prostatic hypertrophy (BPH).

Therefore, the inventor also contemplates numerous pharmaceutical compositions that include the compounds presented herein and it is generally contemplated that compounds according to the inventive subject matter may be formulated into pharmaceutical compositions that have a therapeutically effective amount of contemplated compounds (or pharmaceutically acceptable salt, hydrate, and/or prodrug thereof), and a pharmaceutically acceptable carrier.

Activity, toxicity, and other pharmacological and pharmacodynamic parameters can be established for the compounds presented herein using numerous known protocols. Similarly, cytotoxicity can be established via MTS assay in various cell lines, while disruption of Hec1-Nek2 interaction can be monitored via co-immunoprecipitation or a yeast two-hybrid system. Cell cycle analysis can be performed by monitoring various stage populations (e.g., sub-G1, G0/G1, S, etc.), and metaphase chromosomal misalignment quantitation can be performed using immunofluorescence methods well known in the art. In vivo activity can be established using various animal models, and especially xenograft models. Exemplary results are provided in the attached tables and data. Consequently, the inventors contemplate a pharmaceutical composition that includes a pharmaceutically acceptable carrier and contemplated compounds herein wherein the compounds are present in a concentration effective to disrupt Hec1/Nek2 binding in a patient when the composition is administered to the patient. The inventors have also discovered that numerous compounds according to the inventive subject matter were bioavailable upon oral administration and could be detected in serum over prolonged periods after oral administration or intravenous (i.v.), administration (see below).

Contemplated compounds may be formulated with one or more non-toxic pharmaceutically acceptable carriers, preferably formulated for oral administration in solid or liquid form, or for parenteral injection. Thus, it should be appreciated that pharmaceutical compositions according to the inventive subject matter may be administered to humans and other animals using various routes, including orally, optically, rectally, parenterally, intraperitoneally, vaginally, or topically.

For example, suitable pharmaceutical compositions for injection preferably comprise pharmaceutically acceptable sterile aqueous or nonaqueous solutions, dispersions, emulsions, or suspensions, as well as sterile powders for reconstitution into sterile injectable solutions or dispersions prior to use. Examples of suitable aqueous and nonaqueous carriers, diluents, solvents, or vehicles include water, ethanol, polyols (e.g., glycerol, propylene glycol, polyethylene glycol, etc.), and suitable mixtures thereof, oils, and injectable organic esters (e.g., ethyl oleate). Contemplated compositions may also contain various inactive ingredients, including preservatives, wetting agents, emulsifying agents, and/or dispersing agents. Sterility may be ensured by inclusion of antibacterial and/or antifungal agents (e.g., paraben, phenol sorbic acid, chlorobutanol, etc.). Where appropriate, osmotically active agents may be included (e.g., sugars, sodium chloride, etc.).

Alternatively, contemplated compositions may be formulated into solid dosage forms for oral administration, and may therefore be capsules, tablets, pills, powders, and granules. In preferred solid dosage forms, contemplated compound are mixed with at least one of a pharmaceutically acceptable excipient or carrier (e.g., sodium citrate or dicalcium phosphate), a filler or extender (e.g., starch, lactose, sucrose, glucose, mannitol, or silicic acid), a binder (e.g., carboxymethylcellulose, alginates, gelatin, polyvinylpyrrolidone, sucrose, etc.), a humectant (e.g., glycerol), a disintegrating agent (e.g., agar-agar, calcium carbonate, potato or tapioca starch, alginic acid, certain silicates, or sodium carbonate), a solution retarding agent (e.g., paraffin), an absorption accelerator (e.g., quaternary ammonium compound), a wetting agents (e.g., cetyl alcohol and glycerol monostearate), and absorbents (e.g., kaolin, or bentonite clay), and a lubricant (e.g., talc, calcium stearate, magnesium stearate, solid polyethylene glycols, sodium lauryl sulfate).

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. Contemplated compositions may further be formulated to release the active ingredient(s) only, or preferentially, in a certain part of the intestinal tract, optionally, in a delayed manner. Examples of embedding compositions which can be used include polymeric substances and waxes. Contemplated compounds may also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, liquid dosage forms may contain inert diluents commonly used in the art (e.g., water, or other solvent, solubilizing agents), emulsifiers (e.g., ethyl alcohol, isopropyl alcohol, ethyl carbonate, ethyl acetate, benzyl alcohol, benzyl benzoate, propylene glycol, 1,3-butylene glycol, dimethyl formamide), oils (and in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions may also include adjuvants such as wetting agents, emulsifying and suspending agents, sweetening, flavoring, and perfuming agents.

Compounds according to the inventive subject matter can also be administered in form of liposomes, which may be unilamellar, oligolamellar, or polylamellar. Contemplated compositions in liposome form may further contain stabilizers, preservatives, excipients, etc. Preferred lipids for liposome formation include phospholipids and the phosphatidyl cholines (lecithins), both natural and synthetic. Methods to form liposomes are known in the art (see, for example, Prescott, Ed., *Methods in Cell Biology*, Volume XIV, Academic Press, New York, N.Y. (1976), p. 33 et seq.).

Actual dosage levels of contemplated compounds in pharmaceutical compositions according to the inventive subject matter may be varied so as to obtain an amount of contemplated compound(s) that is effective to achieve the desired therapeutic response for a particular patient, composition, and mode of administration. Thus, the selected dosage level will depend upon various factors, including the activity of the particular compound, the route of administration, the severity of the condition being treated, and the condition and prior medical history of the patient being treated. However, it is within the skill of the art to start doses of the compound at levels lower than required to achieve the desired therapeutic effect and to gradually increase the dosage until the desired effect is achieved. It is contemplated that specific concentration ranges within a patient may have desirable effects not found at concentrations below and above such specific ranges. In some embodiments of the inventive concept, therefore, concentrations of one or more compounds of the inventive concept in a patient-derived sample may be monitored in order to maintain the concentration of such a compound or compounds within the desired range. Similarly, it is contemplated that genetic characterization of a patient may be utilized to provide guidance as to effectiveness and suitable dosages for compounds of the inventive concept. Generally, dosage levels of about 0.01 mg to about 500 mg, more preferably of about 0.5 mg to about 50 mg of contemplated compound per kilogram of body weight per day may be administered orally to a mammalian patient. If desired, the effective daily dose may be divided into multiple doses for purposes of administration, e.g., two to four separate doses per day. Therefore, contemplated formulations especially include those suitable for oral administration, parenteral administration, for administration as cream, or as eye-drops or other liquid topical formulation.

Surprisingly, Hec1 inhibitors were found to exhibit synergistic effect with selected chemotherapeutic inhibitors. Among other chemotherapeutic inhibitors, compounds including Taxol, vincristine, and vinblastine showed synergistic effect. Hec1 inhibitors may also be expected to have synergistic effect with respect to tubulin formation or polymerization inhibitors, as well as pretubulin inhibitors. Thus, suitable chemotherapeutic inhibitors may include one or more drugs that interfere with microtubule formation or degradation. Therefore, any drug that affects cell division and/or any anti-metabolite are deemed useful in combination with the Hec1 inhibitors contemplated herein.

It should still further be appreciated that contemplated pharmaceutical compositions may also include additional pharmaceutically active compounds, and especially contemplated additional pharmaceutically active compounds include antineoplastic agents, which may act on DNA replication, cell cycle, cell metabolism, angiogenesis, or induce apoptosis. Further suitable active agents include immunologically active agents (e.g., anti-inflammatory agents, immunosuppressants, steroids, interferons (alpha, beta, or gamma) and fragments thereof, and those molecules that selectively increase or suppress Th1 and/or Th2 cytokine expression). Still other suitable active agents include antibacterial and antiviral agents, drugs that stimulate or modify metabolism, neurologically active drugs, and/or analgesic drugs. Of course, it should be recognized that additional pharmaceutically active compounds may be included in the same pharmaceutical composition, or may be administered separately, and a person of ordinary skill in the art will readily determine schedule and route of suitable co-administration of the additional pharmaceutically active compounds.

EXAMPLES

Exemplary Synthesis of Hec1 Inhibitors

Contemplated compounds can be prepared by numerous synthetic routes, and the following is provided to give exemplary guidance only. While the below scheme can be used to prepare most of the compounds presented herein, other compounds may require minor modifications to the general scheme that will be readily apparent to the skilled artisan.

Exemplary Route I

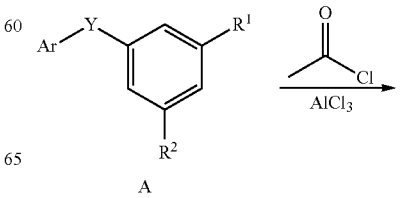

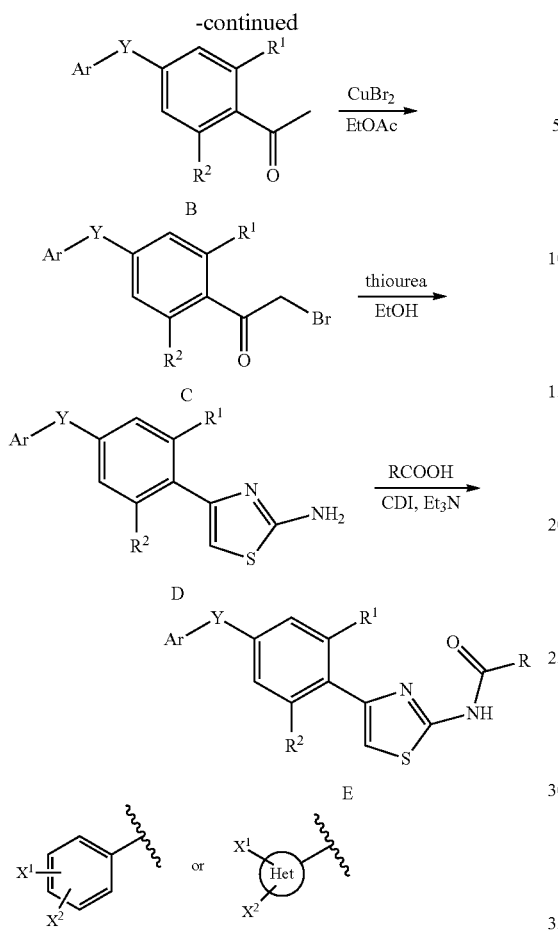

The above scheme illustrates a method for the synthesis of 4-aryl-2-aminothiazoles E.

Aromatic compounds of structure A, including substituted benzene, pyridine, or other heterocyclic compound (5-, 6-, or 7-membered) are reacted with acetyl chloride in the presence of AlCl₃ to afford acetylated arenes B. Bromination of the acetylated arenes give α-Br-acetylated arenes C, which are allowed to reacted thiourea to generate aminothiazoles D with a aryl substituent at the C-4 position. The aminothiazoles react with different acids give the final 4-aryl-2-amidothiazoles E.

Synthesis of A.

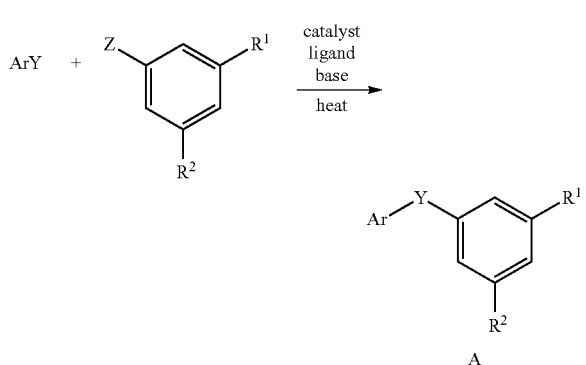

Y = OH, NH₂, NHR, SH
Z = F, Cl, Br, I

Compound A can be prepared by the above two reactants with or without catalyst and/or ligand and/or base. The catalysts include Pd(PPh₃)₄, Pd(OAc)₂, PdCl₂, CuI, Cu, CuBr, CuBr₂, Cu₂O, and other transitional metal. Ligands include PPh₃, X-Phos, and other phosphine ligands. Bases include Et₃N, Me₃N, DIPEA, K₂CO₃, Na₂CO₃, DMAP, K₃PO₄, etc. Compound A can also be prepared by reversal of the substitution Y and Z in the substrates as shown in the scheme below.

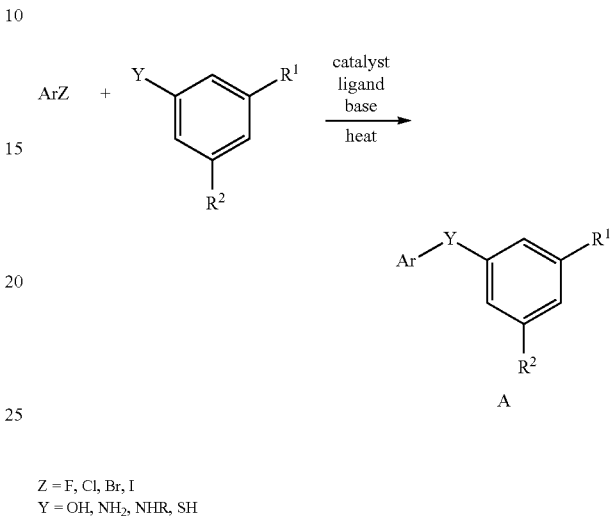

Z = F, Cl, Br, I
Y = OH, NH₂, NHR, SH

Acetylation of A.

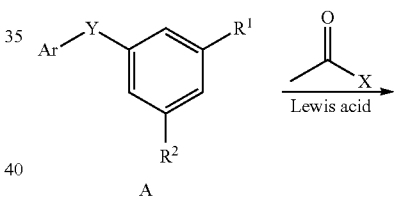

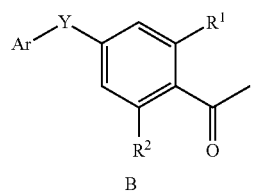

X = OH, Cl, Br, OAlkyl, OAryl
Lewis acid = AlCl₃, ZnCl₃, BiCl₃, conc. acid

The acetylation of A can be achieved by use of different reagents as shown in the above Scheme.

Bromination of B.

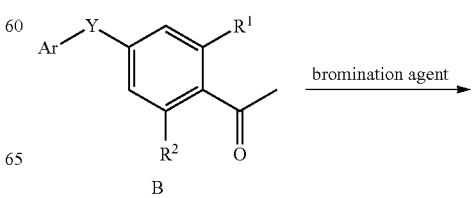

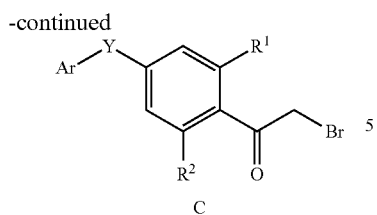

The bromination agents include Br$_2$, HBr, NBS, TBABr$_3$, CuBr$_2$, etc. in various solvents, including ether, THF, halogenated hydrocarbons, ester, etc.

Amidation of Aminothiazoles

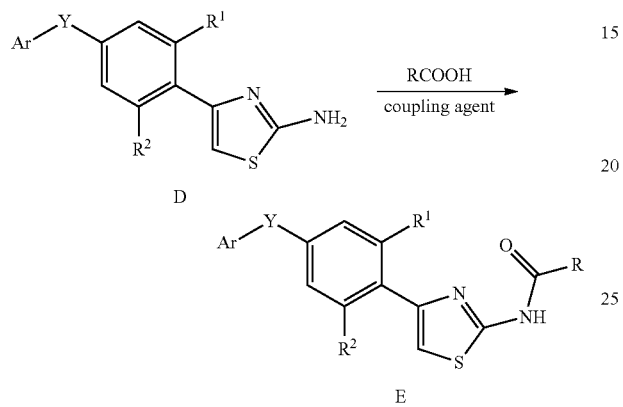

The coupling agents include CDI, EDC, CDC, etc.

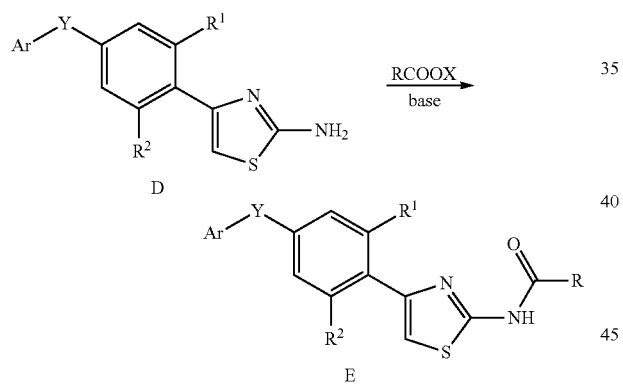

X = Cl or Br;
base = Et$_3$N, Me$_3$N, DIPEA, K$_2$CO$_3$, Na$_2$CO$_3$, DMAP, etc Exemplary Route II ArZ +
Z = F, Cl, Br, I

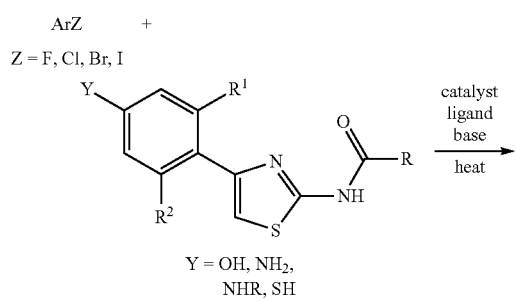

Y = OH, NH$_2$,
NHR, SH

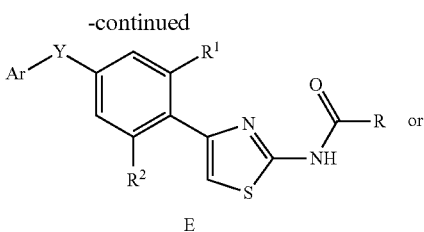

ArZ +
Z = F, Cl, Br, I

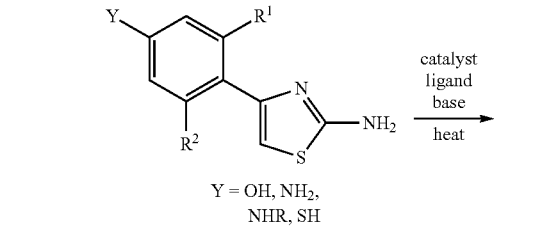

Y = OH, NH$_2$,
NHR, SH

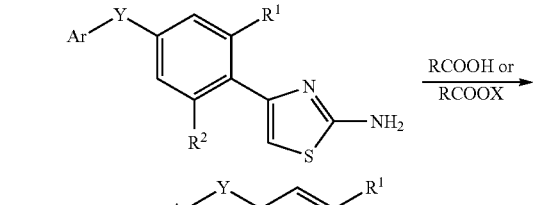

ArY
Y = OH, NH$_2$, +
NHR, SH

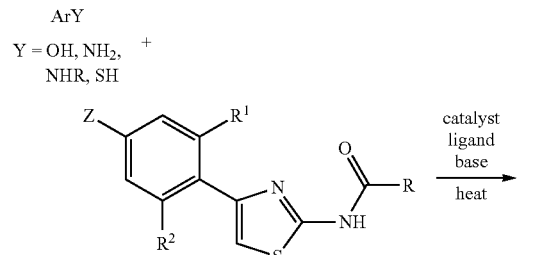

Z = F, Cl, Br, I

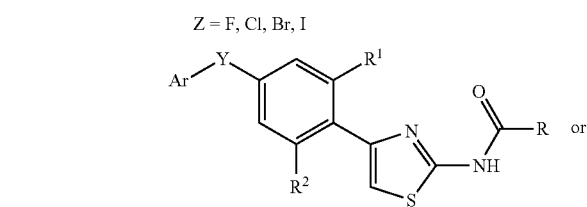

ArY
Y = OH, NH$_2$, +
NHR, SH

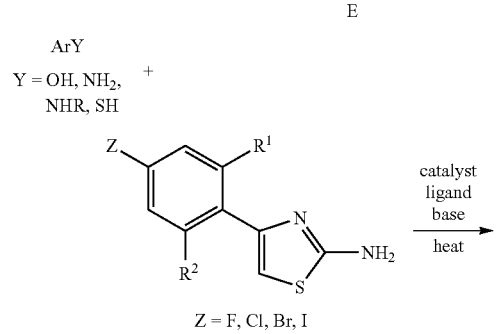

Z = F, Cl, Br, I

-continued

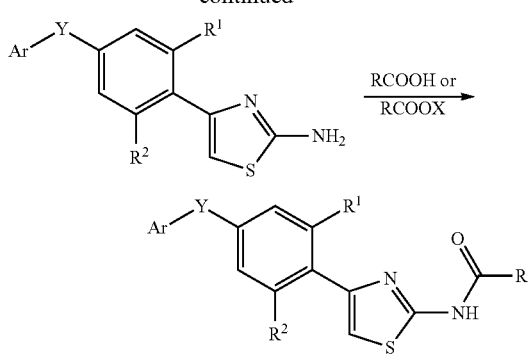

Exemplary Route III

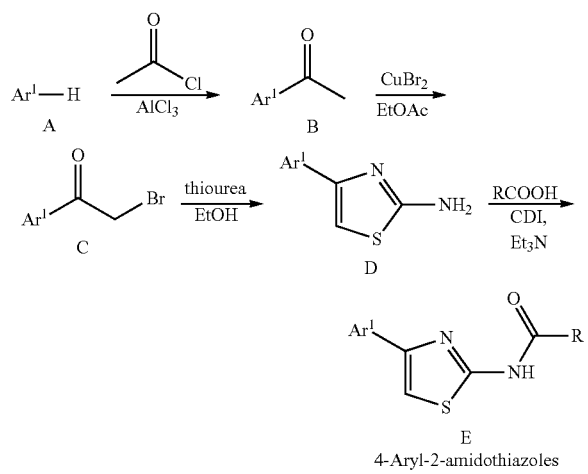

The above scheme illustrates a method for the synthesis of 4-aryl-2-aminothiazoles E. Aromatic compounds of structure A, including substituted benzene, pyridine, or other heterocyclic compound (5-, 6-, or 7-membered) are reacted with acetyl chloride in the presence of $AlCl_3$ to afford acetylated arenes B. Bromination of B give α-Br-acetylated arenes C, which are allowed to react with thiourea to generate aminothiazoles D with an aryl substituent at the C-4 position. The so prepared aminothiazoles then react with different acids give the final 4-aryl-2-amidothiazoles E.

Acetylation of $Ar^1$:

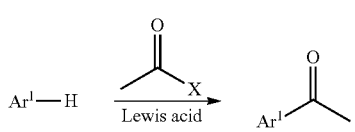

X = OH, Cl, Br, OAlkyl, OAryl
Lewis acid = $AlCl_3$, $ZnCl_3$, $BiCl_3$, conc. acid The acetylation of $Ar^1$ can be achieved by use of different reagents as shown in the above Scheme.

Bromination of Acetyl $Ar^1$:

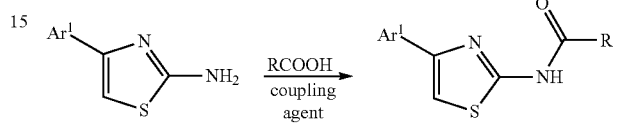

Suitable bromination agents include $Br_2$, HBr, NBS, $TBABr_3$, $CuBr_2$, etc. in various solvents, including ether, THF, halogenated hydrocarbons, ester, etc.

Amidation of Aminothiazoles:

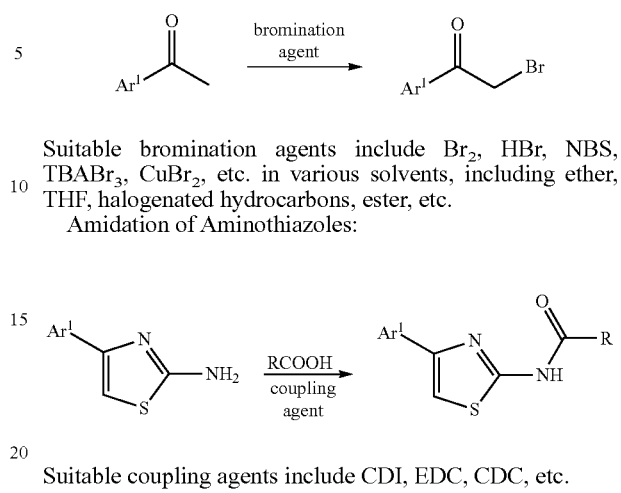

Suitable coupling agents include CDI, EDC, CDC, etc.

X is typically Cl or Br; base is typically $Et_3N$, $Me_3N$, DIPEA, $K_2CO_3$, $Na_2CO_3$, DMAP, etc. Alternatively, 4-Aryl-2-amidothiazoles can be prepared as follows:

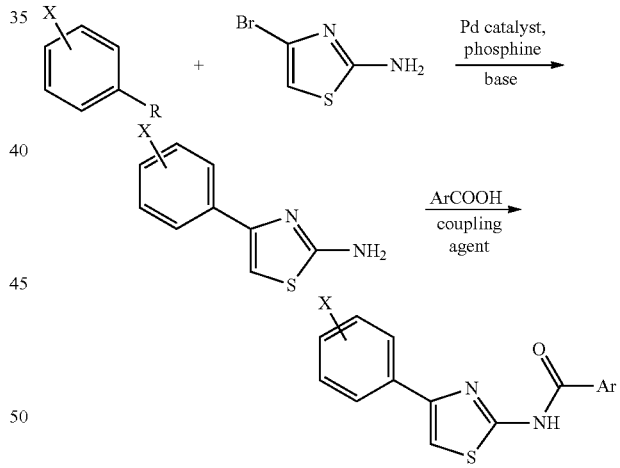

Alternatively, coupling may also be performed as follows:

To a solution of 4-arylthiazol-2-amine (1.0 equiv) in $CH_2Cl_2$ was added triethylamine (3.0 equiv) or DMAP (3.0 equiv)

followed by aryloxy chloride (1.5 equiv) or aryloxychloride hydrochloride (1.5 equiv). The reaction mixture was stirred at room temperature overnight. The solution was concentrated under reduced pressure and added with hot water. The resultant precipitate was filtered, and dried under vacuum to give the corresponding 4-aryl-2-amidothiazoles.

In an alternative procedure for the synthesis of 4-Aryl-2-amidothiazoles, to a suspension of arylcarboxylic acid (1.5 equiv) in dichloromethane was added 1,1'-carbonyldiimidazole (CDI, 3.0 equiv). After being stirred at room temperature for 2.0 h, the solution was added with 4-arylthiazol-2-amine (q.O equiv). The reaction mixture was stirred at room temperature overnight. The solution was concentrated and the residue was re-dissolved in dichloromethane. The solution was washed with brine, dried over MgSO₄, and concentrated under reduced pressure to give the corresponding 4-aryl-2-amidothiazoles. For specific examples of synthesis, see below.

Synthesis of Exemplary Compounds and Related Intermediates

N-{4-(4-(Dimethylamino)-2,6-dimethylphenyl)thiazol-2-yl}isonicotinamide (1)

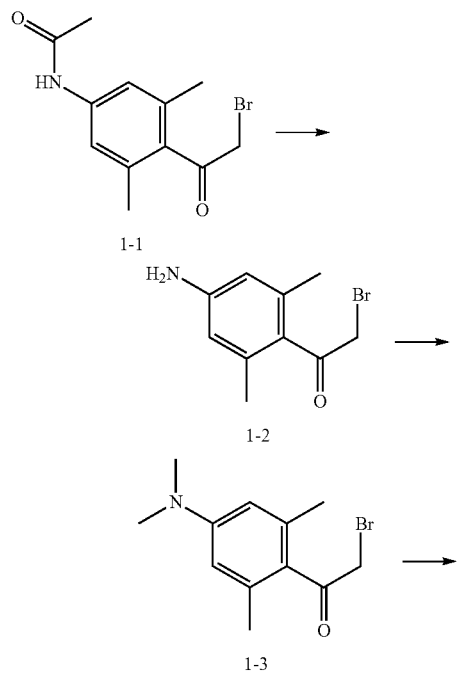

-continued

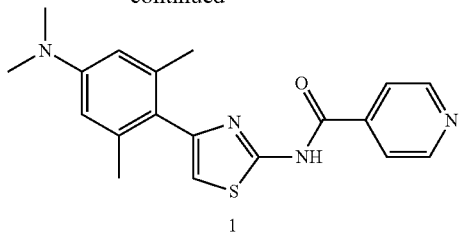

1

1-(4-Amino-2,6-dimethylphenyl)-2-bromoethanone (1-2)

A solution of N-(4-(2-bromoacetyl)-3,5-dimethylphenyl)acetamide (1-1, 6.92 g, 24.4 mmol) in 20.0 mL of ethanol and 10.2 mL of concentrated hydrochloric acid was heated at reflux for 1.5 h. The solution was concentrated and added with ethyl acetate (100 mL) and saturated aqueous Na₂CO₃ (100 mL). The organic layer was collected, dried over anhydrous MgSO₄(s), and concentrated under reduced pressure to give 1-(4-amino-2,6-dimethylphenyl)-2-bromoethanone (1-2, 5.04 g) as yellow solids, which was used directly for the next step without further purification.

2-Bromo-1-(4-(dimethylamino)-2,6-dimethylphenyl)ethanone (1-3)

A mixture of 1-(4-amino-2,6-dimethylphenyl)-2-bromoethanone (1-2, 2.80 g, 11.6 mmol), methyl iodide (8.21 g, 57.8 mmol), and potassium carbonate (4.80 g, 34.7 mmol) in 11.6 mL of acetone was stirred at 40° C. for 2.0 h. The reaction mixture was cooled to room temperature and filtered. The filtrate was concentrated and purified by column chromatography on silica gel (20% EtOAc in hexanes) to give 2-bromo-1-(4-(dimethylamino)-2,6-dimethylphenyl)ethanone (1-3, 0.60 g) as brown oil: ¹H NMR (500 MHz, CDCl₃) δ 6.35 (s, 2 H), 4.23 (s, 2 H), 2.96 (s, 6 H), 2.29 (s, 6 H).

4-(4-(Dimethylamino)-2,6-dimethylphenyl)thiazol-2-amine (1-4)

A mixture of 2-bromo-1-(4-(dimethylamino)-2,6-dimethylphenyl)ethanone (1-3, 0.900 g, 3.33 mmol) and thiourea (0.250 g, 3.33 mmol) in 95% EtOH (4.8 mL) was heated at reflux for 60 min. The solution was concentrated and added with water (30 mL) and saturated aqueous Na₂CO₃ (1.0 mL). The resultant precipitate was filtered and purified by flash column chromatography on silica gel to give 4-(4-(dimethylamino)-2,6-dimethylphenyl)thiazol-2-amine (1-4, 0.50 g) as brown solids in 61% yield: ¹H NMR (500 MHz, CDCl₃) δ 6.45 (s, 2 H), 6.25 (s, 1 H), 4.90 (bs, 2 H), 2.93 (s, 6 H), 2.15 (s, 6 H).

N-{4-(4-(Dimethylamino)-2,6-dimethylphenyl)thiazol-2-yl}isonicotinamide (1)

To a solution of 4-(4-(dimethylamino)-2,6-dimethylphenyl)thiazol-2-amine (1-4, 0.50 g, 2.0 mmol) in CH₂Cl₂ (5.1 mL) was added triethylamine (0.61 g, 6.1 mmol) followed by isonicotinoyl chloride hydrochloride (0.54 g, 3.0 mmol). The reaction mixture was stirred at room temperature overnight. The solution was concentrated under reduced pressure and added with hot water. The resultant precipitate was filtered and dried under vacuum to give N-{4-(4-(dimethylamino)-2,6-dimethylphenyl)thiazol-2-yl}isonicotinamide (1, 0.55 g)

as yellow solids in 77% yield: $^1$H NMR (500 MHz, CDCl$_3$) δ 8.64 (d, J=5.5 Hz, 2 H), 7.55 (d, J=5.5 Hz, 2 H), 6.74 (s, 1 H), 6.12 (s, 2 H), 2.89 (s, 6 H), 1.91 (s, 6 H). ESI-MS: m/z 352.6 (M+H)$^+$.

N-{5-Bromo-4-(4-(4-methoxyphenoxy)-2,6-dimethylphenyl)thiazol-2-yl}isonicotinamide (2)

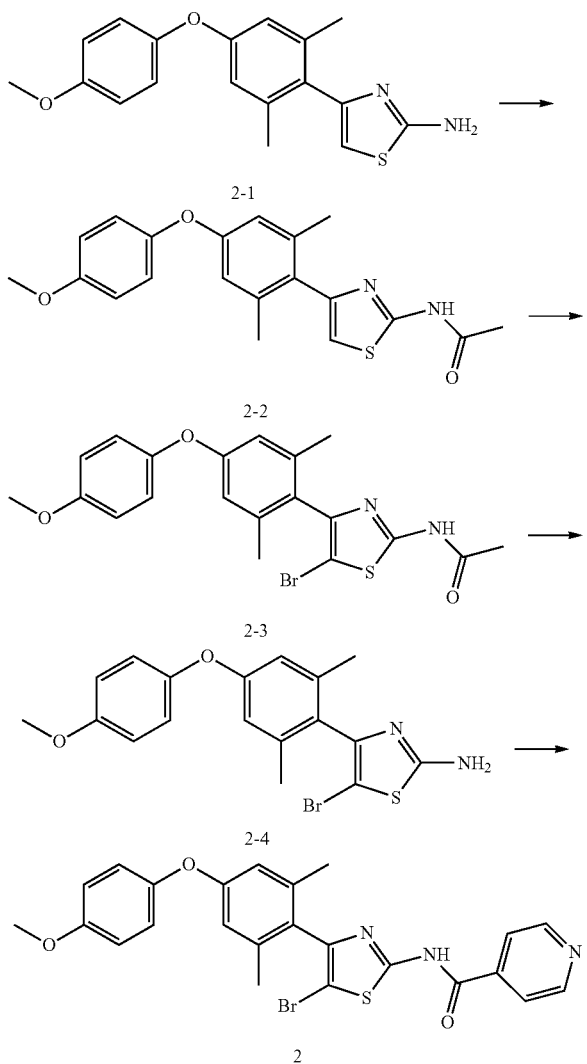

N-{4-(4-(4-Methoxyphenoxy)-2,6-dimethylphenyl)thiazol-2-yl}acetamide (2-2)

To a solution of 4-(4-(4-methoxyphenoxy)-2,6-dimethylphenyl)thiazol-2-amine (2-1, 500 mg, 1.5 mmol) in acetic anhydride (2.0 mL) was added sodium acetate (125.7 mg, 1.5 mmol). The reaction was stirred at room temperature for 1.0 h. The solution was added with water and extracted with ethyl acetate. The organic layer was washed with brine, dried over anhydrous MgSO$_4$(s), and concentrated under reduced pressure to give N-{4-(4-(4-methoxyphenoxy)-2,6-dimethylphenyl)thiazol-2-yl}acetamide (2-2, 465 mg) as yellow oil in 82% yield: $^1$H NMR (500 MHz, DMSO-d$_6$) δ 12.09 (s, 1H), 6.96-7.03 (m, 5 H), 6.64 (s, 2 H), 3.75 (s, 3 H), 2.15 (s, 3 H), 2.01 (s, 6 H). ESI-MS: m/z 368.9 (M+H)$^+$.

N-{5-Bromo-4-(4-(4-methoxyphenoxy)-2,6-dimethylphenyl)thiazol-2-yl}acetamide (2-3)

To a solution of N-{4-(4-(4-methoxyphenoxy)-2,6-dimethylphenyl)thiazol-2-yl}acetamide (2-2, 465 mg, 1.3 mmol) in acetic acid (10.2 mL) was added bromine (0.060 mL, 1.3 mmol) dropwisely. The reaction was stirred at room temperature for 4.0 h. The solution was added with water and extracted with ethyl acetate. The organic layer was washed with brine, dried over anhydrous MgSO$_4$(s), and concentrated under reduced pressure to give N-{5-bromo-4-(4-(4-methoxyphenoxy)-2,6-dimethylphenyl)thiazol-2-yl}acetamide (2-3, 547 mg) as white solids, which was used directly for the next step without further purification.

5-Bromo-4-(4-(4-methoxyphenoxy)-2,6-dimethylphenyl)thiazol-2-amine (2-4)

A methanol solution (10.0 mL) containing N-{5-bromo-4-(4-(4-methoxyphenoxy)-2,6-dimethylphenyl)thiazol-2-yl}acetamide (2-3, 465 mg, 1.3 mmol) and 6 N hydrochloric acid (6.0 mL) was heated at reflux for 4.0 h. The solution was added with 10% aqueous NaOH and the resultant solids were collected to give 5-bromo-4-(4-(4-methoxyphenoxy)-2,6-dimethylphenyl)thiazol-2-amine (2-4, 325 mg) as white solids in 55% yield: $^1$H NMR (500 MHz, DMSO-d$_6$) δ 6.97-7.04 (m, 4H), 6.65 (s, 2 H), 3.76 (s, 3 H), 2.03 (s, 6 H). ESI-MS: m/z 405.3, 407.2 (M+H)$^+$.

N-{5-Bromo-4-(4-(4-methoxyphenoxy)-2,6-dimethylphenyl)thiazol-2-yl}isonicotinamide (2)

To a solution of 5-bromo-4-(4-(4-methoxyphenoxy)-2,6-dimethylphenyl)thiazol-2-amine (2-4, 325 mg, 0.70 mmol) in CH$_2$Cl$_2$ (10 ml) was added triethylamine (0.50 mL, 1.7 mmol) followed by isonicotinoyl chloride hydrochloride (302.5 mg, 3.4 mmol). The reaction mixture was stirred at room temperature overnight. The solution was concentrated under reduced pressure and added with hot water. The resultant precipitate was filtered, and dried under vacuum to give N-{5-bromo-4-(4-(4-methoxyphenoxy)-2,6-dimethylphenyl)thiazol-2-yl}isonicotinamide (2, 345 mg) as white solids in 99% yield: $^1$H NMR (500 MHz, DMSO-d$_6$) δ 13.3 (s, 1 H), 8.82 (m, 2 H), 7.98 (m, 2 H), 7.05 (d, J=9.0 Hz, 2 H), 6.99 (d, J=9.0 Hz, 2 H), 6.70 (s, 2 H), 3.76 (s, 3 H), 1.99 (s, 6 H); ESI-MS: m/z 509.6, 511.1 (M+H)$^+$.

N-{4-(2-Chloro-4-(4-methoxyphenylsulfanyl)-6-methylphenyl)thiazol-2-yl}isonicotinamide (3)

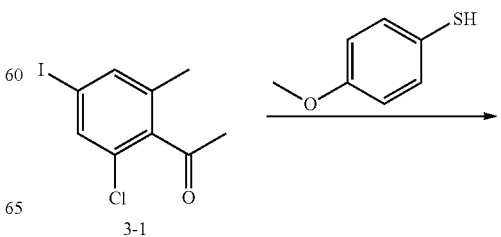

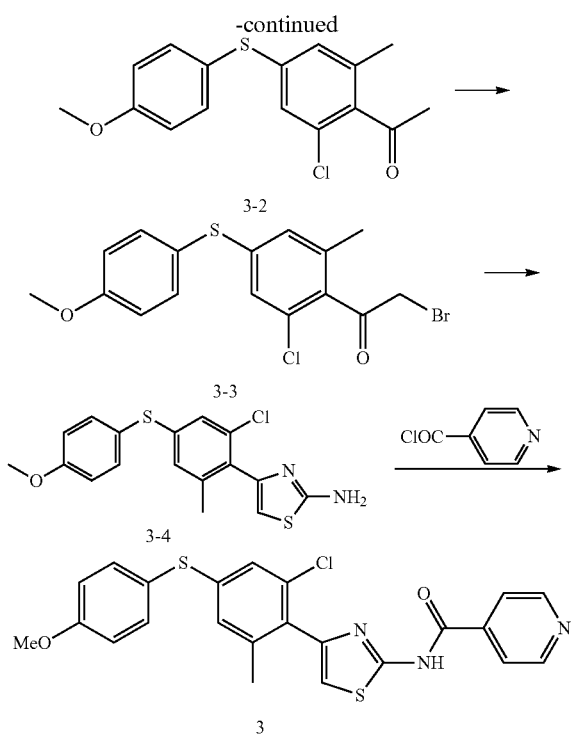

1-(2-Chloro-4-(4-methoxyphenylsulfanyl)-6-methylphenyl)ethanone (3-2)

A mixture of 1-(2-chloro-4-iodo-6-methylphenyl)ethanone (3-1, 0.720 g, 2.44 mmol), 4-methoxybenzenethiol (0.45 mL, 3.7 mmol), copper(I) oxide (17.0 mg, 0.12 mmol), and potassium hydroxide (0.34 g, 6.1 mmol) in DMF (2.2 mL) and H$_2$O (0.5 mL) was heated at reflux for 20 h. The mixture was quenched with H$_2$O and extracted with ethyl acetate. The organic layer was collected, dried over MgSO$_4$(s), and concentrated under reduced pressure. The residue was purified by column chromatography on silica gel to provide 1-(2-chloro-4-(4-methoxyphenylsulfanyl)-6-methylphenyl)ethanone (3-2, 0.10 g, 0.33 mmol) as yellow oil in 13% yield: $^1$H NMR (500 MHz, CDCl$_3$) δ 7.44 (d, J=8.7 Hz, 2 H), 6.94 (d, J=8.7 Hz, 2 H), 6.86 (d, J=8.2 Hz, 2 H), 3.85 (s, 3 H), 2.50 (s, 3 H), 2.17 (s, 3 H).

2-Bromo-1-(2-chloro-4-(4-methoxyphenylsulfanyl)-6-methylphenyl)ethanone (3-3)

To a solution of 1-(2-chloro-4-(4-methoxyphenylsulfanyl)-6-methylphenyl)ethanone (3-2, 0.10 g, 0.33 mmol) in acetonitrile (6.0 mL) was added TBABr$_3$ (0.16 g, 0.33 mmol). The reaction mixture was stirred at room temperature for 30 min. The solution was concentrated under reduced pressure, added with water, and extracted with ethyl acetate. The organic layer was washed with brine, dried over anhydrous MgSO$_4$(s), and concentrated under reduced pressure to give 2-bromo-1-(2-chloro-4-(4-methoxyphenylsulfanyl)-6-methylphenyl)ethanone (3-3, 0.127 g), which was used directly for the next step without further purification.

4-(2-Chloro-4-(4-methoxyphenylsulfanyl)-6-methylphenyl)thiazol-2-ylamine (3-4)

A mixture of 2-bromo-1-(2-chloro-4-(4-methoxyphenylsulfanyl)-6-methylphenyl)ethanone (3-3, 0.127 g) and thiourea (30 mg, 0.33 mmol) in 95% EtOH (3.0 mL) was heated at reflux for 60 min. The solution was concentrated under reduced pressure and the residue was re-dissolved in ethyl acetate. The solution was washed with saturated aqueous NaHCO$_3$, dried over MgSO$_4$(s), and concentrated under reduced pressure. The residue was purified by column chromatography on silica gel to give 4-(2-chloro-4-(4-methoxyphenylsulfanyl)-6-methylphenyl)thiazol-2-ylamine (3-4, 70 mg, 0.19 mmol) as yellow solids in 58% yield: $^1$H NMR (500 MHz, CDCl$_3$) δ 7.44 (m, 2 H), 6.97 (d, J=1.45 Hz, 1 H), 6.93 (m, 3 H), 6.34 (s, 1 H), 3.84 (s, 3 H), 2.13 (s, 3 H); ESI-MS m/z 363.1 (M+H)$^+$.

N-{4-(2-Chloro-4-(4-methoxyphenylsulfanyl)-6-methylphenyl)-thiazol-2-yl}isonicotinamide (3)

Compound 3 was synthesized from the reaction of 3-4 (70 mg, 0.19 mmol) with DMAP (46 mg, 0.38 mmol) and isonicotinoyl chloride hydrochloride (44 mg, 0.25 mmol). The reaction provided compound 3 (42 mg, 89.9 mmol) in 47% yield: $^1$H NMR (500 MHz, CDCl$_3$) δ 8.82 (d, J=6.0 Hz, 2 H), 7.70 (d, J=6.0 Hz, 2 H), 7.46 (d, J=8.8 Hz, 2 H), 6.96 (d, J=8.8 Hz, 2 H), 6.92 (s, 1 H), 6.86 (s, 1 H), 6.82 (s, 1 H), 3.86 (s, 3 H), 2.01 (s, 3 H); ESI-MS: m/z 466.1 (M−H)$^-$.

N-{4-(4-(Cyclopropylmethoxy)-2,6-dimethylphenyl)thiazol-2-yl}isonicotinamide (4)

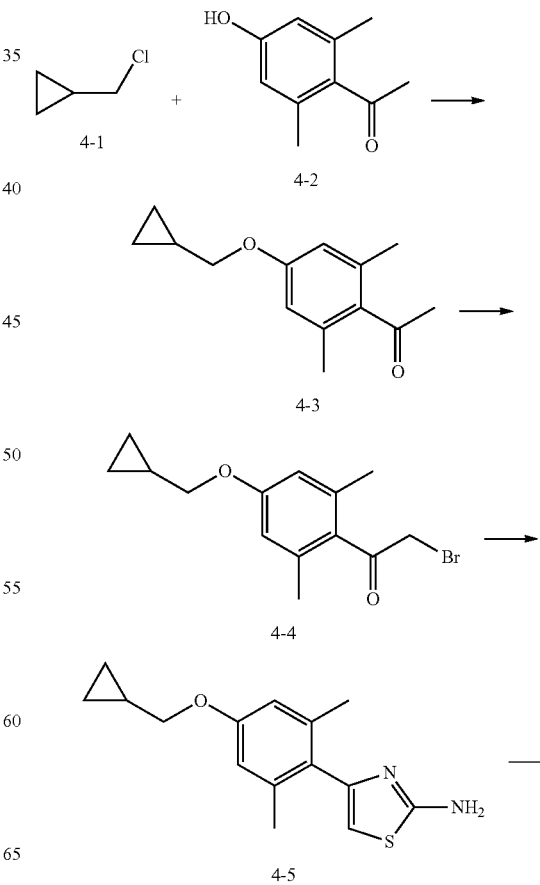

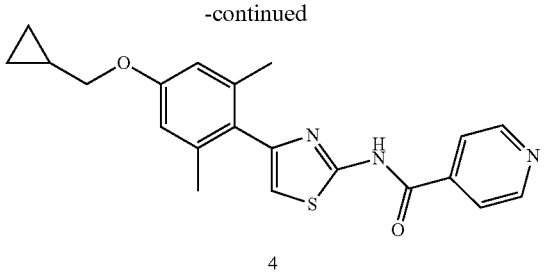

4

1-(4-(Cyclopropylmethoxy)=2,6-dimethylphenyl) ethanone (4-3)

A vigorously stirred mixture of 1-(4-hydroxy-2,6-dimethylphenyl)ethanone (4-2, 1.00 g, 10.9 mmol), chloromethylcyclopropane (4-1, 1.22 g, 7.4 mmol), and powdered potassium carbonate (1.54 g, 11.1 mmol) in DMF (10.0 mL) was heated at 80° C. for 16 h under $N_2$. The mixture was allowed to cool and was filtered through Diatomaceous earth. The filtrate was concentrated under reduced pressure and the residue was extracted with EtOAc. The organic layer was washed with saturated aqueous sodium carbonate and dried over $Na_2SO_4$. The solution was concentrated under reduced pressure to provide 1-(4-(cyclopropylmethoxy)-2,6-dimethylphenyl)ethanone (4-3, 1.61 g) as off-white solids in 99% yield: $^1$H NMR (500 MHz, CDCl$_3$) δ 6.55 (s, 2 H), 3.77 (d, J=6.9 Hz, 2 H), 2.45 (s, 3 H), 2.27 (s, 6 H), 1.19 (s, 1 H), 0.64 (m, 2 H), 0.33 (m, 2 H).

2-Bromo-1-(4-(cyclopropylmethoxy)-2,6-dimethylphenyl)ethanone (4-4)

To a solution of 1-(4-(cyclopropylmethoxy)-2,6-dimethylphenyl)ethanone (4-3, 1.60 g, 7.3 mmol) in acetonitrile (20.0 mL) was added TBABr$_3$ (3.66 g, 7.4 mmol). The reaction was stirred at room temperature for 80 min. The solution was concentrated under reduced pressure, added with water, and extracted with EtOAc. The organic layer was washed with brine, dried over anhydrous MgSO$_4$(s), and concentrated under reduced pressure to give 2-bromo-1-(4-(cyclopropylmethoxy)-2,6-dimethylphenyl)ethanone (4-4, 2.08 g), which was used directly for the next step without further purification: $^1$H NMR (500 MHz, CDCl$_3$) δ 6.57 (s, 2 H), 4.25 (s, 2 H), 3.78 (d, J=6.9 Hz, 2 H), 2.22 (s, 6 H), 1.19 (s, 1 H), 0.64 (m, 2 H), 0.33 (m, 2 H).

4-(4-(Cyclopropylmethoxy)-2,6-dimethylphenyl) thiazol-2-amine (4-5)

A mixture of 2-bromo-1-(4-(cyclopropylmethoxy)-2,6-dimethylphenyl)ethanone (4-4, 2.06 g, 7.0 mmol) and thiourea (0.61 g, 8.0 mmol) in 95% EtOH (30.0 mL) was heated at reflux for 60 min. The solution was concentrated and added with water (50.0 mL) and saturated aqueous Na$_2$CO$_3$ (1.0 mL). The resultant precipitate was filtered and washed with hot water. The solids were filtered and dried under vacuum to give 4-(4-(cyclopropylmethoxy)-2,6-dimethylphenyl)thiazol-2-amine (4-5, 1.18 g) as yellow solids in 61% yield: $^1$H NMR (500 MHz, DMSO-d$_6$) δ 9.00 (s, 2 H), 6.73 (s, 2 H), 3.81 (d, J=7.0 Hz, 1 H), 2.10 (s, 6 H), 1.19 (s, 1 H), 0.55 (m, 2 H), 0.30 (m, 2 H).

N-{4-(4-(Cyclopropylmethoxy)-2,6-dimethylphenyl) thiazol-2-yl}isonicotinamide (4)

To a solution of 4-(4-(cyclopropylmethoxy)-2,6-dimethylphenyl)thiazol-2-amine (4-5, 0.410 g, 1.51 mmol) in CH$_2$Cl$_2$ (10 mL) was added triethylamine (1.0 mL, 7.2 mmol) followed by isonicotinoyl chloride hydrochloride (0.470 g, 2.62 mmol). The reaction mixture was stirred at room temperature overnight. The solution was concentrated under reduced pressure and added with water. The resultant precipitate was filtered, and recrystallized in toluene to give N-{4-(4-(cyclopropylmethoxy)-2,6-dimethylphenyl)thiazol-2-yl}isonicotinamide (4, 0.41 g) as light yellow solids in 72% yield: $^1$H NMR (500 MHz, DMSO-d$_6$) δ 13.0 (s, 1 H), 8.80 (d, J=4.9 Hz, 2 H), 7.99 (d, J=6.0 Hz, 2 H), 7.10 (s, 1 H), 6.68 (s, 2 H), 3.81 (d, J=7.0 Hz, 2 H), 2.06 (s, 6 H), 1.21 (s, 1 H), 0.57 (d, J=6.5 Hz, 2 H), 0.32 (d, J=5.7 Hz, 2 H). ESI-MS: m/z 380.3 (M+H)$^+$.

N-{4-(4-(6-Hydroxypyridin-3-yloxy)-2,6-dimethylphenyl)thiazol-2-yl}isonicotinamide (5)

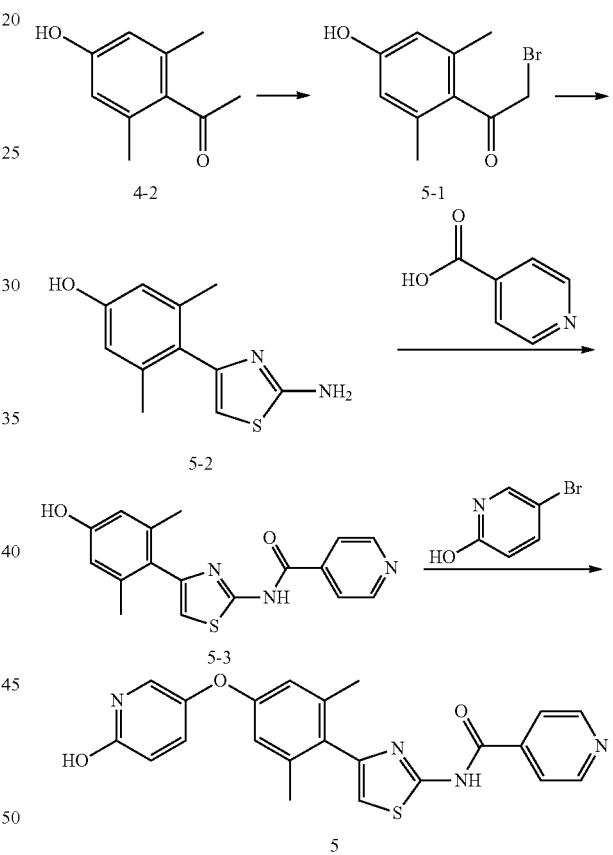

2-Bromo-1-(4-hydroxy-2,6-dimethylphenyl)ethanone (5-1)

To a solution of 1-(4-hydroxy-2,6-dimethylphenyl)ethanone (4-2, 1.60 g, 10.0 mmol) in acetonitrile (30.0 mL) was added TBABr$_3$ (4.82 g, 10.0 mmol). The reaction was stirred at room temperature for 90 min. The solution was concentrated under reduced pressure, added with water, and extracted with ethyl acetate. The organic layer was washed with brine, dried over anhydrous MgSO$_4$(s), and concentrated under reduced pressure to give 2-bromo-1-(4-methoxy-2,6-dimethylphenyl)ethanone (5-1, 2.34 g), which was used directly for the next step without further purification.

4-(2-Aminothiazol-4-yl)-3,5-dimethylphenol (5-2)

A mixture of 2-bromo-1-(4-hydroxy-2,6-dimethylphenyl)ethanone (5-1, 2.43 g, 10.0 mmol) and thiourea (1.37 g, 18.0 mmol) in 95% EtOH (30 mL) was heated at reflux for 120 min. The solution was concentrated and added with water (50 mL) and saturated aqueous $Na_2CO_3$ (5.0 mL). The resultant precipitate was filtered and washed with a solution of 50% EtOAc in hexanes. The solids were dried under vacuum to give 4-(2-aminothiazol-4-yl)-3,5-dimethylphenol (5-2, 1.74 g) as pale yellow solids in 79% yield: $^1$H NMR (500 MHz, $CDCl_3$) δ 8.7 (s, 2 H), 6.17 (s, 2 H), 5.97 (s, 1 H), 1.71 (s, 6 H).

N-(4-(4-Hydroxy-2,6-dimethylphenyl)thiazol-2-yl)isonicotinamide (5-3)

To a suspension of isonicotinic acid hydrochloride (1.48 g, 10.0 mmol, 1.2 equiv) in DMF was added EDC (3.90 g, 2.0 equiv), HOBt (2.7 g, 2.0 equiv) and $NEt_3$ (3.03 g, 3.0 equiv). After being stirred at room temperature for 1.0 h, the solution was added with 4-(2-aminothiazol-4-yl)-3,5-dimethylphenol (5-2, 2.2 g, 1.0 equiv). The reaction mixture was stirred at room temperature overnight. The solution was concentrated and the residue was re-dissolved in EtOAc. The solution was washed with brine, dried over $MgSO_4$, and concentrated under reduced pressure to give brown solid. The brown solid was washed with 50% EtOAc in hexanes to give 5-3 (2.08 g) as white solids in 64% yield: $^1$H NMR (500 MHz, $CDCl_3$) δ 9.29 (s, 1 H), 8.80 (d, 2 H), 7.98 (d, 2 H), 7.06 (s, 1 H), 6.51 (s, 2 H), 2.01 (s, 6H).

N-{4-(4-(6-Hydroxy-pyridin-3-yloxy)-2,6-dimethyl-phenyl)-thiazol-2-yl}isonicotinamide (5)

To a solution of N-(4-(4-hydroxy-2,6-dimethylphenyl)-thiazol-2-yl)isonicotinamide (5-3, 325 mg, 1.0 mmol) in DMF (15 mL) were added cesium carbonate (650 mg, 2.0 mmol, 2.0 equiv) and Cu (19.5 mg, 0.30 mmol, 0.30 equiv). The mixture was stirred at 80-90° C. for 60 min. 5-Bromo-2-hydroxypyridine (261 mg, 1.5 mmol) was added to the solution and the reaction mixture was stirred at 100° C. for additional 24 hr. The solution was quenched with water (40 mL) and extracted with ethyl acetate. The organic layer was washed with saturated brine, and dried over anhydrous magnesium sulfate, and concentrated under reduced pressure. The residue was purified by column chromatography on (NH silica gel, hexane/ethyl acetate=3/1-1/3) to give 5 (0.75 g) in 18% yield: $^1$H NMR (500 MHz, $CDCl_3$) δ 8.31 (d, J=5.0 Hz, 2 H), 8.29 (d, J=5.0 Hz, 2 H), 7.23 (d, J=9.5 Hz, 1 H), 6.81 (s, 1 H), 6.60 (d, J=4.76 Hz, 1 H), 6.49 (s, 2 H), 5.42 (s, 1 H), 2.04 (s, 6 H), ESI-MS=m/z 417.2 (M–H)$^-$.

N-{4-(2,6-Dimethyl-4-(pyrimidin-2-yloxy)phenyl)thiazol-2-yl})isonicotinamide (6)

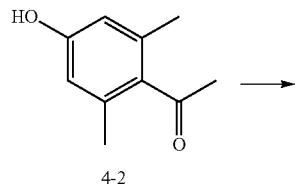

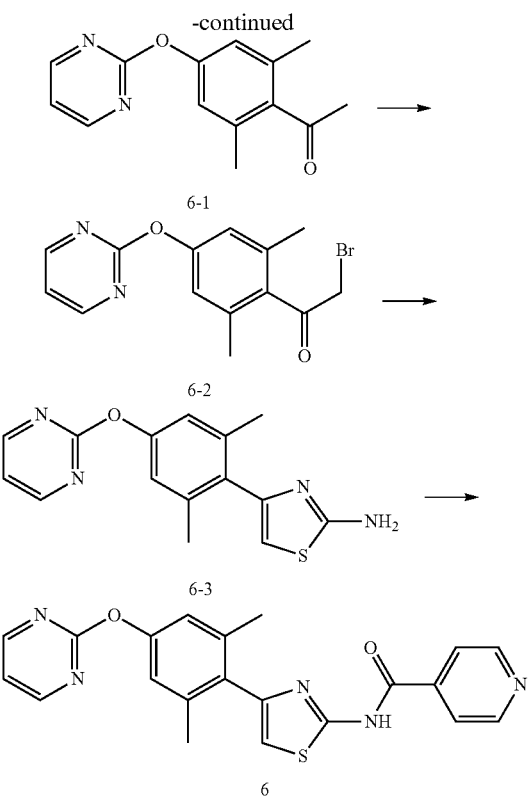

1-(2,6-Dimethyl-4-(pyrimidin-2-yloxy)phenyl)ethanone (6-1)

A mixture of 1-(4-hydroxy-2,6-dimethylphenyl)ethanone (4-2, 2.15 g, 13.1 mmol), 2-chloropyrimidine (1.00 g, 8.73 mmol), copper (55.0 mg, 0.87 mmol), and potassium carbonate (3.62 g, 26.2 mmol) in 17.5 mL of DMF was stirred at 100° C. for 3.0 h. The reaction mixture was cooled to room temperature, added with water, and extracted with ethyl acetate. The organic layer was washed with brine, dried over anhydrous $MgSO_4$(s), and concentrated under reduced pressure. The residue was purified by column chromatography on silica gel (50% EtOAc in hexanes as eluant) to give 1-(2,6-dimethyl-4-(pyrimidin-2-yloxy)phenyl)ethanone (6-1, 1.16 g) as white solids in 55% yield: $^1$H NMR (500 MHz, $CDCl_3$) δ 8.58 (d, J=4.5 Hz, 2 H), 7.05 (t, 1 H), 6.87 (s, 2 H), 2.49 (s, 3 H), 2.27 (s, 6 H).

2-Bromo-1-(2,6-dimethyl-4-(pyrimidin-2-yloxy)phenyl)ethanone (6-2)

To a solution of 1-(2,6-dimethyl-4-(pyrimidin-2-yloxy)phenyl)ethanone (6-1, 1.16 g, 4.79 mmol) in acetonitrile (9.6 mL) was added TBABr$_3$ (2.31 g, 4.79 mmol). The reaction was stirred at room temperature overnight. The solution was concentrated under reduced pressure, added with water, and extracted with ethyl acetate. The organic layer was washed with brine, dried over anhydrous $MgSO_4$(s), and concentrated under reduced pressure to give 2-bromo-1-(2,6-dimethyl-4-(pyrimidin-2-yloxy)phenyl)ethanone (6-2, 1.8 g), which was used directly for the next step without further purification.

4-(2,6-Dimethyl-4-(pyrimidin-2-yloxy)phenyl)thiazol-2-amine (6-3)

A mixture of 2-bromo-1-(2,6-dimethyl-4-(pyrimidin-2-yloxy)phenyl)ethanone (6-2, 1.54 g, 4.79 mmol) and thiourea (0.370 g, 4.86 mmol) in 95% EtOH (6.9 mL) was heated at reflux for 60 min. The solution was concentrated and added with water and saturated aqueous $Na_2CO_3$ (1.0 mL). The resultant precipitate was filtered and recrystallized in toluene. The solids were filtered and dried under vacuum to give 4-(2,6-dimethyl-4-(pyrimidin-2-yloxy)phenyl)thiazol-2-amine (6-3, 0.23 g) as brown solids in 9.1% yield: $^1$H NMR (500 MHz, DMSO-$d_6$) δ 8.64 (d, J=4.5 Hz, 2 H), 7.25 (m, 1 H), 6.99 (bs, 2 H), 6.89 (s, 2 H), 6.41 (s, 1 H), 2.11 (s, 6 H).

N-{4-(2,6-Dimethyl-4-(pyrimidin-2-yloxy)phenyl)thiazol-2-yl}isonicotinamide (6)

To a solution of 4-(2,6-dimethyl-4-(pyrimidin-2-yloxy)phenyl)thiazol-2-amine (6-3, 0.23 g, 0.77 mmol) in THF (3.9 mL) was added triethylamine (0.23 g, 2.30 mmol) followed by isonicotinoyl chloride hydrochloride (0.27 g, 1.52 mmol). The reaction mixture was heated at 60° C. overnight. The solution was concentrated under reduced pressure, added with water, and extracted with ethyl acetate. The organic layer was washed with brine, dried over anhydrous $MgSO_4$(s), and concentrated under reduced pressure. The resultant precipitate was recrystallized in MeOH to give N-{4-(2,6-dimethyl-4-(pyrimidin-2-yloxy)phenyl)thiazol-2-yl}isonicotinamide (6, 0.12 g) as yellow solids in 38% yield: $^1$H NMR (500 MHz, CDCl$_3$) δ 8.75 (d, J=6.0 Hz, 2 H), 8.58 (d, J=4.5 Hz, 2 H), 7.65 (d, J=6.0 Hz, 2 H), 7.04 (t, J=4.8 Hz, 1 H), 6.83 (s, 1 H), 6.70 (s, 2 H), 3.47 (s, 3 H), 1.97 (s, 6 H). ESI-MS: m/z 403.8 (M+H)$^+$.

N-{4-(2,6-Dimethyl-4-(pyrazin-2-yloxy)phenyl)thiazol-2-yl}isonicotinamide (7)

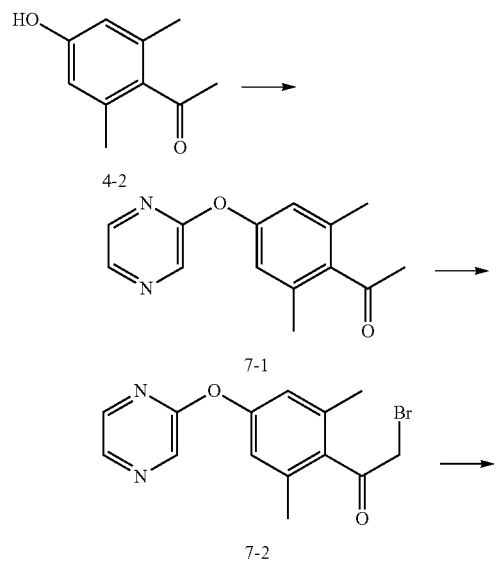

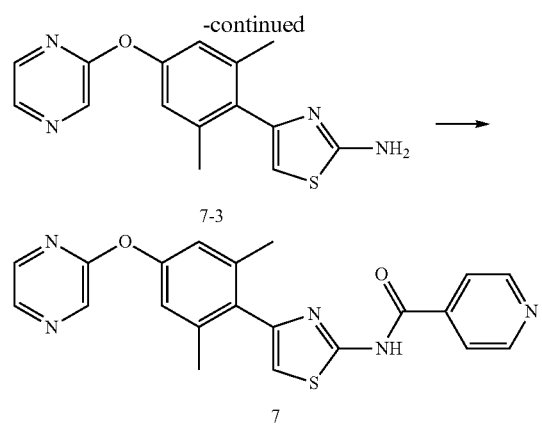

1-(2,6-Dimethyl-4-(pyrazin-2-yloxy)phenyl)ethanone (7-1)

A mixture of 1-(4-hydroxy-2,6-dimethylphenyl)ethanone (4-2, 4.66 g, 28.4 mmol), 2-chloropyrazine (2.50 g, 21.8 mmol), copper (27.7 mg, 4.36 mmol), and potassium carbonate (9.05 g, 65.5 mmol) in 43.7 mL of DMF was stirred at 100° C. overnight. The reaction mixture was added with water and extracted with ethyl acetate. The organic layer was washed with brine, dried over anhydrous $MgSO_4$(s), concentrated under reduced pressure, and purified by column chromatography on silica gel (50% EtOAc in hexanes as eluant) to give 1-(2,6-dimethyl-4-(pyrazin-2-yloxy)phenyl)ethanone (7-1, 4.65 g) as brown oils: $^1$H NMR (500 MHz, CDCl$_3$) δ 8.43 (bs, 1 H), 8.29 (bs, 1 H), 8.14 (bs, 1 H), 6.83 (s, 2 H), 2.49 (s, 3 H), 2.27 (s, 6 H).

2-Bromo-1-(2,6-dimethyl-4-(pyrazin-2-yloxy)phenyl)ethanone (7-2)

To a solution of 1-(2,6-dimethyl-4-(pyrazin-2-yloxy)phenyl)ethanone (7-1, 4.65 g, 19.2 mmol) in acetonitrile (38.4 mL) was added TBABr$_3$ (9.26 g, 19.2 mmol). The reaction was stirred at room temperature overnight. The solution was concentrated under reduced pressure, added with water, and extracted with ethyl acetate. The organic layer was washed with brine, dried over anhydrous $MgSO_4$(s), and concentrated under reduced pressure to give 2-bromo-1-(2,6-dimethyl-4-(pyrazin-2-yloxy)phenyl)ethanone (7-2, 7.6 g), which was used directly for the next step without further purification.

4-(2,6-Dimethyl-4-(pyrazin-2-yloxy)phenyl)thiazol-2-amine (7-3)

A mixture of 2-bromo-1-(2,6-dimethyl-4-(pyrazin-2-yloxy)phenyl)ethanone (7-2, 6.16 g, 19.2 mmol) and thiourea (1.46 g, 19.2 mmol) in 95% EtOH (27.4 mL) was heated at reflux for 60 min. The solution was concentrated and added with water and saturated aqueous $Na_2CO_3$ (1.0 mL). The resultant precipitate was filtered and recrystallized in toluene. The solids were filtered and dried under vacuum to give 4-(2,6-dimethyl-4-(pyrazin-2-yloxy)phenyl)thiazol-2-amine (7-3, 3.07 g) as brown solids in 54% yield: $^1$H NMR (500

MHz, CDCl₃) δ 8.40 (s, 1 H), 8.25 (d, 1 H), 8.14 (s, 1 H), 6.86 (s, 2 H), 6.31 (s, 1 H), 5.09 (s, 2 H), 2.18 (s, 6 H).

N-{4-(2,6-Dimethyl-4-(pyrazin-2-yloxy)phenyl)thiazol-2-yl}isonicotinamide (7)

To a solution of 4-(2,6-dimethyl-4-(pyrazin-2-yloxy)phenyl)thiazol-2-amine (7-3, 0.500 g, 1.68 mmol) in THF (8.4 mL) was added triethylamine (0.510 g, 5.03 mmol) followed by isonicotinoyl chloride hydrochloride (0.750 g, 4.21 mmol). The reaction mixture was stirred at 60° C. overnight. The solution was concentrated under reduced pressure and added with water and extracted with ethyl acetate. The organic layer was washed with brine, dried over anhydrous MgSO₄(s), and concentrated under reduced pressure. The resultant precipitate was recrystallized in toluene to give N-{4-(2,6-dimethyl-4-(pyrazin-2-yloxy)phenyl)thiazol-2-yl}isonicotinamide (0.17 g) as yellow solids in 25% yield: ¹H NMR (500 MHz, CDCl₃) δ 8.76 (d, J=6.0 Hz, 2 H), 8.42 (d, J=1.0 Hz, 1 H), 8.28 (d, J=1.0 Hz, 1 H), 8.13 (m, 1 H), 7.67 (d, J=6.0 Hz, 2 H), 6.84 (s, 1 H), 6.68 (s, 2 H), 1.98 (s, 6 H). ESI-MS: m/z 403.8 (M+H)⁺.

N-{4-(4-(5-Methoxypyrimidin-2-yloxy)-2,6-dimethylphenyl)thiazol-2-yl}isonicotinamide (8)

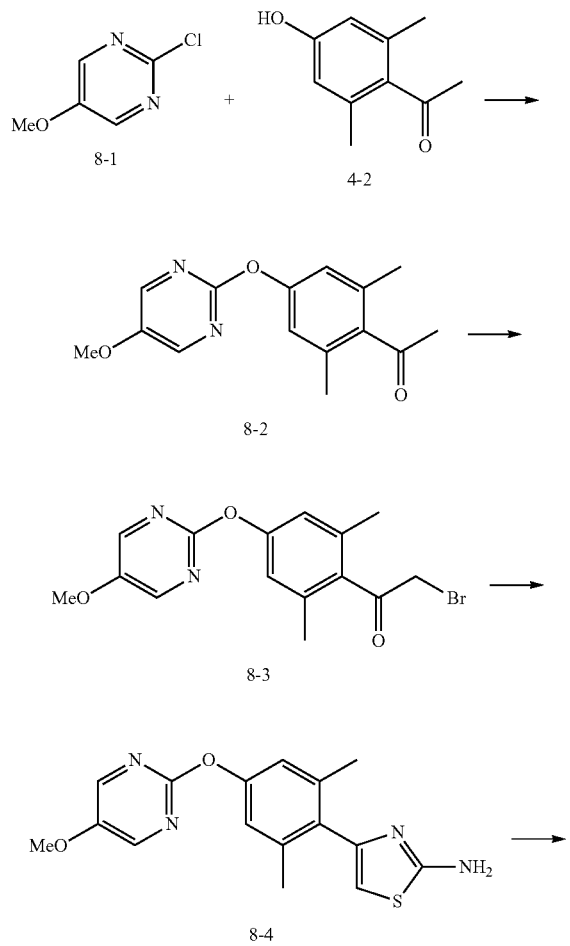

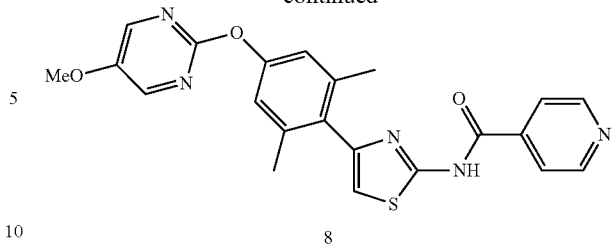

1-{4-(5-Methoxypyrimidin-2-yl)oxy)-2,6-dimethylphenyl}ethanone (8-2)

2-Chloro-5-methoxypyrimidine (8-1, 5.13 g, 35.6 mmol) and 1-(4-hydroxy-2,6-dimethylphenyl)ethanone (4-2, 6.10 g, 37.2 mmol) were suspended in DMF (80.0 ml) and added with copper powder (0.78 g, 7.8 mmol) and potassium carbonate (15.31 g, 0.11 mol). The reaction was heated at 120° C. for 16 h. The reaction was cooled to room temperature and diluted with EtOAc (90 mL). The organic phase was washed with 15% NaOH and water, dried over sodium sulfate, filtered, and concentrated under reduced pressure. The residue was purified by flash column chromatography on silica gel (40% EtOAc in hexanes as eluant) to give 1-{4-((5-methoxypyrimidin-2-yl)oxy)-2,6-dimethylphenyl}ethanone (8-2, 2.33 g) as light yellow solids in 24% yield: ¹H NMR (500 MHz, DMSO-d₆) δ 8.41 (s, 2 H), 6.86 (s, 2 H), 3.86 (s, 3 H), 2.47 (s, 3 H), 2.18 (s, 6 H).

2-Bromo-1-{4-((5-methoxypyrimidin-2-yl)oxy)-2,6-dimethylphenyl}ethanone (8-3)

To a solution of 1-{4-((5-methoxypyrimidin-2-yl)oxy)-2,6-dimethylphenyl}ethanone (8-2, 0.34 g, 1.2 mmol) in acetonitrile (4.0 mL) was added TBABr₃ (0.65 g, 1.3 mmol). The reaction was stirred at room temperature for 80 min. The solution was concentrated under reduced pressure, added with water, and extracted with EtOAc. The organic layer was washed with brine, dried over anhydrous MgSO₄(s), and concentrated under reduced pressure to give 2-bromo-1-{4-((5-methoxypyrimidin-2-yl)oxy)-2,6-dimethylphenyl}ethanone (8-3, 0.51 g), which was used directly for the next step without further purification.

4-{4-((5-Methoxypyrimidin-2-yl)oxy)-2,6-dimethylphenyl}thiazol-2-amine (8-4)

A mixture of 2-bromo-1-{4-((5-methoxypyrimidin-2-yl)oxy)-2,6-dimethylphenyl}ethanone (8-3, 0.51 g, 1.5 mmol) and thiourea (0.13 g, 1.6 mmol) in 95% EtOH (10.0 mL) was heated at reflux for 60 min. The solution was concentrated and added with water (10 mL) and saturated aqueous Na₂CO₃ (1.0 mL). The resultant precipitate was filtered and washed with hot water. The solids were filtered and dried under vacuum to give 4-{4-((5-methoxypyrimidin-2-yl)oxy)-2,6-dimethylphenyl}thiazol-2-amine (8-4, 0.41 g) as yellow solids in 86% yield: ¹H NMR (500 MHz, DMSO-d) 9.00 (s, 2 H), 8.41 (s, 2 H), 6.99 (s, 2 H), 6.88 (s, 1 H), 3.87 (s, 3 H), 2.17 (s, 6 H).

N-(4-{4-((5-Methoxypyrimidin-2-yl)oxy)-2,6-dimethylphenyl}thiazol-2-yl)isonicotinamide (8)

To a solution of 4-{4-((5-methoxypyrimidin-2-yl)oxy)-2,6-dimethylphenyl}thiazol-2-amine (8-4, 0.41 g, 1.23 mmol)

in CH$_2$Cl$_2$ (6.0 mL) was added triethylamine (1.0 mL, 7.2 mmol) followed by isonicotinoyl chloride hydrochloride (0.35 g, 1.94 mmol). The reaction mixture was stirred at room temperature overnight. The solution was concentrated under reduced pressure and added with water. The resultant precipitate was filtered, and recrystallized in toluene to give N-(4-{4-((5-methoxypyrimidin-2-yl)oxy)-2,6-dimethylphenyl}thiazol-2-yl)isonicotinamide (8, 0.37 g) as light yellow solids in 72% yield: $^1$H NMR (500 MHz, DMSO-d$_6$) δ 13.0 (s, 1 H), 8.80 (d, J=4.9 Hz, 2 H), 8.42 (s, 2 H), 7.99 (d, J=6.0 Hz, 2 H), 7.10 (s, 1 H), 6.68 (s, 2 H), 3.81 (d, J=7.0 Hz, 2 H), 2.06 (s, 6 H), 1.21 (s, 1 H), 0.57 (d, J=6.5 Hz, 2 H), 0.32 (d, J=5.7 Hz, 2 H). ESI-MS: m/z 433.8 (M+H)$^+$.

N-{4-(4-(6-Methoxypyridin-3-yloxy)-2,6-dimethylphenyl)thiazol-2-yl}isonicotinamide (9)

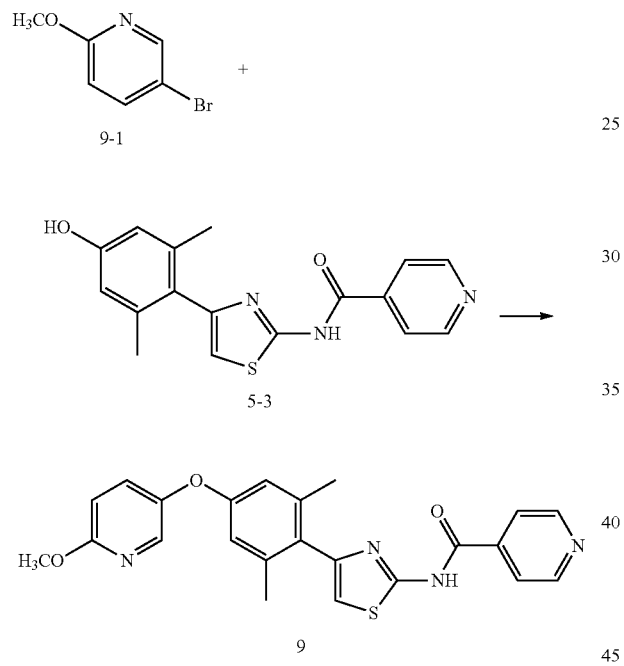

N-{4-(4-(6-Methoxy-pyridin-3-yloxy)-2,6-dimethylphenyl)thiazol-2-yl}isonicotinamide (9)

To a solution of N-(4-(4-hydroxy-2,6-dimethylphenyl)thiazol-2-yl)isonicotinamide (5-3, 1.92 g, 5.91 mmol) in DMF (15 mL) were added cesium carbonate (2.41 g, 7.39 mmol) and Cu (116 mg, 1.78 mmol, 0.30 equiv). The mixture was stirred at 80-90° C. for 60 min. 5-Bromo-2-methoxypyridine (9-1, 1.67 g, 8.87 mmol) was added to the solution and the reaction mixture was stirred at 100° C. for additional 24 hr. The solution was quenched with water (40 mL) and extracted with ethyl acetate. The organic layer was washed with saturated brine, dried over anhydrous magnesium sulfate, and concentrated under reduced pressure. The residue was purified by column chromatography (NH silica gel, hexane/ethyl acetate=3/1-1/3) to give 5 (0.97 g) in 38% yield: $^1$H NMR (CDCl$_3$, 500 MHz) δ 8.89 (d, J=5.0 Hz, 2H), 8.23 (d, J=5.0 Hz, 2 H), 8.02 (s, 1 H), 7.37 (d, J=3.0 Hz, 1 H), 6.89 (s, 1 H), 6.80 (d, J=9.0 Hz, 1 H), 6.69 (s, 2 H), 3.94 (s, 3H), 2.17 (s, 6 H), ESI-MS=m/z 433.2 (M+H)$^+$.

N-(4-(2,6-Dichloro-4-methoxyphenyl)thiazol-2-yl)isonicotinamide (10)

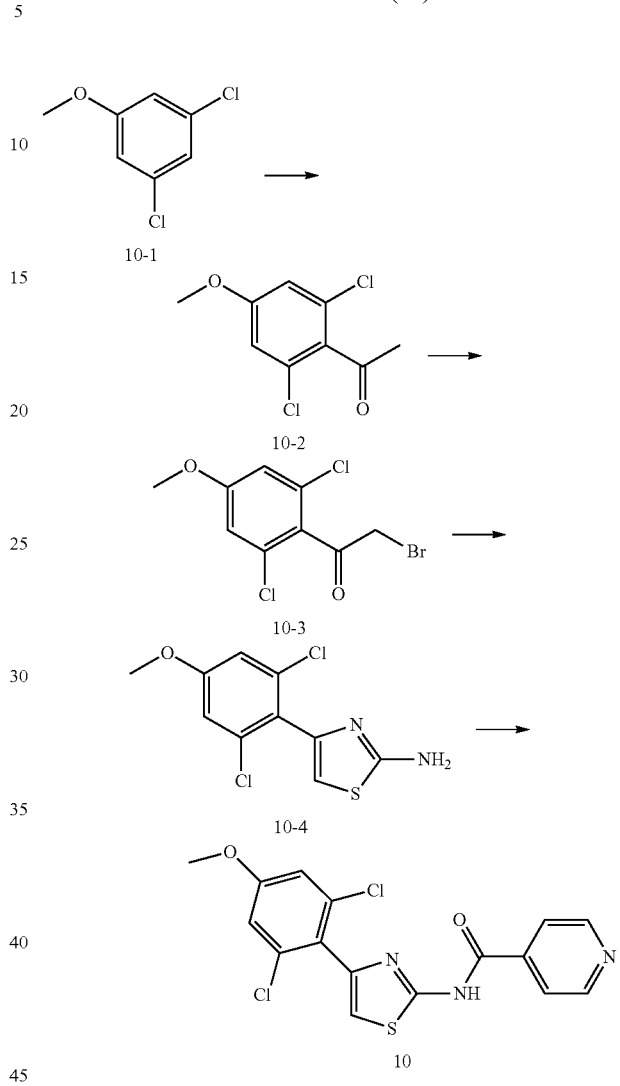

1-(2,6-Dichloro-4-methoxyphenyl)ethanone (10-2)

A mixture of aluminum chloride (4.50 g, 33.9 mmol) and acetyl chloride (2.40 mL, 33.9 mmol) in CH$_2$Cl$_2$ (20.0 mL) was stirred at 0° C. for 30 min. The reaction mixture was slowly added with 1,3-dichloro-5-methoxybenzene (10-1, 2.00 g, 11.3 mmol) in CH$_2$Cl$_2$ (10.0 mL), and the resultant solution was stirred at room temperature for additional 2.0 h. The solution was basified with saturated aqueous NaHCO$_3$. The organic layer was separated, dried over MgSO$_4$(s), and concentrated under reduced pressure. The residue was purified by column chromatography on silica gel to give 1-(2,6-dichloro-4-methoxyphenyl)ethanone (10-2, 1.0 g, 4.6 mmol) as yellow oil in 40% yield: $^1$H NMR (CDCl$_3$, 500 MHz) δ 7.01 (d, J=1.6 Hz, 2 H), 6.82 (d, J=1.6 Hz, 2 H), 3.83 (s, 3 H), 2.49 (s, 3 H).

2-Bromo-1-(2,6-dichloro-4-methoxyphenyl)ethanone (10-3)

To a solution of 1-(2,6-dichloro-4-methoxyphenyl)ethanone (10-2, 1.0 g, 4.6 mmol) in acetonitrile (30.0 mL) was added TBABr₃ (2.2 g, 4.6 mmol). The reaction was stirred at room temperature for 30 min. The solution was concentrated under reduced pressure, added with water, and extracted with ethyl acetate. The organic layer was washed with brine, dried over anhydrous MgSO₄(s), and concentrated under reduced pressure to give 2-bromo-1-(2,6-dichloro-4-methoxyphenyl)ethanone (10-3, 1.3 g), which was used directly for the next step without further purification.

4-(2,6-Dichloro-4-methoxyphenyl)thiazol-2-ylamine (10-4)

To a solution of 2-bromo-1-(2,6-dichloro-4-methoxyphenyl)ethanone (10-3, 1.3 g) and thiourea (0.42 g, 5.5 mmol) in 95% EtOH (15.0 mL) was heated at reflux for 60 min. The solution was concentrated under reduced pressure and the residue was re-dissolved in ethyl acetate. The solution was washed with saturated aqueous NaHCO₃, dried over MgSO₄, and concentrated under reduced pressure. The residue was purified by column chromatography on silica gel to give 4-(2,6-dichloro-4-methoxyphenyl)thiazol-2-ylamine (10-4, 0.60 g, 2.2 mmol) as yellow solids in 47% yield: ¹H NMR (500 MHz, CDCl₃) δ 7.08 (d, J=1.8 Hz, 1 H), 6.83 (d, J=1.8 Hz, 1 H), 6.49 (s, 1 H), 4.88 (brs, 2 H), 3.77 (s, 3 H); ESI-MS m/z 275.1 (M+H)⁺.

N-(4-(2,6-Dichloro-4-methoxyphenyl)thiazol-2-yl)isonicotinamide (10)

To a solution of 4-(2,6-dichloro-4-methoxyphenyl)thiazol-2-ylamine (10-5, 0.10 g, 0.36 mmol) in CH₂Cl₂ (10 mL) was added DMAP (88 mg, 0.72 mmol) followed by isonicotinoyl chloride hydrochloride (83 mg, 0.47 mmol). The reaction mixture was stirred at room temperature overnight. The solution was concentrated under reduced pressure and added with water. The resultant precipitate was collected and recrystallized in toluene to give N-(4-(2,6-dichloro-4-methoxyphenyl)thiazol-2-yl)isonicotinamide (50 mg, 0.13 mmol) as white solids in 37% yield: ¹H NMR (500 MHz, DMSO-d₆) δ 8.80 (d, J=5.8 Hz, 2 H), 7.99 (d, J=6.0 Hz, 2 H), 7.31 (d, J=1.7 Hz, 1 H), 7.26 (s, 1 H), 7.22 (d, J=1.7 Hz, 1 H), 3.75 (s, 3 H). ESI-MS: m/z 381.4 (M+H)⁺.

N-{4-(2,6-Dimethyl-4-(pyrazin-2-ylthio)phenyl)thiazol-2-yl}isonicotinamide (11)

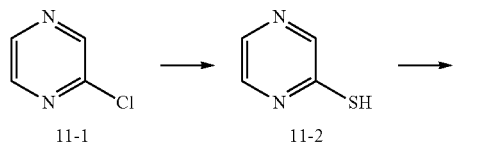

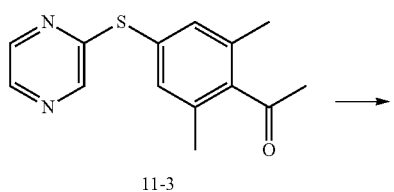

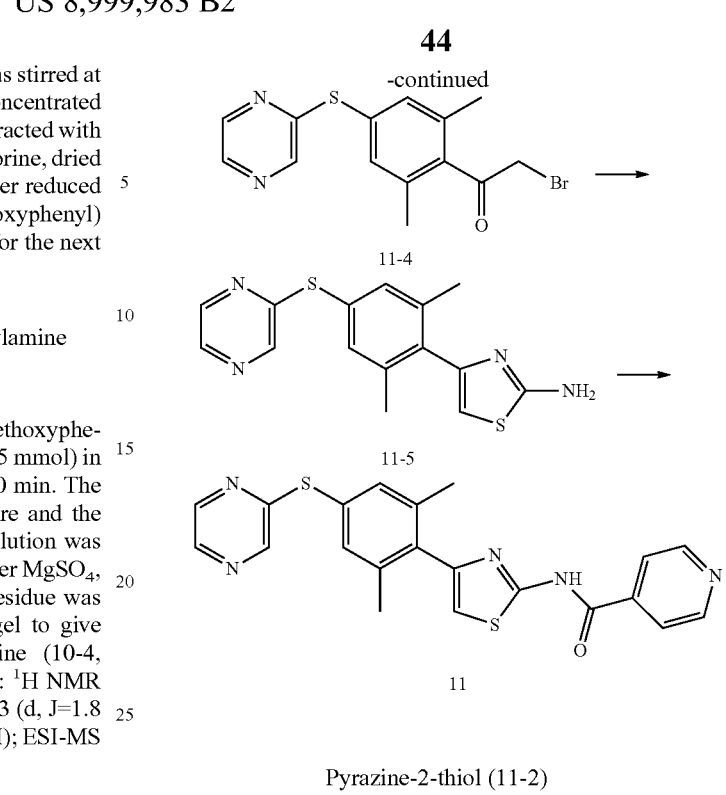

Pyrazine-2-thiol (11-2)

A mixture of 2-chloropyrazine (11-1, 2.00 g, 17.5 mmol) and thiourea (1.30 g, 17.5 mmol) in 95% EtOH (20 mL) was heated at reflux for 16 h. The solution was concentrated, added with 10% aqueous NaOH (20 mL), and extracted with ethyl acetate. The organic layer was washed with brine, dried over anhydrous MgSO₄(s), and concentrated under reduced pressure to give pyrazine-2-thiol (11-2, 1.96 g) as yellow solids in 100% yield: ¹H NMR (500 MHz, DMSO-d₆) δ 8.06 (s, 1 H), 7.70 (d, J=2.6 Hz, 2 H), 7.44 (d, J=2.6 Hz, 1 H); ESI-MS: m/z 113.2 (M+H)⁺.

1-(2,6-Dimethyl-4-(pyrazin-2-ylthio)phenyl)ethanone (11-3)

A mixture of 1-(4-iodo-2,6-dimethylphenyl)ethanone (4-2, 3.20 g, 11.7 mmol), pyrazine-2-thiol (11-1, 1.96 g, 17.5 mmol), copper(I) oxide (83.5 mg, 0.6 mmol), and potassium hydroxide (1.64 g, 29.2 mmol) in DMF (9.6 mL) and H₂O (2.4 mL) was heated at reflux for 24 h. The mixture was quenched with H₂O (10 mL) and extracted with ether (2×50 mL). The organic layer was collected, dried over MgSO₄(s), and concentrated under reduced pressure. The residue was purified by column chromatography on silica gel (3.0% EtOAc in hexanes as eluant) to provide 1-(2,6-dimethyl-4-(pyrazin-2-ylthio)phenyl)ethanone (11-3, 755.2 mg) as yellow oil in 25% yield: ¹H NMR (500 MHz, CDCl₃) δ 8.47 (s, 1 H), 8.27 (s, 1 H), 8.22 (s, 1 H), 7.28 (s, 2 H), 2.51 (s, 3 H), 2.28 (s, 6 H); ESI-MS: m/z 259.3 (M+H)⁺.

2-Bromo-1-(2,6-dimethyl-4-(pyrazin-2-ylthio)phenyl)ethanone (11-4)

To a solution of 1-(2,6-dimethyl-4-(pyrazin-2-ylthio)phenyl)ethanone (11-3, 4.50 g, 17.4 mmol) in acetonitrile (100 mL) was added TBABr₃ (8.3 g, 17.4 mmol). The reaction was stirred at room temperature overnight. The solution was concentrated under reduced pressure, added with water, and extracted with ethyl acetate. The organic layer was washed with brine, dried over anhydrous MgSO$_4$(s), and concentrated under reduced pressure to give 2-bromo-1-(2,6-dimethyl-4-(pyrazin-2-ylthio)phenyl)ethanone (11-4, 4.0 g), which was used directly for the next step without further purification.

4-(2,6-Dimethyl-4-(pyrazin-2-ylthio)phenyl)thiazol-2-amine (11-5)

A mixture of 2-bromo-1-(2,6-dimethyl-4-(pyrazin-2-ylthio)phenyl)ethanone (11-4, 4.00 g, 11.9 mmol) and thiourea (902.9 mg, 11.9 mmol) in 95% EtOH (15 mL) was heated at reflux for 16 hr. The solution was concentrated and added with water (50 mL) and saturated aqueous Na$_2$CO$_3$ (10.0 mL). The resultant precipitate was filtered and recrystallized in toluene (30 mL). The solids were filtered and dried under vacuum to give 4-(2,6-dimethyl-4-(pyrazin-2-ylthio)phenyl)thiazol-2-amine (11-5, 1.56 g) as yellow solids in 42% yield: $^1$H NMR (500 MHz, CDCl$_3$) δ 8.43 (s, 1 H), 8.36 (s, 1 H), 8.31 (s, 1 H), 7.47 (s, 2 H), 6.34 (s, 1 H), 2.24 (s, 6 H). ESI-MS: m/z 315.2 (M+H)$^+$.

N-{4-(2,6-Dimethyl-4-(pyrazin-2-ylthio)phenyl)thiazol-2-yl}isonicotinamide (11)

To a solution of 4-(2,6-dimethyl-4-(pyrazin-2-ylthio)phenyl)thiazol-2-amine (11-5, 500 mg, 1.6 mmol) in CH$_2$Cl$_2$ (10.0 ml) was added triethylamine (0.7 ml, 4.0 mmol) followed by isonicotinoyl chloride hydrochloride (707.7 mg, 4.8 mmol). The reaction mixture was stirred at room temperature overnight. The solution was concentrated under reduced pressure and added with hot water. The resultant precipitate was filtered and dried under vacuum to give N-{4-(2,6-dimethyl-4-(pyrazin-2-ylthio)phenyl)thiazol-2-yl}isonicotinamide (11, 392.5 mg) as white solids in 59% yield: $^1$H NMR (500 MHz, DMSO-d) δ 13.1 (s, 1 H), 8.81 (d, J=5.7 Hz, 2 H), 8.50 (s, 1 H), 8.41 (s, 1 H), 8.36 (s, 1H), 8.00 (d, J=5.7 Hz, 2 H), 7.41 (s, 2 H), 7.30 (s, 1 H), 2.13 (s, 6 H). ESI-MS: m/z 420.2 (M+H)$^+$.

N-(4-{4-(4-(2-Methoxyethoxy)phenoxy)-2,6-dimethylphenyl}thiazol-2-yl)isonicotinamide (12)

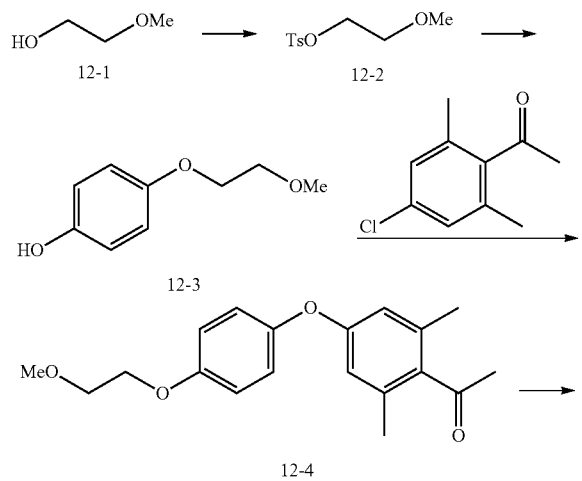

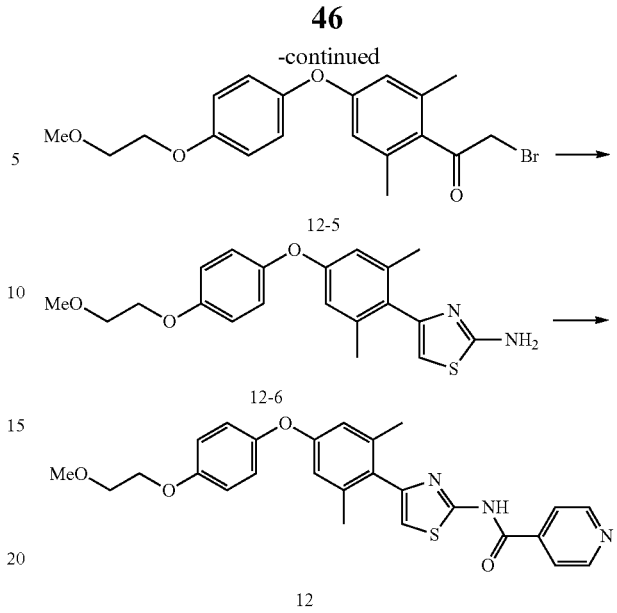

2-Methoxyethyl 4-methylbenzenesulfonate (12-2)

To a solution of 2-methoxyethanol (12-1, 5.00 g, 65.7 mmol) in CH$_2$Cl$_2$ (50.0 mL) was added triethylamine (18.3 mL, 131.4 mmol) followed by 4-methylbenzene-1-sulfonyl chloride (16.3 mg, 85.4 mmol). The reaction mixture was stirred at room temperature overnight. The solution was added with saturated aqueous Na$_2$CO$_3$ (50.0 mL) and extracted with CH$_2$Cl$_2$. The organic layer was washed with brine, dried over anhydrous MgSO$_4$(s), and concentrated under reduced pressure to give 2-methoxyethyl 4-methylbenzenesulfonate (12-2, 10.46 g) as yellow solids in 69% yield: $^1$H NMR (500 MHz, CDCl$_3$) δ 7.80 (d, J=8.3 Hz, 2 H), 7.34 (d, J=8.3 Hz, 2 H), 4.15-4.16 (m, 2 H), 3.57-3.59 (m, 2 H), 3.31 (s, 3H), 2.44 (s, 3 H). ESI-MS: m/z 230.8 (M+H)$^+$.

4-(2-Methoxyethoxy)phenol (12-3)

To a solution of 60% sodium hydride (436 mg, 18.2 mmol) in DMF (2.0 mL) was added hydroquinone (1.0 g, 18.2 mmol) in DMF (10.0 mL) dropwisely. The solution was added with 2-methoxyethyl 4-methylbenzenesulfonate (12-2, 2.10 g, 21.8 mmol) dropwisely. The reaction was stirred at 65° C. for 16 h. The solution was cooled to room temperature, poured into icy H$_2$O, and extracted with ethyl acetate. The organic layer was washed with brine, dried over anhydrous MgSO$_4$(s), and concentrated under reduced pressure to give 4-(2-methoxyethoxy)phenol (12-3, 1.0 g), which was used directly for the next step without further purification.

1-{4-(4-(2-Methoxyethoxy)phenoxy)-2,6-dimethylphenyl}ethanone (12-4)

To a solution of 1-(4-chloro-2,6-dimethylphenyl)ethanone (12-3, 914 mg, 5.00 mmol), K$_3$PO$_4$ (2.10 g, 10.0 mmol), and 4-(2-methoxyethoxy)phenol (12-3, 1.0 g, 6.0 mmol) in toluene (2.0 mL) was added 2-di-tert-butylphosphino-2',4',6'-triisopropylbiphenyl (63.8 mg, 0.15 mmol), Pd(OAc)$_2$ (47.3 mg, 0.10 mmol). The reaction was heated at 100° C. for 16 h under N$_2$. The solution was cooled to room temperature and filtered through a small pad of Diatomaceous earth. The cake was washed with ethyl acetate (50 mL) and the combined filtrate was concentrated under reduced pressure. The residue was purified by flash column chromatography on silica gel to give 1-{4-(4-(2-methoxyethoxy)phenoxy)-2,6- dimethylphenyl}ethanone (12-4, 797.5 mg) as yellow oil in 51% yield: $^1$H NMR (500 MHz, DMSO-$d_6$) δ 6.96-6.97 (m, 4 H), 6.57 (s, 2 H), 4.11-4.13 (m, 2 H), 3.75-3.77 (m, 2 H), 3.46 (s, 3 H), 2.46 (s, 3 H), 2.20 (s, 6 H). ESI-MS: m/z 315.2 (M+H)$^+$.

2-Bromo-1-{4-(4-(2-methoxyethoxy)phenoxy)-2,6-dimethylphenyl}ethanone (12-5)

To a solution of 1-{4-(4-(2-methoxyethoxy)phenoxy)-2,6-dimethylphenyl)}ethanone (12-4, 797.5 mg, 2.5 mmol) in acetonitrile (15 mL) was added TBABr$_3$ (1.22 g, 2.5 mmol). The reaction was stirred at room temperature overnight. The solution was concentrated under reduced pressure, added with water, and extracted with ethyl acetate. The organic layer was washed with brine, dried over anhydrous MgSO$_4$(s), and concentrated under reduced pressure to give 2-bromo-1-{4-(4-(2-methoxyethoxy)phenoxy)-2,6-dimethylphenyl}ethanone (12-5, 835.6 mg), which was used directly for the next step without further purification.

4-{4-(4-(2-Methoxyethoxy)phenoxy)-2,6-dimethylphenyl}thiazol-2-amine (12-6)

A mixture of 2-bromo-1-{4-(4-(2-methoxyethoxy)phenoxy)-2,6-dimethylphenyl}ethanone (12-5, 835.6 mg, 2.1 mmol) and thiourea (161.7 mg, 2.1 mmol) in 95% EtOH (5.0 mL) was heated at reflux for 2.0 h. The solution was concentrated and added with water (10 mL) and saturated aqueous Na$_2$CO$_3$ (10.0 mL). The resultant precipitate was filtered and recrystallized in toluene (30 mL). The solids were collected and dried under vacuum to give 4-{4-(4-(2-methoxyethoxy)phenoxy)-2,6-dimethylphenyl}thiazol-2-amine (12-6, 322.2 mg), which was used directly for the next step without further purification.

N-(4-{4-(4-(2-Methoxyethoxy)phenoxy)-2,6-dimethylphenyl}thiazol-2-yl)isonicotinamide (12)

To a solution of 4-{4-(4-(2-methoxyethoxy)phenoxy)-2,6-dimethylphenyl}thiazol-2-amine (12-6, 322.3 mg, 0.90 mmol) in CH$_2$Cl$_2$ (10.0 ml) was added triethylamine (0.40 mL, 2.6 mmol) followed by isonicotinoyl chloride hydrochloride (387.2 mg, 2.1 mmol). The reaction mixture was stirred at room temperature overnight. The solution was concentrated under reduced pressure and added with hot water. The resultant precipitate was filtered and dried under vacuum to give N-(4-{4-(4-(2-methoxyethoxy)phenoxy)-2,6-dimethylphenyl}thiazol-2-yl)isonicotinamide (12, 230 mg) as white solids in 56% yield: $^1$H NMR (500 MHz, DMSO-$d_6$) δ 13.0 (brs, 1 H), 8.78 (d, J=5.8 Hz, 2 H), 7.98 (d, J=5.8 Hz, 2 H), 7.12 (s, 1 H), 6.96-7.00 (m, 4 H), 6.67 (s, 2 H), 4.01-4.07 (m, 2 H), 3.63-3.64 (m, 2 H), 3.26 (s, 3 H), 2.03 (s, 6 H). ESI-MS: m/z 476.4 (M+H)$^+$.

N-(4-(2-Chloro-6-fluoro-4-methoxyphenyl)thiazol-2-yl)isonicotinamide (13)

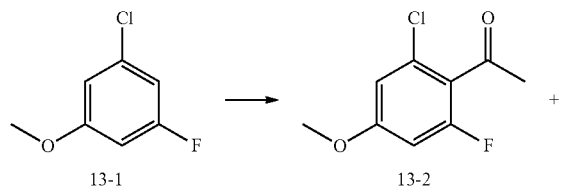

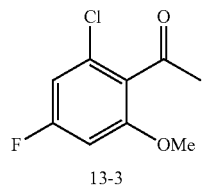

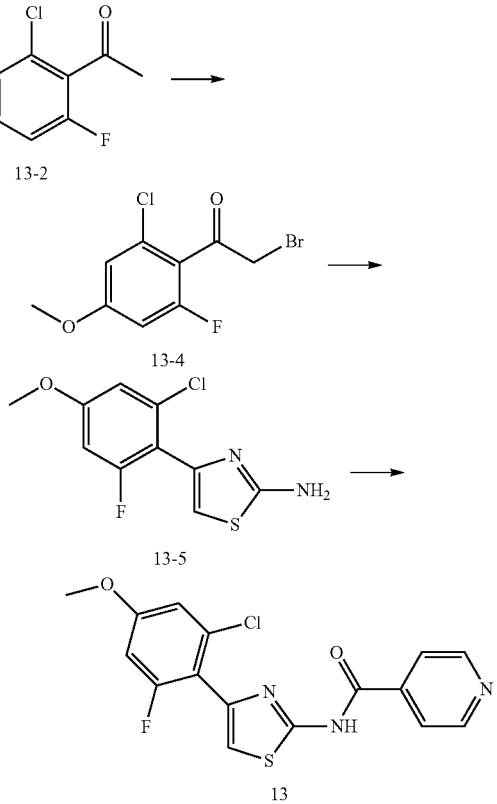

1-(2-Chloro-6-fluoro-4-methoxyphenyl)ethanone (13-2) and 1-(2-chloro-4-fluoro-6-methoxyphenyl)ethanone (13-3)

A mixture of aluminum chloride (2.50 g, 18.7 mmol) and acetyl chloride (1.30 mL, 18.7 mmol) in CH$_2$Cl$_2$ (10.0 mL) was stirred at 0° C. for 30 min. The reaction mixture was slowly added with 1-chloro-3-fluoro-5-methoxybenzene (13-1, 1.00 g, 6.23 mmol) in CH$_2$Cl$_2$ (5.0 mL). The solution was stirred at room temperature for additional 2.0 h. The solution was basified with saturated aqueous NaHCO$_3$, and the organic layer was separated, dried over MgSO$_4$(s), and concentrated under reduced pressure. The residue was purified by column chromatography on silica gel to give a mixture of 1-(2-chloro-6-fluoro-4-methoxyphenyl)ethanone (13-2) and 1-(2-chloro-4-fluoro-6-methoxyphenyl)ethanone (13-3) as yellow oil in 1.2 g (5.9 mmol) total weight (95% yield).

2-Bromo-1-(2-chloro-6-fluoro-4-methoxyphenyl)ethanone (13-4)

To a solution of 1-(2-chloro-6-fluoro-4-methoxyphenyl)ethanone (13-2, 0.60 g, 3.0 mmol) in acetonitrile (15.0 mL) was added TBABr$_3$ (1.4 g, 3.0 mmol). The reaction was stirred at room temperature for 30 min. The solution was concentrated under reduced pressure, added with water, and extracted with ethyl acetate. The organic layer was washed with brine, dried over anhydrous MgSO$_4$(s), and concentrated under reduced pressure 2-bromo-1-(2-chloro-6-fluoro-4-methoxyphenyl)ethanone (13-4, 0.80 g), which was used directly for the next step without further purification.

4-(2-Chloro-6-fluoro-4-methoxyphenyl)thiazol-2-ylamine (13-5)

To a solution of 2-bromo-1-(2-chloro-6-fluoro-4-methoxyphenyl)ethanone (13-4, 0.80 g) and thiourea (0.27 g, 3.6 mmol) in 95% EtOH (8.0 mL) was heated at reflux for 60 min. The solution was concentrated under reduced pressure, and the residue was re-dissolved in ethyl acetate. The solution was washed with saturated aqueous NaHCO$_3$, dried over MgSO$_4$, and concentrated under reduced pressure. The residue was purified by column chromatography on silica gel to give 4-(2-chloro-6-fluoro-4-methoxyphenyl)thiazol-2-ylamine (13-5, 0.30 g, 1.2 mmol) as yellow solids in 39% yield: $^1$H NMR (500 MHz, CDCl$_3$) δ 6.84 (s, 1 H), 6.65 (m, 1 H), 6.57 (s, 1 H), 3.83 (s, 3 H).

N-(4-(2-Chloro-6-fluoro-4-methoxyphenyl)thiazol-2-yl)isonicotinamide (13)

To a solution of 4-(2-chloro-6-fluoro-4-methoxyphenyl)thiazol-2-ylamine (0.10 g, 0.39 mmol) in CH$_2$Cl$_2$ (10 mL) was added DMAP (95 mg, 0.78 mmol) followed by isonicotinoyl chloride hydrochloride (90 mg, 0.51 mmol). The reaction mixture was stirred at room temperature overnight. The solution was concentrated under reduced pressure and added with water. The resultant precipitate was collected and recrystallized in toluene to give N-(4-(2-chloro-6-fluoro-4-methoxyphenyl)thiazol-2-yl)isonicotinamide (13, 60 mg, 0.17 mmol) as white solids in 42% yield: $^1$H NMR (500 MHz, CDCl$_3$) δ 8.76 (s, 2 H), 7.85 (d, J=4.5 Hz, 2 H), 7.12 (s, 1 H), 6.67 (s, 1 H), 6.45 (m, 1 H), 3.79 (s, 3H). ESI-MS: m/z 364.2 (M+H)$^+$.

N-(4-(2-Chloro-4-fluoro-6-methoxyphenyl)thiazol-2-yl)isonicotinamide (14)

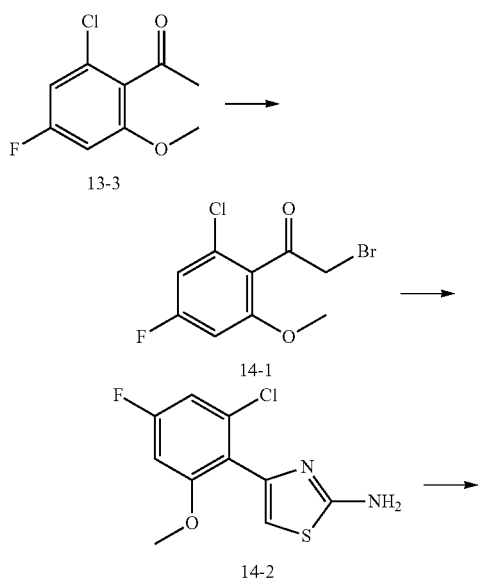

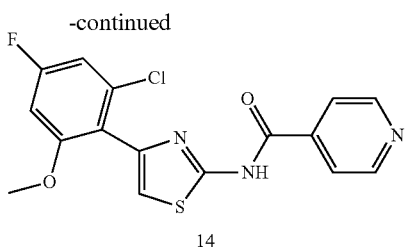

2-Bromo-1-(2-chloro-4-fluoro-6-methoxyphenyl)ethanone (14-1)

To a solution of 1-(2-chloro-4-fluoro-6-methoxyphenyl)ethanone (13-3, 0.60 g, 3.0 mmol) in acetonitrile (15.0 mL) was added TBABr$_3$ (1.4 g, 3.0 mmol). The reaction was stirred at room temperature for 30 min. The solution was concentrated under reduced pressure, added with water, and extracted with ethyl acetate. The organic layer was washed with brine, dried over anhydrous MgSO$_4$(s), and concentrated under reduced pressure 2-bromo-1-(2-chloro-4-fluoro-6-methoxyphenyl)ethanone (14-1, 0.84 g), which was used directly for the next step without further purification.

4-(2-Chloro-4-fluoro-6-methoxyphenyl)thiazol-2-ylamine (14-2).

A solution of 2-bromo-1-(2-chloro-4-fluoro-6-methoxyphenyl)ethanone (14-1, 0.84 g) and thiourea (0.27 g, 3.6 mmol) in 95% EtOH (8.0 mL) was heated at reflux for 60 min. The solution was concentrated under reduced pressure, and the residue was re-dissolved in ethyl acetate. The solution was washed with saturated aqueous NaHCO$_3$, dried over MgSO$_4$, and concentrated under reduced pressure. The residue was purified by column chromatography on silica gel to give 4-(2-chloro-4-fluoro-6-methoxyphenyl)thiazol-2-ylamine (14-2, 0.22 g, 0.85 mmol) as yellow solids in 28% yield: $^1$H NMR (500 MHz, CDCl$_3$) δ 6.81 (m, 1 H), 6.60 (m, 1 H), 6.49 (s, 1 H), 3.79 (s, 3 H).

N-(4-(2-Chloro-4-fluoro-6-methoxy-phenyl)thiazol-2-yl)isonicotinamide (14)

To a solution of 4-(2-chloro-4-fluoro-6-methoxyphenyl)thiazol-2-ylamine (14-2, 0.10 g, 0.39 mmol) in CH$_2$Cl$_2$ (10 mL) was added DMAP (95 mg, 0.78 mmol) followed by isonicotinoyl chloride hydrochloride (90 mg, 0.51 mmol). The reaction mixture was stirred at room temperature overnight. The solution was concentrated under reduced pressure and added with water. The resultant precipitate was collected and recrystallized in toluene to give N-(4-(2-chloro-4-fluoro-6-methoxyphenyl)-thiazol-2-yl)isonicotinamide (14, 55 mg, 0.15 mmol) as white solids in 39% yield: $^1$H NMR (500 MHz, CDCl$_3$) δ 8.81 (s, 2 H), 7.91 (d, J=4.7 Hz, 2 H), 7.12 (s, 1 H), 6.72 (m, 1 H), 6.50 (m, 1 H), 3.75 (s, 3 H); ESI-MS: m/z 364.2 (M+H)$^+$.

N-{4-(4-(5-Methoxypyrazin-2-yloxy)-2,6-dimethylphenyl)thiazol-2-yl}isonicotinamide (15)

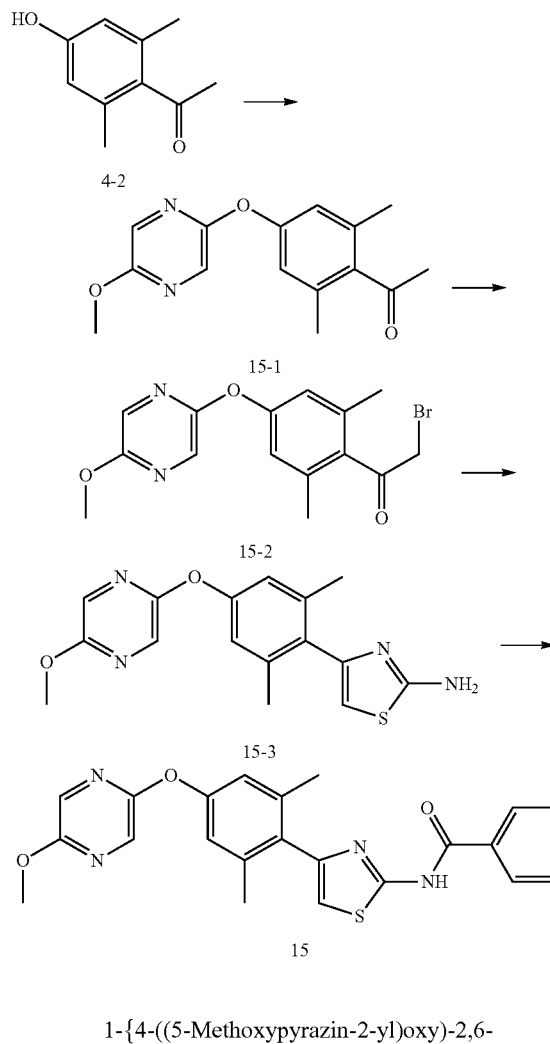

1-{4-((5-Methoxypyrazin-2-yl)oxy)-2,6-dimethylphenyl}ethanone (15-1)

A mixture of 1-(4-hydroxy-2,6-dimethylphenyl)ethanone (4-2, 3.50 g, 21.3 mmol), 2-bromo-5-methoxypyrazine (6.04 g, 32.0 mmol), copper (271 mg, 4.26 mmol), and potassium carbonate (8.84 g, 64.0 mmol) in 35.5 mL of DMF was stirred at 100° C. overnight. The reaction mixture was added with water and extracted with ethyl acetate. The organic layer was washed with brine, dried over anhydrous MgSO$_4$(s), concentrated under reduced pressure, and purified by column chromatography on silica gel (20% EtOAc in hexanes as eluant) to give 1-{4-((5-methoxypyrazin-2-yl)oxy)-2,6-dimethylphenyl}ethanone (15-1, 2.90 g) as yellow oils: $^1$H NMR (500 MHz, CDCl$_3$) δ 7.92 (s, 1 H), 7.87 (s, 1 H), 6.72 (s, 2 H), 3.96 (s, 3 H), 2.47 (s, 3 H), 2.24 (s, 6 H).

2-Bromo-1-{4-((5-methoxypyrazin-2-yl)oxy)-2,6-dimethylphenyl}ethanone (15-2)

To a solution of 1-{4-((5-methoxypyrazin-2-yl)oxy)-2,6-dimethylphenyl}ethanone (15-1, 2.10 g, 7.71 mmol) in acetonitrile (15.4 mL) was added TBABr$_3$ (3.72 g, 7.71 mmol). The reaction was stirred at 50° C. overnight. The solution was concentrated under reduced pressure, added with water, and extracted with ethyl acetate. The organic layer was washed with brine, dried over anhydrous MgSO$_4$(s), and concentrated under reduced pressure to give 2-bromo-1-{4-((5-methoxypyrazin-2-yl)oxy)-2,6-dimethylphenyl}ethanone (15-2, 3.1 g), which was used directly for the next step without further purification.

4-{4-((5-Methoxypyrazin-2-yl)oxy)-2,6-dimethylphenyl}thiazol-2-amine (15-3)

A mixture of 2-bromo-1-{4-((5-methoxypyrazin-2-yl)oxy)-2,6-dimethylphenyl}ethanone (15-2, 2.70 g, 7.69 mmol) and thiourea (0.59 g, 7.69 mmol) in 95% EtOH (11.0 mL) was heated at reflux for 60 min. The solution was concentrated and added with water and saturated aqueous Na$_2$CO$_3$ (1.0 mL). The resultant precipitate was purified by column chromatography on silica gel (EtOAc:hexanes=2:1 as eluant) to give 4-{4-((5-methoxypyrazin-2-yl)oxy)-2,6-dimethylphenyl}thiazol-2-amine (15-3, 0.40 g) as yellow oils in 16% yield: $^1$H NMR (500 MHz, CDCl$_3$) δ 7.91 (s, 1 H), 7.87 (s, 1 H), 6.77 (s, 2 H), 6.28 (s, 1 H), 5.19 (bs, 2 H), 3.96 (s, 3 H), 2.15 (s, 6 H).

N-{4-(4-(5-Methoxypyrazin-2-yloxy)-2,6-dimethylphenyl)thiazol-2-yl}isonicotinamide (15)

To a solution of 4-{4-((5-methoxypyrazin-2-yl)oxy)-2,6-dimethylphenyl}thiazol-2-amine (15-3, 0.40 g, 1.22 mmol) in THF (6.1 mL) was added triethylamine (0.370 g, 3.65 mmol) followed by isonicotinoyl chloride hydrochloride (0.430 g, 2.42 mmol). The reaction mixture was stirred at 60° C. overnight. The solution was concentrated under reduced pressure, added with water, and extracted with ethyl acetate. The organic layer was washed with brine, dried over anhydrous MgSO$_4$(s), and concentrated under reduced pressure. The resultant precipitate was purified by column chromatography on silica gel (EtOAc:hexanes=5:1 as eluant) to give N-(4-(4-(5-methoxypyrazin-2-yloxy)-2,6-dimethylphenyl)thiazol-2-yl)isonicotinamide (15, 0.12 g) as yellow solids in 23% yield: $^1$H NMR (500 MHz, CDCl$_3$) δ 8.87 (d, J=5.0 Hz, 2 H), 8.03 (d, J=6.5 Hz, 2 H), 7.96 (s, 1 H), 7.91 (s, 1 H), 6.81 (s, 3 H), 3.97 (s, 3 H), 2.08 (s, 6 H). ESI-MS: m/z 433.4 (M+H)$^+$.

N-{4-(4-(4-Isopropoxyphenoxy)-2,6-dimethylphenyl)thiazol-2-yl}isonicotinamide (16)

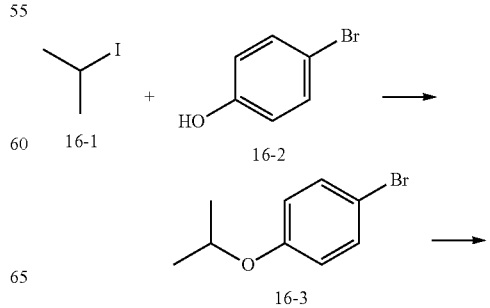

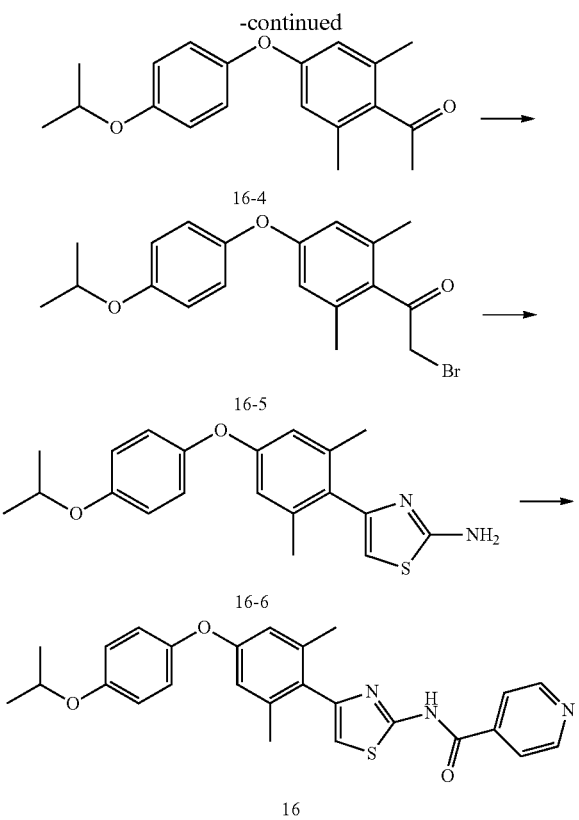

1-Bromo-4-isopropoxybenzene (16-3)

A mixture of 4-bromophenol (16-2, 7.02 g, 39.4 mmol) and potassium carbonate (12.6 g, 90.9 mmol) in DMSO (20.0 mL) was added with 2-iodopropane (16-1, 5.2 mL, 49.0 mmol). The mixture was heated at 60° C. overnight. The solution was cooled to room temperature and added with water (200 mL). The reaction was extracted with EtOAc, dried over MgSO$_4$, and concentrated under reduced pressure. The residue was purified by flash column chromatography on silica gel (EtOAc:hexanes=1:100 as eluant) to give 1-bromo-4-isopropoxybenzene (6.66 g) as colorless oil in 79% yield: $^1$H NMR (CDCl$_3$) δ 7.34 (m, 2 H), 6.77 (dd, J=8.9, 3.1 Hz, 2 H), 4.49 (m, 1 H), 1.33 (s, 3 H), 1.31 (m, 3 H).

1-(4-(4-Isopropoxyphenoxy)-2,6-dimethylphenyl)ethanone (16-4)

A mixture of 1-bromo-4-isopropoxybenzene (16-3, 3.02 g, 14.0 mmol), 1-(4-hydroxy-2,6-dimethylphenyl)ethanone (4-2, 3.54 g, 21.6 mmol), N,N-dimethylglycine HCl salt (0.50 g, 3.5 mmol), copper iodide (0.34 g, 1.8 mmol), and cesium carbonate (9.08 g, 27.9 mmol) in dioxane (30 mL) was heated at 90° C. for 48 h. The reaction mixture was cooled to room temperature, added with water, and extracted with EtOAc. The organic layer was washed with brine, dried over anhydrous MgSO$_4$, concentrated under reduced pressure, and purified by column chromatography on silica gel (EtOAc: hexanes=1:20 as eluant) to give 1-(4-(4-isopropoxyphenoxy)-2,6-dimethylphenyl)ethanone (16-4, 2.07 g) as white solids in 79% yield: $^1$H NMR (500 MHz, CDCl$_3$) δ 6.94 (m, 2 H), 6.87 (m, 2 H), 6.58 (s, 2 H), 4.50 (t, J=6.1 Hz, 1 H), 2.46 (s, 3 H), 2.21 (s, 6 H), 1.34 (s, 6 H), 1.26 (m, 3 H), 0.87 (m, 3 H).

2-Bromo-1-(4-(4-isopropoxyphenoxy)-2,6-dimethylphenyl)ethanone (16-5)

To a solution of 1-(4-(4-isopropoxyphenoxy)-2,6-dimethylphenyl)ethanone (16-4, 2.00 g, 6.7 mmol) in acetonitrile (20.0 mL) was added TBABr$_3$ (3.40 g, 6.9 mmol). The reaction was stirred at room temperature for 16 h. The solution was concentrated under reduced pressure, added with water, and extracted with EtOAc. The organic layer was washed with brine, dried over anhydrous MgSO$_4$, and concentrated under reduced pressure to give 2-bromo-1-(4-(4-isopropoxyphenoxy)-2,6-dimethylphenyl)ethanone (16-5, 2.57 g), which was used directly for the next step without further purification.

4-(4-(4-Isopropoxyphenoxy)-2,6-dimethylphenyl)thiazol-2-amine (16-6)

A mixture of 2-bromo-1-(4-(4-isopropoxyphenoxy)-2,6-dimethylphenyl)ethanone (16-5, 2.57 g, 6.8 mmol) and thiourea (0.60 g, 7.8 mmol) in 95% EtOH (30.0 mL) was heated at reflux for 4.0 h. The solution was concentrated and added with water (10 mL) and saturated aqueous Na$_2$CO$_3$ (1.0 mL). The resultant precipitate was filtered and washed with hot water. The solids were filtered and dried under vacuum to give 4-(4-(4-isopropoxyphenoxy)-2,6-dimethylphenyl)thiazol-2-amine (16-6, 1.48 g) as yellow solids in 61% yield: $^1$H NMR (500 MHz, DMSO-d$_6$) 6.94 (m, 6 H), 6.62 (s, 2 H), 6.33 (s, 1 H), 4.54 (t, J=6.0 Hz, 1 H), 2.05 (s, 6 H), 1.26 (s, 3 H), 1.25 (s, 3 H).

N-{4-(4-(4-Isopropoxyphenoxy)-2,6-dimethylphenyl)thiazol-2-yl}isonicotinamide (16)

To a solution of 4-(4-(4-isopropoxyphenoxy)-2,6-dimethylphenyl)thiazol-2-amine (16-6, 0.25 g, 0.72 mmol) in CH$_2$Cl$_2$ (5.0 mL) was added triethylamine (0.5 mL, 3.59 mmol) followed by isonicotinoyl chloride hydrochloride (0.35 g, 1.94 mmol). The reaction mixture was stirred at room temperature overnight. The solution was concentrated under reduced pressure and added with water. The resultant precipitate was filtered and recrystallized in toluene to give N-{4-(4-(4-isopropoxypherioxy)-2,6-dimethylphenyl)thiazol-2-yl}isonicotinamide (16, 0.26 g) as light yellow solids in 79% yield: $^1$H NMR (500 MHz, DMSO-d$_6$) δ 8.80 (d, J=5.1 Hz, 2 H), 7.98 (d, J=5.7 Hz, 1 H), 7.16 (s, 1 H), 6.95 (m, 4 H), 6.69 (s, 2 H), 4.55 (t, J=6.0 Hz, 2 H), 2.05 (s, 6 H), 1.27 (s, 3 H), 1.26 (s, 3 H). ESI-MS: m/z 460.1 (M+H)$^+$.

N-(4-{4-(6-(2-Methoxyethoxy)pyridin-3-yloxy)-2,6-dimethylphenyl}thiazol-2-yl)isonicotinamide (17)

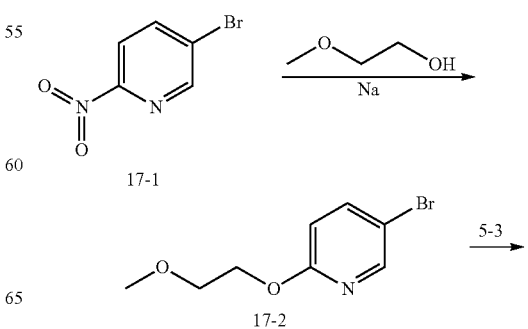

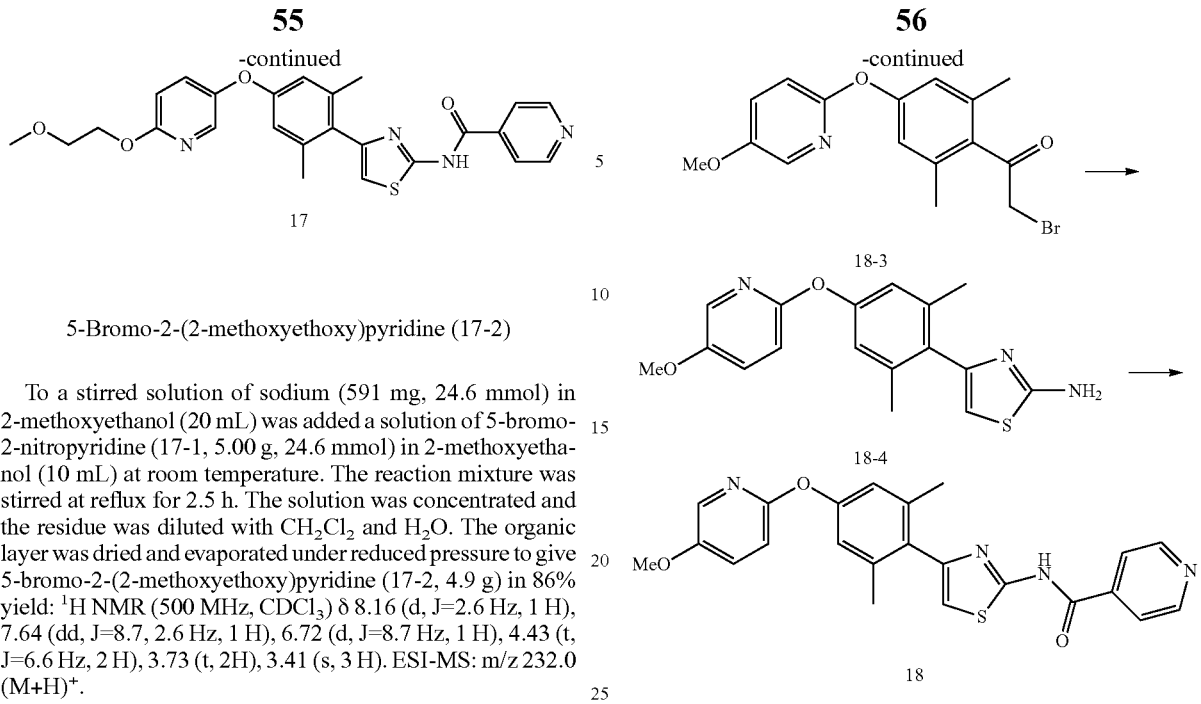

17

5-Bromo-2-(2-methoxyethoxy)pyridine (17-2)

To a stirred solution of sodium (591 mg, 24.6 mmol) in 2-methoxyethanol (20 mL) was added a solution of 5-bromo-2-nitropyridine (17-1, 5.00 g, 24.6 mmol) in 2-methoxyethanol (10 mL) at room temperature. The reaction mixture was stirred at reflux for 2.5 h. The solution was concentrated and the residue was diluted with $CH_2Cl_2$ and $H_2O$. The organic layer was dried and evaporated under reduced pressure to give 5-bromo-2-(2-methoxyethoxy)pyridine (17-2, 4.9 g) in 86% yield: $^1$H NMR (500 MHz, $CDCl_3$) δ 8.16 (d, J=2.6 Hz, 1 H), 7.64 (dd, J=8.7, 2.6 Hz, 1 H), 6.72 (d, J=8.7 Hz, 1 H), 4.43 (t, J=6.6 Hz, 2 H), 3.73 (t, 2H), 3.41 (s, 3 H). ESI-MS: m/z 232.0 $(M+H)^+$.

N-(4-{4-(6-(2-Methoxyethoxy)-pyridin-3-yloxy)-2,6-dimethylphenyl}thiazol-2-yl)isonicotinamide (17)

To a solution of N-(4-(4-Hydroxy-2,6-dimethylphenyl)-thiazol-2-yl)isonicotinamide (5-3, 0.98 g, 3.0 mmol) in DMF (10 mL) were added cesium carbonate (1.95 g, 6.0 mmol, 2.0 equiv) and Cu (58.5 mg, 0.90 mmol, 0.3 equiv). The mixture was stirred at 100-110° C. for 1.0 h and added with 5-bromo-2-(2-methoxyethoxy)pyridine (17-2, 1.04 g, 4.5 mmol). The solution heated at 130° C. for 24 h. The reaction mixture was added with water (40 mL) and extracted with EtOAc. The organic layer was washed with saturated brine and dried over anhydrous magnesium sulfate. The solvent was evaporated under reduced pressure, and the residue was purified by column chromatography (NH silica gel, hexane/ethyl acetate=3/1-1/3) to give 17 (0.94 g) in 66% yield: $^1$H NMR (500 MHz, $CDCl_3$) δ 8.81 (d, 2 H), 7.93 (d, 1 H), 7.88 (d, 2 H), 7.32 (m, 1 H), 6.82 (d, 2 H), 6.57 (s, 2 H), 4.45 (t, 2 H), 3.75 (t, 2 H), 3.44 (s, 3 H), 1.99 (s, 6 H), ESI-MS=m/z 477.2 $(M+H)^+$.

N-(4-{4-((5-Methoxypyridin-2-yl)oxy)-2,6-dimethylphenyl}thiazol-2-yl)isonicotinamide (18)

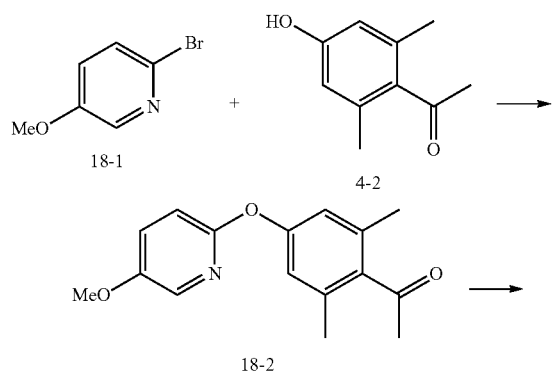

1-{4-((5-Methoxypyridin-2-yl)oxy)-2,6-dimethylphenyl}ethanone (18-2)

A mixture of 2-bromo-5-methoxypyridine (18-1, 1.03 g, 5.46 mmol), 1-(4-hydroxy-2,6-dimethylphenyl)ethanone (4-2, 0.80 g, 4.89 mmol), N,N-dimethylglycine HCl salt (0.28 g, 1.95 mmol), copper iodide (0.24 g, 1.24 mmol), and cesium carbonate (3.57 g, 10.96 mmol) in dioxane (10 mL) was heated at 120° C. for 4.0 h. The reaction mixture was cooled to room temperature, added with water, and extracted with EtOAc. The organic layer was washed with brine, dried over anhydrous $MgSO_4$, and concentrated to give 1-{4-((5-methoxypyridin-2-yl)oxy)-2,6-dimethylphenyl}ethanone (18-2, 1.42 g) as a yellow oil in 96% yield, which was used directly for the next step without further purification.

2-Bromo-1-{4-((5-methoxypyridin-2-yl)oxy)-2,6-dimethylphenyl}ethanone (18-3)

To a solution of 1-{4-((5-methoxypyridin-2-yl)oxy)-2,6-dimethylphenyl}ethanone (18-2, 1.42 g, 5.23 mmol) in acetonitrile (20.0 mL) was added $TBABr_3$ (2.70 g, 5.49 mmol). The reaction was stirred at room temperature for 16 h. The solution was concentrated under reduced pressure, added with water, and extracted with EtOAc. The organic layer was washed with brine, dried over anhydrous $MgSO_4$, and concentrated under reduced pressure to give 2-bromo-1-{4-((5-methoxypyridin-2-yl)oxy)-2,6-dimethylphenyl}ethanone (18-3, 1.89 g), which was used directly for the next step without further purification.

4-{4-((5-Methoxypyridin-2-yl)oxy)-2,6-dimethylphenyl}thiazol-2-amine (18-4)

A mixture of 2-bromo-1-{4-((5-methoxypyridin-2-yl)oxy)-2,6-dimethylphenyl}ethanone (18-3, 1.89 g, 5.40 mmol) and thiourea (0.47 g, 6.18 mmol) in 95% EtOH (20.0 mL) was heated at reflux for 2.0 h. The solution was concentrated and added with water (10 mL) and saturated aqueous $Na_2CO_3$ (1.0 mL). The resultant precipitate was filtered and washed with hot water. The solids were filtered and dried under vacuum to give 4-{4-((5-methoxypyridin-2-yl)oxy)-2,6-dimethylphenyl}thiazol-2-amine (18-4, 0.10 g) as yellow solids in 5.7% yield: $^1$H NMR (500 MHz, CDCl$_3$) δ 7.60 (m, 1 H), 7.30 (m, 1 H), 6.89 (m, 1 H), 6.77 (s, 2 H), 6.25 (s, 1 H), 3.83 (s, 3 H), 2.17 (s, 6 H).

N-(4-{4-((5-Methoxypyridin-2-yl)oxy)-2,6-dimethylphenyl}thiazol-2-yl)isonicotinamide (18)

To a solution of 4-{4-((5-methoxypyridin-2-yl)oxy)-2,6-dimethylphenyl}thiazol-2-amine (18-4, 0.10 g, 0.31 mmol) in CH$_2$Cl$_2$ (5.0 mL) was added triethylamine (0.50 mL, 3.6 mmol) followed by isonicotinoyl chloride hydrochloride (0.15 g, 0.80 mmol). The reaction mixture was stirred at room temperature overnight. The solution was concentrated under reduced pressure and added with water. The resultant precipitate was filtered and recrystallized in toluene to give N-(4-{4-((5-methoxypyridin-2-yl)oxy)-2,6-dimethylphenyl}thiazol-2-yl)isonicotinamide (18, 0.070 g) as light yellow solids in 52% yield: $^1$H NMR (500 MHz, DMSO-d$_6$) δ 8.81 (d, J=5.5 Hz, 2 H), 7.99 (dt, J=3.1, 1.5 Hz, 2 H), 7.92 (d, J=3.1 Hz, 1 H), 7.52 (dt, J=5.7, 3.2 Hz, 1 H), 7.20 (s, 1 H), 7.00 (d, J=8.8 Hz, 1 H), 6.81 (s, 2 H), 3.81 (s, 3 H), 2.08 (s, 6 H). ESI-MS: m/z 433.0 (M+H)$^+$.

N-{4-(2,6-Dimethyl-4-(pyrazin-2-ylthio)phenyl)thiazol-2-yl}-2-fluoroisonicotinamide (19)

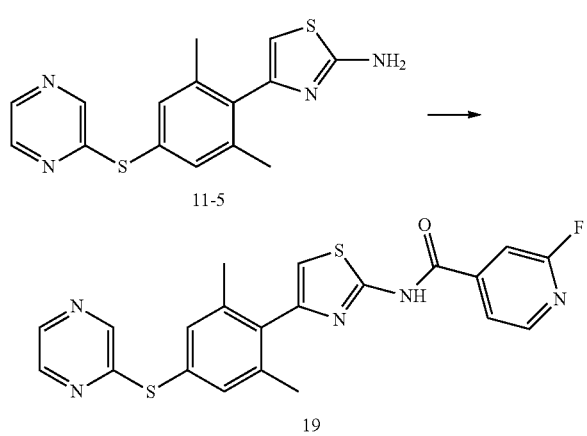

N-{4-(2,6-Dimethyl-4-(pyrazin-2-ylthio)phenyl)thiazol-2-yl}-2-fluoroisonicotinamide (19)

To a solution of 4-(2,6-dimethyl-4-(pyrazin-2-ylthio)phenyl)thiazol-2-amine (11-5, 200 mg, 0.60 mmol) in CH$_2$Cl$_2$ (2.0 mL) was added triethylamine (0.20 mL, 1.9 mmol) followed by 2-fluoroisonicotinic acid (107.7 mg, 1.0 mmol), 1-ethyl-3-(3-dimethylaminopropyl)carbodiimide hydrochloride (243.9 mg, 1.27 mmol) and hydroxybenzotriazole (172.0 mg, 1.27 mmol). The reaction mixture was stirred at room temperature overnight. The solution was concentrated under reduced pressure and added with hot water. The resultant precipitate was filtered, and dried under vacuum to give N-{4-(2,6-dimethyl-4-(pyrazin-2-ylthio)phenyl)thiazol-2-yl}-2-fluoroisonicotinamide (19, 68.4 mg) as yellow solids in 25% yield: $^1$H NMR (500 MHz, DMSO-d$_6$) δ 13.10 (s, 1 H), 8.47-8.50 (m, 2 H), 8.36-8.41 (m, 2 H), 7.96 (s, 1 H), 7.80 (s, 1 H), 7.41 (s, 2 H), 7.33 (s, 1 H), 2.13 (s, 6 H); ESI-MS: m/z 438.1 (M+H)$^+$.

2-Fluoro-N-(4-{4-(4-(2-methoxyethoxy)phenoxy)-2,6-dimethylphenyl}thiazol-2-yl)isonicotinamide (20)

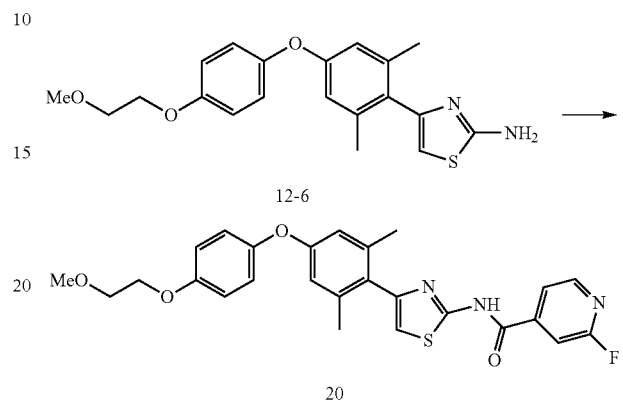

Fluoro-N-(4-{4-(4-(2-methoxyethoxy)phenoxy)-2,6-dimethylphenyl}thiazol-2-yl)isonicotinamide (20)

To a solution of 4-{4-(4-(2-methoxyethoxy)phenoxy)-2,6-dimethylphenyl}thiazol-2-amine (12-6, 180 mg, 0.5 mmol) in CH$_2$Cl$_2$ (2.0 mL) was added triethylamine (0.20 mL, 1.5 mmol) followed by 2-fluoroisonicotinic acid (82.3 mg, 0.70 mmol), 1-ethyl-3-(3-dimethylaminopropyl)carbodiimide hydrochloride (186.3 mg, 1.0 mmol), and hydroxybenzotriazole (131.4 mg, 1.0 mmol). The reaction mixture was stirred at room temperature overnight. The solution was concentrated under reduced pressure and added with hot water. The resultant precipitate was filtered, and dried under vacuum to give fluoro-N-(4-{4-(4-(2-methoxyethoxy)phenoxy)-2,6-dimethylphenyl}thiazol-2-yl)isonicotinamide (20, 186.3 mg) as yellow solids in 35% yield: $^1$H NMR (500 MHz, DMSO-d$_6$) δ 13.10 (s, 1 H), 8.47 (s, 1 H), 7.94-7.95 (m 1H), 7.80 (s, 1 H), 7.19 (s, 1 H), 6.97-7.02 (m, 4 H), 6.69 (s, 2 H), 4.02-4.09 (m, 2 H), 3.65-3.67 (m, 2 H), 3.29 (s, 3 H), 2.05 (m, 6 H). ESI-MS: m/z 494.1 (M+H)$^+$.

N-(4-{4-(4-(3-methoxypropoxy)phenoxy)-2,6-dimethylphenyl}thiazol-2-yl)isonicotinamide (21)

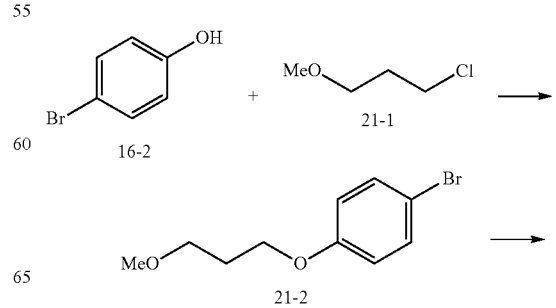

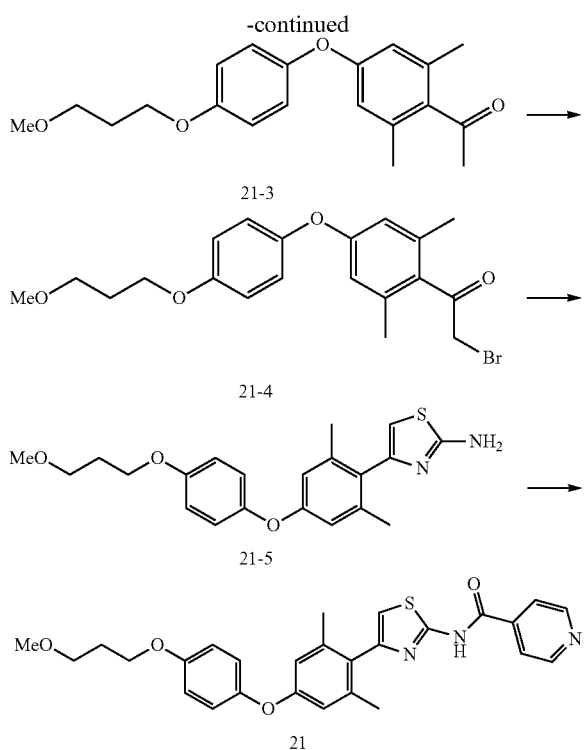

1-Bromo-4-(3-methoxypropoxy)benzene (21-2)

A mixture of 4-bromophenol (16-2, 1.01 g, 5.72 mmol), sodium iodide (1.02 g, 6.83 mmol), and potassium carbonate (1.88 g, 13.6 mmol) in acetonitrile (10.0 mL) was added with 1-chloro-2-methoxyethane (21-1, 0.89 g, 8.0 mmol). The mixture was heated to 60° C. for 48 h. The reaction mixture was cooled to room temperature and added with water (200 mL). The solution was extracted with EtOAc, dried over MgSO$_4$, and concentrated in vacuo. The residue was purified by flash column chromatography on silica gel (EtOAc:hexanes=1:20 as eluant) to give 1-bromo-4-isopropoxybenzene (21-2, 0.95 g) as a colorless oil in 68% yield: $^1$H NMR (CDCl$_3$) δ 7.36 (dt, J=5.0, 2.0 Hz, 2 H), 6.78 (m, 2 H), 4.02 (t, J=6.3 Hz, 2 H), 3.54 (t, J=6.1 Hz, 2 H), 3.35 (s, 3 H), 2.03 (t, J=6.2 Hz, 2 H).

1-{4-(4-(3-Methoxypropoxy)phenoxy)-2,6-dimethylphenyl}ethanone (21-3)

A mixture of 1-bromo-4-isopropoxybenzene (21-2, 0.85 g, 3.9 mmol), 1-(4-hydroxy-2,6-dimethylphenyl)ethanone (4-2, 1.10 g, 6.71 mmol), N,N-dimethylglycine HCl salt (0.21 g, 1.5 mmol), copper iodide (0.12 g, 0.60 mmol), and cesium carbonate (2.90 g, 8.91 mmol) in dioxane (15.0 mL) was stirred at 120° C. for 48 h. The reaction mixture was cooled to room temperature, added with water, and extracted with EtOAc. The organic layer was washed with brine, dried over anhydrous MgSO$_4$, concentrated, and purified by flash column chromatography on silica gel (EtOAc:hexanes=1:5 as eluant) to give 1-{4-(4-(3-methoxypropoxy)phenoxy)-2,6-dimethylphenyl}ethanone (21-3, 0.27 g) as yellow oil in 21% yield: $^1$H NMR (CDCl$_3$) δ 6.96 (dd, J=4.5, 2.2 Hz, 2 H), 6.89 (dd, J=4.3, 2.4 Hz, 2 H), 6.57 (s, 2 H), 4.05 (m, 2 H), 3.57 (t, J=6.2 Hz, 2H), 3.36 (s, 3 H), 2.66 (s, 3 H), 2.20 (s, 6 H), 2.05 (t, J=6.2 Hz, 2H).

2-Bromo-1-{4-(4-(3-methoxypropoxy)phenoxy)-2,6-dimethylphenyl}ethanone (21-4)

To a solution of 1-{4-(4-(3-methoxypropoxy)phenoxy)-2,6-dimethylphenyl}ethanone (21-3, 0.27 g, 0.82 mmol) in acetonitrile (5.0 mL) was added TBABr$_3$ (0.46 g, 0.93 mmol). The reaction was stirred at room temperature for 16 h. The solution was concentrated under reduced pressure, added with water, and extracted with EtOAc. The organic layer was washed with brine, dried over anhydrous MgSO$_4$, and concentrated under reduced pressure to give 2-bromo-1-{4-(4-(3-methoxypropoxy)phenoxy)-2,6-dimethylphenyl}ethanone (21-4, 0.34 g), which was used directly for the next step without further purification.

4-{4-(4-(3-Methoxypropoxy)phenoxy)-2,6-dimethylphenyl}thiazol-2-amine (21-5)

A mixture of 2-bromo-1-{4-(4-(3-methoxypropoxy)phenoxy)-2,6-dimethylphenyl}ethanone (21-4, 0.34 g, 0.82 mmol) and thiourea (0.07 g, 0.96 mmol) in 95% EtOH (5.0 mL) was heated at reflux for 2.0 h. The solution was concentrated and added with water (10 mL) and saturated aqueous Na$_2$CO$_3$ (1.0 mL). The resultant precipitate was filtered and washed with hot water. The solids were filtered and dried under vacuum to give 4-{4-(4-(3-methoxypropoxy)phenoxy)-2,6-dimethylphenyl}thiazol-2-amine (21-5, 0.28 g) as yellow solids in 90% yield, which was used directly for the next step without further purification.

N-(4-{4-(4-(3-Methoxypropoxy)phenoxy)-2,6-dimethylphenyl}thiazol-2-yl)isonicotinamide (21)

To a solution of 4-{4-(4-(3-methoxypropoxy)phenoxy)-2,6-dimethylphenyl}thiazol-2-amine (21-5, 0.28 g, 0.74 mmol) in CH$_2$Cl$_2$ (5.0 mL) was added triethylamine (0.5 mL, 3.59 mmol) followed by isonicotinoyl chloride hydrochloride (0.22 g, 1.22 mmol). The reaction mixture was stirred at room temperature overnight. The solution was concentrated under reduced pressure and added with water. The resultant precipitate was filtered and recrystallized in toluene to give N-{4-(4-(4-(3-methoxypropoxy)phenoxy)-2,6-dimethylphenyl}thiazol-2-yl)isonicotinamide (21, 0.99 mg) as light yellow solids in 27% yield: $^1$H NMR (500 MHz, DMSO-d$_6$) δ 13.00 (s, 1 H), 8.81 (s, 2 H), 7.99 (d, J=5.7 Hz, 2 H), 7.15 (s, 1 H), 6.98 (m, 4 H), 6.68 (s, 2 H), 4.00 (t, J=6.3 Hz, 2 H), 3.47 (t, J=6.3 Hz, 1 H), 2.05 (s, 6 H), 1.94 (t, J=6.3 Hz, 2 H). ESI-MS: m/z 489.7 (M+H)$^+$.

N-(4-{4-(5-(2-Methoxyethoxy)pyrazin-2-yloxy)-2,6-dimethylphenyl}thiazol-2-yl)isonicotinamide (22)

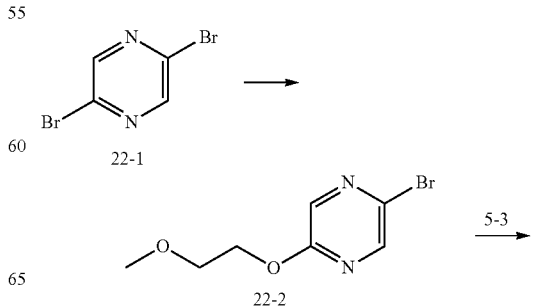

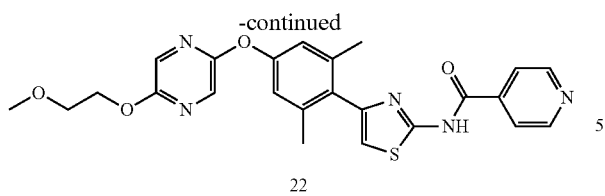

22

2-Bromo-5-(2-methoxyethoxy)pyrazine (22-2)

A mixture of 2,5-dibromopyrazine (22-1, 20.0 g, 84.1 mmol), 2-methoxyethanol (6.40 g, 84.1 mmol), and sodium tert-butoxide (11.3 g, 118 mmol) in 168 mL of THF was stirred at room temperature overnight. The solution was concentrated under reduced pressure and added with ethyl acetate. The mixture was filtered and the filtrate was concentrated under reduced pressure. The residue was purified by column chromatography on silica gel (EtOAc:hexanes=1:5 as eluant) to give 2-bromo-5-(2-methoxyethoxy)pyrazine (22-2, 17.2 g) as yellow oil in 88% yield: $^1$H NMR (500 MHz, CDCl$_3$) δ 8.16 (d, J=1.0 Hz, 1 H), 8.07 (d, J=1.0 Hz, 1 H), 4.46 (t, J=5.0 Hz, 2 H), 3.74 (m, 2 H), 3.43 (s, 3 H).

N-(4-(4-{(5-(2-Methoxyethoxy)pyrazin-2-yl)oxy}-2,6-dimethylphenyl)thiazol-2-yl)isonicotinamide (22)

A mixture of 5-3 (0.50 g, 1.54 mmol), 2-bromo-5-(2-methoxyethoxy)pyrazine (22-2, 0.540 g, 2.32 mmol), copper iodide (15.0 mg, 0.080 mmol), and potassium carbonate (0.64 g, 4.63 mmol) in 3.1 mL of DMF was heated at 100° C. for 6.0 h. The reaction mixture was concentrated under reduced pressure and purified by column chromatography on silica gel (EtOAc:hexanes=5:1 as eluant) to give N-(4-(4-{(5-(2-methoxyethoxy)pyrazin-2-yl)oxy}-2,6-dimethylphenyl)thiazol-2-yl)isonicotinamide (22, 0.19 g) as brown solids: $^1$H NMR (500 MHz, CDCl$_3$) δ 8.77 (d, J=4.5 Hz, 2 H), 7.91 (d, J=1.0 Hz, 1 H), 7.88 (d, J=1.0 Hz, 1 H), 7.73 (d, J=5.5 Hz, 2 H), 6.79 (s, 1 H), 6.63 (s, 2 H), 4.46 (t, J=4.5 Hz, 2 H), 3.75 (t, J=4.5 Hz, 2 H), 3.43 (s, 3 H), 1.98 (s, 6 H). ESI-MS: m/z 478.2 (M+H)$^+$.

N-(4-{4-(2-(Dimethylamino)ethoxy)-2,6-dimethylphenyl}thiazol-2-yl)isonicotinamide (23)

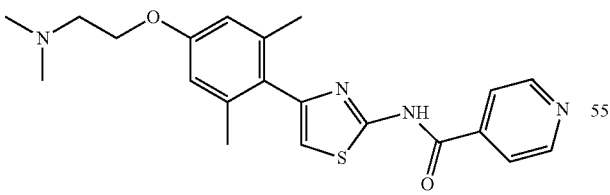

23

N-(4-{4-(2-(Dimethylamino)ethoxy)-2,6-dimethylphenyl}thiazol-2-yl)isonicotinamide (23)

From the reaction of 5-3 with equal molar of 2-chloro-N,N-dimethylethanamine and NaH in DMF: $^1$H NMR (500 MHz, DMSO-d$_6$) δ 8.72 (s, 2 H), 8.19 (d, J=5.9 Hz, 2 H), 6.91 (s, 1 H), 6.70 (s, 2 H), 4.63 (s, 1 H), 4.31 (t, J=6.8 Hz, 2 H), 2.92 (s, 2 H), 2.50 (s, 6 H), 2.11 (s, 6 H). ESI-MS: m/z 397.2 (M+H)$^+$.

N-{4-(2,6-Dimethyl-4-(6-nitropyridin-3-yloxy)phenyl)thiazol-2-yl}isonicotinamide (24)

N-{4-(2,6-Dimethyl-4-(6-nitropyridin-3-yloxy)phenyl)thiazol-2-yl}isonicotinamide (24)

A solution of 5-3 (1.92 g, 5.91 mmol) in DMF (15 mL) was added with cesium carbonate (2.41 g, 7.39 mmol). The reaction mixture was heated at 50° C. for 60 min and added with 5-bromo-2-nitropyridine (24-1, 1.80 g). The reaction mixture was heated at 50° C. for 4.0 h. The solution was quenched with water (40 mL) and the mixture was extracted with ethyl acetate. The organic layer was washed with saturated brine and dried over anhydrous magnesium sulfate. The solvent was evaporated under reduced pressure and the residue was purified by column chromatography (NH silica gel, hexane/ethyl acetate=3/1-1/3) to give 24 (1.76 g) in 67% yield: $^1$H NMR (500 MHz, DMSO-d$_6$) δ 8.78 (d, 2 H), 8.42 (d, 1 H), 8.33 (d, 1 H), 7.96 (d, 2 H), 7.63 (m, 1 H), 7.21 (s, 1 H), 7.01 (s, 2 H), 2.08 (s, 6 H), ESI-MS=m/z 447.5 (M+H)$^+$.

N-{4-(4-(5-Methoxypyrazin-2-ylthio)-2,6-dimethylphenyl)thiazol-2-yl}isonicotinamide (25)

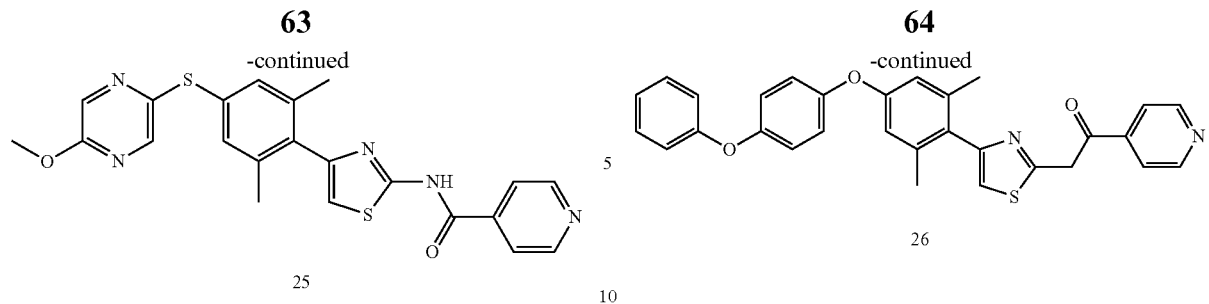

25

N-{4-(4-(5-Methoxypyrazin-2-ylthio)-2,6-dimethylphenyl)thiazol-2-yl}isonicotinamide (25)

A mixture of N-(4-(4-iodo-2,6-dimethylphenyl)thiazol-2-yl)isonicotinamide (25-1, 173.5 mg, 0.40 mmol), 5-methoxypyrazine-2-thiol (25-2, 170 mg, 17.5 mmol), copper iodide (3.8 mg, 0.02 mmol), and potassium carbonate (165.3 mg, 1.2 mmol) in DMF (2 mL) was heated at 80° C. for 16 h. The solution was added with water and extracted with ethyl acetate. The organic layer was collected, dried over MgSO$_4$(s), and concentrated under reduced pressure. The residue was purified by flash column chromatography on silica gel (20% EtOAc in hexanes as eluant) to provide N-{4-(4-(5-methoxypyrazin-2-ylthio)-2,6-dimethylphenyl)thiazol-2-yl}isonicotinamide (25, 135 mg) as yellow solids in 24% yield: $^1$H NMR (500 MHz, DMSO-d$_6$) δ 8.77 (s, 2 H), 8.28 (s, 1 H), 8.18 (s, 1 H), 7.94-7.95 (m, 2 H), 7.14-7.21 (m, 3 H), 3.88 (s, 3 H), 2.03 (s, 6 H). ESI-MS: m/z 450.3 (M+H)$^+$.

N-{4-(2,6-Dimethyl-4-(4-phenoxyphenoxy)phenyl)thiazol-2-yl}isonicotinamide (26)

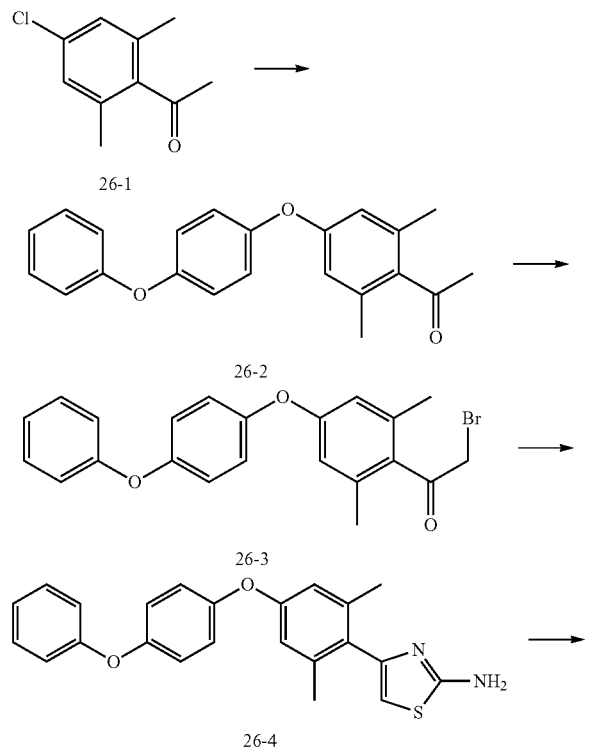

1-(2,6-Dimethyl-4-(4-phenoxyphenoxy)phenyl)ethanone (26-2)

To a solution of 1-(4-chloro-2,6-dimethylphenyl)ethanone (26-1, 5.00 g, 27.4 mmol), K$_3$PO$_4$ (11.6 g, 54.6 mmol), and 4-phenoxyphenol (6.12 g, 32.9 mmol) in toluene (39.1 mL) was added 2-di-tert-butylphosphino-2',4',6'-triisopropylbiphenyl (349 mg, 0.82 mmol) and Pd(OAc)$_2$ (259 mg, 1.15 mmol). The reaction was heated at 100° C. for 4.0 h under N$_2$. The solution was cooled to room temperature and filtered through a small pad of diatomaceous earth. The cake was washed with ethyl acetate (50 mL) and the combined filtrate was concentrated under reduced pressure. The residue was purified by column chromatography on silica gel (EtOAc: hexanes=1:10 as eluant) to give 1-(2,6-dimethyl-4-(4-phenoxyphenoxy)phenyl)ethanone (26-2, 7.70 g) as white solids in 85% yield: $^1$H NMR (500 MHz, CDCl$_3$) δ 7.34-7.37 (m, 2 H), 7.10-7.13 (m, 1 H), 6.99-7.04 (m, 6 H), 6.65 (s, 2 H), 2.49 (s, 3 H), 2.24 (s, 6 H).

2-Bromo-1-(2,6-dimethyl-4-(4-phenoxyphenoxy)phenyl)ethanone (26-3)

To a solution of 1-(2,6-dimethyl-4-(4-phenoxyphenoxy)phenyl)ethanone (26-2, 7.70 g, 23.2 mmol) in acetonitrile (46.3 mL) was added TBABr$_3$ (11.2 g, 23.2 mmol). The reaction mixture was stirred at room temperature overnight. The solution was concentrated under reduced pressure, added with water, and extracted with ethyl acetate. The organic layer was washed with brine, dried over anhydrous MgSO$_4$(s), and concentrated under reduced pressure to give 2-bromo-1-(2,6-dimethyl-4-(4-phenoxyphenoxy)phenyl)ethanone (26-3, 11.2 g), which was used directly for the next step without further purification.

4-(2,6-Dimethyl-4-(4-phenoxyphenoxy)phenyl)thiazol-2-amine (26-4)

A mixture of 2-bromo-1-(2,6-dimethyl-4-(4-phenoxyphenoxy)phenyl)ethanone (26-3, 9.53 g, 23.2 mmol) and thiourea (1.76 g, 23.1 mmol) in 95% EtOH (33.1 mL) was heated at reflux for 60 min. The solution was concentrated and added with water (100 mL) and saturated aqueous Na$_2$CO$_3$ (5.0 mL). The resultant precipitate was filtered and washed with ethyl acetate. The solids were dried under vacuum to give 4-(2,6-dimethyl-4-(4-phenoxyphenoxy)phenyl)thiazol-2-amine (26-4, 9.00 g) as brown solids in 100% yield, which was used directly for the next step without further purification.

N-{4-(2,6-Dimethyl-4-(4-phenoxyphenoxy)phenyl)thiazol-2-yl}isonicotinamide (26)

To a solution of 4-(2,6-dimethyl-4-(4-phenoxyphenoxy)phenyl)thiazol-2-amine (26-4, 0.500 g, 1.29 mmol) in THF (6.4 mL) was added triethylamine (0.39 g, 3.86 mmol) followed by isonicotinoyl chloride hydrochloride (0.46 g, 2.58 mmol). The reaction mixture was stirred at 60° C. overnight. The solution was concentrated under reduced pressure and added with water. The resultant precipitate was filtered and dried to give N-{4-(2,6-dimethyl-4-(4-phenoxyphenoxy)phenyl)thiazol-2-yl}isonicotinamide (26, 0.51 g) as light yellow solids in 80% yield: $^1$H NMR (500 MHz, CDCl$_3$) δ 8.72 (m, 2 H), 7.61 (m, 2 H), 7.31-7.34 (m, 2 H), 7.08-7.10 (m, 1 H), 6.94-7.02 (m, 6 H), 6.80 (s, 1H), 6.49 (s, 2 H), 1.94 (s, 6 H). ESI-MS: m/z 494.2 (M+H)$^+$.

N-(4-{4-(5-(2-methoxyethoxy)pyrazin-2-ylthio)-2,6-dimethylphenyl}thiazol-2-yl)isonicotinamide (27)

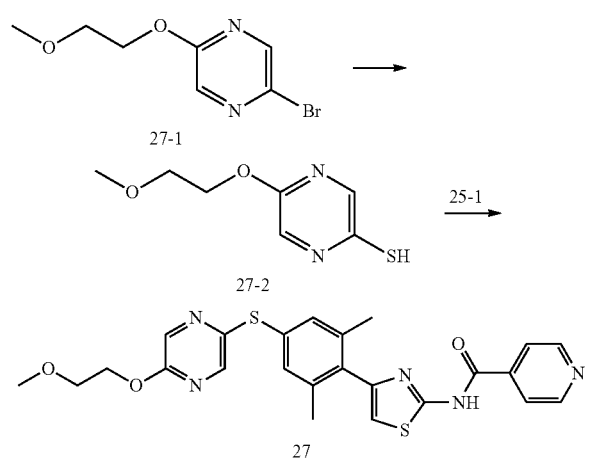

5-(2-Methoxyethoxy)pyrazine-2-thiol (27-2)

A mixture of 2-bromo-5-(2-methoxyethoxy)pyrazine (27-1, 5.00 g, 21.5 mmol) and NaSH.xH$_2$O (4.81 g, 85.8 mmol) in 35.5 mL of DMF was stirred at 80° C. for 3.0 h. The reaction mixture was concentrated under reduced pressure and added with methanol. The mixture was filtered and the filtrate was concentrated under reduced pressure and washed with ethyl acetate. The resultant precipitate was dried under reduced pressure to give 5-(2-methoxyethoxy)pyrazine-2-thiol (27-2, 3.90 g) as yellow solids.

N-(4-{4-(5-(2-Methoxyethoxy)pyrazin-2-ylthio)-2,6-dimethylphenyl}thiazol-2-yl)isonicotinamide (27)

A mixture of 25-1 (3.00 g, 6.89 mmol), 5-(2-methoxyethoxy)pyrazine-2-thiol (27-2, 2.57 g, 13.8 mmol), copper iodide (66.0 mg, 0.35 mmol), and potassium carbonate (2.86 g, 20.7 mmol) in 13.8 mL of DMF was stirred at 100° C. for 7.0 h. The reaction mixture was concentrated under reduced pressure and purified by column chromatography on silica gel (EtOAc:hexnaes=2:1 as eluant) to give N-(4-{4-(5-(2-methoxyethoxy)pyrazin-2-ylthio)-2,6-dimethylphenyl}thiazol-2-yl)isonicotinamide (27, 2.00 g) as light yellow solids in 59% yield: $^1$H NMR (500 MHz, CDCl$_3$) δ 8.75 (d, J=4.0 Hz, 2 H), 8.19 (d, J=1.0 Hz, 1 H), 8.00 (d, J=1.0 Hz, 1H), 7.63 (d, J=5.0 Hz, 2 H), 6.96 (s, 1 H), 6.79 (s, 2 H), 4.44 (t, J=4.5 Hz, 2 H), 3.72 (t, J=4.5 Hz, 2 H), 3.41 (s, 3 H), 1.95 (s, 6 H). ESI-MS: m/z 494.2 (M+H)$^+$.

N-(4-(4-{5-(2-(Dimethylamino)ethoxy)pyrazin-2-ylthio}-2,6-dimethylphenyl)thiazol-2-yl)isonicotinamide (28)

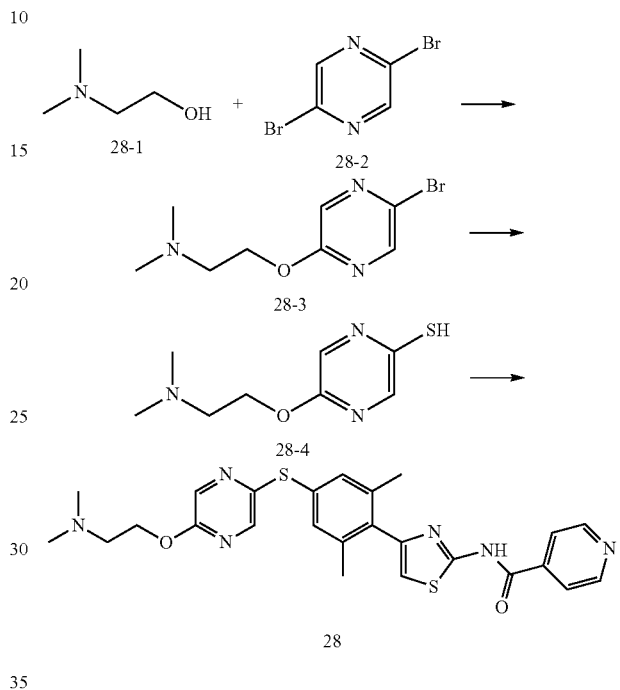

2-((5-Bromopyrazin-2-yl)oxy)-N,N-dimethylethanamine (28-3)

To a solution of 2-(dimethylamino)ethanol (28-1, 8.00 g, 78.9 mmol) in THF (100 mL) was added sodium tert-butoxide (10.0 g, 102.0 mmol) at room temperature. The reaction was stirred for 15 min. The reaction mixture was cooled to 0° C. and added with a solution of 2,5-dibromopyrazine (28-2, 20.0 g, 82.4 mmol) in THF (100 ml) slowly in a period of 5.0 min. The reaction mixture was warmed to room temperature and stirred for 16 h. The mixture was diluted with ethyl acetate and washed with saturated NH$_4$Cl. The organic layer was dried over MgSO$_4$, filtered, and concentrated under reduced pressure to give 2-((5-bromopyrazin-2-yl)oxy)-N,N-dimethylethanamine (28-3, 17.0 g) as yellow oils in 88% yield: $^1$H NMR (500 MHz, CDCl$_3$) δ 8.46 (s, 1 H), 8.16 (d, J=1.1 Hz, 1 H), 8.06 (d, J=1.1 Hz, 1 H), 4.68 (t, J=4.8 Hz, 2 H), 3.20 (s, 2 H), 2.70 (s, 6 H).

5-(2-(Dimethylamino)ethoxy)pyrazine-2-thiol (28-4)

A mixture of 2-((5-bromopyrazin-2-yl)oxy)-N,N-dimethylethanamine (28-3, 3.10 g, 12.6 mmol) and NaSH.xH$_2$O (5.20 g, 92.8 mmol) in DMF (30 mL) was heated at 80° C. for 3.0 h. The reaction mixture was concentrated under reduced pressure and added with methanol. The mixture was filtered and the filtrate was concentrated under reduced pressure and washed with ethyl acetate. The resultant precipitate was dried to give 5-(2-(dimethylamino)ethoxy)pyrazine-2-thiol (28-4, 1.87 g) as yellow solids, which was used directly for the next step without further purification.

N-(4-(4-{5-(2-(Dimethylamino)ethoxy)pyrazin-2-ylthio}-2,6-dimethylphenyl)thiazol-2-yl)isonicotinamide (28)

A mixture of N-(4-(4-iodo-2,6-dimethylphenyl)thiazol-2-yl)isonicotinamide (0.51 g, 1.2 mmol), 5-(2-(dimethylamino)ethoxy)pyrazine-2-thiol (28-4, 0.96 g, 4.8 mmol), copper iodide (73.0 mg, 0.38 mmol), and potassium carbonate (0.64 g, 4.6 mmol) in 5.0 mL of DMF was heated at 100° C. for 16 h. The reaction mixture was concentrated under reduced pressure and purified by column chromatography on silica gel (MeOH:CH$_2$Cl$_2$=1:10 as eluant) to give N-(4-(4-{5-(2-(dimethylamino)ethoxy)pyrazin-2-ylthio}-2,6-dimethylphenyl)thiazol-2-yl)isonicotinamide (28, 0.28 g) as light yellow solids in 47% yield: $^1$H NMR (500 MHz, CD$_3$OD) δ 8.75 (s, 2 H), 8.14 (d, J=1.1 Hz, 1 H), 8.04 (s, 1 H), 7.97 (d, J=5.9 Hz, 2 H), 7.18 (s, 2 H), 7.00 (s, 1 H), 4.58 (s, 3 H), 4.46 (t, J=5.5 Hz, 2 H), 2.81 (t, J=5.4 Hz, 2 H), 2.37 (s, 6 H), 2.10 (s, 6 H). ESI-MS: m/z 507.1 (M+H)$^+$.

N-(4-{4-(6-(2-Methoxyethylamino)pyridin-3-yloxy)-2,6-dimethylphenyl}thiazol-2-yl)isonicotinamide (29)

To a solution of 5-3 (325 mg, 1.0 mmol) in DMF (15 mL) were added cesium carbonate (650 mg, 2.0 mmol, 2.0 equiv) and Cu (19.5 mg, 0.30 mmol, 0.3 equiv). The solution was stirred at 100-110° C. for 60 min and added with 5-bromo-N-(2-methoxyethyl)pyridin-2-amine (29-2, 347 mg). The reaction mixture was stirred at 140° C. for 48 h. The reaction was quenched with water (40 mL) and extracted with ethyl acetate. The organic layer was washed with brine, dried over anhydrous magnesium sulfate, and concentrated under reduced pressure. The residue was purified by column chromatography (NH silica gel, hexane/ethyl acetate=3/1-1/3) to give 29 (96 mg) in 16% yield: $^1$H NMR (500 MHz, CDCl$_3$) δ 8.81 (d, 1 H), 7.72 (d, 1 H), 7.71 (d, 1H), 7.24 (m, 1 H), 6.81 (s, 1 H), 6.72 (d, 1 H), 6.49 (s, 1 H), 3.59 (t, 1 H), 3.51 (t, 1 H), 3.35 (s, 3 H), 2.01 (s, 6 H), ESI-MS=m/z 447.5 (M+H)$^+$.

N-{4-(2-Fluoro-4-(4-methoxyphenoxy)-6-methylphenyl)thiazol-2-yl}isonicotinamide (30)

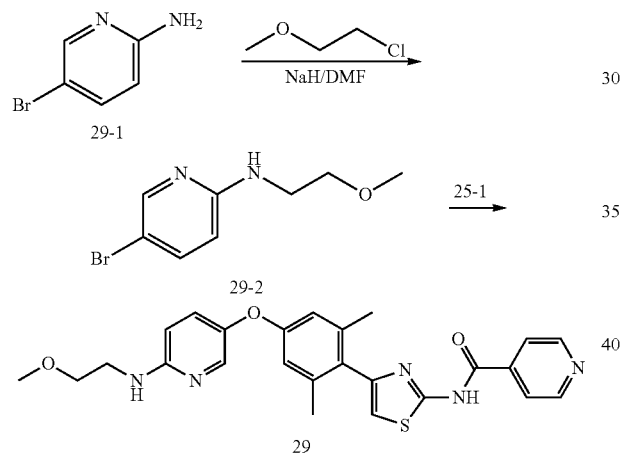

5-Bromo-N-(2-methoxyethyl)pyridin-2-amine (29-2)

5-Bromo-pyridin-2-ylamine (29-1, 1.43 g, 8.27 mmol) was dissolved in anhydrous DMF (20 mL) under N$_2$. The solution was cooled to 0-5° C. and added with NaH (>1.0 equiv) until no hydrogen was formed. The solution was added with 1-chloro-2-methoxy-ethane (2.5 ml, 14 mmol) dropwise at 0-5° C. The reaction mixture was stirred at 0° C. for 50 min. The solution was quenched with methanol and saturated aqueous NH$_4$Cl. The solution was concentrated under reduced pressure and distributed between water, brine, and dichloromethane. The aqueous phase was then extracted with dichloromethane and the combined organic phases were dried over sodium sulfate, filtered, and concentrated. The residue was purified by flash column chromatography on silica gel to give 5-bromo-N-(2-methoxyethyl)pyridin-2-amine (29-2, 1.01 g) as brown solids in 53% yield: $^1$H NMR (500 MHz, CDCl$_3$) δ 8.01 (d, 1 H), 7.57 (d, 1 H), 6.57 (d, 1 H), 3.97 (t, 2 H), 3.49 (t, 2 H), 3.35 (s, 3 H). ESI-MS: m/z 231.0 (M+H)$^+$.

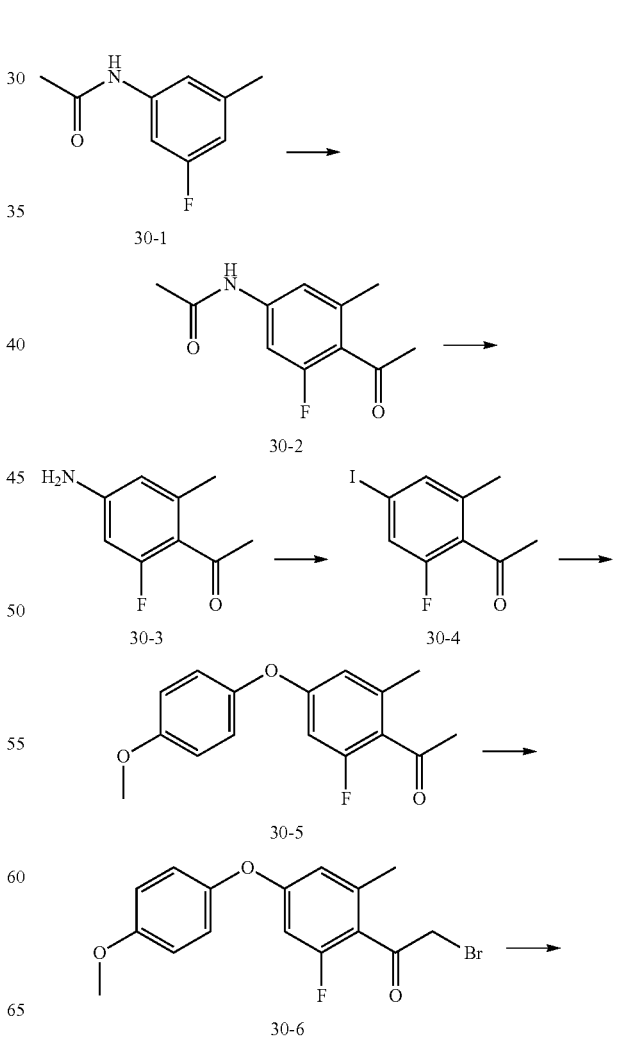

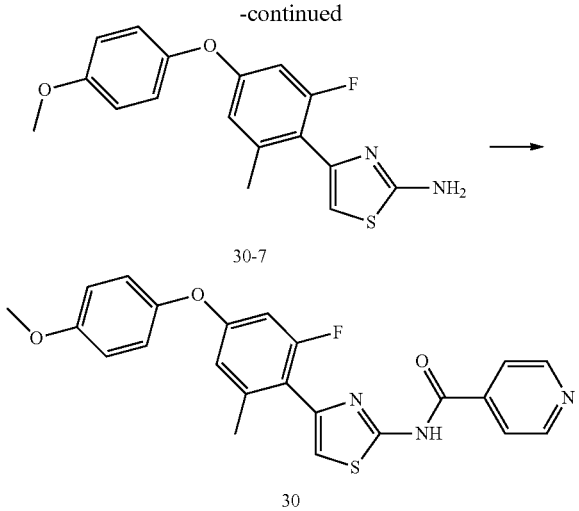

30-7

30

N-(4-Acetyl-3-fluoro-5-methylphenyl)acetamide (30-2)

A dry $CS_2$ solution (42 mL) containing N-(3-fluoro-5-methylphenyl)acetamide (30-1, 5.00 g, 29.9 mmol) and acetyl chloride (3.2 mL, 45 mmol) was slowly added with aluminum chloride (10 g, 74.8 mmol). The reaction mixture was heated at reflux for 2.0 h. The solution was cooled to room temperature and $CS_2$ was decanted. The remaining syrup was poured into icy HCl, and the resultant solids were collected, re-dissolved in EtOH, and decolorized by charcoal. The solution was filtered and the filtrate was concentrated under vacuum to give N-(4-acetyl-3-fluoro-5-methyl-phenyl)acetamide (30-2, 6.10 g, 29.2 mmol) as light yellow solids in 97% yield: $^1$H NMR (500 MHz, $CDCl_3$) δ 7.46 (d, J=12.4 Hz, 1 H), 6.93 (s, 1 H), 2.53 (d, J=3.8 Hz, 3 H), 2.31 (s, 3 H), 2.18 (s, 3 H).

1-(4-Amino-2-fluoro-6-methylphenyl)ethanone (30-3)

An ethanol solution (51 mL) containing N-(4-acetyl-3-fluoro-5-methylphenyl)acetamide (30-2, 5.80 g, 27.7 mmol) and concentrated hydrochloric acid (20.0 mL) was heated at reflux for 15 h. The solution was added with 10% aqueous NaOH and the resultant solids were collected to give 1-(4-amino-2-chloro-6-methylphenyl)ethanone (30-3, 4.00 g, 23.9 mmol) as light yellow solids in 86% yield: $^1$H NMR (500 MHz, DMSO-$d_6$) δ 6.22 (m, 2 H), 2.37 (m, 3 H), 2.22 (s, 3 H). ESI-MS: m/z 167.8 (M+H)$^+$.

1-(2-Fluoro-4-iodo-6-methylphenyl)ethanone (30-4)

A $CH_3CN$ solution (48 mL) containing KI (4.80 g, 28.8 mmol) and tert-butyl nitrite (3.90 mL, 32.4 mmol) was added with 1-(4-amino-2-fluoro-6-methylphenyl)ethanone (30-3, 4.0 g, 24.0 mmol) in $CH_3CN$ (32 mL) at –10° C. The reaction mixture was warmed to room temperature and poured into aqueous HCl. The solution was extracted with EtOAc, and the organic layer was separated, washed with $H_2O$, dried over $MgSO_4(s)$, and concentrated under reduced pressure. The residue was purified by flash column chromatography on silica gel to give 1-(2-fluoro-4-iodo-6-methylphenyl)ethanone (30-4, 1.4 g, 5.0 mmol) as brown oil in 21% yield: $^1$H NMR (500 MHz, $CDCl_3$) δ 7.36 (s, 1 H), 7.29 (d, J=9.2 Hz, 1H), 2.49 (d, J=3.2 Hz, 3 H), 2.26 (s, 3 H).

1-(2-Fluoro-4-(4-methoxyphenoxy)-6-methylphenyl)ethanone (30-5)

To a solution of 1-(2-fluoro-4-iodo-6-methylphenyl)ethanone (30-4, 1.1 g, 4.0 mmol), $K_3PO_4$ (1.7 g, 8.0 mmol), 4-methoxy-phenol (0.60 g, 4.8 mmol) in toluene (20 mL) was added 2-di-tert-butylphosphino-2',4',6'-triisopropylbiphenyl (51 mg, 0.12 mmol), $Pd(OAc)_2$ (38 mg, 0.08 mmol). The reaction was heated at 100° C. overnight under $N_2$. The solution was cooled to room temperature and filtered through a small pad of diatomaceous earth. The cake was washed with ethyl acetate (50 mL) and combined filtrate was concentrated under reduced pressure. The residue was purified by flash column chromatography on silica gel to give 1-(2-fluoro-4-(4-methoxyphenoxy)-6-methylphenyl)ethanone (0.47 g, 1.7 mmol) as yellow oil in 43% yield: $^1$H NMR (500 MHz, $CDCl_3$) δ 6.97 (m, 2 H), 6.90 (m, 2 H), 6.54 (s, 1 H), 6.42 (m, 1 H), 3.80 (s, 3 H), 2.50 (d, J=4.1 Hz, 3 H), 2.30 (s, 3 H). ESI-MS: m/z 275.0 (M+H)$^+$.

2-Bromo-1-(2-fluoro-4-(4-methoxyphenoxy)-6-methylphenyl)ethanone (30-6)

To a solution of 1-(2-fluoro-4-(4-methoxyphenoxy)-6-methylphenyl)ethanone (0.470 g, 1.71 mmol) in acetonitrile (23.0 mL) was added $TBABr_3$ (0.830 g, 1.71 mmol). The reaction was stirred at room temperature for 30 min. The solution was concentrated under reduced pressure, added with water, and extracted with ethyl acetate. The organic layer was washed with brine, dried over anhydrous $MgSO_4(s)$, and concentrated under reduced pressure to give 2-bromo-1-(2-fluoro-4-(4-methoxyphenoxy)-6-methylphenyl)ethanone (30-6, 0.60 g), which was used directly for the next step without further purification.

4-(2-Fluoro-4-(4-methoxyphenoxy)-6-methylphenyl)thiazol-2-ylamine (30-7)

A mixture of 2-bromo-1-(2-fluoro-4-(4-methoxyphenoxy)-6-methylphenyl)ethanone (30-6, 0.60 g) and thiourea (0.160 mg, 2.05 mmol) in 95% EtOH (12.0 mL) was heated at reflux for 60 min. The solution was concentrated under reduced pressure, and the residue was re-dissolved in ethyl acetate. The solution was washed with saturated aqueous $NaHCO_3$, dried over $MgSO_4$, and concentrated under reduced pressure. The residue was purified by column chromatography on silica gel to give 4-(2-fluoro-4-(4-methoxyphenoxy)-6-methylphenyl)thiazol-2-ylamine (30-7, 0.450 g, 1.36 mmol) as yellow solids in 80% yield: $^1$H NMR (500 MHz, $CDCl_3$) δ 6.98 (d, J=9.0 Hz, 2 H), 6.89 (d, J=9.0 Hz, 2 H), 6.60 (s, 1 H), 6.49 (d, J=10.9 Hz, 1 H), 6.41 (s, 0.1 H), 3.80 (d, J=3.4 Hz, 3 H), 2.26 (s, 3H). ESI-MS: m/z 331.0 (M+H)$^+$.

N-{4-(2-Fluoro-4-(4-methoxyphenoxy)-6-methylphenyl)thiazol-2-yl}isonicotinamide (30)

To a solution of 4-(2-fluoro-4-(4-methoxyphenoxy)-6-methylphenyl)thiazol-2-ylamine (30-7, 0.10 g, 0.30 mmol) in $CH_2Cl_2$ (10 mL) was added DMAP (73 mg, 0.60 mmol) followed by isonicotinoyl chloride hydrochloride (69 mg, 0.39 mmol). The reaction mixture was stirred at room temperature overnight. The solution was concentrated under reduced pressure and added with water. The resultant precipitate was collected and recrystallized in toluene to give N-{4-

(2-dluoro-4-(4-methoxyphenoxy)-6-methylphenyl)thiazol-2-yl}isonicotinamide (30, 42 mg, 0.10 mmol) as white solids in 32% yield: $^1$H NMR (500 MHz, CDCl$_3$) δ 8.86 (d, J=5.8 Hz, 2 H), 8.04 (d, J=5.6 Hz, 2H), 6.99 (d, J=7.2 Hz, 3 H), 6.92 (d, J=9.0 Hz, 2 H), 6.61 (s, 1 H), 6.50 (m, 1 H), 3.82 (s, 3 H), 2.26 (s, 3 H). ESI-MS: m/z 436.1 (M+H)$^+$.

N-(4-{4-(5-(2-Methoxyethoxy)pyrazin-2-ylsulfonyl)-2,6-dimethylphenyl}thiazol-2-yl)isonicotinamide (31)

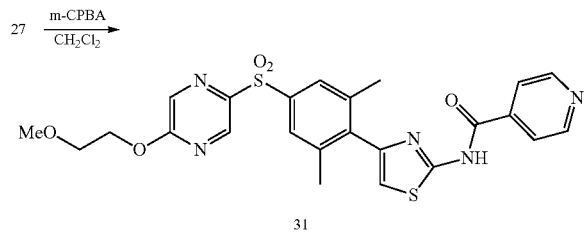

31

N-(4-{4-(5-(2-Methoxyethoxy)pyrazin-2-ylsulfonyl)-2,6-dimethylphenyl}thiazol-2-yl)isonicotinamide (31)

A mixture of 27 and m-chloroperoxybenzoic acid (249.7 mg, 1.01 mmol, 2.5 equiv) in dichloromethane (2.0 mL) was stirred at room temperature for 16 h. The solution was concentrated under reduced pressure, and the residue was re-dissolved in EtOAc (30 mL). The solution was washed with saturated aqueous NaHCO$_3$ (20 mL), dried over MgSO$_4$, and concentrated under reduced pressure to give 31 (88.8 mg, 0.17 mmol) as light-yellow solids in 42% yield: $^1$H NMR (DMSO-d$_6$, 500 MHz) δ 13.09 (s, 1 H), 8.98 (d, J=0.95 Hz, 1 H), 8.81 (d, J=5.7 Hz, 2 H), 8.46 (d, J=0.95 Hz, 1 H), 7.98 (d, J=5.7 Hz, 2 H), 7.75 (s, 2 H), 7.31 (s, 1 H), 4.52-4.53 (m, 2 H), 3.69-3.70 (m, 2 H), 3.29 (s, 3 H), 2.17 (s, 6 H). ESI-MS: m/z 526.1 (M+H)$^+$.

N-(4-{4-(5-(2-Methoxyethoxy)pyrazin-2-ylsulfinyl)-2,6-dimethylphenyl}thiazol-2-yl)isonicotinamide (32)

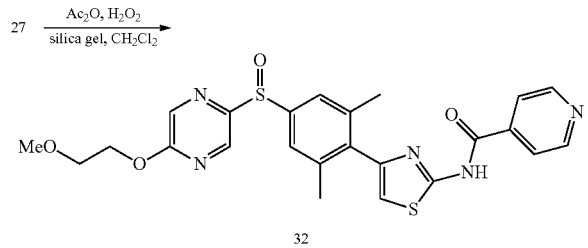

32

N-(4-{4-(5-(2-Methoxyethoxy)pyrazin-2-ylsulfinyl)-2,6-dimethylphenyl}thiazol-2-yl)isonicotinamide (32)

A mixture of 27 (200.0 mg, 0.41 mmol, 1.0 equiv), acetic anhydride (0.040 mL, 0.45 mmol, 1.1 equiv), 30% hydrogen peroxide (201.1 mg, 5.94 mmol, 4.4 equiv), and silica gel (81.1 mg, 230-400 mesh) in dichloromethane (5.0 mL) was stirred at room temperature for 16 h. The solution was concentrated under reduced pressure, and the residue was re-dissolved in EtOAc (30 mL). The solution was washed with saturated aqueous NaHCO$_3$ (20 mL), dried over MgSO$_4$, and concentrated under reduced pressure. The residue was purified by column chromatography on silica gel (90% EtOAc in hexanes as eluant) to provide to provide N-(4-{4-(5-(2-methoxyethoxy)pyrazin-2-ylsulfinyl)-2,6-dimethylphenyl}thiazol-2-yl)isonicotinamide (32, 100.3 mg, 0.2 mmol) as yellow solids in 49% yield: $^1$H NMR (DMSO-d$_6$, 500 MHz) δ 13.05 (s, 1 H), 8.81 (d, J=5.5 Hz, 2 H), 8.68 (s, 1 H), 8.40 (s, 1 H), 7.98 (d, J=5.5 Hz, 2 H), 7.50 (s, 2 H), 7.26 (s, 1 H), 4.47-4.48 (m, 2 H), 3.67-3.69 (m, 2 H), 3.29 (s, 3 H), 2.14 (s, 6 H); ESI-MS: m/z 510.1 (M+H)$^+$.

N-{4-(4-(3,4-Dimethoxyphenylsulfanyl)-2,6-dimethylphenyl)thiazol-2-yl}isonicotinamide (33)

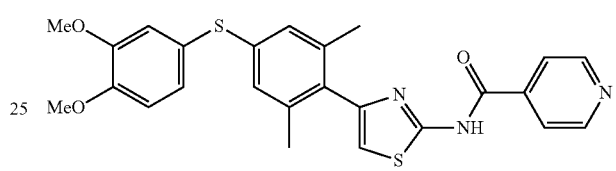

33

N-{4-(4-(3,4-Dimethoxyphenylsulfanyl)-2,6-dimethylphenyl)thiazol-2-yl}isonicotinamide (33)

$^1$H NMR (500 MHz, CDCl$_3$) δ 8.69 (t, J=4.5 Hz, 2 H), 7.53 (d, J=6.0 Hz, 2 H), 7.08 (m, 1 H), 6.99 (d, J=2.0 Hz, 1 H), 6.87 (d, J=8.0 Hz, 1 H), 6.74 (s, 1 H), 6.54 (s, 2H), 3.90 (s, 3 H), 3.87 (s, 3 H), 1.81 (s, 6 H). ESI-MS: m/z 478.3 (M+H)$^+$.

N-{4-(4-(4-Hydroxyphenylsulfanyl)-2,6-dimethylphenyl)thiazol-2-yl}isonicotinamide (34)

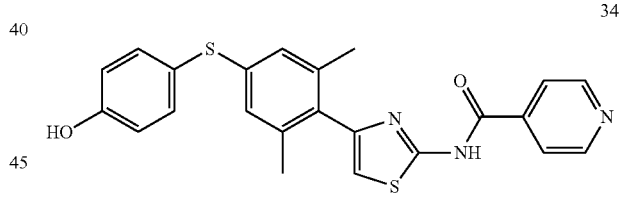

34

N-{4-(4-(4-Hydroxyphenylsulfanyl)-2,6-dimethylphenyl)thiazol-2-yl}isonicotinamide (34)

$^1$H NMR (500 MHz, CDCl$_3$) δ 8.77 (d, J=6.0 Hz; 2 H), 7.70 (d, J=6.00 Hz, 2 H), 7.37 (d, J=8.5 Hz, 2 H), 6.80 (m, 3 H), 6.70 (s, 1 H), 1.91 (s, 6 H). ESI-MS: m/z 434.1 (M+H)$^+$.

N-{4-(4-(4-Aminophenylsulfanyl)-2,6-dimethylphenyl)thiazol-2-yl}isonicotinamide (35)

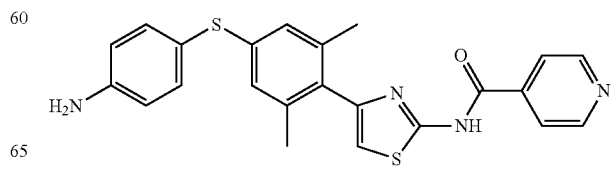

35

N-{4-(4-(4-Aminophenylsulfanyl)-2,6-dimethylphenyl)thiazol-2-yl}isonicotinamide (35)

¹H NMR (500 MHz, CDCl₃) δ 8.69 (m, 2 H), 7.52 (m, 2 H), 7.30 (m, 2 H), 6.74 (s, 1 H), 6.70 (m, 2 H), 6.53 (s, 2 H), 1.81 (s, 6 H). ESI-MS: m/z 433.2 (M+H)⁺.

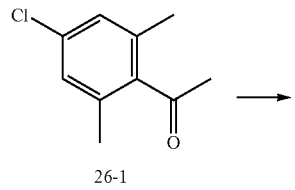

26-1

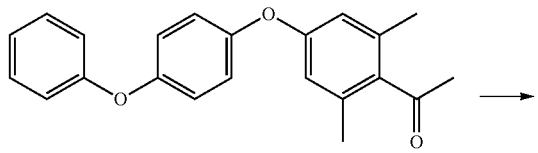

26-2

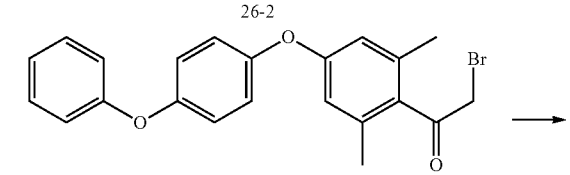

26-3

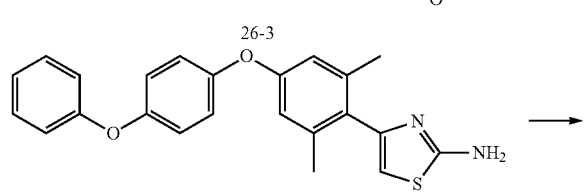

26-4

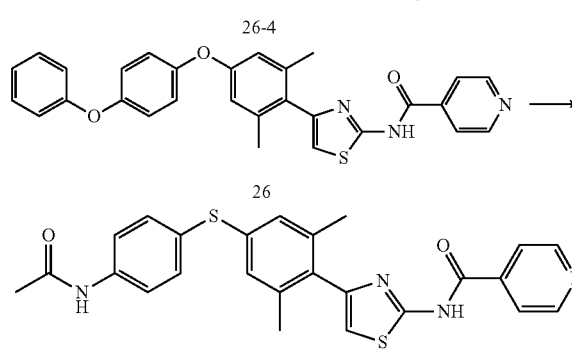

26

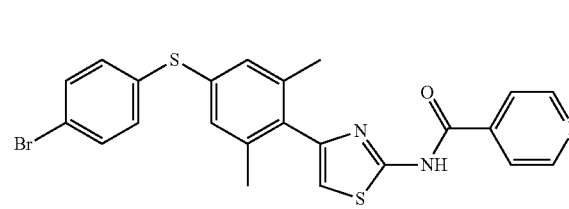

36

N-{4-(4-(4-Acetylaminophenylsulfanyl)-2,6-dimethylphenyl)thiazol-2-yl}isonicotinamide (36)

¹H NMR (500 MHz, CDCl₃) δ 10.11 (s, 1 H), 8.70 (bs, 2 H), 8.00 (s, 2 H), 7.64 (d, J=8.5 Hz, 2 H), 7.39 (d, J=8.0 Hz, 2 H), 7.16 (s, 1 H), 6.95 (s, 2 H), 2.05 (s, 6 H). ESI-MS: m/z 475.2 (M+H)⁺.

N-{4-(4-(4-Bromophenylsulfanyl)-2,6-dimethylphenyl)thiazol-2-yl}isonicotinamide (37)

37

N-{4-(4-(4-Bromophenylsulfanyl)-2,6-dimethylphenyl)thiazol-2-yl}isonicotinamide (37)

¹H NMR (500 MHz, CDCl₃) δ 8.76 (d, J=5.8 Hz, 2 H), 7.60 (d, J=5.8 Hz, 2 H), 7.44 (d, J=8.4 Hz, 2 H), 7.20 (d, J=8.4 Hz, 2 H), 6.83 (m, 3 H), 1.93 (s, 6 H). ESI-MS: m/z 496.3 (M+H)⁺.

N-{4-(4-(3-Chlorophenylsulfanyl)-2,6-dimethylphenyl)thiazol-2-yl}isonicotinamide (38)

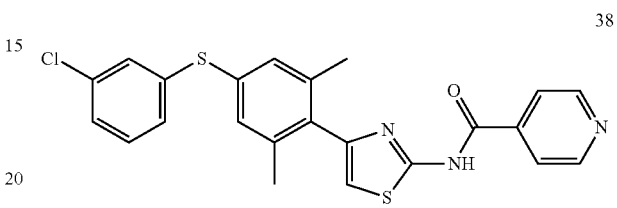

38

N-{4-(4-(3-Chlorophenylsulfanyl)-2,6-dimethylphenyl)thiazol-2-yl}isonicotinamide (38)

¹H NMR (500 MHz, CDCl₃) δ 8.78 (d, J=4.7 Hz, 2 H), 7.62 (d, J=4.3 Hz, 2 H), 7.22 (m, 4H), 6.93 (d, J=2.3 Hz, 2 H), 6.83 (s, 1 H), 1.96 (s, 6 H). ESI-MS: m/z 452.1 (M+H)⁺.

N-{4-(4-(2-Chlorophenylsulfanyl)-2,6-dimethylphenyl)thiazol-2-yl}isonicotinamide (39)

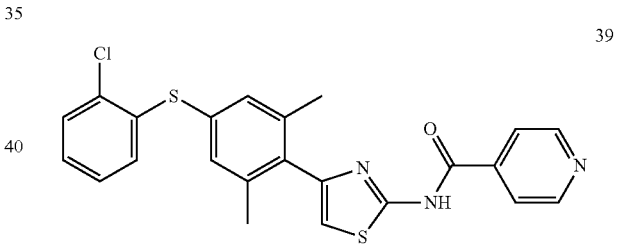

39

N-{4-(4-(2-Chlorophenylsulfanyl)-2,6-dimethylphenyl)thiazol-2-yl}isonicotinamide (39)

¹H NMR (500 MHz, CDCl₃) δ 8.75 (d, J=5.9 Hz, 2 H), 7.60 (d, J=6.0 Hz, 2 H), 7.22 (m, 4H), 6.91 (s, 2 H), 6.85 (s, 1 H), 1.95 (s, 6 H). ESI-MS: m/z 452.3 (M+H)⁺.

N-{4-(4-(4-Chlorophenylsulfanyl)-2,6-dimethylphenyl)thiazol-2-yl}isonicotinamide (40)

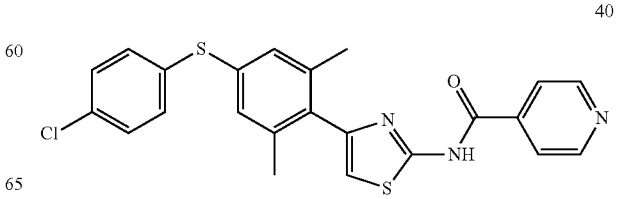

40

N-{4-(4-(4-Chlorophenylsulfanyl)-2,6-dimethylphenyl)thiazol-2-yl}isonicotinamide (40)

¹H NMR (500 MHz; CDCl₃) δ 8.68 (m, 2 H), 7.53 (d, J=5.7 Hz, 13.5 Hz, 2 H), 7.26 (d, J=8.7 Hz, 4.3 Hz, 4 H), 6.78 (d, J=11.9 Hz, 1 H), 6.66 (s, 2 H), 1.83 (s, 6 H). ESI-MS: m/z 452.3 (M+H)⁺.

N-(4-(2,6-Dimethyl-4-((1-methyl-1H-imidazol-2-yl)thio)phenyl)thiazol-2-yl)isonicotinamide (41)

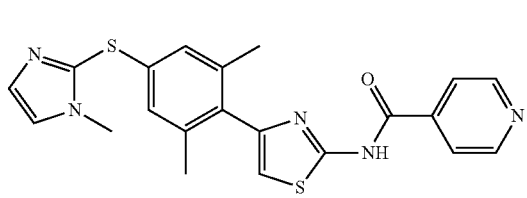

41

N-(4-(2,6-Dimethyl-4-((1-methyl-1H-imidazol-2-yl)thio)phenyl)thiazol-2-yl)isonicotinamide (41)

¹H NMR (500 MHz, CDCl₃) δ 8.78 (m, 2 H), 7.85 (m, 2 H), 7.19 (d, J=1.0 Hz, 1 H), 7.08 (d, J=1.0 Hz, 1 H), 6.75 (m, 3 H), 3.66 (s, 3 H), 1.95 (s, 6 H). ESI-MS: m/z 422.4 (M+H)⁺.

N-(4-(2,6-Dimethyl-4-((4-(N-(methylsulfonyl)methylsulfonamido)phenyl)thio)phenyl)thiazol-2-yl)isonicotinamide (42)

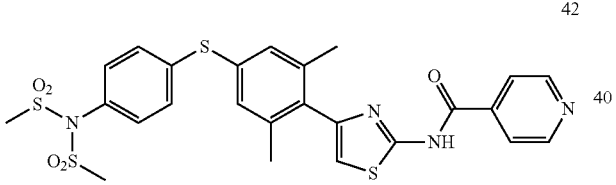

42

N-(4-(2,6-Dimethyl-4-((4-(N-(methylsulfonyl)methylsulfonamido)phenyl)thio)phenyl)thiazol-2-yl)isonicotinamide (42)

¹H NMR (500 MHz, CDCl₃) δ 8.86 (d, J=5.5 Hz, 2 H), 7.99 (d, J=5.5 Hz, 2 H), 7.25 (m, 6 H), 6.85 (s, 1 H), 3.39 (s, 6 H), 2.10 (s, 6 H). ESI-MS: m/z 589.0 (M+H)⁺.

N-(4-(2,6-Dimethyl-4-((4-(methylsulfonamido)phenyl)thio)phenyl)thiazol-2-yl)isonicotinamide (43)

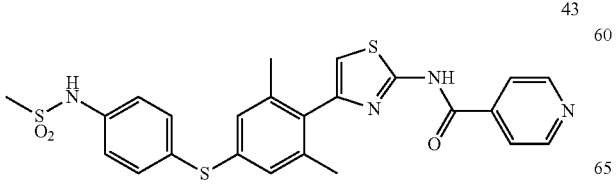

43

N-(4-(2,6-Dimethyl-4-((4-(methylsulfonamido)phenyl)thio)phenyl)thiazol-2-yl)isonicotinamide (43)

¹H NMR (500 MHz, CDCl₃) δ 8.90 (d, J=6.0 Hz, 2 H), 8.37 (d, J=6.5 Hz, 2 H), 7.39 (d, J=8.5 Hz, 2 H), 7.25 (d, J=8.5 Hz, 2 H), 6.99 (m, 3 H), 3.05 (s, 3 H), 2.08 (s, 6H). ESI-MS: m/z 511.1 (M+H)⁺.

N-(4-(4-Methoxy-2,6-dimethylphenyl)thiazol-2-yl)isonicotinamide (44)

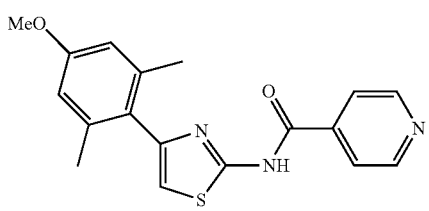

44

N-(4-(4-Methoxy-2,6-dimethylphenyl)thiazol-2-yl)isonicotinamide (44)

¹H NMR (500 MHz, CDCl₃) δ 8.67 (d, J=5.5 Hz, 2 H), 7.55 (d, J=6.0 Hz, 2 H), 6.77 (s, 1 H), 6.32 (s, 2 H), 3.73 (s, 3 H), 1.91 (s, 6 H); ESI-MS: m/z 340.0 (M+H)⁺.

1-(4-(4-Methoxy-2,6-dimethylphenyl)thiazol-2-yl)-3-(pyridin-4-yl)urea (45)

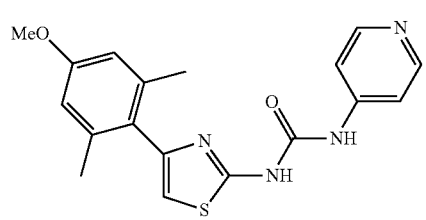

45

1-(4-(4-Methoxy-2,6-dimethylphenyl)thiazol-2-yl)-3-(pyridin-4-yl)urea (45)

¹H NMR (500 MHz, DMSO-d₆) δ 10.49 (bs, 1 H), 8.54 (d, J=6.5 Hz, 2 H), 7.94 (s, 2 H), 6.88 (s, 1 H), 6.74 (s, 2 H), 3.76 (s, 3 H), 2.10 (s, 6 H); ESI-MS: m/z 354.8 (M+H)⁺.

N-(4-(4-Isopropoxy-2,6-dimethylphenyl)thiazol-2-yl)isonicotinamide (46)

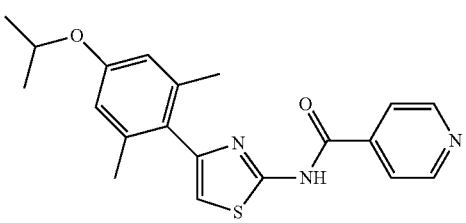

46

N-(4-(4-Isopropoxy-2,6-dimethylphenyl)thiazol-2-yl)isonicotinamide (46)

$^1$H NMR (500 MHz, CDCl$_3$) δ 8.67 (d, J=6.0 Hz, 2 H), 7.55 (d, J=6.0 Hz, 2 H), 6.77 (s, 1 H), 6.30 (s, 2 H), 4.43 (m, 1 H), 1.89 (s, 6 H), 1.31 (d, J=6.0 Hz, 6 H); ESI-MS: m/z 368.1 (M+H)$^+$.

N-(4-Mesitylthiazol-2-yl)-2-(pyridin-4-yl)acetamide (47)

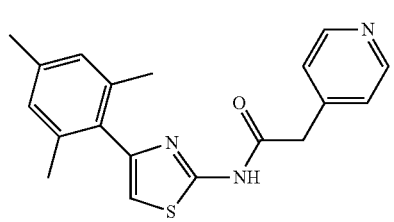

N-(4-Mesitylthiazol-2-yl)-2-(pyridin-4-yl)acetamide (47)

$^1$H NMR (500 MHz, DMSO-d$_6$) δ 8.52-8.53 (m, 2 H), 7.35-7.36 (m, 2 H), 6.99 (s, 1 H), 6.91 (s, 1 H), 3.84 (s, 1 H), 2.25 (s, 3 H), 2.02 (s, 6 H); ESI-MS: m/z 338.1 (M+H)$^+$.

N-(4-(4-(4-Methoxyphenoxy)-2,6-dimethylphenyl)thiazol-2-yl)isonicotinamide (48)

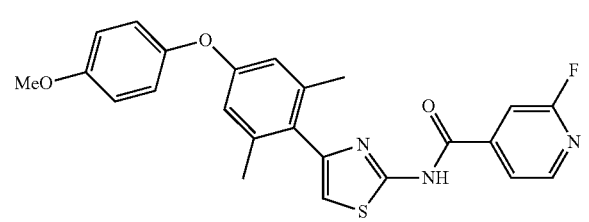

N-(4-(4-(4-Methoxyphenoxy)-2,6-dimethylphenyl)thiazol-2-yl)isonicotinamide (48)

$^1$H NMR (500 MHz, CDCl$_3$) δ 8.73 (m, 2 H), 7.62 (m, 2 H), 6.90-6.96 (m, 4 H), 6.80 (s, 1 H), 6.45 (s, 2 H), 3.83 (s, 3 H), 1.92 (s, 6 H); ESI-MS: m/z 431.7 (M+H)$^+$.

2-Fluoro-N-(4-(4-(4-methoxyphenoxy)-2,6-dimethylphenyl)thiazol-2-yl)isonicotinamide (49)

2-Fluoro-N-(4-(4-(4-methoxyphenoxy)-2,6-dimethylphenyl)thiazol-2-yl)isonicotinamide (49)

$^1$H-NMR (500 MHz, CDCl$_3$) δ 8.38-8.40 (m, 1 H), 7.66-7.67 (m, 2 H), 7.43 (s, 1 H), 6.98-7.00 (m, 2 H), 6.91-6.93 (m, 2 H), 6.84 (s, 1 H), 6.54 (s, 1 H), 3.83 (s, 3 H), 2.0 (s, 6 H); ESI-MS: m/z 450.0 (M+H)$^+$.

(E)-N-(4-Mesitylthiazol-2-yl)-3-(pyridin-3-yl)acrylamide (50)

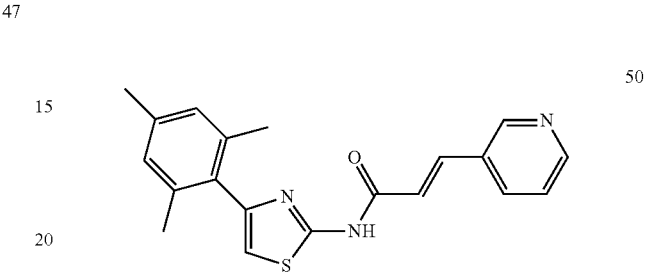

(E)-N-(4-Mesitylthiazol-2-yl)-3-(pyridin-3-yl)acrylamide (50)

$^1$H NMR (DMSO-d$_6$, 500 MHz) δ 12.48 (s, 1 H), 8.82-8.83 (m, 1 H), 8.60-8.61 (m, 1 H), 8.04-8.05 (m, 1 H), 7.76-7.79 (m, 1 H), 7.49-7.51 (m, 1 H), 7.00-7.03 (m, 2 H), 6.92 (s, 2 H), 2.26 (s, 3 H), 2.05 (s, 6 H); ESI-MS: m/z 350.7 (M+H)$^+$.

N-(4-(4-(4-Methoxybenzyl)-2,6-dimethylphenyl)thiazol-2-yl)isonicotinamide (51)

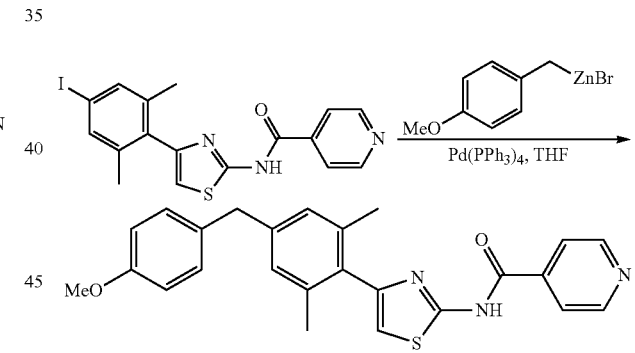

N-(4-(4-(4-Methoxybenzyl)-2,6-dimethylphenyl)thiazol-2-yl)isonicotinamide (51)

A THF solution of 4-methoxylbenzylzinc(II) bromide (4.0 mL, 2.0 mmol) was added to a degassed solution of N-(4-(4-iodo-2,6-dimethylphenyl)thiazol-2-yl)isonicotinamide (435 mg, 1.0 mmol) and tetrakistriphenylphosphine palladium (57.8 mg, 0.10 mmol) in THF (5.0 mL). The reaction mixture was heated at reflux for 16 h under N$_2$ then poured into saturated aqueous NaHCO$_3$. The mixture was extracted with ethyl acetate, washed with brine, dried MgSO$_4$, and concentrated under reduced pressure. The residue was purified by flash column chromatography on silica gel to give N-(4-(4-(4-methoxybenzyl)-2,6-dimethylphenyl)thiazol-2-yl)isonicotinamide: $^1$H NMR (500 MHz, CDCl$_3$) δ 8.69 (d, J=5.2 Hz, 2 H), 7.66 (d, J=4.9 Hz, 2 H), 7.11 (d, J=8.4 Hz, 2 H), 6.86 (d, 2 H), 6.80 (s, 1H), 6.75 (s, 2 H), 3.80 (s, 2 H), 3.78 (s, 2 H), 1.98 (s, 6 H); ESI-MS: m/z 399.9 (M+H)+.

N-(4-(4-(4-Bromophenylamino)-2,6-dimethylphenyl)thiazol-2-yl)isonicotinamide (52)

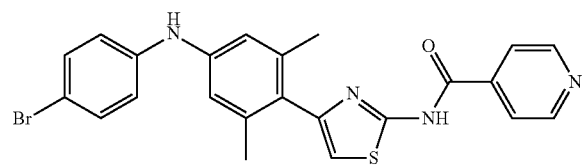

52

N-(4-(4-(4-Bromophenylamino)-2,6-dimethylphenyl)thiazol-2-yl)isonicotinamide (52)

¹H NMR (500 MHz, CDCl₃) δ 8.79 (d, J=4.5 Hz, 2 H), 7.85 (d, J=4.5 Hz, 2 H), 7.39 (d, J=8.6 Hz, 2 H), 6.97 (d, J=8.6 Hz, 2 H), 6.83 (s, 1 H), 2.05 (s, 6 H); ESI-MS: m/z 479.2 (M+H)+.

N-(4-(4-(4-methoxyphenoxy)-2,6-dimethylphenyl)thiazol-2-yl)isonicotinamide (53)

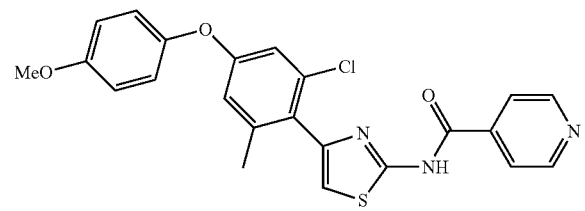

53

N-(4-(4-(4-methoxyphenoxy)-2,6-dimethylphenyl)thiazol-2-yl)isonicotinamide (53)

Yield: 24%; ¹H NMR (500 MHz, CDCl₃) δ 8.80 (s, 2 H), 7.70 (d, J=5.1 Hz, 2 H), 6.97 (m, 2 H), 6.92 (m, 3 H), 6.70 (d, J=2.4 Hz, 1 H), 6.61 (d, J=2.3, 1 H), 3.83 (s, 3 H), 2.02 (s, 3 H); ESI-MS: m/z 452.4 (M+H)+.

N-(4-Mesitylthiazol-2-yl)-2-morpholinoisonicotinamide (II-83)

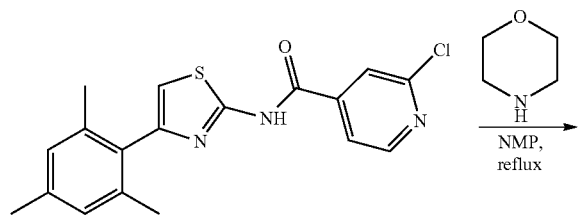

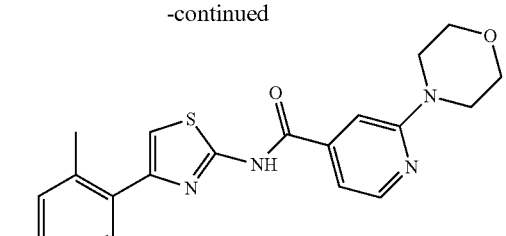

II-83

N-(4-Mesitylthiazol-2-yl)-2-morpholinoisonicotinamide (II-83)

A mixture of 2-chloro-N-(4-mesitylthiazol-2-yl)isonicotinamide (500.0 mg, 1.4 mmol, 1.0 equiv) and morpholine (1.5 mL, 16.8 mmol, 12 equiv) in methylpyrrolidone (15.0 mL) was stirred at 150° C. for 16 h. The mixture was poured into icy H₂O (20.0 mL), and the resultant solids were filtered to provide N-(4-mesitylthiazol-2-yl)-2-morpholinoisonicotinamide (358.6 mg, 0.90 mmol) as yellow solids in 63% yield: ¹H NMR (DMSO-d₆, 500 MHz) δ 8.30 (d, J=5.1 Hz, 2 H), 7.50 (s, 1 H), 7.22 (d, J=5.1 Hz, 2 H), 7.10 (s, 1H), 6.92 (s, 2 H), 3.70-3.73 (m, 4 H), 3.53-3.55 (m, 4 H), 2.26 (s, 3 H), 2.05 (s, 6H); ESI-MS: m/z 409.3 (M+H)+.

N-(4-Mesitylthiazol-2-yl)-2-(4-methylpiperazin-1-yl)isonicotinamide (II-84)

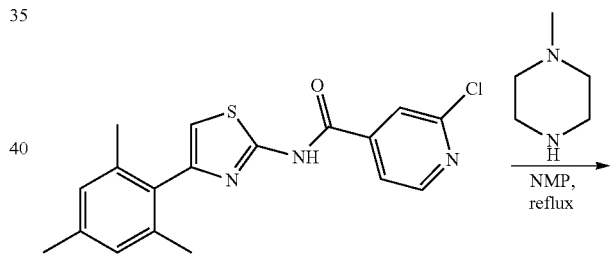

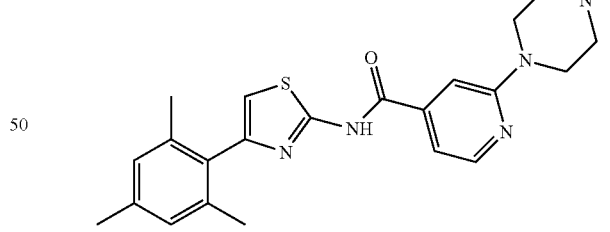

II-84

N-(4-Mesitylthiazol-2-yl)-2-(4-methylpiperazin-1-yl)isonicotinamide (II-84)

A mixture of 2-chloro-N-(4-mesitylthiazol-2-yl)isonicotinamide (300.0 mg, 0.8 mmol, 1.0 equiv) and 1-methylpiperazine (1.12 mL, 10.1 mmol, 12 equiv) in methylpyrrolidone (9.0 mL) was stirred at 150° C. for 16 h. The mixture was poured into icy H₂O (15.0 mL) and the resultant solids were filtered to provide N-(4-mesitylthiazol-2-yl)-2-(4-methylpiperazin-1-yl)isonicotinamide (95.6 mg, 0.20 mmol) as yellow solids in 27% yield: $^1$H NMR (CDCl$_3$, 500 MHz) δ 8.27 (d, J=5.1 Hz, 1 H), 7.12 (s, 1 H), 6.83-6.86 (m, 3 H), 6.78 (s, 1 H), 3.63-3.65 (m, 4 H), 2.35 (s, 3 H), 2.27 (s, 3 H), 2.04 (s, 6 H); ESI-MS: m/z 422.1 (M+H)$^+$.

N-(4-Mesitylthiazol-2-yl)-2-(piperidin-1-yl)isonicotinamide (II-91)

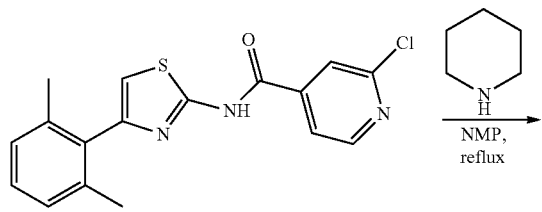

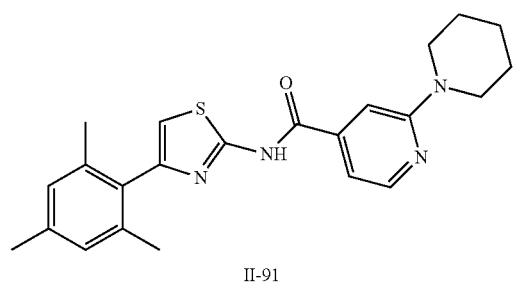

II-91

N-(4-Mesitylthiazol-2-yl)-2-(piperidin-1-yl)isonicotinamide (II-91)

A mixture of 2-chloro-N-(4-mesitylthiazol-2-yl)isonicotinamide (200 mg, 0.60 mmol, 1.0 equiv) and piperidine (0.70 mL, 6.7 mmol, 12 equiv) in methylpyrrolidone (6.0 mL) was stirred at 150° C. for 16 h. The mixture was poured into icy H$_2$O (10.0 mL) and the resultant solids were filtered. The solids were purified by column chromatography on silica gel (15% EtOAc in hexanes as eluant) to provide N-(4-mesitylthiazol-2-yl)-2-(piperidin-1-yl)isonicotinamide (87.2 mg, 0.20 mmol) as yellow solids in 38% yield: $^1$H NMR (CDCl$_3$, 500 MHz) δ 8.29 (d, J=5.1 Hz, 1 H), 7.15 (s, 1 H), 6.83-6.90 (m, 3 H), 6.79 (s, 1 H), 3.61-3.63 (m, 4 H), 2.31 (s, 3 H), 2.08 (s, 6 H), 1.57-1.67 (m, 6 H); ESI-MS: m/z 407.2 (M+H)$^+$.

2-(Dimethylamino)-N-(4-mesitylthiazol-2-yl)isonicotinamide (II-92)

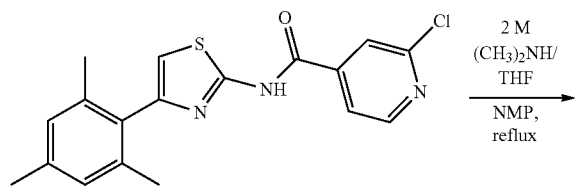

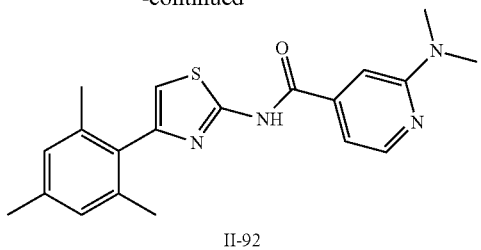

II-92

2-(Dimethylamino)-N-(4-mesitylthiazol-2-yl)isonicotinamide (II-92)

A mixture of 2-chloro-N-(4-mesitylthiazol-2-yl)isonicotinamide (200 mg, 0.60 mmol, 1.0 equiv), cesium carbonate (2.73 g, 0.6 mmol, 15 equiv) and 2.0 M dimethylamine in THF (3.4 mL, 6.7 mmol, 12 equiv) in DMF (6.0 mL) was heated at reflux for 16 h. The mixture was poured into icy H$_2$O (10.0 mL) and extracted with EtOAc. The organic layer was collected, dried over MgSO$_4$(s), and concentrated under reduced pressure. The residue was purified by column chromatography on silica gel (15% EtOAc in hexanes as eluant) to provide 2-(dimethylamino)-N-(4-mesityl-thiazol-2-yl)isonicotinamide (5.5 mg, 0.10 mmol) as yellow solids in 3.0% yield: $^1$H NMR (CDCl$_3$, 500 MHz) δ 8.32 (d, J=5.1 Hz, 1 H), 7.02 (s, 1 H), 6.92 (s, 2 H), 6.85 (d, J=5.1 Hz, 1 H), 6.80 (s, 1 H), 3.16 (s, 6 H), 2.31 (s, 3 H), 2.09 (s, 6 H); ESI-MS: m/z 367.1 (M+H)$^+$.

N-(4-(4-Benzyl-2,6-dimethylphenyl)thiazol-2-yl)isonicotinamide (II-118)

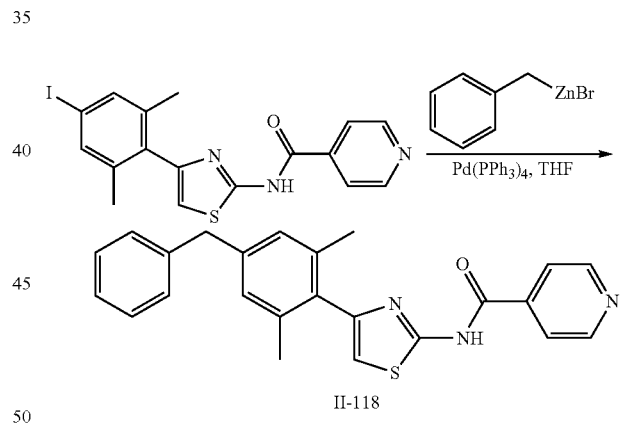

II-118

N-(4-(4-Benzyl-2,6-dimethylphenyl)thiazol-2-yl)isonicotinamide (II-118)

A THF solution of benzylzinc(II) bromide (4.0 mL, 2.0 mmol) was added to a degassed solution of N-(4-(4-iodo-2,6-dimethylphenyl)thiazol-2-yl)isonicotinamide (435 mg, 1.0 mmol) and tetrakistriphenylphosphine palladium (57.8 mg, 0.10 mmol) in THF (5.0 mL). The reaction mixture was heated at reflux for 16 h under N$_2$ and then poured into saturated aqueous NaHCO$_3$. The mixture was extracted with ethyl acetate, washed with brine, dried MgSO$_4$, and concentrated under reduced pressure. The residue was purified by flash column chromatography on silica gel to give N-(4-(4-benzyl-2,6-dimethylphenyl)thiazol-2-yl)isonicotinamide: $^1$H NMR (500 MHz, CDCl$_3$ δ 8.70 (d, J=4.9 Hz, 2 H), 7.67 (d, J=4.9 Hz, 2 H), 7.33 (d, J=8.6 Hz, 2 H), 7.10-7.26 (m, 3 H), 6.80 (s, 1 H), 6.24 (s, 1 H), 3.86 (s, 2 H), 2.04 (s, 6 H); ESI-MS: m/z 399.9 (M+H)+.

N-(4-(4-(4-Methoxybenzyl)-2,6-dimethylphenyl) thiazol-2-yl)isonicotinamide (II-119)

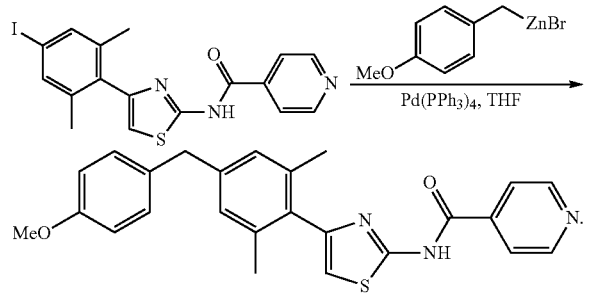

N-(4-(4-(4-Methoxybenzyl)-2,6-dimethylphenyl) thiazol-2-yl)isonicotinamide (II-119)

A THF solution of 4-methoxylbenzylzinc(II) bromide (4.0 mL, 2.0 mmol) was added to a degassed solution of N-(4-(4-iodo-2,6-dimethylphenyl)thiazol-2-yl)isonicotinamide (435 mg, 1.0 mmol) and tetrakistriphenylphosphine palladium (57.8 mg, 0.10 mmol) in THF (5.0 mL). The reaction mixture was heated at reflux for 16 h under $N_2$ then poured into saturated aqueous $NaHCO_3$. The mixture was extracted with ethyl acetate, washed with brine, dried $MgSO_4$, and concentrated under reduced pressure. The residue was purified by flash column chromatography on silica gel to give N-(4-(4-(4-methoxybenzyl)-2,6-dimethylphenyl)thiazol-2-yl)isonicotinamide: $^1$H NMR (500 MHz, $CDCl_3$) δ 8.69 (d, J=5.2 Hz, 2 H), 7.66 (d, J=4.9 Hz, 2 H), 7.11 (d, J=−8.4 Hz, 2 H), 6.86 (d, 2 H), 6.80 (s, 1 H), 6.75 (s, 2 H), 3.80 (s, 2 H), 3.78 (s, 2 H), 1.98 (s, 6 H); ESI-MS: m/z 399.9 (M+H)+.

2-Bromo-1-mesitylethanone

To a solution of 1-mesitylethanone (1.02 g, 6.27 mmol) in EtOAc (50 mL) was added copper(I) bromide ($CuBr_2$, 2.85 g, 12.8 mmol). The reaction mixture was heated at reflux for 90 min. The solution was allowed to cool down, and the resultant solids were filtered off and washed with EtOAc. The filtrate was concentrated under reduced pressure to give crude 2-bromo-1-mesitylethanone (1.67 g) as yellow oil: $^1$H NMR (500 MHz, $CDCl_3$) δ 6.87 (s, 2 H), 4.27 (s, 2 H), 2.31 (s, 3 H), 2.22 (s, 6 H).

4-Mesitylthiazol-2-amine

2-Bromo-1-mesitylethanone (2.43 g, 10.1 mmol) and thiourea (0.810 g, 10.6 mmol) were dissolved in 95% ethanol (20 mL). The reaction mixture was heated at reflux for 2.0 h. The solution was concentrated under reduced pressure, and the residue was recrystallized from 2-propanol to give the desired 4-mesitylthiazol-2-amine (2.36 g) as white solids: $^1$H NMR (500 MHz, $CD_3OD$) δ 7.00 (s, 2 H), 6.67 (s, 1 H), 2.31 (s, 3 H), 2.19 (s, 6 H).

4-(p-Tolyl)thiazol-2-amine

A mixture of 2-bromo-1-(p-tolyl)ethanone. (5.00 g, 23.5 mmol) and thiourea (1.97 g, 25.9 mmol) in 95% EtOH (33.5 mL) was heated at reflux for 60 min. The solution was concentrated and added with water (50 mL) and saturated aqueous $Na_2CO_3$ (1.05 mL). The resultant precipitate was filtered and washed with hot water. The solids were filtered and dried under vacuum to give 4-(p-tolyl)thiazol-2-amine (4.40 g) as white solids in 99% yield: $^1$H NMR (500 MHz, $CDCl_3$) δ 7.66 (d, J=8.0 Hz, 2 H), 7.18 (d, J=7.5 Hz, 2 H), 6.66 (s, 1 H), 5.25 (s, 2 H), 2.36 (s, 6 H).

5-Methyl-4-(p-tolyl)thiazol-2 amine. A mixture of 2-bromo-1-(p-tolyl)propan-1-one (6.88 g, 30.3 mmol) and thiourea (2.54 g, 33.4 mmol) in 95% EtOH (43 mL) was heated at reflux for 60 min. The solution was concentrated and added with water (100 mL) and saturated aqueous Na2CO3 (5.0 mL). The resultant precipitate was filtered and recrystallized in toluene. The solid were filtered and dried under vacuum to give 5-methyl-4-(p-tolyl) thiazol-2-amine (6.10 g) as white solids in 99% yield: $^1$H NMR (500 MHz, $CDCl_3$) δ 7.40 (d, J=8.0 Hz, 2 H), 7.23 (d, J=8.0 Hz, 2 H), 3.18 (s, 2 H), 2.37 (s, 3 H), 2.35 (s, 3 H).

2-Bromo-1-(4-methoxy-2,6-dimethylphenyl)ethanone

To a solution of 1-(4-methoxy-2,6-dimethylphenyl)ethanone (5.7 g, 32 mmol) in acetonitrile (64 mL) was added tetrabutylammoniumtribromide ($TBABr_3$, 15.4 g, 32.0 mmol). The reaction was stirred at room temperature for 80 min. The solution was concentrated under reduced pressure, added with water, and extracted with ethyl acetate. The organic layer was washed with brine, dried over anhydrous $MgSO_4$(s), and concentrated under reduced pressure to give 2-bromo-1-(4-methoxy-2,6-dimethylphenyl)ethanone (9.14 g), which was used directly for the next step without further purification.

4-(4-Methoxy-2,6-dimethylphenyl)thiazol-2-amine

A mixture of 2-bromo-1-(4-methoxy-2,6-dimethylphenyl) ethanone (8.65 g, 33.6 mmol) and thiourea (2.56 g, 33.6 mmol) in 95% EtOH (48 mL) was heated at reflux for 60 min. The solution was concentrated and added with water (50 mL) and saturated aqueous $Na_2CO_3$ (5.0 mL). The resultant precipitate was filtered and recrystallized in toluene (50 mL). The solids were filtered and dried under vacuum to give 4-(4-methoxy-2,6-dimethylphenyl)thiazol-2 amine (5.9 g) as white solids in 66% yield: $^1$H NMR (500 MHz, $CDCl_3$) δ 6.61 (s, 2 H), 627 (s, 1 H), 4.91 (s, 2 H), 3.79 (s, 3 H), 2.15 (s, 6 H).

2-Bromo-1-(2,4,6-trimethylpyridin-3-yl)ethanone hydrobromide

To a solution of 1-(2,4,6-trimethylpyridin-3-yl)ethanone (5.0 g, 30.6 mmol) in 33% HBr in acetic acid solution (10.2 mL) was added bromine (1.57 ml, 30.6 mmol) in acetic acid (10.2 mL) dropwisely. The reaction was stirred at 70° C. for 2.0 h. The solution was cooled to room temperature and washed with ether. The residue was dried under reduced pressure to give 2-bromo-1-(2,4,6-trimethylpyridin-3-yl) ethanone hydrobromide, which was used directly for the next step without further purification.

4-(2,4,6-Trimethylpyridin-3-yl)thiazol-2-amine

A mixture of 2-bromo-1-(2,4,6-trimethylpyridin-3-yl) ethanone hydrobromide (9.00 g, 27.9 mmol) and thiourea (2.12 g, 27.9 mmol) in 95% EtOH (39.8 mL) was heated at reflux for 120 min. The solution was concentrated and added with water (50 mL) and saturated aqueous $Na_2CO_3$ (5.0 mL). The resultant precipitate was filtered and recrystallized in toluene. The solids were filtered and dried under vacuum to give 4-(2,4,6-trimethylpyridin-3-yl)thiazol-2-amine (3.80 g) as yellow solids in 62% yield: $^1$H NMR (500 MHz, $CDCl_3$) δ 6.87 (s, 1 H), 6.31 (s, 1 H), 5.07 (s, 2 H), 2.49 (s, 3 H), 2.38 (s, 3 H), 2.14 (s, 3 H).

2-Bromo-1-(4-ethoxy-2,6-dimethylphenyl)ethanone

To a solution of 1-(4-ethoxy-2,6-dimethylphenyl)ethanone (4.00 g, 20.8 mmol) in acetonitrile (41.6 mL) was added tetrabutylammoniumtribromide ($TBABr_3$, 10.0 g, 20.8 mmol). The reaction was stirred at room temperature overnight. The solution was concentrated under reduced pressure, added with water, and extracted with ethyl acetate. The organic layer was washed with brine, dried over anhydrous $MgSO_4$(s), and concentrated under reduced pressure to give 2-bromo-1-(4-ethoxy-2,6-dimethylphenyl)ethanone (6.40 g), which was used directly for the next step without further purification.

4-(4-Ethoxy-2,6-dimethylphenyl)thiazol-2-amine

A mixture of 2-bromo-1-(4-ethoxy-2,6-dimethylphenyl) ethanone (6.35 g, 23.4 mmol) and thiourea (1.78 g, 23.4 mmol) in 95% EtOH (33.5 mL) was heated at reflux for 60 min. The solution was concentrated and added with water (50 mL) and saturated aqueous $Na_2CO_3$ (5.0 mL). The resultant precipitate was filtered and recrystallized in toluene (30 mL). The solids were filtered and dried under vacuum to give 4-(4-ethoxy-2,6-dimethylphenyl)thiazol-2-amine (4.18 g) as white solids in 72% yield: $^1$H NMR (500 MHz, DMSO-$d_6$) δ 6.84 (s, 2 H), 6.60 (s, 2 H), 6.27 (s, 1 H), 3.99 (q, J=6.5 Hz, 2 H), 2.06 (s, 6 H), 1.31 (t, J=6.95 Hz, 3 H).

4-Acetyl-3,5-dimethylphenyl trifluoromethanesulfonate

A solution of 1-(4-hydroxy-2,6-dimethylphenyl)ethanone (3.30 g, 20.1 mmol), triethylamine (4.07 g, 40.2 mmol) in anhydrous $CH_2Cl_2$ (20.1 mL) was cooled to 0° C., and then added with trifluoromethanesulfonic anhydride (4.0 mL, 24 mmol) dropwise. After the addition was completed, the reaction mixture was warmed to room temperature and stirred for 1.0 h. The solution was added with water and extracted with ethyl acetate (60 mL). The organic layer was separated, dried over $MgSO_4$(s), concentrated under reduced pressure. The residue was purified by flash chromatography on silica gel to give 4-acetyl-3,5-dimethylphenyl trifluoromethanesulfonate (5.0 g) as yellow oil in 85% yield.

1-(3,5-Dimethyl-(1,1'-biphenyl)-4-yl)ethanone

To a solution of 4-acetyl-3,5-dimethylphenyl trifluoromethanesulfonate (1.00 g, 3.38 mmol), KF (0.65 g, 11 mmol), and phenylboronic acid (0.49 g, 4.0 mmol) in THF (4.0 mL) was added tricyclohexylphosphine (11.4 mg, 0.04 mmol) and $Pd(OAc)_2$ (7.6 mg, 0.03 mmol). The reaction mixture was stirred at room temperature for 5.0 h under $N_2$. The reaction mixture was filtered through a small pad of diatomaceous earth, and the cake was washed with ethyl acetate (40 mL). The filtrate was concentrated under reduced pressure, and the residue was purified by flash chromatography on silica gel to give 1-(3,5-dimethyl-(1,1'-biphenyl)-4-yl)ethanone (0.68 g) in 90% yield: $^1$H NMR (500 MHz, $CDCl_3$) δ 7.56 (d, J=8.0 Hz, 2 H), 7.44 (t, J=7.0 Hz, 2 H), 7.35 (m, 1H), 7.25 (s, 2 H), 2.52 (s, 3H), 2.33 (s, 6 H).

2-Bromo-1-(3,5-dimethyl-(1,1'-biphenyl)-4-yl)ethanone

To a solution of 1-(3,5-dimethyl-(1,1'-biphenyl)-4-yl)ethanone (1.89 g, 8.43 mmol) in acetonitrile (16.9 mL) was added tetrabutylammoniumtribromide ($TBABr_3$, 4.07 g, 8.43 mmol). The reaction was stirred at room temperature overnight. The solution was concentrated under reduced pressure, added with water, and extracted with ethyl acetate. The organic layer was washed with brine, dried over anhydrous $MgSO_4$(s), and concentrated under reduced pressure to give 2-bromo-1-(3,5-dimethyl-(1,1'-biphenyl)-4-yl)ethanone (3.2 g), which was used directly for the next step without further purification.

4-(3,5-Dimethyl-(1,1'-biphenyl)-4-yl)thiazol-2-amine

A mixture of 2-bromo-1-(3,5-dimethyl-(1,1'-biphenyl)-4-yl)ethanone (2.56 g, 8.44 mmol) and thiourea (0.64 g, 8.44 mmol) in 95% EtOH (12.1 mL) was heated at reflux for 60 min. The solution was concentrated and added with water (50 mL) and saturated aqueous $Na_2CO_3$ (1.0 mL). The resultant precipitate was filtered and recrystallized in toluene (10 mL). The solids were filtered and dried under vacuum to give 4-(3,5-dimethyl-(1,1'-biphenyl)-4-yl)thiazol-2-amine (0.66 g) as yellow solids in 28% yield: $^1$H NMR (500 MHz, $CDCl_3$) δ 7.60 (d, J=1 Hz, 2 H), 7.43 (t, J=7.5 Hz, 1 H), 7.32 (m, 1 H), 7.25 (s, 2 H), 6.34 (s, 1 H), 5.03 (s, 2 H), 2.24 (s, 6 H).

1-(4-Chloro-2,6-dimethylphenyl)ethanone

Anhydrous copper(II) chloride (98.9 g, 0.74 mol) was mixed with tert-butyl nitrite (94.8 g, 0.83 mol) in acetonitrile (1.02 L). The solution was cooled to 0° C. and slowly added with 1-(4-amino-2,6 dimethylphenyl)ethanone (100 g, 0.61 mol) in a period of 5.0 min. After the addition was completed, the reaction mixture was warmed to room temperature, and was poured into an aqueous hydrochloric acid solution (20%, 1.0 L). The solution was extracted with EtOAc (800 mL), and the organic layer was separated, washed with $H_2O$ (1.0 L), dried over $MgSO_4$ (s), and concentrated under reduced pressure. The liquid was distilled to give 1-(4-chloro-2,6-dimethylphenyl)ethanone (85.0 g) as yellow oil in 76% yield: $^1$H NMR (500 MHz, $CDCl_3$) δ 7.02 (s, 2 H), 2.45 (s, 3 H), 2.22 (s, 6 H).

2-bromo-1-(4-chloro-2,6-dimethylphenyl)ethanone

To a solution of 1-(4-chloro-2,6-dimethylphenyl)ethanone (5.0 g, 27 mmol) in acetonitrile (54.8 mL) was added tetrabutylammoniumtribromide ($TBABr_3$, 13.2 g, 27.4 mmol). The reaction was stirred at room temperature overnight. The solution was concentrated under reduced pressure, added with water, and extracted with ethyl acetate. The organic layer was washed with brine, dried over anhydrous $MgSO_4$(s), and concentrated under reduced pressure to give 2-bromo-1-(4-chloro-2,6-dimethylphenyl)ethanone (7.2 g), which was used directly for the next step without further purification.

4-(4-Chloro-2,6-dimethylphenyl)thiazol-2-amine

A mixture of 2-bromo-1-(4-chloro-2,6-dimethylphenyl) ethanone (6.54 g, 25.0 mmol) and thiourea (1.90 g, 25.0 mmol) in 95% EtOH (35.7 mL) was heated at reflux for 60 min. The solution was concentrated and added with water (50 mL) followed by saturated aqueous $Na_2CO_3$ (4.0 mL). The resultant precipitate was filtered and recrystallized in toluene (30 mL). The solids were filtered and dried under vacuum to give 4-(4-chloro-2,6-dimethylphenyl)thiazol-2-amine (4.30 g) as white solids in 72% yield: $^1$H NMR (500 MHz, DMSO-d) δ 7.16 (s, 2 H), 6.43 (s, 1 H), 2.10 (s, 6 H).

N-(4-(2-Bromoacetyl)-3,5-dimethylphenyl)acetamide

To a solution of N-(4-acetyl-3,5-dimethylphenyl)acetamide (5.00 g, 24.4 mmol) in acetonitrile (48.7 mL) was added tetrabutylammoniumtribromide ($TBABr_3$, 11.7 g, 24.4 mmol). The reaction was stirred at room temperature overnight. The solution was concentrated under reduced pressure, added with water, and extracted with ethyl acetate. The organic layer was washed with brine, dried over anhydrous $MgSO_4$(s), and concentrated under reduced pressure to give N-(4-(2-bromoacetyl)-3,5-dimethylphenyl)acetamide (7.00 g), which was used directly for the next step without further purification.

N-(4-(2-aminothiazol-4-yl)-3,5-dimethylphenyl) acetamide

A mixture of N-(4-(2-bromoacetyl)-3,5-dimethylphenyl) acetamide (7.34 g, 25.9 g mmol) and thiourea (1.97 g, 25.9 mmol) in 95% EtOH (36.9 mL) was heated at reflux for 120 min. The solution was concentrated and added with water (100 mL) and saturated aqueous $Na_2CO_3$ (5.0 mL). The resultant precipitate was filtered and recrystallized in toluene (50 mL). The solids were filtered and dried under vacuum to give N-(4-(2-aminothiazol-4-yl)-3,5-dimethylphenyl)acetamide (5.83 g) as yellow solids in 86% yield: $^1$H NMR (500 MHz, DMSO-$d_6$) δ 9.80 (s, 1 H), 7.26 (s, 2 H), 6.90 (s, 2 H), 6.30 (s, 1 H), 2.06 (s, 6 H), 2.02 (s, 3 H).

2-Bromo-1-(2,4,6-triisopropylphenyl)ethanone

To a solution of 1 (2,4,6-triisopropylphenyl)ethanone (10.0 g, 65.3 mmol) in acetonitrile (81 mL) was added tetrabutylammoniumtribromide ($TBABr_3$, 19.6 g, 40.6 mmol). The reaction was stirred at room temperature for 3.0 h. The solution was concentrated under reduced pressure, added with water, and extracted with ethyl acetate. The organic layer was washed with brine, dried over anhydrous MgSO4(s), and concentrated under reduced pressure to give 2-bromo-1-(2,4,6-triisopropylphenyl)ethanone (13.2 g), which was used directly for the next step without further purification.

4-(2,4,6-Triisopropylphenyl)thiazol-2-amine

A mixture of 2-bromo-1-(2,4,6-triisopropylphenyl)ethanone (13.9 g, 42.7 mmol) and thiourea (3.24 g, 42.6 mmol) in 95% EtOH (60.9 mL) was heated at reflux overnight. The solution was concentrated and added with water (100 mL), saturated aqueous Na2CO3 (10 mL), and extracted with ethyl acetate. The organic layer was washed with brine, dried over anhydrous $MgSO_4$(s), and concentrated under reduced pressure, which was purified by column chromatography on silica gel (33% EtOAc in hexanes as eluant) to give 4-(2,4,6-triisopropylphenyl)thiazol-2-amine (3.28 g) as white solids in 25% yield: $^1$H NMR (500 MHz, $CDCl_3$) δ 7.03 (s, 2 H), 6.22 (s, 1 H), 4.75 (s, 2 H), 2.89 (m, 1 H), 2.68 (m, 2 H), 1.27-1.14 (m, 18H).

1-(2,6-Dimethyl-4-phenoxyphenyl)ethanone

To a solution of 1-(4-chloro-2,6-dimethylphenyl)ethanone (4.50 g, 24.6 mmol), $K_3PO_4$ (10.5 g, 49.3 mmol), and phenol (2.78 g, 29.5 mmol) in toluene (49.3 mL) was added 2-(di-tert-butylphosphino)biphenyl (221 mg, 0.74 mmol) and $Pd(OAc)_2$ (233 mg, 1.04 mmol). The reaction was heated at 100° C. for 2.0 h under $N_2$. The solution was cooled to room temperature and filtered through a small pad of diatomaceous earth. The cake was washed with ethyl acetate (50 mL) and the combined filtrate was concentrated under reduced pressure. The residue was purified by flash column chromatography on silica gel to give 1-(2,6-dimethyl-4-phenoxyphenyl) ethanone as a yellow oil in 68% yield: $^1$H NMR (500 MHz, $CDCl_3$) δ 7.35 (t, J=8.0 Hz, 2 H), 7.12 (t, J=7.5 Hz, 1 H), 7.00 (d, J=7.5 Hz, 2 H), 6.65 (s, 2 H), 2.48 (s, 3H), 2.22 (s, 6 H).

2-Bromo-1-(2,6-dimethyl-4-phenoxyphenyl)ethanone

To a solution of 1-(2,6-dimethyl-4-phenoxyphenyl)ethanone (3.60 g, 15.0 mmol) in acetonitrile (30 mL) was added tetrabutylammoniumtribromide ($TBABr_3$, 7.95 g, 15.0 mmol). The reaction was stirred at room temperature overnight. The solution was concentrated under reduced pressure, added with water, and extracted with ethyl acetate. The organic layer was washed with brine, dried over anhydrous $MgSO_4$(s), and concentrated under reduced pressure to give 2-bromo-1-(2,6-dimethyl-4-phenoxyphenyl)ethanone (4.8 g), which was used directly for the next step without further purification.

4-(2,6-Dimethyl-4-phenoxyphenyl)thiazol-2-amine

A mixture of 2-bromo-1-(2,6-dimethyl-4-phenoxyphenyl) ethanone (5.18 g, 16.2 mmol) and thiourea (1.24 g. 16.3 mmol) in 95% EtOH (23.2 mL) was heated at reflux for 60 min. The solution was concentrated and added with water (50 mL) and saturated aqueous $Na_2CO_3$ (5.0 mL). The resultant precipitate was filtered and recrystallized in toluene (30 mL). The solids were filtered and dried under vacuum to give 4-(2,6-dimethyl-4-phenoxyphenyl)thiazol-2-amine (2.84 g) as yellow solids in 59% yield: $^1$H NMR (500 MHz, $CDCl_3$) δ 7.33 (t, J=7.5 Hz, 2 H), 7.26 (t, J=7.5 Hz, 1 H), 7.10 (d, J=7.3, 2 H), 6.72 (s, 2 H), 6.30 (s, 1 H), 5.18 (s, 2 H), 2.14 (s, 6 H).

2-Bromo-1-(4-isopropoxy-2,6-dimethylphenyl)ethanone

To a solution of 1-(4-isopropoxy-2,6-dimethylphenyl) ethanone (4.3 g, 20.9 mmol) in acetonitrile (41.7 mL) was added tetrabutylammoniumtribromide ($TBABr_3$, 11.1 g, 22.9 mmol). The reaction was stirred at room temperature overnight. The solution was concentrated under reduced pressure, added with water, and extracted with ethyl acetate. The organic layer was washed with brine, dried over anhydrous MgSO4(s), and concentrated under reduced pressure to give 2-bromo-1-(4-isopropoxy-2,6-dimethylphenyl)ethanone (5.9 g), which was used directly for the next step without further purification.

4-(4-Isopropoxy-2,6-dimethylphenyl)thiazol-2-amine

A mixture of 2-bromo-1-(4-isopropoxy-2,6-dimethylphenyl)ethanone (5.18 g, 18.2 mmol) and thiourea (1.38 g, 18.2 mmol) in 95% EtOH (26 mL) was heated at reflux for 60 min. The solution was concentrated and added with water (50 mL) and saturated aqueous $Na_2CO_3$ (5.0 mL). The resultant precipitate was filtered and recrystallized in toluene (30 mL). The solids were filtered and dried under vacuum to give 4-(4-isopropoxy-2,6 dimethylphenyl)thiazol-2-amine (3.44 g) as yellow solids in 72.2% yield: $^1$H NMR (500 MHz, CDCl$_3$) δ 6.60 (s, 2 H), 6.26 (s, 1 H), 4.97 (s, 2 H), 4.54 (m, 1 H), 2.13 (s, 6 H), 1.32 (d, J=6.1 Hz, 6 H).

2-Bromo-1-(4-(cyclopentyloxy)-2,6-dimethylphenyl)ethanone

To a solution of 1-(4-(cyclopentyloxy)-2,6-dimethylphenyl)ethanone (4.60 g, 19.8 mmol) in acetonitrile (39.6 mL) was added tetrabutylammoniumtribromide (TBABr$_3$, 10.5 g, 21.8 mmol). The reaction was stirred at room temperature overnight. The solution was concentrated under reduced pressure, added with water, and extracted with ethyl acetate. The organic layer was washed with brine, dried over anhydrous MgSO$_4$(s), and concentrated under reduced pressure to give 2-bromo-1-(4-(cyclopentyloxy)-2,6-dimethylphenyl)ethanone (6.2 g), which was used directly for the next step without further purification.

4-(4-(Cyclopentyloxy)-2,6-dimethylphenyl)thiazol-2-amine

A mixture of 2-bromo-1-(4-(cyclopentyloxy)-2,6-dimethylphenyl)ethanone (6.16 g, 19.8 mmol) and thiourea (1.51 g, 19.8 mmol) in 95% EtOH (28.3 mL) was heated at reflux for 90 min. The solution was concentrated and added with water (50 mL) and saturated aqueous Na$_2$CO$_3$ (5.0 mL). The resultant precipitate was filtered and recrystallized in toluene (30 mL). The solids were filtered and dried under vacuum to give 4-(4-(cyclopentyloxy)-2,6-dimethylphenyl)thiazol-2-amine (4.2 g) as white solids in 73.7% yield: $^1$H NMR (500 MHz, CDCl$_3$) δ 6.58 (s, 2 H), 6.24 (s, 1 H), 4.75 (m, 1 H), 2.13 (s, 6 H), 1.88-1.78 (m, 6 H), 1.62-1.59 (m, 2 H).

1-(4-(4-Methoxyphenoxy)-2,6-dimethylphenyl)ethanone

To a solution of 1-(4-chloro-2,6-dimethylphenyl)ethanone (10.0 g, 54.8 mmol), K$_3$PO$_4$ (23.2 g, 110 mmol) 4-methoxyphenol (8.16 g, 65.7 mmol) in toluene (78.2 mL), was added 2-di-tert-Butylphosphino-2',4',6'-triisopropylbiphenyl (349 mg, 0.82 mmol), Pd(OAc)$_2$ (259 mg, 1.15 mmol). The reaction was heated at 100° C. for 5.0 h under N$_2$. The solution was cooled to room temperature and filtered through a small pad of diatomaceous earth. The cake was washed with ethyl acetate (50 mL) and combined filtrate was concentrated under reduced pressure. The residue was recrystallized in MeOH to give 1-(4-(4-methoxyphenoxy)-2,6-dimethylphenyl)ethanone (11.1 g) as white solids in 75.0%: $^1$H NMR (500 MHz, CDCl$_3$) δ 6.96 (m, 2 H), 6.88 (m, 2 H), 6.57 (s, 2 H), 3.81 (s, 3 H), 2.46 (s, 3 H), 2.20 (s, 6 H).

2-Bromo-1-(4-(4-methoxyphenoxy)-2,6-dimethylphenyl)ethanone

To a solution of 1-(4-(4-methoxyphenoxy)-2,6-dimethylphenyl)ethanone (3.80 g, 14.1 mmol) in acetonitrile (28.1 mL) was added tetrabutylammoniumtribromide (TBABr$_3$, 7.46 g, 15.5 mmol). The reaction was stirred at room temperature overnight. The solution was concentrated under reduced pressure, added with water, and extracted with ethyl acetate. The organic layer was washed with brine, dried over anhydrous MgSO$_4$(s), and concentrated under reduced pressure to give 2-bromo-1-(4-(4-methoxyphenoxy)-2,6-dimethylphenyl)ethanone (5.25 g), which was used directly for the next-step without further purification.

4-(4-(4-Methoxyphenoxy)-2,6-dimethylphenyl)thiazol-2-amine

A mixture of 2-bromo-1-(4-(4-methoxyphenoxy)-2,6-dimethylphenyl)ethanone (4.90 g, 14.0 mmol) and thiourea (1.07 g, 14.1 mmol) in 95% EtOH (20.0 mL) was heated at reflux for 100 min. The solution was concentrated and added with water (100 mL) and saturated aqueous Na$_2$CO$_3$ (5.0 mL). The resultant precipitate was filtered and recrystallized in toluene. The solids were filtered and dried under vacuum to give 4-(4-(4-methoxyphenoxy)-2,6-dimethylphenyl)thiazol-2-amine (3.10 g) as yellow solids in 68% yield: $^1$H NMR (500 MHz, CDCl$_3$) 6.98 (m, 2 H), 6.88 (m, 2 H), 6.64 (s, 2 H), 6.27 (s, 1 H), 5.40 (s, 2 H), 3.81 (s, 3 H), 2.13 (s, 6 H).

1-(4-(4-Fluorophenoxy)-2,6-dimethylphenyl)ethanone

To a solution of 1-(4-chloro-2,6-dimethylphenyl)ethanone (4.50 g, 24.6 mmol), K3PO4 (10.5 g, 49.3 mmol), 4-fluorophenol (3.31 g, 29.5 mmol) in toluene (49.3 mL), was added 2-di-tert-butylphosphino-2',4',6'-triisopropylbiphenyl (314 mg, 0.74 mmol), Pd(OAc)$_2$ (233 mg, 1.04 mmol). The reaction was heated at 100° C. overnight under N$_2$. The solution was cooled to room temperature and filtered through a small pad of diatomaceous earth. The cake was washed with ethyl acetate (100 mL), and combined filtrate was concentrated under reduced pressure. The residue was purified by flash column chromatography on silica gel to give 1-(4-(4-Fluorophenoxy)-2,6-dimethylphenyl)ethanone (4.40 g) as yellow oil in 68% yield: $^1$H NMR (500 MHz, CDCl$_3$) δ 7.03 (m, 2 H), 6.98 (m, 2 H), 6.60 (s, 2 H), 2.47 (s, 3 H), 2.22 (s, 6 H).

2-Bromo-1-(4-(4-fluorophenoxy)-2,6-dimethylphenyl)ethanone

To a solution of 1-(4-(4-fluorophenoxy)-2,6-dimethylphenyl)ethanone (4.40 g, 17.0 mmol) in acetonitrile (34.1 mL) was added tetrabutylammoniumtribromide (TBABr$_3$, 9.04 g, 18.8 mmol). The reaction was stirred at room temperature overnight. The solution was concentrated under reduced pressure, added with water, and extracted with ethyl acetate. The organic layer was washed with brine, dried over anhydrous MgSO$_4$(s), and concentrated under reduced pressure to give 2-bromo-1-(4-(4-fluorophenoxy)-2,6-dimethylphenyl)ethanone (5.8 g), which was used directly for the next step without further purification.

4-(4-(4-Fluorophenoxy)-2,6-dimethylphenyl)thiazol-2-amine

A mixture of 2-bromo-1-(4-(4-fluorophenoxy)-2,6-dimethylphenyl)ethanone (5.74 g, 17.0 mmol) and thiourea (1.30 g, 17.1 mmol) in 95% EtOH (24.3 mL) was heated at reflux for 60 min. The solution was concentrated and added with water (100 mL) and saturated aqueous Na$_2$CO$_3$ (5.0 mL). The resultant precipitate was filtered and recrystallized in toluene. The solids were filtered and dried under vacuum to give 4-(4-(4-fluorophenoxy)-2,6-dimethylphenyl)thiazol-2-amine (4.50 g) as yellow solids in 84% yield: $^1$H NMR (500 MHz, CDCl$_3$) δ 7.05-6.97 (m, 4 H), 6.66 (s, 2 H), 6.28 (s, 1H), 5.95 (s, 2 H), 2.14 (s, 6H).

2-Bromo-1-(4-isobutoxy-2,6-dimethylphenyl)ethanone

To a solution of 1-(4-isobutoxy-2,6-dimethylphenyl)ethanone (4.3 g, 19.5 mmol) in acetonitrile (39 mL) was added tetrabutylammoniumtribromide (TBABr$_3$, 9.41 g, 19.5 mmol). The reaction was stirred at room temperature overnight. The solution was concentrated under reduced pressure, added with water, and extracted with ethyl acetate. The organic layer was washed with brine, dried over anhydrous MgSO$_4$(s), and concentrated under reduced pressure to give 1-(4-isobutoxy-2,6-dimethylphenyl)ethanone (6.1 g), which was used directly for the next step without further purification.

4-(4-Isobutoxy-2,6-dimethylphenyl)thiazol-2-amine

A mixture of 2-bromo-1-(4-isobutoxy-2,6-dimethylphenyl)ethanone (5.84 g, 19.5 mmol) and thiourea (1.49 g, 19.6 mmol) in 95% EtOH (28 mL) was heated at reflux for 60 min. The solution was concentrated and added with water (50 mL) and saturated aqueous Na$_2$CO$_3$ (5.0 mL). The resultant precipitate was filtered and recrystallized in toluene (30 mL). The solids were filtered and dried under vacuum to give 4-(4-isobutoxy-2,6-dimethylphenyl)thiazol-2-amine (4.4 g) as white solids in 82% yield: $^1$H NMR (500 MHz, CDCl$_3$) δ 6.61 (s, 2 H), 6.24 (s, 1H), 3.70 (d, J=6.5 Hz, 2 H), 2.15 (s, 6 H), 2.07 (m, 1H), 1.01 (d, J=6.7 Hz, 6 H).

1-(4-(Benzo(d)(1,3)dioxol-5-yloxy)-2,6-dimethylphenyl)ethanone

To a solution of 1-(4-chloro-2,6-dimethylphenyl)ethanone (5.0 g, 27.4 mmol), K$_3$PO$_4$ (11.6 g, 54.7 mmol), sesamol (4.54 g, 32.9 mmol) in toluene (54.8 mL), was added 2-di-tert-butylphosphino-2',4',6'-triisopropylbiphenyl (349 mg, 0.82 mmol), Pd(OAc)$_2$ (259 mg, 1.15 mmol). The reaction was heated at 100° C. overnight under N$_2$. The solution was cooled to room temperature and filtered through a small pad of diatomaceous earth. The cake was washed with ethyl acetate (50 mL) and combined filtrate was concentrated under reduced pressure. The residue was recrystallized in MeOH to give 1-(4-(benzo(d)(1,3)dioxol-5-yloxy)-2,6-dimethylphenyl)ethanone (4.80 g) as white solids in 62% yield: $^1$H NMR (500 MHz, CDCl$_3$) δ 6.77 (d, J=8.5 Hz, 1H), 6.59 (s, 2 H), 6.56 (s, 1 H), 6.48 (m, 1 H), 5.98 (s, 2 H), 2.46 (s, 3 H), 2.21 (s, 6 H).

1-(4-(Benzo(d)(1,3)dioxol-5-yloxy)-2,6-dimethylphenyl)-2-bromoethanone

To a solution of 1-(4-(benzo(d)(1,3)dioxol-5-yloxy)-2,6-dimethylphenyl)ethanone (4.80 g, 16.9 mmol) in acetonitrile (33.8 mL) was added tetrabutylammoniumtribromide (TBABr$_3$, 8.14 g, 16.9 mmol). The reaction was stirred at room temperature overnight. The solution was concentrated under reduced pressure, added with water, and extracted with ethyl acetate. The organic layer was washed with brine, dried over anhydrous MgSO$_4$(s), and concentrated under reduced pressure to give 1-(4-(benzo(d)(1,3)dioxol-5-yloxy)-2,6-dimethylphenyl)-2-bromoethanone (6.70 g), which was used directly for the next step without further purification.

4-(4-(Benzo(d)(1,3)dioxol-5-yloxy)-2,6-dimethylphenyl)thiazol-2-amine

A mixture of 1-(4-(benzo(d)(1,3)dioxol-5-yloxy)-2,6-dimethylphenyl)-2-bromoethanone (6.13 g, 16.9 mmol) and thiourea (1.29 g, 16.9 mmol) in 95% EtOH (24.1 mL) was heated at reflux for 90 min. The solution was concentrated and added with water (100 mL) and saturated aqueous Na$_2$CO$_3$ (5.0 mL). The resultant precipitate was filtered and recrystallized in toluene. The solids were filtered and dried under vacuum to give 4-(4-(benzo(d)(1,3)dioxol-5-yloxy)-2,6-dimethylphenyl)thiazol-2-amine (5.50 g) as yellow solids 20 in 96% yield: $^1$H NMR (500 MHz, CDCl$_3$) δ 6.75 (d, J=8.5 Hz, 1 H), 6.66 (s, 2 H), 6.58 (m, 1 H), 6.49 (m, 1 H), 6.28 (s, 1 H), 5.98 (s, 2 H), 5.05 (s, 2 H), 2.13 (s, 6 H).

1-(4-(3,5-Dimethylphenoxy)-2,6-dimethylphenyl)ethanone

To a solution of 1-(4-chloro-2,6-dimethylphenyl)ethanone (5.0 g, 27.4 mmol), K$_3$PO$_4$ (11.6 g, 54.7 mmol), 3,5-dimethylphenol (4.01 g, 32.8 mmol) in toluene (54.8 mL), was added 2-di-tert-butylphosphino-2',4',6'-triisopropylbiphenyl (349 mg, 0.82 mmol), Pd(OAc)$_2$ (259 mg, 1.15 mmol). The reaction was heated at 100° C. overnight under N$_2$. The solution was cooled to room temperature and filtered through a small pad of diatomaceous earth. The cake was washed with ethyl acetate (50 mL) and combined filtrate was concentrated under reduced pressure. The residue was purified by flash column chromatography on silica gel to give 1-(4-(3,5-dimethylphenoxy)-2,6-dimethylphenyl)ethanone (6.3 g) as yellow solids in 86% yield: $^1$H NMR (500 MHz, CDCl$_3$) δ 6.76 (s, 1 H), 6.63 (s, 2 H), 6.62 (s, 2 H), 2.48 (s, 3 H), 2.29 (s, 6 H), 2.22 (s, 6 H).

2-Bromo-1-(4-(3,5-dimethylphenoxy)-2,6-dimethylphenyl)ethanone

To a solution of 1-(4-(3,5-dimethylphenoxy)-2,6-dimethylphenyl)ethanone (6.30 g, 23.5 mmol) in acetonitrile (47.0 mL) was added tetrabutylammoniumtribromide (TBABr$_3$, 11.9 g, 24.7 mmol). The reaction was stirred at room temperature overnight. The solution was concentrated under reduced pressure, added with water, and extracted with ethyl acetate. The organic layer was washed with brine, dried over anhydrous MgSO$_4$(s), and concentrated under reduced pressure to give 2-bromo-1-(4-(3,5-dimethylphenoxy)-2,6-dimethylphenyl)ethanone (8.3 g), which was used directly for the next step without further purification.

4-(4-(3,5-Dimethylphenoxy)-2,6-dimethylphenyl)thiazol-2-amine

A mixture of 2-bromo-1-(4-(3,5-dimethylphenoxy)-2,6-dimethylphenyl)ethanone (8.15 g, 23.5 mmol) and thiourea (1.79 g, 23.5 mmol) in 95% EtOH (33.5 mL) was heated at reflux for 120 min. The solution was concentrated and added with water (100 mL) and saturated aqueous Na$_2$CO$_3$ (5.0 mL). The resultant precipitate was filtered and recrystallized in toluene. The solids were filtered and dried under vacuum to give 4-(4-(3,5 dimethylphenoxy)-2,6-dimethylphenyl)thiazol-2-amine (4.50 g) as yellow solids in 59% yield: $^1$H NMR (500 MHz, CDCl$_3$) δ 6.76 (s, 1H), 6.68 (s, 2 H), 6.64 (s, 2 H), 6.26 (s, 1 H), 2.29 (s, 6 H), 2.16 (s, 6 H).

1-(4-(3-Methoxyphenoxy)-2,6-dimethylphenyl)ethanone

To a solution of 1-(4-chloro-2,6-dimethylphenyl)ethanone (5.00 g, 27.4 mmol), K3PO4 (11.6 g, 54.7 mmol), 3-methoxyphenol (4.08 g, 32.9 mmol) in toluene (54.8 mL) was added 2-di-tert-butylphosphino-2',4',6'-triisopropylbiphenyl (349 mg, 0.82 mmol), Pd(OAc)$_2$ (259 mg, 1.15 mmol). The reaction was heated at 100° C. overnight under N$_2$. The solution was cooled to room temperature and filtered through a small pad of diatomaceous earth. The cake was washed with ethyl acetate (50 mL) and combined filtrate was concentrated under reduced pressure. The residue was purified by flash column chromatography on silica gel to give 1-(4-(3-methoxyphenoxy)-2,6-dimethylphenyl)ethanone (5.4 g) as yellow oil in 73% yield: $^1$H NMR (500 MHz, CDCl$_3$) δ 7.24 (m, 1H), 6.68-6.66 (m, 3 H), 6.57-6.56 (m, 2 H), 3.79 (s, 3 H), 2.48 (s, 3 H), 2.22 (s, 6 H).

2-Bromo-1-(4-(3-methoxyphenoxy)-2,6-dimethylphenyl)ethanone

To a solution of 1-(4-(3-methoxyphenoxy)-2,6-dimethylphenyl)ethanone (5.40 g, 20.0 mmol) in acetonitrile (40.0 mL) was added tetrabutylammoniumtribromide (TBABr$_3$, 10.1 g, 21.0 mmol). The reaction was stirred at room temperature overnight. The solution was concentrated under reduced pressure, added with water, and extracted with ethyl acetate. The organic layer was washed with brine, dried over anhydrous MgSO$_4$(s), and concentrated under reduced pressure to give 2-bromo-1-(4-(3-methoxyphenoxy)-2,6-dimethylphenyl)ethanone (7.00 g), which was used directly for the next step without further purification.

4-(4-(3-Methoxyphenoxy)-2,6-dimethylphenyl)thiazol-2-amine

A mixture of 2-bromo-1-(4-(3-methoxyphenoxy)-2,6-dimethylphenyl)ethanone (6.98 g, 20.0 mmol) and thiourea (1.52 g, 20.0 mmol) in 95% EtOH (28.5 mL) was heated at reflux for 5.0 h. The solution was concentrated and added with water (50 mL) and saturated aqueous Na$_2$CO$_3$ (1.0 mL), and extracted with ethyl acetate (100 ml). The organic layer was washed with brine, dried over anhydrous MgSO$_4$(s), and concentrated under reduced pressure to give 4-(4-(3-methoxyphenoxy)-2,6-dimethylphenyl)thiazol-2-amine (4.30 g) as deep-brown oil, which was used directly for the next step without further purification.

1-(2,6-Dimethyl-4-(4-(trifluoromethyl)phenoxy)phenyl)ethanone

To a solution of 1-chloro-4-(trifluoromethyl)benzene (6.60 g, 36.6 mmol), K$_3$PO$_4$ (12.9 g, 60.9 mmol), 1-(4-hydroxy-2,6-dimethylphenyl)ethanone (5.00 g, 30.5 mmol) in toluene (60.9 mL) was added 2-di-tert-butylphosphino-2',4',6'-triisopropylbiphenyl (388 mg, 0.91 mmol) and Pd(OAc)$_2$ (288 mg, 1.28 mmol). The reaction was heated at 100° C. for 120 min under N$_2$. The solution was cooled to room temperature and filtered through a small pad of diatomaceous earth. The cake was washed with ethyl acetate (50 mL) and combined filtrate was concentrated under reduced pressure. The residue was purified by flash column chromatography on silica gel to give 1-(2,6-dimethyl-4-(4-(trifluoromethyl)phenoxy)phenyl)ethanone (1.8 g) as yellow oil in 19% yield: $^1$H NMR (500 MHz, CDCl$_3$) δ 7.58 (d, J=8.5 Hz, 2 H), 7.04 (d, J=8.5 Hz, 2 H), 6.70 (s, 2 H), 2.50 (s, 3 H), 2.25 (s, 6H).

2-Bromo-1-(2,6-dimethyl-4-(4-(trifluoromethyl)phenoxy)phenyl)ethanone

To a solution of 1-(2,6-dimethyl-4-(4-(trifluoromethyl)phenoxy)phenyl)ethanone (1.80 g, 5.84 mmol) in acetonitrile (11.7 mL) was added tetrabutylammoniumtribromide (TBABr$_3$, 2.82 g, 5.84 mmol). The reaction was stirred at room temperature overnight. The solution was concentrated under reduced pressure, added with water, and extracted with ethyl acetate. The organic layer was washed with brine, dried over anhydrous MgSO$_4$(s), and concentrated under reduced pressure to give 2-bromo-1-(2,6-dimethyl-4-(4-(trifluoromethyl)phenoxy)phenyl)ethanone (2.16 g), which was used directly for the next step without further purification.

4-(2,6-Dimethyl-4-(4-(trifluoromethyl)phenoxy)phenyl)thiazol-2-amine

A mixture of 2-bromo-1-(2,6-dimethyl-4-(4-(trifluoromethyl)phenoxy)phenyl)ethanone (2.20 g, 5.68 mmol) and thiourea (0.43 g, 5.68 mmol) in 95% EtOH (8.1 mL) was heated at reflux for 60 min. The solution was concentrated and added with water (50 mL) and saturated aqueous Na$_2$CO$_3$ (1.0 mL). The resultant precipitate was filtered and recrystallized in toluene. The solids were filtered and dried under vacuum to give 4-(2,6-dimethyl-4-(4-(trifluoromethyl)phenoxy)phenyl)thiazol-2-amine (1.30 g) as yellow solids in 63% yield: $^1$H NMR (500 MHz, CDCl$_3$) δ 7.56 (d, J=8.5 Hz, 2 H), 7.05 (d, J=8.5 Hz, 2 H), 6.76 (s, 2 H), 6.32 (s, 1 H), 5.03 (s, 2 H), 2.17 (s, 6 H).

1-(4-(4-Ethylphenoxy)-2,6-dimethylphenyl)ethanone

To a solution of 1-(4-chloro-2,6-dimethylphenyl)ethanone (5.0 g, 27.4 mmol), K$_3$PO$_4$ (11.6 g, 54.7 mmol), 4-ethylphenol (4.01 g, 32.8 mmol) in toluene (54.8 mL) was added 2-di-tert-butylphosphino-2',4',6'-triisopropylbiphenyl (349 mg, 0.82 mmol) and Pd(OAc)$_2$ (259 mg, 1.15 mmol). The reaction was heated at 100° C. overnight under N$_2$. The solution was cooled to room temperature and filtered through a small pad of diatomaceous earth. The cake was washed with ethyl acetate (50 mL) and combined filtrate was concentrated under reduced pressure. The residue was purified by flash column chromatography on silica gel to give 1-(4-(4-ethylphenoxy)-2,6-dimethylphenyl)ethanone (6.0 g) as yellow oil in 82% yield: $^1$H NMR (500 MHz, CDCl$_3$) δ 7.17 (d, J=8.5 Hz, 2 H), 6.93 (d, J=8.5 Hz, 2 H), 6.63 (s, 2H), 2.64 (q, J=7.5 Hz, 2 H), 2.47 (s, 3 H), 2.21 (s, 6 H), 1.25 (t, J=75 Hz, 3 H).

2-Bromo-1-(4-(4-ethylphenoxy)-2,6-dimethylphenyl)ethanone

To a solution of 1-(4-(4-ethylphenoxy)-2,6-dimethylphenyl)ethanone (6.00 g, 22.4 mmol) in acetonitrile (44.7 mL) was added tetrabutylammoniumtribromide (TBABr$_3$, 10.8 g, 22.4 mmol). The reaction was stirred at room temperature overnight. The solution was concentrated under reduced pressure, added with water, and extracted with ethyl acetate. The organic layer was washed with brine, dried over anhydrous MgSO4(s), and concentrated under reduced pressure to give 2-bromo-1-(4-(4-ethylphenoxy)-2,6-dimethylphenyl)ethanone (8.2 g), which was used directly for the next step without further purification.

4-(4-(4-Ethylphenoxy)-2,6-dimethylphenyl)thiazol-2-amine

A mixture of 2-bromo-1-(4-(4-ethylphenoxy)-2,6-dimethylphenyl)ethanone (7.70 g, 2212 mmol) and thiourea (1.69 g, 22.2 mmol) in 95% EtOH (31.7 mL) was heated at reflux for 180 min. The solution was concentrated and added with water (100 mL) and saturated aqueous Na$_2$CO$_3$ (5.0 mL). The resultant precipitate was filtered and recrystallized in toluene. The solids were filtered and dried under vacuum to give 4-(4-(4-ethylphenoxy)-2,6-dimethylphenyl)thiazol-2-amine (6.30 g) as yellow solids in 88% yield: $^1$H NMR (500 MHz, CDCl$_3$) δ 7.18 (d, J=7.5 Hz, 2 H), 6.95 (d, J=8.5, 2 H), 6.71 (s, 2 H), 6.29 (s, 1H), 5.45 (bs, 2 H), 2.64 (q, J=7.5 Hz, 2 H), 2.14 (s, 6 H), 1.25 (t, J=8.0 Hz, 3 H).

2-Bromo-1-(3,5-difluoro-4-methoxyphenyl)ethanone

To a CH$_3$CN solution (56 mL) containing 1-(3,5-difluoro-4-methoxyphenyl)ethanone (5.0 g, 26.9 mmol, 1.0 equiv) was added TBABr$_3$ (12.95 g, 26.9 mmol, 1.0 equiv). The reaction mixture was stirred at room temperature for 16 h. The solution was concentrated under reduced pressure, and the residue was re-dissolved in EtOAc (50 mL). The solution was washed with saturated aqueous NaHCO$_3$ (30 mL), dried over MgSO$_4$, and concentrated under reduced pressure. The residue was purified by column chromatography on silica gel (2.0% EtOAc in hexanes as eluant) to provide 2-bromo-1-(3,5-difluoro-4-methoxyphenyl)ethanone (5.05 g, 19.0 mmol) as white solids in 71% yield: $^1$H NMR (DMSO-d$_6$, 500 MHz) δ 7.76-7.81 (m, 2 H), 4.91 (s, 2 H), 4.07 (s, 3 H).

4-(3,5-Difluoro-4-methoxyphenyl)thiazol-2-amine

A reaction mixture containing 2-bromo-1-(3,5-difluoro-4-methoxyphenyl)ethanone (2.0 g, 7.5 mmol, 1.0 equiv) and thiourea (0.57 g, 7.5 mmol, 1.0 equiv) in EtOH (20.0 mL) was heated at reflux for 3.0 h. The residue was basified with saturated aqueous Na$_2$CO$_3$ (20 mL) and extracted with EtOAc (3×30 mL). The organic layer was separated, dried over MgSO$_4$(s), and concentrated under reduced pressure. The resultant solids were washed with hexanes to give 4-(3,5-difluoro-4-methoxyphenyl)thiazol-2-amine (1.54 g, 6.4 mmol) as white solids in 84% yield: $^1$H NMR (DMSO-d$_6$, 500 MHz) δ 7.49-7.54 (m, 2 H), 7.12-7.14 (m, 3 H), 3.92 (s, 3 H); ESI-MS: m/z 243.0 (M+H)$^+$.

1-(2,6-Difluoro-4-methoxyphenyl)ethanone

A mixture of aluminium chloride (10.0-15 g, 69.4 mmol, 5.0 equiv) and acetyl chloride (2.0 mL, 28 mmol, 2.0 equiv) in CH$_2$Cl$_2$ (50.0 mL) was stirred at 0° C. for 30 min. The reaction mixture was slowly added with 1,3-difluoro-5-methoxybenzene (2.0 g, 13.9 mmol, 1.0 equiv) in CH$_2$Cl$_2$ (10.0 mL), and the resultant solution was stirred at room temperature for additional 2.0 h. The solution was basified with saturated aqueous NaHCO$_3$ (20 mL) to pH 8-9. The organic layer was separated, dried over MgSO$_4$(s), and concentrated under reduced pressure. The residue was purified by column chromatography on silica gel (15% EtOAc in hexanes as eluant) to give 1-(2,6-difluoro-4-methoxyphenyl)ethanone (1.5 g, 8.1 mmol) as yellow oil in 58% yield: $^1$H NMR (CDCl$_3$, 500 MHz) δ 6.46-6.48 (m, 2 H), 3.83 (s, 3 H), 2.56 (s, 3 H); ESI-MS: m/z 187.0 (M+H)$^+$.

2-Bromo-1-(2,5-difluoro-4-methoxyphenyl)ethanone

A CH$_3$CN solution (20 mL) containing 1-(2,6-difluoro-4-methoxyphenyl)ethanone (1.5 g, 8.1 mmol, 1.0 equiv) was added with TBABr$_3$ (3.88 g, 8.1 mmol, 1.0 equiv). The reaction mixture was stirred at room temperature for 16 h. The solution was concentrated under reduced pressure, and the residue was re-dissolved in EtOAc (50 mL). The solution was washed with saturated aqueous NaHCO$_3$ (30 mL), dried over MgSO$_4$, and concentrated under reduced pressure. The residue was purified by column chromatography on silica gel (2.0% EtOAc in hexanes as eluant) to provide 2-bromo-1-(2,5-difluoro-4-methoxyphenyl)ethanone (5.05 g, 19.1 mmol) as yellow oil in 84% yield: $^1$H NMR (CDCl$_3$, 500 MHz) δ 6.50-6.52 (m, 2 H), 4.34 (s, 2 H), 3.85 (s, 3 H).

4-(2,6-Difluoro-4-methoxyphenyl)thiazol-2-amine

A reaction mixture containing 2-bromo-1-(2,5-difluoro-4-methoxyphenyl)ethanone (1.5 g, 5.7 mmol, 1.0 equiv) and thiourea (430.8 mg, 5.7 mmol, 1.0 equiv) in EtOH (15.0 mL) was heated at reflux for 6.0 h. The residue was basified with saturated aqueous NaHCO$_3$ (20 mL) and extracted with EtOAc (3×30 mL). The organic layer was separated, dried over MgSO$_4$(s), and concentrated under reduced pressure. The residue was purified by column chromatography on silica gel (3.0% EtOAc in hexanes as eluant) to provide 4-(2,6-difluoro-4-methoxy-phenyl)-thiazol-2-amine (928.6 mg, 3.8 mmol) as white solids in 68% yield: $^1$H NMR (CDCl$_3$, 500 MHz) 6.68 (s, 1H), 6.50-6.52 (m, 2 H), 5.07 (s, 2 H), 3.81 (s, 3 H); ESI-MS: m/z 243.7 (M+H)$^+$.

1-(4-(2-Hydroxypropoxy)-2,6-dimethylphenyl)ethanone

A pressure glass vessel charged with 1-(4-hydroxy-2,6-dimethylphenyl)ethanone (500 mg, 3.1 mmol, 1.0 equiv) and 2-methyloxirane (0.22 mL, 3.1 mmol, 1.0 equiv) in 50% aqueous NaOH solution (5.0 mL) was stirred at 140° C. for 4.0 h. The mixture was diluted with H$_2$O (20 mL) and extracted with EtOAc. The organic layer was collected, dried over MgSO$_4$(s), and concentrated under reduced pressure. The residue was purified by column chromatography on silica gel (30% EtOAc in hexanes as eluant) to provide 1-(4-(2-hydroxypropoxy)-2,6-dimethylphenyl)ethanone (445.9 mg. 2.1 mmol) as yellow oil in 66% yield: $^1$H NMR (CDCl$_3$, 500 MHz) δ 6.57 (s, 2 H), 4.10-4.20 (s, 1 H), 3.90-3.93 (m, 2 H), 3.75-3.79 (m, 1 H), 2.45 (s, 3 H), 2.23 (s, 6 H), 1.25-1.28 (m, 3 H); ESI-MS: m/z 223.4 (M+H)$^+$.

2-Bromo-1-(4-(2-hydroxypropoxy)-2,6-dimethylphenyl)ethanone

To a CH$_3$CN solution (6.0 mL) containing 1-(4-(2-hydroxypropoxy)-2,6-dimethylphenyl)ethanone (445.9 mg, 2.0 mmol, 1.0 equiv) was added TBABr$_3$ (967.3 mg, 2.0 mmol, 1.0 equiv). The reaction mixture was stirred at room temperature for 16 h. The solvent was concentrated under reduced pressure, and the residue was re-dissolved in EtOAc (50 mL). The solution was washed with saturated aqueous NaHCO$_3$ (30 mL), dried over MgSO$_4$, and concentrated under reduced pressure. 2-Bromo-1-(4-(2-hydroxypropoxy)-2,6-dimethylphenyl)ethanone (547.8 mg, 1.8 mmol) was obtained as brown oil in 91% yield: $^1$H NMR (CDCl$_3$, 500 MHz) δ 6.60 (s, 2 H), 4.25 (s, 2 H), 4.10-4.20 (s, 1 H), 3.91-3.94 (m, 2 H), 3.79-3.80 (s, 1 H), 2.24 (s, 6 H), 1.27-1.29 (m, 3 H).

1-(4-(2-Aminothiazol-4-yl)-3,5-dimethylphenoxy)propan-2-ol

A reaction mixture containing 2-bromo-1-(2,5-difluoro-4-methoxyphenyl)ethanone (547.8 mg, 1.8 mmol, 1.0 equiv) and thiourea (138.5 mg, 1.8 mmol, 1.0 equiv) in EtOH (3.0 mL) was heated at reflux for 16 h. The solution was concentrated under reduced pressure, and the residue was re-dissolved in EtOAc (30 mL). The solution was washed with saturated aqueous NaHCO$_3$ (30 mL), dried over MgSO$_4$, and concentrated under reduced pressure. The residue was purified by column chromatography on silica gel (30% EtOAc in hexanes as eluant) to provide 1-(4-(2-aminothiazol-4-yl)-3, 5-dimethylphenoxy)propan-2-ol (332.5 mg, 1.2 mmol) as yellow oil in 66% yield: $^1$H NMR (CDCl$_3$, 500 MHz) δ 6.62 (s, 2 H), 6.26 (s, 1H), 4.95 (s, 2 H), 4.10-4.20 (s, 1H), 3.91-3.94 (m, 2 H), 3.75-3.79 (m, 1 H), 2.15 (s, 6 H), 1.26-1.28 (m, 3 H); ESI-MS: m/z 279.7 (M+H)$^+$.

1-(4-(2,3-Dihydroxypropoxy)-2,6-dimethylphenyl) ethanone

A pressure glass vessel charged with 1-(4-hydroxy-2,6-dimethylphenyl)ethanone (2.00 g, 12.2 mmol, 1.0 equiv) and 3-chloropropane-1,2-diol (1.02 mL, 12.2 mmol, 1.0 equiv) in 50% aqueous NaOH solution (20.0 mL) was heated at 140° C. for 16 h. The mixture was diluted with H$_2$O (20 mL) and extracted with EtOAc. The organic layer was collected, dried over MgSO$_4$(s), and concentrated under reduced pressure. The residue was purified by column chromatography on silica gel (30% EtOAc in hexanes as eluant) to provide 1-(4-(2,3-dihydroxypropoxy)-2,6-dimethylphenyl)ethanone (1.66 g, 7.0 mmol) as yellow oil in 57% yield: $^1$H NMR (CDCl$_3$, 500 MHz) δ o 6.57 (s, 2 H), 4.10-4.11 (m, 1 H), 4.08-4.09 (m, 2 H), 4.01-4.02 (m, 1 H), 3.74-3.75 (m, 1 H), 2.58-2.59 (s, 1 H), 2.45 (s, 3 H), 2.23 (s, 6 H), 2.05-2.10 (s, 1 H); ESI-MS: m/z 239.9 (M+H)$^+$.

2-Bromo-1-(4-(2,3-dihydroxypropoxy)-2,6-dimethylphenyl)ethanone

To a CH$_3$CN solution (10.0 mL) containing 1-(4-(2,3-dihydroxypropoxy)-2,6 dimethylphenyl)ethanone (1.0 g, 4.2 mmol, 1.0 equiv) was added TBABr$_3$ (2.04 g, 4.2 mmol, 1.0 equiv). The reaction mixture was stirred at room temperature for 16 h. The solution was concentrated under reduced pressure, and the residue was re-dissolved in EtOAc (50 mL). The solution was washed with saturated aqueous NaHCO$_3$ (30 mL), dried over MgSO$_4$, and concentrated under reduced pressure. 2-Bromo-1-(4-(2,3-dihydroxypropoxy)-2,6-dimethylphenyl)ethanone (741.9 mg, 2.3 mmol) was obtained as yellow solids in 56% yield: $^1$H NMR (CDCl$_3$, 500 MHz) δ 6.60 (s, 2 H), 4.25 (s, 2 H), 4.10-4.11 (m, 1 H), 4.03-4.04 (m, 2 H), 3.82-3.85 (m, 1 H), 3.75-3.76 (m, 1 H), 2.24 (s, 6 H).

3-(4-(2-Aminothiazol-4-yl)-3,5-dimethylphenoxy) propane-1,2-diol

A reaction mixture containing 2-bromo-1-(4-(2,3-dihydroxypropoxy)-2,6-dimethylphenyl)ethanone (741.9 mg, 2.3 mmol, 1.0 equiv) and thiourea (178.1 mg, 2.3 mmol, 1.0 equiv) in EtOH (10.0 mL) was heated at reflux for 16 h. The solution was concentrated under reduced pressure, and the residue was re-dissolved in EtOAc (30 mL). The solution was washed with saturated aqueous NaHCO$_3$ (30 mL), dried over MgSO$_4$, and concentrated under reduced pressure. The residue was purified by column chromatography on silica gel (30.0% EtOAc in hexanes as eluant) to provide 3-(4-(2-aminothiazol-4-yl)-3,5-dimethylphenoxy)propane-1,2-diol (694.1 mg, 2.4 mmol) as yellow solids in >99% yield: $^1$H NMR (CDCl$_3$, 500 MHz) δ 6.76 (s, 2 H), 5.31-5.32 (m, 1 H), 3.99-4.00 (m, 1 H), 3.79-3.87 (m, 1H), 3.78-3.79 (m, 1 H), 3.43-3.44 (m, 2 H), 3.37 (s, 2 H), 2.15 (s, 6 H); ESI-MS: m/z 295.6 (M+H)$^+$.

1-(4-(2-Methoxyethoxy)-2,6-dimethylphenyl)ethanone

A pressure glass vessel charged with 1-(4-hydroxy-2,6-dimethylphenyl)ethanone (500 mg, 3.1 mmol, 1.0 equiv) and 1-chloro-2-methoxyethane (0.28 mL, 3.1 mmol, 1.0 equiv) in 50% aqueous NaOH solution (5.0 mL) was heated at 140° C. for 16 h. The residue was diluted with H$_2$O (20 mL) and extracted with EtOAc (3×30 mL). The organic layer was separated, dried with MgSO$_4$, and concentrated under reduced pressure to give 1-(4-(2-methoxyethoxy)-2,6-dimethylphenyl)ethanone (430.9 mg, 1.9 mmol) as yellow oil in 64% yield: $^1$H NMR (CDCl$_3$, 500 MHz) δ 6.58 (s, 2 H), 4.09-4.10 (m, 2 H), 3.72-3.74 (m, 2 H), 3.44 (s, 3 H), 2.45 (s, 3 H), 2.23 (s, 6 H); ESI-MS: m/z 223.6 (M+H)$^+$.

2-Bromo-1-(4-(2-methoxyethoxy)-2,6-dimethylphenyl)ethanone

To a CH$_3$CN solution (6.0 mL) containing 1-(4-(2-methoxyethoxy)-2,6-dimethylphenyl)ethanone (400 mg, 1.8 mmol, 1.0 equiv) was added TBABr$_3$ (867.7 mg, 1.8 mmol, 1.0 equiv). The reaction mixture was stirred at room temperature for 16 h. The solution was concentrated under reduced pressure, and the residue was re-dissolved in EtOAc (50 mL). The solution was washed with saturated aqueous NaHCO$_3$ (30 mL), dried over MgSO$_4$(s), and concentrated under reduced pressure. 2-Bromo-1-(4-(2-methoxyethoxy)-2,6-dimethylphenyl)ethanone (322.9 mg, 1.1 mmol) was obtained as yellow solids in 60% yield: $^1$H NMR (CDCl$_3$, 500 MHz) δ 6.61 (s, 2 H), 4.25 (s, 2 H), 4.09-4.11 (m, 2 H), 3.73-3.75 (m, 2 H), 3.45 (s, 3 H), 2.24 (s, 6 H).

4-(4-(2-Methoxyethoxy)-2,6-dimethylphenyl)thiazol-2-amine

A reaction mixture containing 2-bromo-1-(4-(2-methoxyethoxy)-2,6-dimethylphenyl)ethanone (322.9 mg, 1.1 mmol, 1.0 equiv) and thiourea (81.61 mg, 1.1 mmol, 1.0 equiv) in EtOH (3.0 mL) was heated at reflux for 16 h. The solution was concentrated under reduced pressure, and the residue was re-dissolved in EtOAc (20 mL). The solution was washed with saturated aqueous NaHCO$_3$ (30 mL), dried over MgSO$_4$, and concentrated under reduced pressure. The residue was purified by column chromatography on silica gel (30% EtOAc in hexanes as eluant) to provide 4-(4-(2-methoxyethoxy)-2,6-dimethylphenyl)thiazol-2-amine (281.0 mg, 1.0 mmol) as yellow solids in 94% yield: $^1$H NMR (DMSO-d$_6$, 500 MHz) δ 6.76 (s, 2 H), 5.31-5.33 (m, 1 H), 4.09-4.11 (m, 2 H), 3.64-3.65 (m, 2 H), 3.30 (s, 3 H), 2.12 (s, 6 H); ESI-MS: m/z 279.7 (M+H)$^+$.

1-(4-(3-Methoxypropoxy)-2,6-dimethylphenyl)ethanone

A pressure glass vessel charged with 1-(4-hydroxy-2,6-dimethylphenyl)ethanone (800 mg, 4.9 mmol, 1.0 equiv) and 1-chloro-3-methoxypropane (528.97 mg, 4.9 mmol, 1.0 equiv) in 50% aqueous NaOH solution (10.0 mL) was stirred at 140° C. for 16 h. The residue was diluted with H$_2$O (20 mL) and extracted with EtOAc (3×30 mL). The organic layer was separated, dried over MgSO$_4$(s), and concentrated under reduced pressure to give 1-(4-(3-methoxypropoxy)-2,6-dimethylphenyl)ethanone (987.8 mg, 4.2 mmol) as yellow oil in 86% yield: $^1$H NMR (DMSO-d$_6$, 500 MHz) δ 6.56 (s, 2 H), 4.02-4.04 (m, 2H), 3.53-3.55 (m, 2 H), 3.36 (s, 3 H), 2.45 (s, 3 H), 2.23 (s, 6 H), 2.02-2.04 (m, 3H); ESI-MS: m/z 237.7 (M+H)$^+$.

2-Bromo-1-(4-(3-methoxypropoxy)-2,6-dimethylphenyl)ethanone

To a CH$_3$CN solution (15.0 mL) containing 1-(4-(3-methoxypropoxy)-2,6-dimethylphenyl)ethanone (987.8 mg, 4.2 mmol, 1.0 equiv) was added TBABr$_3$ (2.02 g, 4.2 mmol, 1.0 equiv). The reaction mixture was stirred at room temperature for 16 h. The solution was concentrated under reduced pressure, and the residue was re-dissolved in EtOAc (50 mL). The solution was washed with saturated aqueous NaHCO$_3$ (30 mL), dried over MgSO$_4$(s), and concentrated under reduced pressure. 2-Bromo-1-(4-(3-methoxypropoxy)-2,6-dimethylphenyl)ethanone (1.23 g, 3.9 mmol) was obtained as yellow oil in 93% yield: $^1$H NMR (CDCl$_3$, 500 MHz) δ 6.58 (s, 2 H), 4.24-4.35 (m, 2 H), 4.03-4.05 (m, 2 H), 3.53-3.55 (m, 2 H), 3.35 (s, 3 H), 2.24 (s, 6 H), 2.01-2.06 (m, 2 H).

4-(4-(3-Methoxypropoxy)-2,6-dimethylphenyl)thiazol-2-amine

A reaction mixture containing 2-bromo-1-(4-(3-methoxypropoxy)-2,6-dimethylphenyl)ethanone (500.0 mg, 1.6 mmol, 1.0 equiv) and thiourea (126.8 mg, 1.6 mmol, 1.0 equiv) in EtOH (10.0 mL) was heated at reflux for 16 h. The solution was concentrated under reduced pressure, and the residue was re-dissolved in EtOAc (50 mL). The solution was washed with saturated aqueous NaHCO$_3$ (30 mL), dried over MgSO$_4$(s), and concentrated under reduced pressure. The residue was purified by column chromatography on silica gel (30% EtOAc in hexanes as eluant) to provide 4-(4-(3-methoxypropoxy)-2,6-dimethylphenyl)thiazol-2-amine (328.9 mg, 1.1 mmol) as yellow 10 solids in 71% yield: $^1$H NMR (CDCl$_3$, 500 MHz) δ 9.35 (s, 1H), 9.00 (s, 1 H), 6.64 (s, 2 H), 6.22 (s, 1 H), 4.04-4.05 (m, 2 H), 3.54-3.56 (m, 2 H), 3.37 (s, 3 H), 2.19 (s, 6 H), 2.03-2.06 (m, 2 H); ESI-MS m/z 293.8 (M+H)$^+$.

1-(2,6-Dimethyl-4-(phenylthio)phenyl)ethanone

A mixture of 1-(4-iodo-2,6-dimethylphenyl)ethanone (1.5 g, 5.5 mmol, 1.0 equiv), benzenethiol (0.60 mL, 8.2 mmol, 1.5 equiv), copper(I) oxide (39.2 mg, 0.3 mmol, 0.05 equiv), and potassium hydroxide (614.1 mg, 11.0 mmol, 2.0 equiv) in DMF (4.4 mL) and H$_2$O (1.1 mL) was heated at reflux for 20 h. The mixture was quenched with H$_2$O (10 mL) and extracted with ether (2×20 mL). The organic layer was collected, dried over MgSO$_4$(s), and concentrated under reduced pressure. The residue was purified by column chromatography on silica gel (3.0% EtOAc in hexanes as eluant) to provide 1-(2,6-dimethyl-4-(phenylthio)phenyl)ethanone (931 mg, 3.6 mmol) as yellow oil in 66% yield: $^1$H NMR (CD$_3$OD, 500 MHz) δ 7.34-7.35 (m, 5 H); 6.97 (s, 2 H), 2.46 (s, 3 H), 2.17 (s, 6 H); ESI-MS: m/z 257.0 (M+H)$^+$.

2-Bromo-1-(2,6-dimethyl-4-(phenylthio)phenyl)ethanone

To a CH$_3$CN solution (15.0 mL) containing 1-(2,6-dimethyl-4-(phenylthio)phenyl)ethanone (816.3 mg, 3.2 mmol, 1.0 equiv) was added TBABr$_3$ (1.54 g, 3.2 mmol, 1.0 equiv). The reaction mixture was stirred at room temperature for 16 h. The solution was concentrated under reduced pressure, and the residue was re-dissolved in EtOAc (50 mL). The solution was washed with saturated aqueous NaHCO$_3$ (30 mL), dried over MgSO$_4$(s), and concentrated under reduced pressure. The residue was purified by column chromatography on silica gel (3.0% EtOAc in hexanes as the eluant) to provide 2-bromo-1-(2,6-dimethyl-4-(phenylthio)phenyl)ethanone (591.7 mg, 1.6 mmol) as yellow oil in 55% yield: $^1$H NMR (DMSO-d$_6$, 500 MHz) G 7.36-7.42 (m, 5 H), 7.01 (s, 2 H), 4.75 (s, 2 H), 2.13 (s, 6 H).

4-(2,6-Dimethyl-4-(phenylthio)phenyl)thiazol-2-amine

A reaction mixture containing 2-bromo-1-(2,6-dimethyl-4-(phenylthio)phenyl)ethanone (591.7 mg, 1.8 mmol, 1.0 equiv) and thiourea (134.3 mg, 1.8 mmol, 1.0 equiv) in EtOH (15.0 mL) was heated at reflux for 16 h. The solution was concentrated under reduced pressure, and the residue was re-dissolved in EtOAc (50 mL). The solution was washed with saturated aqueous NaHCO$_3$ (30 mL), dried over MgSO$_4$(s), and concentrated under reduced pressure. The residue was purified by column chromatography on silica gel (5.0% EtOAc in hexanes as eluant) to provide 4-(2,6-dimethyl-4-(phenylthio)phenyl)thiazol-2-amine (483.7 mg, 1.6 mmol) as yellow solids in 88% yield: $^1$H NMR (DMSO-d$_6$, 500 MHz) δ 7.33-7.38 (m, 2 H), 7.29-7.33 (m, 3 H), 7.06 (s, 2 H), 6.89 (s, 2 H), 6.38 (s, 1 H), 2.07 (s, 6 H); ESI-MS: m/z 313.8 (M+H)$^+$.

1-(2,6-Dimethyl-4-(p-tolylthio)phenyl)ethanone. A mixture of 1-(4-iodo-2,6-dimethylphenyl)ethanone (1.5 g, 5.5 mmol, 1.0 equiv), 4-methylbenzenethiol (1.02 g, 8.2 mmol, 1.5 equiv), copper(I) oxide (39.2 mg, 0.3 mmol, 0.05 equiv), and potassium hydroxide (614.1 mg, 11.0 mmol, 2.0 equiv) in DMF (4.4 mL) and H$_2$O (1.1 mL) was heated at reflux for 20 h. The mixture was quenched with H$_2$O (10 mL) and extracted with ether (2×20 mL). The organic layer was collected, dried over MgSO$_4$(s), and concentrated under reduced pressure. The residue was purified by column chromatography on silica gel (3.0% EtOAc in hexanes as eluant) to provide 1-(2,6-dimethyl-4-(p-tolylthio)phenyl)ethanone (1.16 g, 4.3 mmol) as yellow oil in 79% yield: $^1$H NMR (CD$_3$OD, 500 MHz) δ 7.29 (d, J=8.0 Hz, 2 H), 7.20 (d, J=8.0 Hz, 2 H), 6.88 (s, 2 H), 2.45 (s, 3 H), 2.35 (s, 3 H), 2.15 (s, 6 H); ESI-MS: m/z 271.8 (M+H)$^+$.

2-Bromo-1-(2,6-dimethyl-4-(p-tolylthio)phenyl)ethanone. To a CH$_3$CN solution (20.0 mL) containing 1-(2,6-dimethyl-4-(p-tolylthio)phenyl)ethanone (1.0 g, 3.7 mmol, 1.0 equiv) was added TBABr$_3$ (1.79 g, 3.7 mmol, 1.0 equiv). The reaction mixture was stirred at room temperature for 16 h. The solution was concentrated under reduced pressure, and the residue was re-dissolved in EtOAc (50 mL). The solution was washed with saturated aqueous NaHCO$_3$ (30 mL), dried over MgSO$_4$(s), and concentrated under reduced pressure. The residue was purified by column chromatography on silica gel (3.0% EtOAc in hexanes as the eluant) to provide 2-bromo-1-(2,6-dimethyl-4-(p-tolylthio)phenyl)ethanone (394.8 mg, 1.1 mmol) as yellow oil in 31% yield: $^1$H NMR (DMSO-d$_6$, 500 MHz) δ 7.33 (d, J=8.0 Hz, 2 H), 7.2 (d, J=8.0 Hz, 2 H), 6.92 (s, 2 H), 4.76 (s, 2H), 2.32 (s, 3 H), 2.11 (s, 6 H).

4-(2,6-Dimethyl-4-(p-tolylthio)phenyl)thiazol-2-amine. A reaction mixture containing 2-bromo-1-(2,6-dimethyl-4-(p-tolylthio)phenyl)ethanone (394.8 mg, 1.1 mmol, 1.0 equiv) and thiourea (86.04 mg, 1.1 mmol, 1.0 equiv) in EtOH (10.0 mL) was heated at reflux for 16 h. The solution was concentrated under reduced pressure, and the residue was re-dissolved in EtOAc (50 mL). The solution was washed with saturated aqueous NaHCO$_3$ (30 mL), dried over MgSO$_4$(s), and concentrated under reduced pressure. The residue was purified by column chromatography on silica gel (5.0% EtOAc in hexanes as eluant) to provide 4-(2,6-dimethyl-4-(p-tolylthio)phenyl)thiazol-2-amine (371.9 mg, 1.1 mmol) as yellow solids in >99% yield: $^1$H NMR (DMSO-d$_6$, 500 MHz) δ 7.27 (d, J=8.0 Hz, 2 H), 7.21 (d, J=8.0 Hz, 2 H), 6.97 (s, 2 H), 6.87 (s, 2 H), 6.36 (s, 1 H), 2.30 (s, 3 H), 2.05 (s, 6 H); ESI-MS: m/z 327.0 (M+H)$^+$.

1-(4-(4-Methoxyphenylthio)-2,6-dimethylphenyl)ethanone. A mixture of 1-(4-iodo-2,6-dimethylphenyl)ethanone (1.5 g, 5.5 mmol, 1.0 equiv), 4-methoxybenzenethiol (1.01 mL, 8.2 mmol, 1.5 equiv), copper(I) oxide (39.2 mg, 0.3 mmol, 0.05 equiv), and potassium hydroxide (614.1 mg, 11.0 mmol, 2.0 equiv) in DMF (4.4 mL) and H$_2$O (1.1 mL) was heated at reflux for 20 h. The mixture was quenched with H$_2$O (10 mL) and extracted with ether (2×20 mL). The organic layer was collected, dried over MgSO$_4$(s), and concentrated under reduced pressure. The residue was purified by column chromatography on silica gel (3.0% EtOAc in hexanes as eluant) to provide 1-(4-(4-methoxyphenylthio)-2,6-dimethylphenyl)ethanone (1.41 g, 4.9 mmol) as yellow oil in 90% yield: $^1$H NMR (DMSO-d$_6$, 500 MHz) δ 7.39 (d, J=8.5 Hz, 2 H), 6.96 (d, J=8.5 Hz, 2 H), 6.79 (s, 2 H), 3.82 (s, 3 H), 2.43 (s, 3 H), 2.13 (s, 6 H); ESI-MS: m/z 287.6 (M+H)$^+$.

2-Bromo-1-(4-(4-methoxyphenylthio)-2,6-dimethylphenyl)ethanone. To a CH$_3$CN solution (20.0 mL) containing 1-(4-(4-methoxyphenylthio)-2,6 dimethylphenyl)ethanone (1.0 g, 3.5 mmol, 1.0 equiv) was added TBABr$_3$ (1.684 g, 3.5 mmol, 1.0 equiv). The reaction mixture was stirred at room temperature for 16 h. The solution was concentrated under reduced pressure, and the residue was re-dissolved in EtOAc (50 mL). The solution was washed with saturated aqueous NaHCO$_3$ (30 mL), dried over MgSO$_4$(s), and concentrated under reduced pressure. The residue was purified by column chromatography on silica gel (3.0% EtOAc in hexanes as eluant) to provide 2-bromo-1-(4-(4-methoxyphenylthio)-2,6-dimethylphenyl)ethanone (1.06 g, 2.9 mmol) as yellow oil in 83% yield: $^1$H NMR (DMSO-d$_6$, 500 MHz) δ 7.44 (d, J=8.7 Hz, 2 H), 7.03 (d, l=8.7 Hz, 2 H), 6.83 (s, 2 H), 4.71 (s, 2 H), 3.80 (s, 3 H), 2.10 (s, 6 H).

4-(4-(4-Methoxyphenylthio)-2,6-dimethylphenyl)thiazol-2-amine. A reaction mixture containing 2-bromo-1-(4-(4-methoxyphenylthio)-2,6-dimethylphenyl)ethanone (1.06 g, 2.9 mmol, 1.0 equiv) and thiourea (221.5 mg, 2.9 mmol, 1.0 equiv) in EtOH (20.0 mL) was heated at reflux for 16 h. The solution was concentrated under reduced pressure, and the residue was re-dissolved in EtOAc (50 mL). The solution was washed with saturated aqueous NaHCO$_3$ (30 mL), dried over MgSO$_4$(s), and concentrated under reduced pressure. The residue was purified by column chromatography on silica gel (5.0% EtOAc in hexanes as eluant) to provide 4-(4-(4-methoxyphenylthio)-2,6-dimethylphenyl)thiazol-2-amine (890.9 mg, 2.6 mmol) as yellow solids in 90% yield: $^1$H NMR (DMSO-d$_6$, 500 MHz) δ 7.40 (d, J=8.7 Hz, 2 H), 7.00 (d, J=8.7 Hz, 2 H), 6.86-6.87 (m, 4 H), 6.33 (s, 1 H), 3.78 (s, 3 H), 2.03 (s, 6 H); ESI-MS m/z 343.9 (M+H)$^+$.

2-Bromo-1-(4-(4-methoxyphenylsulfonyl)-2,6-dimethylphenyl)ethanone. A mixture of 2-bromo-1-(4-(4-methoxyphenylthio)-2,6-dimethylphenyl)ethanone (1.0 g, 2.7 mmol, 1.0 equiv) and m-chloroperoxybenzoic acid (1.69 g, 6.8 mmol, 2.5 equiv) in dichloromethane (10.0 mL) was stirred at room temperature for 16 h. The solution was concentrated under reduced pressure, and the residue was re-dissolved in EtOAc (50 mL). The solution was washed with saturated aqueous NaHCO$_3$ (30 mL), dried over MgSO$_4$(s), and concentrated under reduced pressure to give 2-bromo-1-(4-(4 methoxyphenylsulfonyl)-2,6-dimethylphenyl)ethanone (1.09 g, 2.7 mmol) as white solids in >99% yield: $^1$H NMR (CDCl$_3$, 500 MHz) δ 7.85-7.90 (m, 2 H), 7.57-7.60 (m, 2 H), 6.97-6.90 (m, 2H), 4.21 (s, 2 H), 3.85 (s, 3 H), 2.30 (s, 6 H).

4-(4-(4-Methoxyphenylsulfonyl)-2,6-dimethylphenyl)thiazol-2-amine. A reaction mixture containing 2-bromo-1-(4-(4-methoxyphenylsulfonyl)-2,6 dimethylphenyl)ethanone (1.33 g, 3.4 mmol, 1.0 equiv) and thiourea (254.8 mg, 3.4 mmol, 1.0 equiv) in EtOH (5.0 mL) was heated at reflux for 1.0 h. The solution was concentrated under reduced pressure, and the residue was re-dissolved in EtOAc (50 mL). The solution was washed with saturated aqueous NaHCO 3 (30 mL), dried over MgSO4, and concentrated under reduced pressure. The resultant solids were washed with hexanes to give 4-(4-(4-methoxyphenylsulfonyl)-2,6-dimethylphenyl)thiazol-2-amine (839.2 mg, 2.2 mmol) as yellow solids in 65% yield: $^1$H NMR (DMSO-d$_6$, 500 MHz) δ 7.89 (d, J=8.9 Hz, 2 H), 7.61 (s, 2 H), 7.13 (d, J=8.9 Hz, 2 H), 6.95 (brs, 2 H), 6.43 (s, 1 H), 3.83 (s, 3 H), 2.16 (s, 6 H); ESI-MS: m/z 375.6 (M+H)$^+$.

2-Bromo-1-(4-(4-methoxyphenylsulfinyl)-2,6-dimethylphenyl)ethanone. A mixture of 2-bromo-1-(4-(4-methoxyphenylthio)-2,6-dimethylphenyl)ethanone (500.0 mg, 1.3 mmol, 1.0 equiv), acetic anhydride (0.14 mL, 1.5 mmol, 1.1 equiv), 30% hydrogen peroxide (55.86 mg, 1.6 nm 101, 1.2 equiv) and silica gel (273.75 mg, 230-400 mesh) in dichloromethane (10.0 mL) was stirred at room temperature for 16 h. The solution was concentrated under reduced pressure, and the residue was re-dissolved in EtOAc (50 mL). The solution was washed with saturated aqueous NaHCO$_3$ (30 mL), dried over MgSO$_4$(s), and concentrated under reduced pressure to give 2-bromo-1-(4-(4 methoxyphenylsulfinyl)-2,6-dimethylphenyl)ethanone (235.4 mg, 0.6 mmol) as pale yellow oil in 48% yield: $^1$H NMR (DMSO-d$_6$, 500 MHz) δ 7.65 (d, J=8.8 Hz, 2 H), 7.41 (s, 2 H), 7.09 (d, J=8.8 Hz, 2 H), 4.78 (s, 2 H), 3.79 (s, 3 H), 2.21 (s, 6 H).

N-(4-(4-(4-Methoxyphenylsulfinyl)-2,6-dimethylphenyl)thiazol-2-yl)isonicotinamide.

A reaction mixture containing 2-bromo-1-(4-(4-methoxyphenylsulfinyl)-2,6-dimethylphenyl)ethanone (235.4 mg, 0.6 mmol, 1.0 equiv) and thiourea (47.0 mg, 0.60 mmol, 1.0 equiv) in EtOH (5.0 mL) was heated at reflux for 1.0 h. The solution was concentrated under reduced pressure, and the residue was re-dissolved in EtOAc (50 mL). The solution was washed with saturated aqueous NaHCO$_3$ (30 mL), dried over MgSO$_4$, and concentrated under reduced pressure. The resultant solids were washed with hexanes to give N-(4-(4-(4-methoxyphenylsulfinyl)-2,6-dimethylphenyl)thiazol-2 yl)isonicotinamide (236.7 mg, 0.70 mmol) as yellow solids in >99% yield: $^1$H NMR (DMSO-d$_6$, 500 MHz) δ 7.64 (d, J=8.9 Hz, 2 H), 7.34 (s, 2 H), 7.09 (d, J=8.9 Hz, 2H), 6.90 (s, 2 H), 6.39 (s, 1 H), 3.79 (s, 3 H), 2.13 (s, 6 H); ESI-MS m/z 359.0 (M+H)$^+$.

5-Methyl-4-phenylthiazol-2-amine. A mixture of 2-bromo-1-phenylpropan-1-one (3.00 g, 19.5 mmol) and thiourea (1.56 g, 20.5 mmol) in 95% EtOH (30 mL) was heated at reflux for 60 min. The solution was concentrated and mixed with water (100 mL) and saturated aqueous Na$_2$CO$_3$ (5.0 mL). The resultant precipitate was filtered and recrystallized in toluene. The solids were filtered and dried under vacuum to give 5-methyl-4-phenylthiazol-2-amine (4.07 g) as yellow solids in 77% yield: $^1$H NMR (500 MHz, DMSO-d$_6$) δ 8.85 (s, 2 H), 7.54-7.49 (m, 5 H), 2.28 (s, 3 H).

2-Bromo-1-(4-methoxyphenyl)propan-1-one. To a solution of 1-(4-methoxyphenyl)propan-1-one (5.01 g, 30.2 mol) in EtOAc (120 mL) was added copper(II) bromide (CuBr$_2$, 13.6 g, 6.8 mmol). The reaction mixture was heated at reflux for 90 min. The solution was allowed to cool down, and the resultant solids were filtered off and washed with EtOAc. The filtrate was concentrated under reduced pressure to give crude 2-bromo-1-(4-methoxyphenyl)propan-1-one (10.4 g) as yellow oil: $^1$H NMR (500 MHz, CDCl$_3$) δ 8.02 (m, 2 H), 6.96 (m, 2 H), 5.28-5.25 (m, 1H), 3.89 (s, 3 H), 1.89 (d, 3 H).

4-(4-Methoxyphenyl)-5-methylthiazol-2-amine. A mixture of 2-bromo-1-(4-methoxyphenyl)propan-1-one (10.4 g, 36.1 mmol) and thiourea (2.76 g, 36.2 mmol) in 95% EtOH (70 mL) was heated at reflux for 60 min. The solution was concentrated and mixed with water (100 mL) and saturated aqueous Na2CO3 (5.0 mL). The resultant precipitate was filtered and recrystallized in toluene. The solids were filtered and dried under vacuum to give 4-(4-methoxyphenyl)-5-methylthiazol-2-amine (6.16 g) as yellow solids in 78% yield: $^1$H NMR (500 MHz, DMSO-$d_6$) δ 8.90 (s, 2 H), 7.46-7.44 (m, 2 H), 7.09-7.07 (m, 2 H), 3.81 (s, 3 H), 2.47 (s, 3 H).

2-Bromo-1-(2,4,6-trimethoxyphenyl)ethanone. To a solution of 1-(2,4,6-trimethoxyphenyl)ethanone (5.0 g, 23.3 mmol) in EtOAc (100 mL) was added copper(II) bromide (CuBr$_2$, 10.4 g, 46.7 mmol). The reaction mixture was heated at reflux for 90 min. The solution was allowed to cool down, and the resultant solids were filtered off and washed with EtOAc. The filtrate was concentrated under reduced pressure to give crude 2-bromo-1-(2,4,6-trimethoxyphenyl)ethanone (2.70 g) 2-bromo-1-(2,4,6-trimethoxyphenyl)ethanone as yellow oil: $^1$H NMR (500 MHz, CDCl$_3$) δ 6.11 5 (m, 2 H), 4.36 (m, 2 H), 3.86 (s, 3 H), 3.82 (s, 6 H).

4-(2,4,6-Trimethoxyphenyl)thiazol-2-amine. A mixture of 2-bromo-1-(2,4,6-trimethoxyphenyl)ethanone (2.49 g, 8.6 mmol) and thiourea (0.67 g, 8.7 mmol) in 95% EtOH (16 mL) was heated at reflux for 60 min. The solution was concentrated and mixed with water (100 mL) and saturated aqueous Na$_2$CO$_3$ (5.0 mL). The resultant precipitate was filtered and recrystallized in toluene. The solids were filtered and dried under vacuum to give 4-(2,4,6-trimethoxyphenyl)thiazol-2-amine (1.75 g) as yellow solids in >99% yield: $^1$H NMR (500 MHz, DMSO-$d_6$) δ 9.00 (s, 2 H), 6.78 (s, 1 H), 6.36 (s, 2 H), 3.84 (s, 3 H), 3.79 (s, 6 H).

2-Bromo-1-(4-methoxyphenyl)ethanone. To a solution of 1-(4-methoxyphenyl)ethanone (15.2 g, 0.10 mol) in EtOAc (250 mL) was added copper(II) bromide (CuBr2, 45.1 g, 0.20 mol). The reaction mixture was heated at reflux for 90 min. The solution was allowed to cool down, and the resultant solids were filtered off and washed with EtOAc. The filtrate was concentrated under reduced pressure to give crude 2-bromo-1-(4-methoxyphenyl)ethanone (15.8 g) as yellow oil: $^1$H NMR (500 MHz, CDCl$_3$) δ 7.98 (m, 2 H), 6.97 (m, 2 H), 4.41 (s, 3 H), 3.89 (s, 6H).

4-(4-Methoxyphenyl)thiazol-2-amine. A mixture of 2-bromo-1-(4-methoxyphenyl)ethanone (5.00 g, 21.8 mmol) and thiourea (1.72 g, 22.6 mmol) in 95% EtOH (40 mL) was heated at reflux for 60 min. The solution was concentrated and mixed with water (100 mL) and saturated aqueous Na$_2$CO$_3$ (5.0 mL). The resultant precipitate was filtered and recrystallized in toluene. The solids were filtered and dried under vacuum to give 4-(4-methoxyphenyl)thiazol-2-amine (5.24 g) as yellow solids in >99% yield: $^1$H NMR (500 MHz, DMSO-$d_6$) δ 7.72 (d, 2 H), 6.99 (s, 2 H), 6.92-6.91 (m, 2 H), 6.82 (s, 1 H), 3.76 (s, 3 H).

2-Bromo-1-(2,4-dimethoxyphenyl)ethanone. To a solution of 1-(2,4-dimethoxyphenyl)ethanone (10.0 g, 54.4 mmol) in EtOAc (220 mL) was added copper(II) bromide (CuBr$_2$, 24.3 g, 0.11 mol). The reaction mixture was heated at reflux for 90 min. The solution was allowed to cool down, and the resultant solids were filtered off and washed with EtOAc. The filtrate was concentrated under reduced pressure to give crude 2-bromo-1-(2,4-dimethoxyphenyl)ethanone (14.5 g) as yellow oil: $^1$H NMR (500 MHz, CDCl$_3$) δ 7.91 (m, 2 H), 6.52 (m, 2 H), 4.57 (s, 3 H), 3.98 (s, 3 H), 3.85 (s, 3 H).

4-(2,4-Dimethoxyphenyl)thiazol-2-amine. A mixture of 2-bromo-1-(2,4-dimethoxyphenyl)ethanone (14.5 g, 55.8 mmol) and thiourea (4.32 g, 56.7 mmol) in 95% EtOH (110 mL) was heated at reflux for 60 min. The solution was concentrated and mixed with water (100 mL) and saturated aqueous Na$_2$CO$_3$ (5.0 mL). The resultant precipitate was filtered and recrystallized in toluene. The solids were filtered and dried under vacuum to give 4-(2,4-dimethoxyphenyl)thiazol-2-amine (10.9 g) as yellow solids in 62% yield: $^1$H NMR (500 MHz, DMSO-$d_6$) δ 8.60 (s, 2 H), 7.53 (s, 1 H), 6.97 (s, 1 H), 6.69 (s, 1 H), 6.67-6.63 (m, 1 H), 3.86 (s, 3 H), 3.80 (s, 3 H).

2-Chloro-1-(2,4,6-trifluorophenyl)ethanone. To a mechanically stirred solution of 1,3,5-trifluorobenzene (6.0 mL, 58 mmol) in dichloroethane (14.0 mL) was added gradually AlCl$_3$ (15.5 g, 116 mmol) in a period of 15 min with caution. Violent bumping and HCl gas evolution was observed. The mixture was carefully heated to reflux, and chloroacetyl chloride (5.5 mL, 69 mmol) was added drop wisely in a period of 45 min. The reaction mixture was heated at reflux for an additional 6.0 h. The solution was cooled, carefully poured onto an ice/water slush (200 mL) and the aqueous solution was extracted with ether (3×50 mL). The combined ethereal layers were washed with 10% aqueous HCl (2×30 mL), 1.0 N aqueous NaOH (3×30 mL), and brine (25 mL). The solution was dried over MgSO$_4$(s) and concentrated under reduced pressure to give 2-chloro-1-(2,4,6-trifluorophenyl)ethanone (5.28 g) as yellow solids in 51% yield: $^1$H NMR (500 MHz, CDCl$_3$) δ 6.79-6.76 (m, 2 H), 4.50 (s, 2 H).

4-(2,4,6-Trifluorophenyl)thiazol-2-amine. A mixture of 2-chloro-1-(2,4,6-trifluorophenyl)ethanone (9.04 g, 43.5 mmol) and thiourea (3.51 g, 46.1 mmol) in 95% EtOH (50 mL) was heated at reflux overnight. The solution was concentrated and mixed with water (100 mL) and saturated aqueous Na2CO3 (5.0 mL). The solids were filtered and dried under vacuum to give 4-(2,4,6-trifluorophenyl)thiazol-2-amine (9.71 g) as pink-white solids in 97% yield: $^1$H NMR (500 MHz, DMSO-$d_6$) δ 7.26-7.22 (m, 2 H), 7.09 (s, 2 H), 6.77 (s, 1 H).

1-(2,6-Dimethyl-4-(phenylamino)phenyl)ethanone. To a solution of 1-(4-amino-2,6-dimethylphenyl)ethanone (3.26 g, 20.0 mmol), K3PO4 (9.2 g, 40 mmol), and 1-iodobenzene (4.08 g, 20.0 mmol) in DMF (35.0 mL) was added CuI (761.8 mg, 40 mmol). The reaction was heated at 110° C. overnight under N$_2$. The solution was cooled to room temperature and filtered through a small pad of diatomaceous earth. The cake was washed with ethyl acetate (50 mL) and the combined filtrate was concentrated under reduced pressure. The residue was purified by flash column chromatography on silica gel to give 1-(2,6-dimethyl-4-(phenylamino)phenyl)ethanone as red-brown syrup: $^1$H NMR (500 MHz, CDCl$_3$) δ 7.30 (d, J=8.2 Hz, 2 H), 7.10 (d, J=7.7 Hz, 2 H), 6.99 (d, J=4.2 Hz, 1 H), 6.71 (s, 1 H), 2.47 (s, 3 H), 2.18 (s, 6 H); ESI-MS: m/z 239.5 (M+H)$^+$.

1-(4-(4-Bromophenylamino)-2,6-dimethylphenyl)-2-bromoethanone. To a solution of 1-(2,6-dimethyl-4-(phenylamino)phenyl)ethanone (2.10 g, 8.78 mmol) in acetonitrile (50 mL) was added tetrabutylammoniumtribromide (TBABr$_3$, 4.24 g, 8.78 mmol). The reaction was stirred at room temperature for 60 min. The solution was concentrated under reduced pressure, added with water, and extracted with ethyl acetate. The organic layer was washed with brine, dried over anhydrous MgSO$_4$(s), and concentrated under reduced pressure to give 1-(4-(4-bromophenylamino)-2,6-dimethylphenyl)-2-bromoethanone (2.01 g), which was used directly for the next step without further purification.

4-(4-(4-Bromophenylamino)-2,6-dimethylphenyl)thiazol-2-amine. A solution of 1-(4-(4-bromophenylamino)-2,6-dimethylphenyl)-2-bromoethanone (1.6 g, 4.0 mmol) and thiourea (0.79 g, 7.2 mmol) in acetonitrile (30 mL) was heated at reflux for 90 min. The solution was concentrated and added with water (50 mL) and saturated aqueous Na$_2$CO$_3$ (1.0 mL), and extracted with ethyl acetate. The organic layer was washed with brine, dried over anhydrous MgSO₄(s), and concentrated under reduced pressure to give product (1.1 g), which was used directly for the next step without further purification.

3-Chloro-5-methyl-phenylamine. An ethanol solution (75 mL) containing 1-chloro-3-methyl-5-nitro-benzene (5.0 g, 29 mmol) were mixed with SnCl$_2$.2H$_2$O (32.8 g, 146 mmol). The reaction mixture was refluxed for 3.0 h. The solution was concentrated under vacuum, and the residue was re-dissolved in aqueous NaOH, filtered, and extracted with EtOAc. The organic layer was collected, washed with brine, dried over MgSO₄(s), and concentrated under reduced pressure. The residue was purified by column chromatography on silica gel to give 3-chloro-5-methyl-phenylamine (4.0 g) as light yellow solids in 97% yield: $^1$H NMR (500 MHz, CDCl$_3$) δ 6.56 (s, 1 H), 6.48 (s, 1 H), 6.36 (s, 1), 3.66 (s, 2 H), 2.23 (s, 3 H); ESI-MS: m/z 141.7 (M+H)$^+$.

N-(3-Chloro-5-methyl-phenyl)-acetamide. Acetic anhydride (6.7 mL) and 3-chloro-5-methyl-phenylamine (5.0 g, 35 mmol) was mixed and stand for 2.0 h. The reaction mixture was cooled to room temperature to give N-(3-chloro-5-methyl-phenyl)acetamide (5.1 g) as light yellow solids in 79% yield: $^1$H NMR (500 MHz, CDCl$_3$) δ 7.38 (s, 1 H), 7.19 (s, 1 H), 7.12 (s, 1 H), 6.91 (s, 1 H), 2.31 (s, 3 H), 2.16 (s, 3 H).

N-(4-Acetyl-3-chloro-5-methyl-phenyl)-acetamide. A dry CS$_2$ solution (30 mL) containing N-(3-chloro-5-methyl-phenyl)acetamide (5.0 g, 27 mmol) and acetyl chloride (2.9 ml, 40.8 mmol) was slowly mixed with aluminum chloride (9.1 g, 68 mmol). The reaction mixture was heated at reflux for 30 min, cooled to room temperature, and allowed to stand for 4.0 h. The CS$_2$ was decanted and the remaining syrup was poured into icy HCl. The resultant solids were collected, re-dissolved in EtOH, and decolorized with charcoal. The solution was filtered and the filtrate was concentrated under vacuum to give N-(4-acetyl-3-chloro-5-methylphenyl)acetamide (5.2 g) as light yellow solids in 85% yield: $^1$H NMR (500 MHz, CDCl$_3$) δ 7.48 (s, 1 H), 7.26 (s, 1 H), 7.21 (s, 1 H), 2.52 (s, 3 H), 2.24 (s, 3 H), 2.18 (s, 3 H).

1-(4-Amino-2-chloro-6-methylphenyl)ethanone. An ethanol solution (4.0 mL) containing N-(4-acetyl-3-chloro-5-methylphenyl)acetamide (0.53 g, 2.3 mmol) and concentrated hydrochloric acid (1.6 mL) was heated at reflux for 15 h. The solution was added with 10% aqueous NaOH and the resultant solids were collected to give 1-(4-amino-2-chloro-6-methylphenyl)ethanone (0.37 g) as light yellow solids in 88% yield: $^1$H NMR (500 MHz, CDCl$_3$) δ 6.46 (d, J=1.77 Hz, 1 H), 6.34 (s, 1 H), 3.85 (bs, 2 H), 2.49 (s, 3 H), 2.14 (s, 3 H): ESI-MS: m/z 183.4 (M+H)$^+$.

1-(2-Chloro-4-iodo-6-methyl-phenyl)-ethanone. A CH$_3$CN solution (20 mL) containing KI (2.5 g, 15 mmol) and tert-butyl nitrite (2.00 mL, 16.9 mmol) was added with 1-(4-amino-2-chloro-6-methyl-phenyl)ethanone (2.3 g, 12.5 mmol) in CH$_3$CN (13 mL) at −10° C. The reaction mixture was warmed to room temperature and poured into aqueous HCl (20%, 23 mL). The solution was extracted with EtOAc (20 mL), and the organic layer was separated, washed with H$_2$O (23 mL), dried over MgSO₄(s), and concentrated under reduced pressure. The residue was purified by flash column chromatography on silica gel to give 1-(2-chloro-4-iodo-6-methylphenyl)ethanone (1.28 g) as yellow oil in 35% yield: $^1$H NMR (500 MHz, CDCl$_3$) δ 7.58 (s, 1 H), 7.49 (s, 1 H), 2.51 (s, 3 H), 2.21 (s, 3 H).

1-(2-Chloro-4-(4-methoxy-phenoxy)-6-methyl-phenyl)-ethanone To a solution of 1-(2-chloro-4-iodo-6-methylphenyl)ethanone (1.1 g, 3.7 mmol), K$_3$PO$_4$ (1.6 g, 7.4 mmol), and 4-methoxyphenol (0.55 g, 4.44 mmol) in DMF (55 mL) was added tetrabutylammonium bromide (0.12 g, 0.37 mmol) and copper(I) iodide (70 mg, 0.37 mmol). The reaction was heated at reflux for 22 h. The solution was extracted with EtOAc (10 mL), and the organic layer was separated, washed with H$_2$O (11 mL), dried over MgSO₄(s), and concentrated under reduced pressure. The residue was purified by flash column chromatography on silica gel to give 1-(2-chloro-4-(4-methoxyphenoxy)-6-methylphenyl)ethanone as yellow oil in 19% yield: $^1$H NMR (500 MHz, CDCl$_3$) δ 6.97 (m, 2 H), 6.90 (m, 2 H), 6.73 (d, J=2.19 Hz, 1 H), 6.67 (d, J=1.99 Hz, 1 H), 3.81 (s, 3 H), 2.52 (s, 3 H), 2.20 (s, 3 H).

2-Bromo-1-(2-chloro-4-(4-methoxyphenoxy)-6-methylphenyl)ethanone. To a solution of 1-(2-chloro-4-(4-methoxyphenoxy)-6-methylphenyl)ethanone (0.20 g, 0.69 mmol) in acetonitrile (6.0 mL) was added TBABr$_3$ (0.33 g, 0.69 mmol). The reaction was stirred at room temperature for 30 min. The solution was concentrated under reduced pressure, added with water, and extracted with ethyl acetate. The organic layer was washed with brine, dried over anhydrous MgSO₄(s), and concentrated under reduced pressure to give 2-bromo-1-(2,6-dimethyl-4-phenoxyphenyl)ethanone, which was used directly for the next step without further purification.

4-(2-Chloro-4-(4-methoxy-phenoxy)-6-methyl-phenyl)-thiazol-2-ylamine. A mixture of 2-bromo-1-(2,6-dimethyl-4-phenoxyphenyl)ethanone and thiourea (63 mg, 0.83 mmol) in 95% EtOH (3.0 mL) was heated at reflux for 60 min. The solution was concentrated and added with water (50 mL) and saturated aqueous NaHCO$_3$ (5.0 mL). The resultant precipitate was filtered and recrystallized in toluene (30 mL). The solids were filtered and dried under vacuum to give 4-(2-chloro-4-(4-methoxyphenoxy)-6-methylphenyl)thiazol-2-ylamine (0.10 g) as yellow solids in 42% yield: $^1$H NMR (500 MHz, CDCl$_3$) δ 6.98 (m, 2 H), 6.90 (m, 2 H), 6.83 (d, J=2.4 Hz, 1 H), 6.73 (d, J=2.3 Hz, 1 H), 6.41 (s, 1 H), 4.97 (s, 2 H), 3.81 (s, 3 H), 2.16 (s, 3 H).

2-Bromo-1-(2,6-dimethyl-4-(methylthio)phenyl)ethanone. To a solution of 1-(4-(cyclopentyloxy)-2,6-dimethylphenyl)ethanone (3.30 g, 17.0 mmol) in acetonitrile (34.0 mL) was added tetrabutylammoniumtribromide (TBABr$_3$, 8.19 g, 17.0 mmol). The reaction was stirred at room temperature overnight. The solution was concentrated under reduced pressure, mixed with water, and extracted with ethyl acetate. The organic layer was washed with brine, dried over anhydrous MgSO₄(s), and concentrated under reduced pressure to give 2-bromo-1-(2,6-dimethyl-4-(methylthio)phenyl) ethanone (5.2 g), which was used directly for the next step without further purification.

4-(2,6-Dimethyl-4-(methylthio)phenyl)thiazol-2-amine. A mixture of 2-bromo-1-(2,6-dimethyl-4-(methylthio)phenyl)ethanone (4.64 g, 17.0 mmol) and thiourea (1.29 g, 17.0 mmol) in 95% EtOH (24.3 mL) was heated at reflux for 120 min. The solution was concentrated and mixed with water (50 mL) and saturated aqueous Na$_2$CO$_3$ (4.0 mL). The resultant precipitate was filtered and recrystallized in toluene (30 mL). The solids were filtered and dried under vacuum to give 4-(2,6-dimethyl-4 (methylthio)phenyl)thiazol-2-amine (1.9 g) as light yellow solids in 45% yield: $^1$H NMR (500 MHz, CDCl$_3$) δ 6.97 (s, 2 H), 6.26 (s, 1 H), 2.47 (s, 3 H), 2.15 (s, 6 H).

(2-Bromo-1-(2,6-dimethyl-4-(methylsulfonyl)phenyl) ethanone. To a solution of 2-bromo-1-(2,6-dimethyl-4-(methylthio)phenyl)ethanone (4.92 g, 0.653 mol) in CH$_2$Cl$_2$, (36 mL) at 0° C. was added mCPBA (70%, 11.1 g, 1.63 mol). The mixture was stirred at room temperature for 7.0 h. The solution was filtered, and the filtrate was added with saturated aqueous NaHCO3 (50 mL). The organic layer was dried over anhydrous MgSO₄(s) and concentrated under reduced pressure to give 2-bromo-1-(2,6-dimethyl-4-(methylsulfonyl)phenyl)ethanone (7.6 g), which was used directly for the next step without further purification.

4-(2,6-Dimethyl-4-(methylsulfonyl)phenyl)thiazol-2-amine

A mixture of 2-bromo-1-(2,6-dimethyl-4-(methylsulfonyl)phenyl)ethanone (7.60 g, 24.9 mmol) and thiourea (1.90 g, 25.0 mmol) in 95% EtOH (35.6 mL) was heated at reflux for 90 min. The solution was concentrated and mixed with water (100 mL) and saturated aqueous $Na_2CO_3$ (5.0 mL). The resultant precipitate was filtered and recrystallized in toluene (20 mL). The solids were filtered and dried under vacuum to give 4-(2,6-dimethyl-4-(methylsulfonyl)phenyl)thiazol-2-amine (3.28 g) as yellow solids in 47% yield: $^1$H NMR (500 MHz, $CDCl_3$) δ 7.64 (s, 2 H), 6.34 (s, 1 H), 5.19 (m, 1 H), 3.04 (s, 3 H), 2.26 (s, 6 H).

2-Amino-N-(4-(4-(4-methoxyphenoxy)-2,6-dimethylphenyl)thiazol-2-yl)isonicotinamide. A mixture of N-(4-(4-(4-methoxyphenoxy)-2,6-dimethylphenyl)thiazol-2-yl)-2-nitroisonicotinamide (0.20 g, 0.40 mmol) and Pd/C (0.15 g, 10% w/w) in ethanol (10 mL) was stirred under $H_2$ overnight. The reaction was filtered through diatomaceous earth and concentrated under reduced pressure to provide 2-amino-N-(4-(4-(4-methoxyphenoxy)-2,6-dimethylphenyl)thiazol-2-yl)isonicotinamide (0.11 g) as yellow solids in 59% yield: $^1$H NMR (500 MHz, DMSO-$d_6$) δ 7.88-7.89 (m, 1 H), 7.10-7.11 (m, 2 H), 6.95-6.97 (m, 2 H), 6.62 (s, 1 H), 5.76 (s, 1 H), 3.29 (s, 3 H), 2.03 (s, 6 H); ESI-MS: m/z 446.6 (M+H)$^+$.

N-(4-Mesitylthiazol-2-yl)-2-morpholinoisonicotinamide. A mixture of 2-chloro-N-(4-mesitylthiazol-2-yl)isonicotinamide (500.0 mg, 1.4 mmol, 1.0 equiv) and morpholine (1.5 mL, 16.8 mmol, 12 equiv) in methylpyrrolidone (15.0 mL) was stirred at 150° C. for 16 h. The mixture was poured into icy $H_2O$ (20.0 mL), and the resultant solids were filtered to provide N-(4-mesitylthiazol-2-yl)-2-morpholinoisonicotinamide (358.6 mg, 0.90 mmol) as yellow solids in 63% yield: $^1$H NMR (DMSO-$d_6$, 500 MHz) δ 8.30 (d, J=5.1 Hz, 2 H), 7.50 (s, 1 H), 7.22 (d, J=5.1 Hz, 2 H), 7.10 (s, 1H), 6.92 (s, 2 H), 3.70-3.73 (m, 4 H), 3.53-3.55 (m, 4 H), 2.26 (s, 3 H), 2.05 (s, 6 H); ESI-MS: m/z 409.3 (M+H)$^+$.

Exemplary Compounds and Physicochemical Data

N-(4-Mesitylthiazol-2-yl)isonicotinamide (II-1)

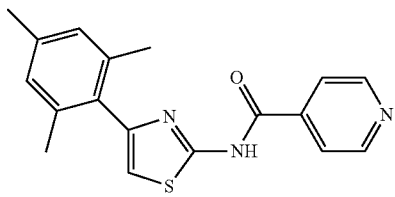 [SMILES: Cc1cc(C)c(-c2csc(NC(=O)c3ccncc3)n2)c(C)c1]

N-(4-Mesitylthiazol-2-yl)isonicotinamide compound II-1

N-(4-Mesitylthiazol-2-yl)isonicotinamide (II-1) Yield: 77%; $^1$H NMR (500 MHz, $CD_3OD$) δ 8.75-8.76 (m, 2 H), 7.96-7.99 (m, 2 H), 6.90-6.92 (m, 3 H), 2.29 (s, 3 H), 2.08 (s, 6 H); ESI-MS: m/z 324.0 (M+H)$^+$.

N-(5-Methyl-4-phenylthiazol-2-yl)isonicotinamide (II-2)

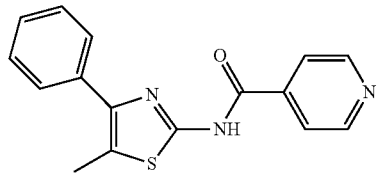

1-(5-Methyl-4-phenylthiazol-2-yl)isonicotinamide compound II-2

N-(5-Methyl-4-phenylthiazol-2-yl)isonicotinamide (II-2) Yield: 77%; $^1$H NMR (500 MHz, $CDCl_3$) δ 11.7 (s, 1 H), 8.61-8.62 (m, 2 H), 7.51-7.53 (m, 2 H), 7.41-7.43 (m, 2 H), 7.26-7.30 (m, 2 H), 7.20-7.22 (m, 1 H), 2.54 (s, 3 H); ESI-MS: m/z 295.3 (M+H)$^+$.

N-(5-Methyl-4-phenylthiazol-2-yl)nicotinamide (II-3)

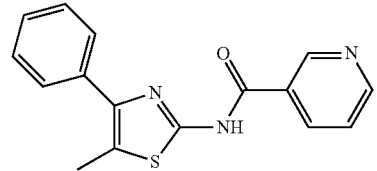 [SMILES: Cc1sc(NC(=O)c2cccnc2)nc1-c1ccccc1]

N-(5-Methyl-4-phenylthiazol-2-yl)nicotinamide compound II-3

N-(5-Methyl-4-phenylthiazol-2-yl)nicotinamide (II-3) Yield: 15%; $^1$H NMR (500 MHz, $CDCl_3$) δ 11.7 (s, 1 H), 9.03 (s, 1 H), 8.68-8.69 (m, 1 H), 8.06-8.08 (m, 1 H), 7.45-7.47 (m, 2H), 7.22-7.31 (m, 4 H), 2.54 (s, 3 H); ESI-MS: m/z 295.9 (M+H)$^+$.

4-Cyano-N-(4-mesitylthiazol-2-yl)benzamide (II-4)

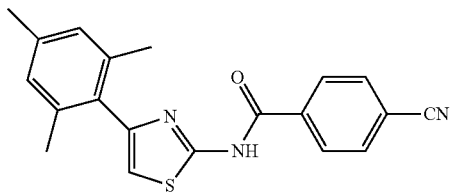 [SMILES: Cc1cc(C)c(-c2csc(NC(=O)c3ccc(C#N)cc3)n2)c(C)c1]

4-Cyano-N-(4-mesitylthiazol-2-yl)benzamide compound I-4

4-Cyano-N-(4-mesitylthiazol-2-yl)benzamide (1-4) Yield: 67%; ¹H NMR (500 MHz, DMSO-d₆) δ 8.23 (d, 2 H), 8.02 (d, 2 H), 7.09 (s, 1 H), 6.92 (s, 2 H), 2.26 (s, 3 H), 2.05 (s, 6 H); ESI-MS: m/z 348.0 (M+H)⁺.

N-(4-mesitylthiazol-2-yl)pyrimidine-4-carboxamide (II-5)

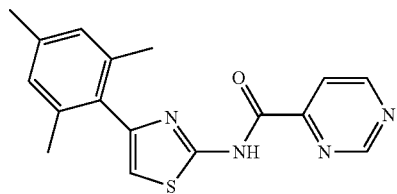 [SMILES: Cc1cc(C)c(-c2csc(NC(=O)c3ccncn3)n2)c(C)c1]

N-(4-mesitylthiazol-2-yl)pyrimidine-4-carboxamide compound II-5

N-(4-mesitylthiazol-2-yl)pyrimidine-4-carboxamide (II-5)
Yield: 62%; ¹H NMR (500 MHz, DMSO-d₆) δ 9.41 (s, 1 H), 9.15 (d, 1 H), 8.14 (d, 1 H), 7.17 (s, 1 H), 6.89 (s, 2 H), 2.25 (s, 3H), 2.03 (s, 6 H); ESI-MS: m/z 325.1 (M+H)⁺.

N-(4-p-Tolylthiazol-2-yl)isonicotinamide (II-6)

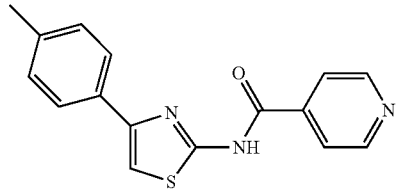 [SMILES: Cc1ccc(-c2csc(NC(=O)c3ccncc3)n2)cc1]

N-(4-p-Tolylthiazol-2-yl)isonicotinamide compound II-6

N-(4-p-Tolylthiazol-2-yl)isonicotinamide (II-6) Yield: 8.6%; ¹H NMR (500 MHz, CDCl₃) δ 8.70 (d, J=5.5 Hz, 2 H), 7.65-7.63 (m, 2 H), 7.60 (d, J=8.0 Hz, 2 H), 7.17 (s, 1 H), 7.14 (d, J=7.5 Hz, 2 H), 2.34 (s, 6 H); ESI-MS: m/z 295.9 (M+H)⁺.

4-Cyano-N-(4-p-tolylthiazol-2-yl)benzamide (II-7)

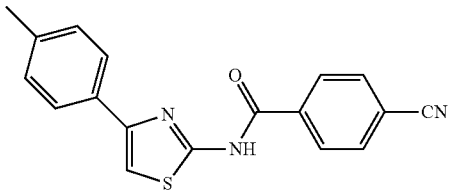 [SMILES: Cc1ccc(-c2csc(NC(=O)c3ccc(C#N)cc3)n2)cc1]

4-Cyano-N-(4-p-tolylthiazol-2-yl)benzamide compound II-7

4-Cyano-N-(4-p-tolylthiazol-2-yl)benzamide (II-7) Yield: 63%; ¹H NMR (500 MHz, CDCl₃) δ 7.89 (d, J=8.5 Hz, 2 H), 7.62 (d, J=8.5 Hz, 2 H), 7.55 (d, J=8.5 Hz, 2 H), 7.17 (s, 1 H), 7.12 (d, J=8.0 Hz, 2 H), 2.34 (s, 6 H); ESI-MS: m/z 317.9 (M−H)⁻.

N-(4-Mesitylthiazol-2-yl)pyridazine-4-carboxamide (II-8)

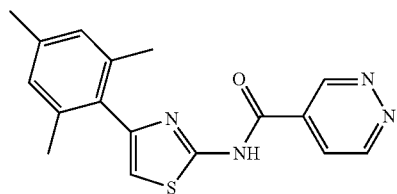

N-(4-Mesitylthiazol-2-yl)pyridazine-4-carboxamide compound II-8

N-(4-Mesitylthiazol-2-yl)pyridazine-4-carboxamide (II-8) Yield: 62%; ¹H NMR (500 MHz, DMSO-d₆) δ 9.72 (s, 1 H), 9.50 (d, 1 H), 8.21 (m, 1 H), 7.13 (s, 1 H), 6.94 (s, 2 H), 2.27 (s, 3H), 2.06 (s, 6 H); EST-MS: m/z 324.5 (M+H)⁺.

N-(4-mesitylthiazol-2-yl)thiazole-5-carboxamide (II-9)

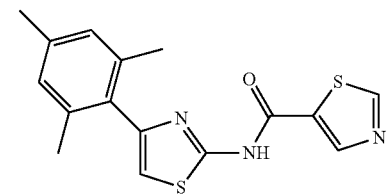 [SMILES: Cc1cc(C)c(-c2csc(NC(=O)c3cncs3)n2)c(C)c1]

N-(4-mesitylthiazol-2-yl)thiazole-5-carboxamide compound II-9

N-(4-mesitylthiazol-2-yl)thiazole-5-carboxamide (II-9) Yield: 40%; ¹H NMR (500 MHz, DMSO-d₆) δ 9.36 (s, 1 H), 8.82 (s, 1 H), 7.06 (s, 1 H), 6.93 (s, 2 H), 2.26 (s, 3 H), 2.05 (s, 6 H); ESI-MS: m/z 329.3 (M+H)⁺.

N-(4-(4-Methoxyphenyl)-5-methylthiazol-2-yl)isonicotinamide (II-10)

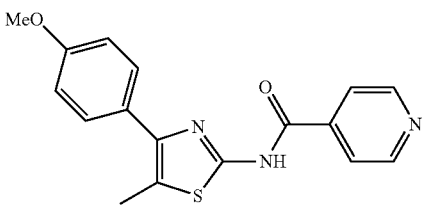 [SMILES: COc1ccc(-c2nc(NC(=O)c3ccncc3)sc2C)cc1]

N-(4-(4-Methoxyphenyl)-5-methylthiazol-2-yl)isonicotinamide compound II-10

N-(4-(4-Methoxyphenyl)-5-methylthiazol-2-yl)isonicotinamide (II-10) Yield: 12%; ¹H NMR (500 MHz, DMSO-d$_6$) δ 12.9 (s, 1 H), 8.80-8.81 (m, 2 H), 7.99-8.00 (m, 2 H), 7.61-7.63 (m, 2 H), 7.02-7.04 (m, 2 H), 3.80 (s, 3 H), 2.49 (s, 3 H); ESI-MS: m/z 326.0 (M+H)$^+$.

N-(4-(2,4,6-Trimethoxyphenyl)thiazol-2-yl)isonicotinamide (II-11)

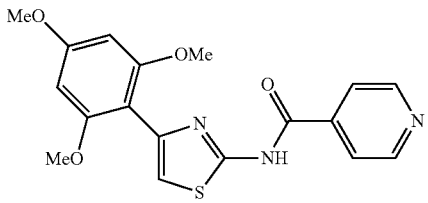 [SMILES: COc1cc(OC)c(-c2csc(NC(=O)c3ccncc3)n2)c(OC)c1]

N-(4-(2,4,6-Trimethoxyphenyl)thiazol-2-yl)isonicotinamide compound II-11

N-(4-(2,4,6-Trimethoxyphenyl)thiazol-2-yl)isonicotinamide (II-11)
Yield: 12%; ¹H NMR (500 MHz, DMSO-d$_6$) δ 13.0 (s, 1 H), 8.78 (s, 2 H), 7.98-8.00 (m, 3 H), 6.98 (s, 1 H), 6.29 (s, 2 H), 3.82 (s, 3 H), 3.68 (s, 3 H); ESI-MS: m/z 369.9 (M–H)$^-$.

N-(4-(4-Methoxyphenyl)thiazol-2-yl)isonicotinamide (II-12)

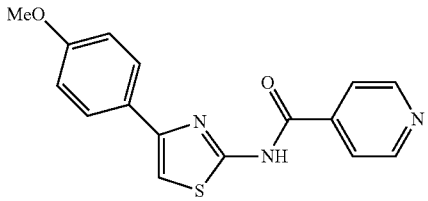

N-(4-(4-Methoxyphenyl)thiazol-2-yl)isonicotinamide compound II-12

N-(4-(4-Methoxyphenyl)thiazol-2-yl)isonicotinamide (II-12) Yield: 50%; ¹H NMR (500 MHz, CDCl$_3$) δ 11.7 (s, 1 H), 8.61-8.62 (m, 2 H), 7.51-7.53 (m, 2 H), 7.41-7.43 (m, 2 H), 7.26-7.30 (m, 2 H), 7.20-7.22 (m, 1 H), 2.54 (s, 3 H); ESI-MS: m/z 310.1 (M–H)$^-$.

N-(4-(2,4-Dimethoxyphenyl)thiazol-2-yl)isonicotinamide (II-13)

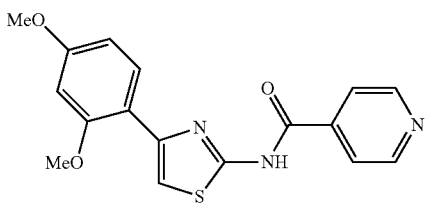 [SMILES: COc1ccc(-c2csc(NC(=O)c3ccncc3)n2)c(OC)c1]

N-(4-(2,4-Dimethoxyphenyl)thiazol-2-yl)isonicotinamide compound II-13

N-(4-(2,4-Dimethoxyphenyl)thiazol-2-yl)isonicotinamide (II-13) Yield: 10%; ¹H NMR (500 MHz, DMSO-d$_6$) δ 12.97 (s, 1 H), 8.81-8.82 (m, 2 H), 8.00-8.07 (m, 3 H), 7.59 (s, 1 H), 6.64-6.68 (m, 2 H), 3.92 (s, 3 H), 3.81 (s, 3 H); ESI-MS: m/z 340.3 (M–H)$^-$.

N-(4-(4-Methoxyphenyl)-5-methylthiazol-2-yl)nicotinamide (II-14)

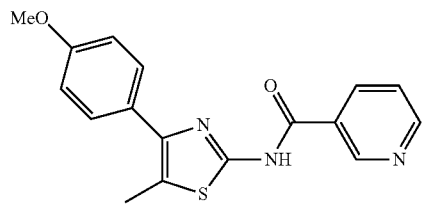 [SMILES: COc1ccc(-c2nc(NC(=O)c3cccnc3)sc2C)cc1]

N-(4-(4-Methoxyphenyl)-5-methylthiazol-2-yl)nicotinamide compound II-14

N-(4-(4-Methoxyphenyl)-5-methylthiazol-2-yl)nicotinamide (II-14) Yield: 74%; ¹H NMR (500 MHz, CDCl$_3$) δ 9.09 (d, 1 H), 8.73-8.72 (m, 1 H), 8.15-8.14 (m, 1 H), 7.42-7.41 (m, 2 H), 7.35 (m, 1 H), 6.87-6.85 (m, 2 H), 3.82 (s, 3 H), 2.51 (s, 6 H): ESI-MS: m/z 325.3 (M+H)$^+$.

N-(4-(2,4-Dimethoxyphenyl)thiazol-2-yl)nicotinamide (II-15)

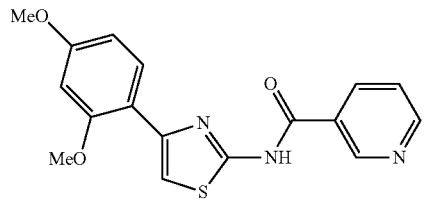

N-(4-(2,4-Dimethoxyphenyl)thiazol-2-yl)nicotinamide compound II-15

N-(4-(2,4-Dimethoxyphenyl)thiazol-2-yl)nicotinamide (II-15) Yield: 87%; ¹H NMR (500 MHz, CDCl$_3$) δ 9.30 (s, 1 H), 8.82-8.81 (m, 1 H), 8.39-8.36 (m, 1 H), 7.80-7.79 (m, 1 H), 7.48-7.46 (m, 1 H), 7.43-7.39 (m, 1 H), 6.58-6.55 (m, 2 H), 3.92 (s, 3 H), 3.86 (s, 3 H); ESI-MS: m/z 341.4 (M+H)$^+$.

N-(4-(4-Methoxyphenyl)-5-methylthiazol-2-yl)picolinamide (II-16)

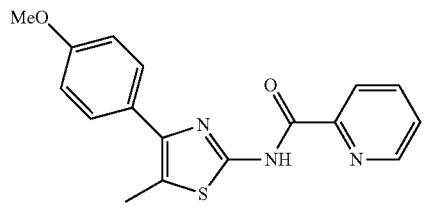

N-(4-(4-Methoxyphenyl)-5-methylthiazol-2-yl)picolinamide compound II-16

N-(4-(4-Methoxyphenyl)-5-methylthiazol-2-yl)picolinamide (II-16)
Yield: >99%; $^1$H NMR (500 MHz, CDCl$_3$) δ 10.55 (s, 1 H), 8.65-8.64 (m, 1 H), 8.30-8.29 (m, 1 H), 7.93 (m, 1 H), 7.60-7.58 (m, 2 H), 7.54-7.53 (m, 1 H), 6.99-6.98 (m, 2 H), 3.86 (s, 3 H), 2.54 (s, 3 H); ESI-MS: m/z 325.6 (M+H)$^+$.

N-(4-(4-Methoxyphenyl)thiazol-2-yl)picolinamide (II-17)

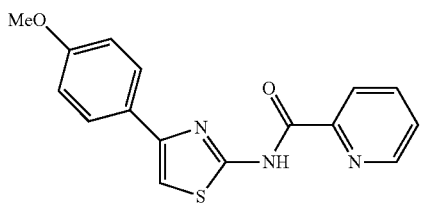

N-(4-(4-Methoxyphenyl)thiazol-2-yl)picolinamide compound II-17

N-(4-(4-Methoxyphenyl)thiazol-2-yl)picolinamide (II-17) Yield: >99%; $^1$H NMR (500 MHz, DMSO-d$_6$) δ 11.98 (s, 1 H), 8.78-8.77 (m, 1 H), 8.19-8.17 (m, 1 H), 8.11-8.09 (m, 1 H), 7.89-7.87 (m, 2 H), 7.74-7.71 (m, 1 H), 7.58 (m, 1 H), 7.00-6.99 (m, 2 H), 3.79 (s, 3 H), 2.54 (s, 3 H); ESI-MS: m/z 310.0 (M−H)$^−$.

N-(4-(2,4-Dimethyoxyphenyl)thiazol-2-yl)picolinamide (II-18)

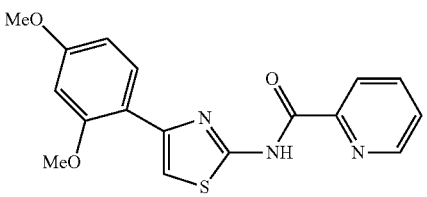 [SMILES: COc1ccc(-c2csc(NC(=O)c3ccccn3)n2)c(OC)c1]

N-(4-(2,4-Dimethoxyphenyl)thiazol-2-yl)picolinamide compound II-18

N-(4-(2,4-Dimethyoxyphenyl)thiazol-2-yl)picolinamide (II-18) Yield: 89%; $^1$H NMR (500 MHz, DMSO-d$_6$) δ 11.9 (s, 1 H), 8.79-8.78 (m, 1 H), 8.20-8.19 (m, 1 H), 8.12-8.07 (m, H), 7.75-7.74 (m, 2 H), 7.61 (s, 1 H), 6.68-6.63 (m, 2 H), 3.92 (s, 3 H), 3.82 (s, 3 H); ESI MS: m/z 340.3 (M−H)$^−$.

N-(5-Methyl-4-phenylthiazol-2-yl)picolinamide (II-19)

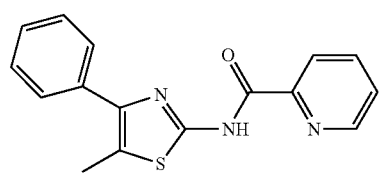 [SMILES: Cc1sc(NC(=O)c2ccccn2)nc1-c1ccccc1]

N-(5-Methyl-4-phenylthiazol-2-yl)picolinamide compound II-19

N-(5-Methyl-4-phenylthiazol-2-yl)picolinamide (II-19) Yield 90%: $^1$H NMR (500 MHz, DMSO-d$_6$) δ 11.9 (s, 1 H), 8.76-8.77 {m, 1 H), 8.18-8.19 (m, 1 H), 8.10 (m, 1 H), 7.69-7.73 (m, 3 H), 7.45-7.48 (m, 1 H), 7.36-7.38 {m, 1 H), 2.50 (s, 3 H); ESI-MS: m/z 295.4 (M+H)$^+$.

N-(4-(3,4,5-Trimethoxyphenyl)thiazol-2-yl)nicotinamide (II-20)

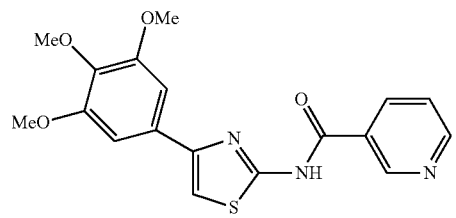 [SMILES: COc1cc(-c2csc(NC(=O)c3cccnc3)n2)cc(OC)c1OC]

N-(4-(3,4,5-Trimethoxyphenyl)thiazol-2-yl)nicotinamide compound II-20

N-(4-(3,4,5-Trimethoxyphenyl)thiazol-2-yl)nicotinamide (II-20) Yield 78%: $^1$H NMR (500 MHz, DMSO-d$_6$) δ 9.24 (d, 1 H), 8.79 (t, 1 H), 8.44 (d, 1 H), 7.75 (s, 1 H), 7.58-7.60 (m, 1 H), 7.26 (s, 2 H), 3.85 (s, 6 H), 3.69 (s, 3 H); ESI-MS: m/z 372.5 (M+H)$^+$.

N-(4-(2-Fluoro-4-methoxyphenyl)thiazol-2-yl)nicotinamide (II-21)

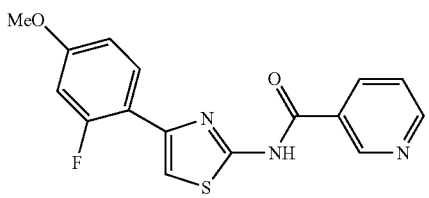 [SMILES: COc1ccc(-c2csc(NC(=O)c3cccnc3)n2)c(F)c1]

N-(4-(2-Fluoro-4-methoxyphenyl)thiazol-2-yl)nicotinamide compound II-21

N-(4-(2-Fluoro-4-methoxyphenyl)thiazol-2-yl)nicotinamide (II-21) Yield 81%: $^1$H NMR (500 MHz, DMSO-d$_6$) δ 9.23 (d, 1 H), 8.80 (t, 1 H), 8.44 (d, 1 H), 8.00-8.03 (m, 1 H), 7.58-7.60 (m, 1 H), 7.46 (d, 1 H), 6.90-6.98 (m, 2 H), 3.82 (s, 3 H); ESI-MS: m/z 330.0 (M+H)$^+$.

N-(4-(2-Fluoro-4-methoxyphenyl)thiazol-2-yl)-3-(4-methoxyphenyl)propanamide (II-22)

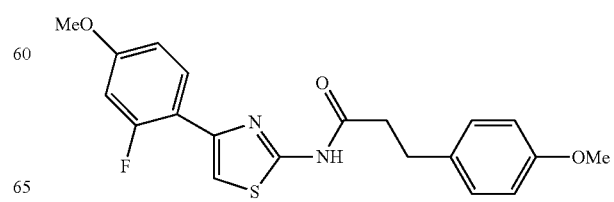

N-(4-(2-Fluoro-4-methoxyphenyl)thiazol-2-yl)-3-(4-methoxyphenyl)propanamide compound II-22

N-(4-(2-Fluoro-4-methoxyphenyl)thiazol-2-yl)-3-(4-methoxyphenyl)propanamide (II-22) Yield 53%: $^1$H NMR (500 MHz, CDCl$_3$) δ 11.01 (s, 1 H), 7.82-7.86 (m, 1 H), 7.27 (d, 1 H), 6.63-6.84 (m, 6 H), 3.80 (s, 3 H), 3.76 (s, 3 H), 2.77 (t, 2 H), 2.29 (t, 3 H); ESI-MS: m/z 387.0 (M+H)$^+$.

N-(4-(2-Fluoro-4-methoxyphenyl)thiazol-2-yl)-3-phenylpropanamide (II-23)

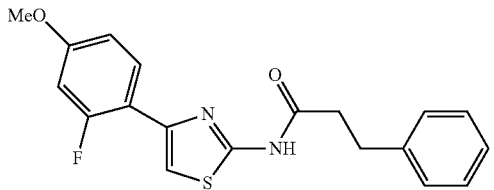 [SMILES: COc1ccc(-c2csc(NC(=O)CCc3ccccc3)n2)c(F)c1]

N-(4-(2-Fluoro-4-methoxyphenyl)thiazol-2-yl)-3-phenylpropanamide compound II-23

N-(4-(2-Fluoro-4-methoxyphenyl)thiazol-2-yl)-3-phenylpropanamide (II-23) Yield 45%: $^1$H NMR (500 MHz, CDCl$_3$) δ 10.87 (s, 1 H), 7.83-7.87 (m, 1 H), 7.15-7.27 (m, 5 H), 7.95 (d, 2 H), 6.62-6.73 (m, 2 H), 3.80 (s, 3 H), 2.86 (t, 2 H), 2.36 (t, 2 H); ESI-MS: m/z 356.0 (M+H)$^+$.

N-(4-(2-Fluoro-4-methoxyphenyl)thiazol-2-yl)picolinamide (II-24)

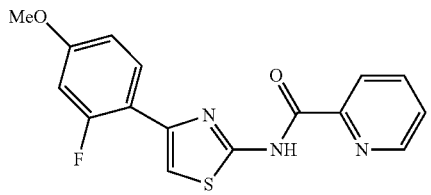 [SMILES: COc1ccc(-c2csc(NC(=O)c3ccccn3)n2)c(F)c1]

N-(4-(2-Fluoro-4-methoxyphenyl)thiazol-2-yl)picolinamide compound II-24

N-(4-(2-Fluoro-4-methoxyphenyl)thiazol-2-yl)picolinamide (II-24) Yield 77%: $^1$H NMR (500 MHz, DMSO-d$_6$) δ 12.04 (s, 1 H), 8.79 (d, 2 H), 8.02-8.21 (m, 3 H), 7.74 (t, 1 H), 7.49 (d, 2 H), 6.90-6.97 (m, 2 H), 3.82 (s, 3 H); ESI-MS: m/z 330.0 (M+H)$^+$.

N-(4-(3,4,5-Trimethoxyphenyl)thiazol-2-yl)picolinamide (II-25)

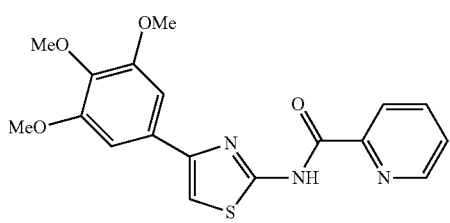 [SMILES: COc1cc(-c2csc(NC(=O)c3ccccn3)n2)cc(OC)c1OC]

N-(4-(3,4,5-Trimethoxyphenyl)thiazol-2-yl)picolinamide compound II-25

N-(4-(3,4,5-Trimethoxyphenyl)thiazol-2-yl)picolinamide (II-25) Yield 75%: $^1$H NMR (500 MHz, DMSO-d$_6$) δ 12.04 (s, 1 H), 8.78 (s, 1 H), 8.18 (d, 1 H), 8.11 (t, 1 H), 7.78-7.82 (m, 2 H), 7.28 (s, 2 H), 3.86 (s, 6 H), 3.69 (s, 3 H); ESI-MS: m/z 372.0 (M+H)$^+$.

N-(4-(2-Fluoro-4-methoxyphenyl)thiazol-2-yl)isonicotinamide II-26

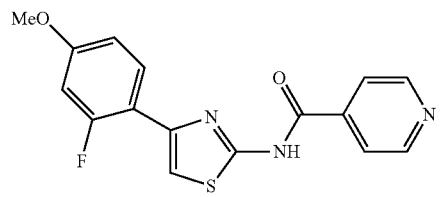 [SMILES: COc1ccc(-c2csc(NC(=O)c3ccncc3)n2)c(F)c1]

N-(4-(2-Fluoro-4-methoxyphenyl)thiazol-2-yl)isonicotinamide compound II-26

N-(4-(2-Fluoro-4-methoxyphenyl)thiazol-2-yl)isonicotinamide II-26
Yield 84%: $^1$H NMR (500 MHz, DMSO-d$_6$) δ 8.82 (d, 2 H), 7.99-8.03 (m, 3 H), 7.48 (d, 1 H), 6.91-6.98 (m, 2 H), 3.83 (s, 3 H); ESI-MS: m/z 330.0 (M+H)$^+$.

N-(4-(3,4,5-Trimethoxyphenyl)thiazol-2-yl)isonicotinamide (II-27)

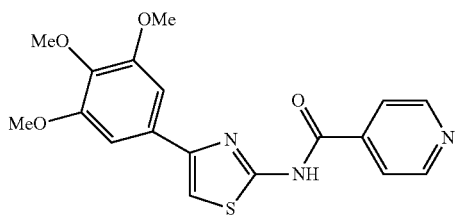 [SMILES: COc1cc(-c2csc(NC(=O)c3ccncc3)n2)cc(OC)c1OC]

N-(4-(3,4,5-Trimethoxyphenyl)thiazol-2-yl)isonicotinamide compound II-27

N-(4-(3,4,5-Trimethoxyphenyl)thiazol-2-yl)isonicotinamide (II-27) Yield 82%: $^1$H NMR (500 MHz, DMSO-d$_6$) δ 8.79 (d, 2 H), 8.00-8.01 (m, 2 H), 7.71 (s, 1 H), 7.26 (s, 2 H), 3.85 (s, 6 H), 3.70 (s, 3 H); ESI-MS: m/z 72.0 (M+H)$^+$.

N-(4-p-Tolylthiazol-2-yl)picolinamide (II-28)

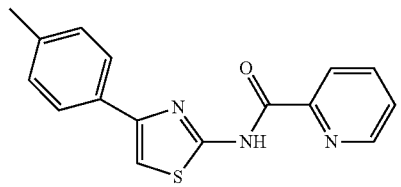 [SMILES: Cc1ccc(-c2csc(NC(=O)c3ccccn3)n2)cc1]

N-(4-p-Tolyithiazol-2-yl)picolinamide compound II-28

N-(4-p-Tolylthiazol-2-yl)picolinamide (II-28)
Yield: 6.7%; $^1$H NMR (500 MHz, CDCl$_3$) δ 10.96 (s, 1 H), 9.11 (s, 1 H), 8.75 (s, 1 H), 8.14 (d, J=8.0 Hz, 1 H), 7.60 (d, J=7.5 Hz, 2H), 7.34 (s, 1 H), 7.15 (s, 1 H), 7.12 (d, J=7.5 Hz, 2 H), 2.33 (s, 6 H); ESI-MS: m/z 293.7 (M–H)$^-$.

N-(4-p-Tolylthiazol-2-yl)nicotinamide (II-29)

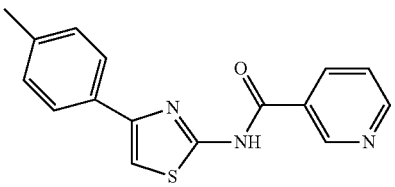 [SMILES: Cc1ccc(-c2csc(NC(=O)c3cccnc3)n2)cc1]

N-(4-p-Tolylthiazol-2-yl)nicotinamide compound II-29

N-(4-p-Tolylthiazol-2-yl)nicotinamide (II-29) Yield: 83%; $^1$H NMR (500 MHz, CDCl$_3$) δ 11.24 (s, 1 H), 8.68 (d, J=4.5 Hz, 1 H), 8.31 (d, J=8.0 Hz, 1 H), 7.95 (m, 1 H), 7.78 (d, J=8.0 Hz, 2 H), 7.54 (m, 1 H), 7.24 (m, 2 H), 7.17 (s, 1 H), 2.39 (s, 6 H); ESI-MS: m/z 295.6 (M+H)$^+$.

4-Cyano-N-(5-methyl-4-p-tolylthiazol-2-yl)benzamide (II-30)

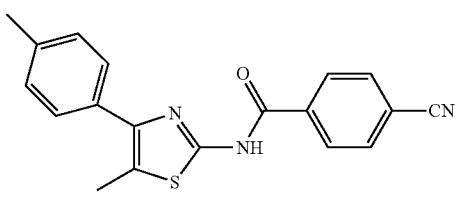 [SMILES: Cc1ccc(-c2nc(NC(=O)c3ccc(C#N)cc3)sc2C)cc1]

4-Cyano-N-(5-methyl-4-p-tolylthiazol-2-yl)benzamide compound II-30

4-Cyano-N-(5-methyl-4-p-tolylthiazol-2-yl)benzamide (II-30) Yield: 36%; $^1$H NMR (500 MHz, CDCl$_3$) δ7.72 (d, J=8.5 Hz, 2 H), 7.49 (d, J=8.5 Hz, 2 H), 7.20 (d, j=8.0 Hz, 2 H), 6.99 (d, J=8.0 Hz, 2 H), 2.51 (s, 3 H), 2.27 (s, 3 H); ESI-MS: m/z 332.0 (M–H)$^-$.

N-(5-Methyl-4-p-tolylthiazol-2-yl)nicotinamide (II-31)

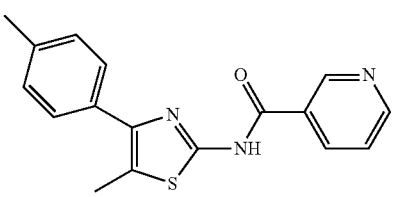 [SMILES: Cc1ccc(-c2nc(NC(=O)c3cccnc3)sc2C)cc1]

N-(5-Methyl-4-p-tolylthiazol-2-yl)nicotinamide compound II-31

N-(5-Methyl-4-p-tolylthiazol-2-yl)nicotinamide (II-31) Yield: 56%; $^1$H NMR (500 MHz, CDCl$_3$) δ 8.99 (s, 1 H), 8.63 (d, J=5.0 Hz, 1 H), 8.01 (d, J=7.9 Hz, 1 H), 7.29-7.21 (m, 3 H), 7.03 (d, J=7.8 Hz, 2 H), 2.49 (s, 3 H), 2.29 (s, 3 H); ESI-MS: m/z 310.3 (M+H)$^+$.

N-(5-Methyl-4-p-tolylthiazol-2-yl)picolinamide (II-32)

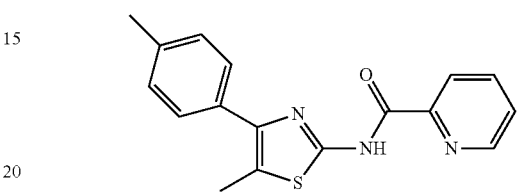

N-(5-Methyl-4-p-tolylthiazol-2-yl)picolinamide compound II-32

N-(5-Methyl-4-p-tolylthiazol-2-yl)picolinamide (II-32) Yield: 79%; $^1$H NMR (500 MHz, CDCl$_3$) δ 11.11 (s, 1 H), 8.64 (d, J=4.5 Hz, 1 H), 8.29 (d, J=7.5 Hz, 1 H), 7.93 (t, J=8.0 Hz, 1 H), 7.55-7.51 (m, 3 H), 7.25 (d, J=7.5 Hz, 1 H), 2.54 (s, 3 H), 2.40 (s, 3 H); ESI-MS: m/z 309.0 (M–H)$^-$.

N-(4-Mesitylthiazol-2-yl)thiophene-3-carboxamide (II-33)

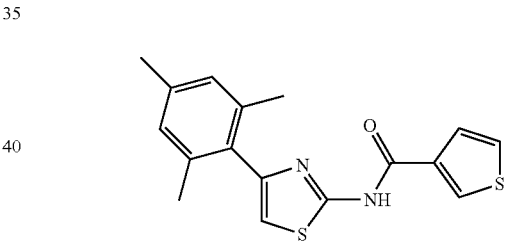

N-(4-Mesitylthiazol-2-yl)thiophene-3-carboxamide compound II-33

N-(4-Mesitylthiazol-2-yl)thiophene-3-carboxamide (II-33) Yield: 37%; $^1$H NMR (500 MHz, DMSO-d$_6$) δ 12.59 (s, 1 H), 8.60 (s, 1 H), 7.69-7.76 (m, 2 H), 7.04 (s, 1 H), 6.93 (s, 2 H), 2.27 (s, 3 H), 2.06 (s, 6 H); ESI-MS: m/z 327.1 (M–H)$^-$.

N-(4-(4-Hydroxy-3-methoxyphenyl)thiazol-2-yl)isonicotinamide (II-34)

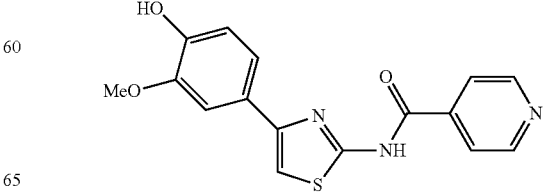

N-(4-(4-Hydroxy-3-methoxyphenyl)thiazol-2-yl) isonicotinamide compound II-34

N-(4-(4-Hydroxy-3-methoxyphenyl)thiazol-2-yl)isonicotinamide (II-34) Yield: 54%; $^1$H NMR (500 MHz, DMSO-d$_6$) δ 8.89 (d, 2H), 8.00 (d, 2H), 7.57 (d, 1H), 7.44-7.46 (m, 1H), 7.26 (d, 1H), 7.11 (s, 3H), 3.81 (s, 3H); ESI-MS: m/z 327.9 (M+H)$^+$.

N-(4-(4-Hydroxy-3-methoxyphenyl)thiazol-2-yl) nicotinamide (II-35)

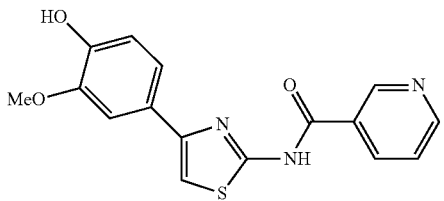

N-(4-(4-Hydroxy-3-methoxyphenyl)thiazol-2-yl) nicotinamide compound II-35

N-(4-(4-Hydroxy-3-methoxyphenyl)thiazol-2-yl)nicotinamide (II-35) Yield: 44%; $^1$H NMR (500 MHz, DMSO-d$_6$) δ 9.25 (s, 1H), 8.91 (s, 1H), 8.45-8.48 (m, 1H), 7.65-7.67 (m, 1H), 7.57 (d, 1H), 7.44-7.46 (m, 1H), 7.26 (d, 1H), 7.10 (s, 2H), 3.81 (s, 3H); ESI-MS: m/z 328.0 (M+H)$^+$.

N-(4-(4-Hydroxy-3-methoxyphenyl)thiazol-2-yl) picolinamide (II-36)

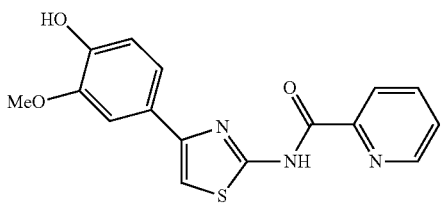 [SMILES: COc1cc(-c2csc(NC(=O)c3ccccn3)n2)ccc1O]

N-(4-(4-Hydroxy-3-methoxyphenyl)thiazol-2-yl) picolinamide compound II-36

N-(4-(4-Hydroxy-3-methoxyphenyl)thiazol-2-yl)picolinamide (II-36) Yield: 37%; $^1$H NMR (500 MHz, DMSO-d$_6$) δ 8.82 (d, 1H), 8.23 (d, 1H), 8.08 (d, 1H), 7.74-7.75 (m, 1H), 7.57 (d, 1H), 7.44-7.46 (m, 1H), 7.23 (d, 1H), 7.10 (s, 2H), 3.81 (s, 3H); ESI-MS: m/z 328.1 (M+H)$^+$.

N-(4-(4-Methoxyphenyl)thiazol-2-yl)nicotinamide (II-37)

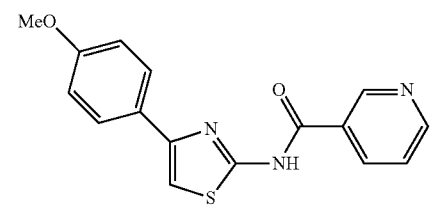

N-(4-(4-Methoxyphenyl)thiazol-2-yl)nicotinamide compound II-37

N-(4-(4-Methoxyphenyl)thiazol-2-yl)nicotinamide (II-37) Yield: 94%; $^1$H NMR (500 MHz, DMSO-d$_6$) δ 12.98 (s, 1H), 9.23 (m, 1H), 8.80 (m, 1H), 8.46-8.43 (m, 1H), 7.90-7.88 (m, 2H), 7.61-7.56 (m, 1H), 7.02-7.00 (m, 2H), 3.80 (s, 3H); ESI-MS: m/z 310.0 (M–H)$^-$.

4-Cyano-N-(5-methyl-4-phenylthiazol-2-yl)benzamide II-38)

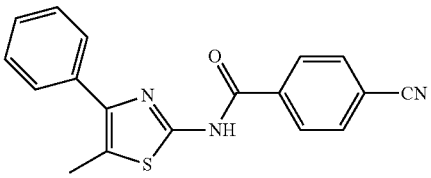 [SMILES: Cc1sc(NC(=O)c2ccc(C#N)cc2)nc1-c1ccccc1]

4-Cyano-N-(5-methyl-4-phenylthiazol-2-yl)benzamide compound II-38

4-Cyano-N-(5-methyl-4-phenylthiazol-2-yl)benzamide (II-38) Yield: 99%; $^1$H NMR (500 MHz, DMSO-d$_6$) δ 7.82-7.80 (m, 2H), 7.60-7.58 (m, 2H), 7.41-7.40 (m, 2H), 7.30-7.29 (m, 2H), 7.22-7.19 (m, 1H), 2.54 (s, 3H); ESI-MS: m/z 320.0 (M+H)$^+$.

4-Cyano-N-(4-(4-methoxyphenyl)-5-methylthiazol-2-yl)benzamide (II-39)

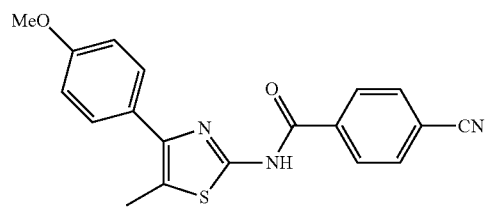 [SMILES: COc1ccc(-c2nc(NC(=O)c3ccc(C#N)cc3)sc2C)cc1]

4-Cyano-N-(4-(4-methoxyphenyl)-5-methylthiazol-2-yl)benzamide compound II-39

4-Cyano-N-(4-(4-methoxyphenyl)-5-methylthiazol-2-yl)benzamide (II-39) Yield: 66%; $^1$H NMR (500 MHz, CD$_3$OD) δ 8.18-8.17 (m, 2H), 7.92-7.90 (m, 2H), 7.60-7.58 (m, 2H), 7.01-7.00 (m, 2H), 3.84 (s, 3H), 2.50 (s, 2H); ESI-MS m/z 349.5 (M+H)$^+$.

N-(4-(2,4-Dimethoxyphenyl)thiazol-2-yl)-2-(2-methoxy enyl)acetamide (II-40)

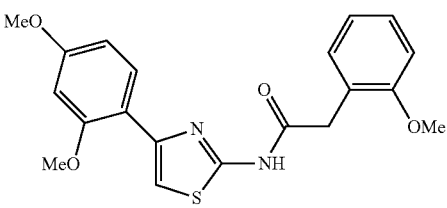 [SMILES: COc1ccc(-c2csc(NC(=O)Cc3ccccc3OC)n2)c(OC)c1]

N-(4-(2,4-Dimethoxyphenyl)thiazol-2-yl)-2-(2-methoxyphenyl)acetamide compound II-40

N-(4-(2,4-Dimethoxyphenyl)thiazol-2-yl)-2-(2-methoxyphenyl)acetamide (II-40)
Yield: 85%; $^1$H NMR (500 MHz, DMSO-$d_6$) δ 12.3 (s, 1 H), 7.99-7.97 (m, 1 H), 7.64 (s, 1 H), 7.24 (m, 1 H), 6.91 (m, 2 H), 6.90 (m, 1 H), 6.66-6.61 (m, 2 H), 3.89 (s, 3 H), 3.80 (s, 3 H), 3.75-3.74 (m, 5H); ESI-MS: m/z 385.1 (M+H)$^+$.

2-(2-Methoxyphenyl)-N-(5-methyl-4-phenylthiazol-2-yl)acetamide (II-41)

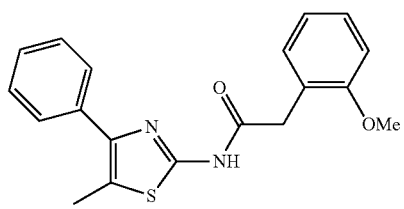 [SMILES: COc1ccccc1CC(=O)Nc1nc(-c2ccccc2)c(C)s1]

2-(2-Methoxyphenyl)-N-(5-methyl-4-phenylthiazol-2-yl)acetamide compound II-41

2-(2-Methoxyphenyl)-N-(5-methyl-4-phenylthiazol-2-yl)acetamide (II-41) Yield: 76%; $^1$H NMR (500 MHz, CDCl$_3$) δ 8.90 (s, 1 H), 7.56-7.55 (m, 2 H), 7.43-7.40 (m, 2 H), 7.34-7.33 (m, 1 H), 7.26-7.22 (m, 1 H), 3.77 (s, 3 H), 3.47 (s, 2 H), 2.49 (s, 3 H); ESI-MS: m/z 339.2 (M+H)$^+$.

N-(4-(4-Methoxy-2,6-dimethylphenyl)thiazol-2-yl)isonicotinamide (II-42)

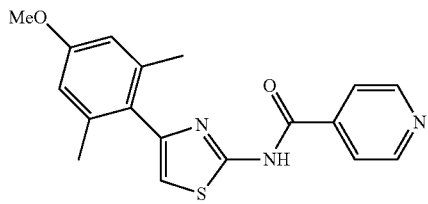

N-(4-(4-Methoxy-2,6-dimethylphenyl)thiazol-2-yl)isonicotinamide compound II-42

N-(4-(4-Methoxy-2,6-dimethylphenyl)thiazol-2-yl)isonicotinamide (II-42) Yield: 69%; $^1$H NMR (500 MHz, CDCl$_3$) δ 8.67 (d, J=5.5 Hz, 2 H), 7.55 (d, J=6.0 Hz, 2 H), 6.77 (s, 1 H), 6.32 (s, 2 H), 3.73 (s, 3 H), 1.91 (s, 6 H); ESI-MS: m/z 340.0 (M+H)$^+$.

N-(5-Methyl-4-p-tolylthiazol-2-yl)isonicotinamide (II-43)

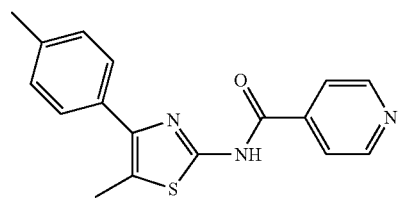 [SMILES: Cc1ccc(-c2nc(NC(=O)c3ccncc3)sc2C)cc1]

N-(5-Methyl-4-p-tolylthiazol-2-yl)isonicotinamide compound II-43

N-(5-Methyl-4-p-tolylthiazol-2-yl)isonicotinamide (II-43) Yield: 54%; $^1$H NMR (500 MHz, CDCl$_3$) δ 8.57 (d, J=5.0 Hz, 2 H), 7.46 (d, J=5.5 Hz, 2 H), 7.25 (d, J=4.5 Hz, 2 H), 7.02 (d, J=7.5 Hz, 2 H), 2.51 (s, 3 H), 2.28 (s, 3 H); ESI-MS: m/z 309.9 (M+H)$^+$.

N-(4-(2,4,6-Trimethylpyridin-3-yl)thiazol-2-yl)isonicotinamide (II-44)

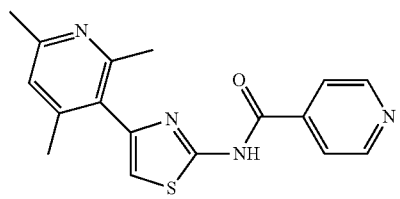 [SMILES: Cc1cc(C)c(-c2csc(NC(=O)c3ccncc3)n2)c(C)n1]

N-(4-(2,4,6-Trimethylpyridin-3-yl)thiazol-2-yl)isonicotinamide compound II-44

N-(4-(2,4,6-Trimethylpyridin-3-yl)thiazol-2-yl)isonicotinamide (II-44) Yield: 51%; $^1$H NMR (500 MHz, CDCl$_3$) δ 8.79 (d, J=5.5 Hz, 2 H), 7.70 (d, J=5.5 Hz, 2 H), 6.86 (s, 1 H), 6.77 (s, 1 H), 2.45 (s, 3 H), 2.23 (s, 3 H), 2.03 (s, 3 H); ESI-MS: m/z 324.5 (M+H)$^+$.

N-(4-(2,4,6-Trimethylpyridin-3-yl)thiazol-2-yl)picolinamide II-45

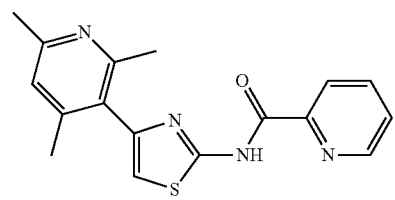 [SMILES: Cc1cc(C)c(-c2csc(NC(=O)c3ccccn3)n2)c(C)n1]

N-(4-(2,4,6-Trimethylpyridin-3-yl)thiazol-2-yl)picolinamide compound II-45

N-(4-(2,4,6-Trimethylpyridin-3-yl)thiazol-2-yl)picolinamide (II-45) Yield: 18%; $^1$H NMR (500 MHz, CDCl$_3$) δ 11.22 {s, 1 H), 8.65 (d, J=4.5 Hz, 1 H), 8.31 (d, J=7.5 Hz, 1 H), 7.96 (t, J=7.5 Hz, 1 H), 7.54 (m, 1 H), 6.92 (s, 1 H), 6.85 {s, 1 H), 2.52 (s, 3 H), 2.37 (s, 3 H), 2.133 (s, 3H); ESI-MS: m/z 325.0 (M+H)$^+$.

N-(4-(2,4,6-Trimethylpyridin-3-yl)thiazol-2-yl)nicotinamide (II-46)

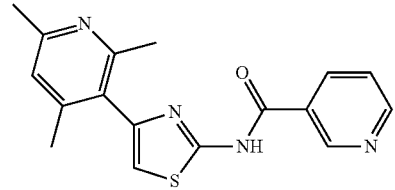 [SMILES: Cc1cc(C)c(-c2csc(NC(=O)c3cccnc3)n2)c(C)n1]

N-(4-(2,4,6-Trimethylpyridin-3-yl)thiazol-2-yl)nicotinamide compound II-46

N-(4-(2,4,6-Trimethylpyridin-3-yl)thiazol-2-yl)nicotinamide (II-46) Yield: 18%; $^1$H NMR (500 MHz, CDCl$_3$) δ 9.11 {s, 1 H), 8.77 (s, 1 H), 8.17 (d, J=7.5 Hz, 1 H), 7.42 (m, 1 H), 6.85 {s, 1 H), 6.78 (s, 1 H), 2.45 (s, 3 H), 2.27 (s, 3 H), 2.02 (s, 3 H); ESI-MS: m/z 325.1 (M+H)$^+$.

N-(4-(4-Hydroxy-3-methoxyphenyl)thiazol-2-yl) pyridazine-4-carboxamide (II-47)

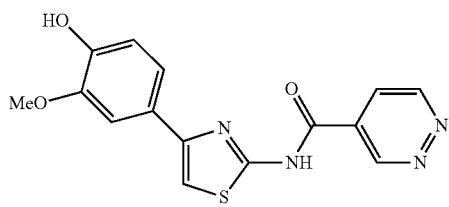 [SMILES: COc1cc(-c2csc(NC(=O)c3ccnnc3)n2)ccc1O]

N-(4-(4-Hydroxy-3-methoxyphenyl)thiazol-2-yl) pyridazine-4-carboxamide compound II-47

N-(4-(4-Hydroxy-3-methoxyphenyl)thiazol-2-yl)pyridazine-4-carboxamide (II-47)
Yield: 54%; $^1$H NMR (500 MHz, DMSO-d$_6$) δ 9.75 (s, 1 H), 9.61 (s, 1 H), 8.28-8.30 (m, 1 H), 7.58 (d, 1 H), 7.46-7.48 (m, 1 H), 7.29 (d, 1 H), 7.12 (s, 3 H), 3.82 (s, 3 H); ESI-MS: m/z 329.4 (M+H)$^+$.

N-(4-(4-Hydroxy-3-methoxyphenyl)thiazol-2-yl) pyrimidine-4-carboxamide (II-48)

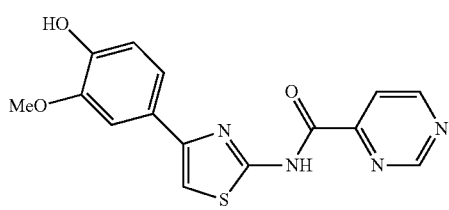

N-(4-(4-Hydroxy-3-methoxyphenyl)thiazol-2-yl) pyrimidine-4-carboxamide compound II-48

N-(4-(4-Hydroxy-3-methoxyphenyl)thiazol-2-yl)pyrimidine-4-carboxamide (II-48)
Yield: 44%; $^1$H NMR (500 MHz, DMSO-d$_6$) δ 9.49 (d, 1 H), 9.19 (d, 1 H), 8.22-8.23 (m, 1 H), 7.58 (d, 1 H), 7.45-7.47 (m, 1 H), 7.27 (d, 1 H), 7.12 (s, 3 H), 3.82 (s, 3 H); ESI-MS: m/z 328.9 (M+H)$^+$.

N-(4-(4-Hydroxy-3-methoxyphenyl)thiazol-2-yl) thiophene-3-carboxamide (II-49)

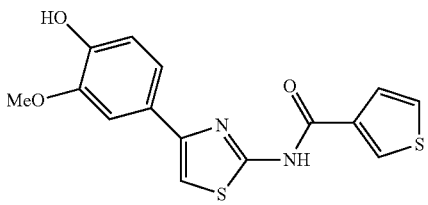

N-(4-(4-Hydroxy-3-methoxyphenyl)thiazol-2-yl) thiophene-3-carboxamide compound II-49

N-(4-(4-Hydroxy-3-methoxyphenyl)thiazol-2-yl) thiophene-3-carboxamide (II-49)
Yield: 37%; $^1$H NMR (500 MHz, DMSO-d$_6$) δ 8.58 (d, 1 H), 7.73-7.75 (m, 1 H), 7.60 (d, 1 H), 7.55 (d, 1 H), 7.42-7.44 (m, 1 H), 7.18 (d, 1 H), 7.09 (m, 3 H); ESI-MS: m/z 333.0 (M+H)$^+$.

N-(4-(4-Hydroxy-3-methoxyphenyl)thiazol-2-yl) thiazole-5-carboxamide (II-50)

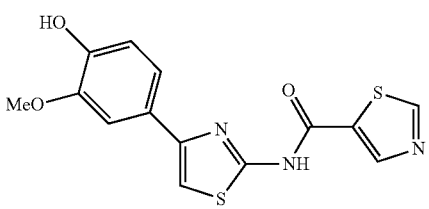 [SMILES: COc1cc(-c2csc(NC(=O)c3cncs3)n2)ccc1O]

N-(4-(4-Hydroxy-3-methoxyphenyl)thiazol-2-yl) thiazole-5-carboxamide compound II-50

N-(4-(4-Hydroxy-3-methoxyphenyl)thiazol-2-yl)thiazole-5-carboxamide (II-50)
Yield: 37%; $^1$H NMR (500 MHz, DMSO-d$_6$) δ 9.49 (s, 1 H), 8.75 (s, 1 H), 7.56 (s, 1 H), 7.43-7.45 (m 1 H), 7.24 (d, 1 H), 7.11 (m, 3 H), 3.81 (s, 3 H); ESI-MS: m/z 333.9 (M+H)$^+$.

N-(4-(4-Hydroxy-3-methoxyphenyl)thiazol-2-yl) furan-3-carboxamide (II-51)

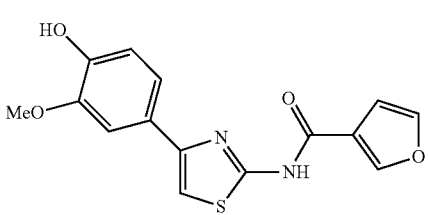 [SMILES: COc1cc(-c2csc(NC(=O)c3ccoc3)n2)ccc1O]

N-(4-(4-Hydroxy-3-methoxyphenyl)thiazol-2-yl) furan-3-carboxamide compound II-51

N-(4-(4-Hydroxy-3-methoxyphenyl)thiazol-2-yl)furan-3-carboxamide (II-51) Yield: 32%; $^1$H NMR (500 MHz, DMSO-$d_6$) δ 8.63 (s, 1 H), 7.91 (s, 1 H), 7.54 (s, 1 H), 7.41-7.43 (m, 1 H), 7.08-7.18 (m, 4 H), 6.93 (s, 1 H), 3.80 (s, 3 H); ESI-MS: m/z 316.9 (M+H)$^+$.

N-(4-(4-Ethoxy-2,6-dimethylphenyl)thiazol-2-yl) isonicotinamide (II-52)

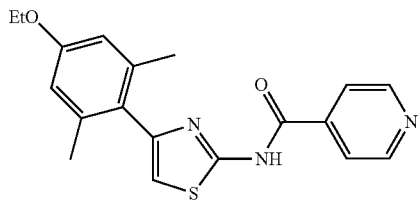 [SMILES: CCOc1cc(C)c(-c2csc(NC(=O)c3ccncc3)n2)c(C)c1]

N-(4-(4-Ethoxy-2,6-dimethylphenyl)thiazol-2-yl) isonicotinamide compound II-52

N-(4-(4-Ethoxy-2,6-dimethylphenyl)thiazol-2-yl)isonicotinamide (II-52) Yield: 88%; $^1$H NMR (500 MHz, CDCl$_3$) δ 8.70 (d, J=6.0 Hz, 2 H), 7.58 (d, J=6.0 Hz, 2 H), 6.78 (s, 1 H), 6.37 (s, 2 H), 3.95 (q, J=7.0 Hz, 2 H), 1.94 (s, 6 H), 1.41 (t, J=7.0 Hz, 3 H); ESI-MS: m/z 353.6 (M+H)$^+$.

N-(4-(3,5-Dimethylbiphenyl-4-yl)thiazol-2-yl)isonicotinamide (II-53)

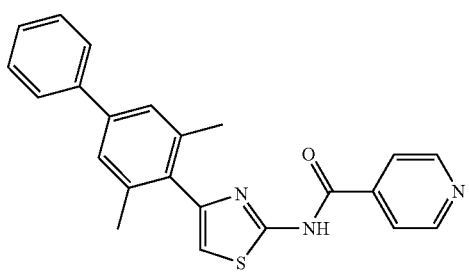 [SMILES: Cc1cc(-c2ccccc2)cc(C)c1-c1csc(NC(=O)c2ccncc2)n1]

N-(4-(3,5-Dimethylbiphenyl-4-yl)thiazol-2-yl)isonicotinamide compound II-53

N-(4-(3,5-Dimethylbiphenyl-4-yl)thiazol-2-yl)isonicotinamide (II-53) Yield: 78%; $^1$H NMR (500 MHz, CDCl$_3$) δ 8.58 (m, 2 H), 7.53-7.44 (m, 5 H), 7.37 (m, 1 H), 7.03 (s, 2 H), 6.86 (s, 1H), 2.02 (s, 6 H); ESI-MS: m/z 385.7 (M+H)$^+$.

2-Chloro-N-(4-(4-methoxyphenyl)thiazol-2-yl)isonicotinamide (II-54)

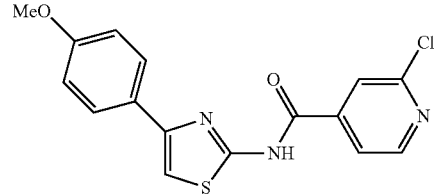 [SMILES: COc1ccc(-c2csc(NC(=O)c3ccnc(Cl)c3)n2)cc1]

2-Chloro-N-(4-(4-methoxyphenyl)thiazol-2-yl)isonicotinamide compound II-54

2-Chloro-N-(4-(4-methoxyphenyl)thiazol-2-yl)isonicotinamide (II-54) Yield: 95%; $^1$H NMR (500 MHz, CDCl$_3$) δ 8.33-8.34 (m, 1 H), 7.47-7.54 (m, 4 H), 7.11 (s, 1 H), 6.79-6.80 (m, 2H), 3.81 (s, 3 H); ESI-MS: m/z 345.7 (M+H)$^+$.

N-(4-(4-Chloro-2,6-dimethylphenyl)thiazol-2-yl) isonicotinamide (II-55)

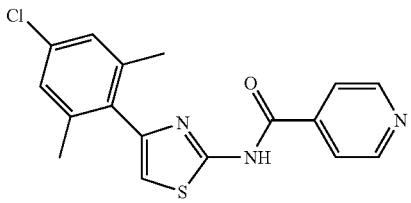 [SMILES: Cc1cc(Cl)cc(C)c1-c1csc(NC(=O)c2ccncc2)n1]

N-(4-(4-Chloro-2,6-dimethylphenyl)thiazol-2-yl) isonicotinamide compound II-55

N-(4-(4-Chloro-2,6-dimethylphenyl)thiazol-2-yl)isonicotinamide (II-55) Yield: 89%; $^1$H NMR (500 MHz, CDCl$_3$) δ 8.76 (d, J=6.0 Hz, 2 H), 7.57 (m, 2 H), 6.81 (m, 3 H), 1.92 (s, 6 H); ESI-MS: m/z 343.8 (M+H)$^+$.

4-Cyano-N-(4-(4-hydroxyphenyl)thiazol-2-yl)benzamide (II-56)

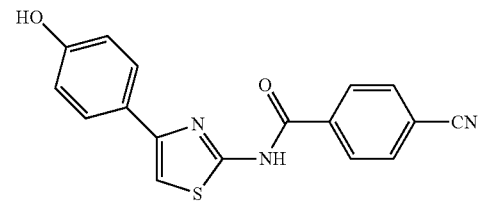 [SMILES: N#Cc1ccc(C(=O)Nc2nc(-c3ccc(O)cc3)cs2)cc1]

4-Cyano-N-(4-(4-hydroxyphenyl)thiazol-2-yl)benzamide compound II-56

4-Cyano-N-(4-(4-hydroxyphenyl)thiazol-2-yl)benzamide (II-56) Yield: 38%; $^1$H NMR (500 MHz, DMSO-$d_6$) δ 8.28 (d, 2 H), 8.09 (d, 2 H), 7.88 (d, 2 H), 7.31 (d, 2 H), 7.04-7.08 (m, 3 H); ESI-MS: m/z 322.0 (M+H)⁺.

N-(4-(4-Hydroxyphenyl)thiazol-2-yl)isonicotinamide (II-57)

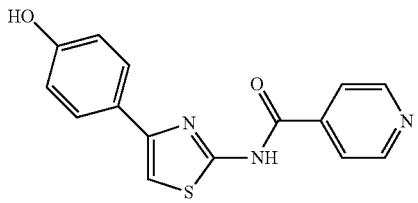 [SMILES: O=C(Nc1nc(-c2ccc(O)cc2)cs1)c1ccncc1]

N-(4-(4-Hydroxyphenyl)thiazol-2-yl)isonicotinamide compound II-57

N-(4-(4-Hydroxyphenyl)thiazol-2-yl)isonicotinamide (II-57) Yield: 75%; $^1$H NMR (500 MHz, DMSO-d$_6$) δ 8.89 (d, 2 H), 8.01-8.06 (m, 2 H), 7.89 (d, 2 H), 7.32 (d, 2 H), 7.05-7.09 (m, 3 H); ESI-MS: m/z 297.6 (M+H)⁺.

N-(4-(4-Hydroxyphenyl)thiazol-2-yl)pyrimidine-4-carboxamide (II-58)

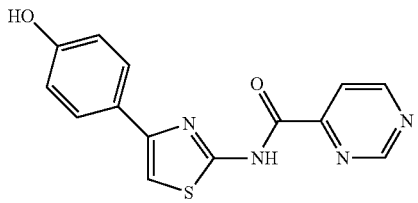

N-(4-(4-Hydroxyphenyl)thiazol-2-yl)pyrimidine-4-carboxamide compound II-58

N-(4-(4-Hydroxyphenyl)thiazol-2-yl)pyrimidine-4-carboxamide (II-58) Yield: 48%; $^1$H NMR (500 MHz, DMSO-d$_6$) δ 9.49 (s, 1 H), 9.18 (d, 1 H), 8.23 (d, 1 H), 7.86-7.91 (m, 2 H), 7.33 (d, 2 H), 7.06-7.09 (m, 3 H); ESI-MS: m/z 192.5 (M−106, aminothiazole).

N-(4-(4-Hydroxyphenyl)thiazol-2-yl)picolinamide (II-59)

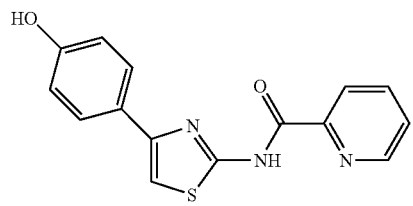 [SMILES: O=C(Nc1nc(-c2ccc(O)cc2)cs1)c1ccccn1]

N-(4-(4-Hydroxyphenyl)thiazol-2-yl)picolinamide compound II-59

N-(4-(4-Hydroxyphenyl)thiazol-2-yl)picolinamide (II-59) Yield: 49%; $^1$H NMR (500 MHz, DMSO-d$_6$) δ 8.82 (d, 1 H), 8.24 (d, 1 H), 8.07-8.1 (m, 1 H), 7.88 (d, 2 H), 7.73-7.75 (m, 1 H), 7.30 (d, 2 H), 7.05-7.08 (m, 3 H); ESI-MS: m/z 297.7 (M+H)⁺.

N-(4-(4-Hydroxyphenyl)thiazol-2-yl)nicotinamide (II-60)

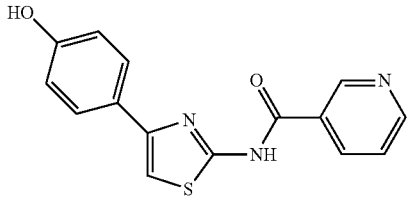

N-(4-(4-Hydroxyphenyl)thiazol-2-yl)nicotinamide compound II-60

N-(4-(4-Hydroxyphenyl)thiazol-2-yl)nicotinamide (II-60) Yield: 49%; $^1$H NMR (500 MHz, DMSO-d$_6$) δ 9.26 (d, 1 H), 8.91 (d, 1 H), 8.47 (d, 1 H), 7.89 (d, 2 H), 7.65-7.67 (m, 1 H), 7.32 (d, 2 H), 7.05-7.08 (m, 3 H); ESI-MS: m/z 297.6 (M+H)⁺.

4-Cyano-N-(4-(4-hydroxy-2-methylphenyl)thiazol-2-yl)benzamide (II-61)

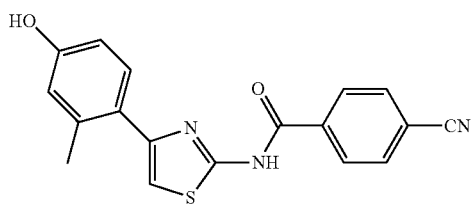 [SMILES: Cc1cc(O)ccc1-c1csc(NC(=O)c2ccc(C#N)cc2)n1]

4-Cyano-N-(4-(4-hydroxy-2-methylphenyl)thiazol-2-yl)benzamide compound II-61

4-Cyano-N-(4-(4-hydroxy-2-methylphenyl)thiazol-2-yl)benzamide (II-61) Yield: 48%; $^1$H NMR (500 MHz, DMSO-d$_6$) δ 8.24-8.30 (m, 2 H), 8.04-8.11 (m, 2 H), 7.63 (d, 1 H), 7.00-7.20 (m, 4 H), 6.67 (s, 1 H); ESI-MS: m/z 335.7 (M+H)⁺.

N-(4-(3,5-Difluoro-4-methoxyphenyl)thiazol-2-yl)isonicotinamide (II-62)

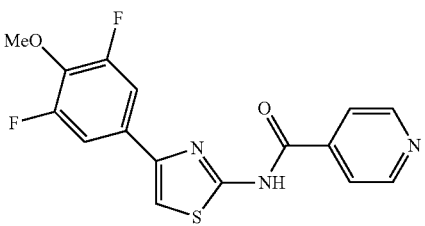 [SMILES: COc1c(F)cc(-c2csc(NC(=O)c3ccncc3)n2)cc1F]

N-(4-(3,5-Difluoro-4-methoxyphenyl)thiazol-2-yl)isonicotinamide compound II-62

N-(4-(3,5-Difluoro-4-methoxyphenyl)thiazol-2-yl)isonicotinamide (II-62) Yield: 67%; $^1$H NMR (DMSO-d$_6$, 500 MHz) δ 13.10 (s, 1 H), 8.82 (d, J=5.6 Hz, 2 H), 8.00 (d, J=5.6 Hz, 2 H), 7.88 (s, 1 H), 7.70-7.72 (m, 2 H), 3.96 (s, 3 H); ESI-MS m/z 348.0 (M+H)⁺.

2-Chloro-N-(4-(3-fluoro-4-methoxyphenyl)thiazol-2-yl)isonicotinamide (II-63)

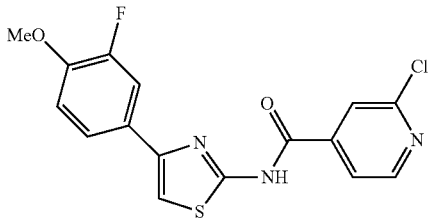 [SMILES: COc1ccc(-c2csc(NC(=O)c3ccnc(Cl)c3)n2)cc1F]

2-Chloro-N-(4-(3-fluoro-4-methoxyphenyl)thiazol-2-yl)isonicotinamide compound II-63

2-Chloro-N-(4-(3-fluoro-4-methoxyphenyl)thiazol-2-yl)isonicotinamide (II-63)
Yield: 83%; $^1$H NMR (500 MHz, CDCl$_3$) δ 8.52-8.53 (m, 1 H), 7.69-7.70 (m, 1 H), 7.59-7.60 (m, 1H), 7.28-7.47 (m, 2 H), 7.16 (s, 1 H), 6.93-6.97 (m, 1 H), 3.93 (s, 3 H); ESI-MS: m/z 363.7 (M+H)$^+$.

2-Chloro-N-(4-mesitylthiazol-2-yl)isonicotinamide (II-64)

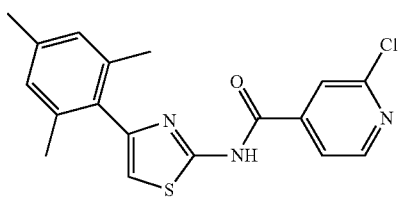 [SMILES: Cc1cc(C)c(-c2csc(NC(=O)c3ccnc(Cl)c3)n2)c(C)c1]

2-Chloro-N-(4-mesitylthiazol-2-yl)isonicotinamide compound II-64

2-Chloro-N-(4-mesitylthiazol-2-yl)isonicotinamide (II-64) Yield: 87%; $^1$H NMR (500 MHz, CDCl$_3$) δ 8.49-8.50 (m, 1 H), 7.74 (m, 1 H), 7.62 (m, 1 H), 6.83 (s, 1 H), 6.72 (m, 2 H), 2.26 (s, 3 H), 1.97 (s, 6 H); ESI-MS: m/z 357.7 (M+H)$^+$.

2-Chloro-N-(4-(4-methoxy-2,6-dimethylphenyl)thiazol-2-yl)isonicotinamide (II-65)

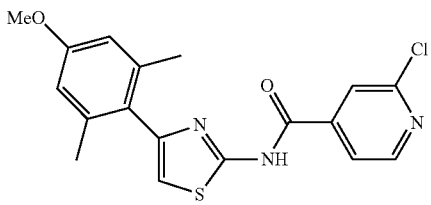 [SMILES: COc1cc(C)c(-c2csc(NC(=O)c3ccnc(Cl)c3)n2)c(C)c1]

2-Chloro-N-(4-(4-methoxy-2,6-dimethylphenyl)thiazol-2-yl)isonicotinamide compound II-65

2-Chloro-N-(4-(4-methoxy-2,6-dimethylphenyl)thiazol-2-yl)isonicotinamide (II-65)
Yield: 63%; $^1$H NMR (500 MHz, CDCl$_3$) δ 8.60-8.61 (m, 1 H), 7.91-7.96 (m, 2 H), 6.87 (s, 1 H), 6.58 (m, 2 H), 3.81 (s, 3 H), 2.11 (s, 6 H); ESI-MS: m/z 373.9 (M+H)$^+$.

2-Chloro-N-(4-(4-ethoxy-2,6-dimethylphenyl)thiazol-2-yl)isonicotinamide (II-66)

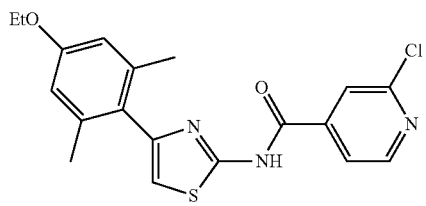 [SMILES: CCOc1cc(C)c(-c2csc(NC(=O)c3ccnc(Cl)c3)n2)c(C)c1]

2-Chloro-N-(4-(4-ethoxy-2,6-dimethylphenyl)thiazol-2-yl)isonicotinamide compound II-66

2-Chloro-N-(4-(4-ethoxy-2,6-dimethylphenyl)thiazol-2-yl)isonicotinamide (II-66)
Yield: 95%; $^1$H NMR (500 MHz, CDCl$_3$) δ 8.53-8.54 (m, 1 H), 7.74-7.84 (m, 2 H), 6.83 (s, 1 H), 6.48 (m, 2 H), 3.98-4.02 (m, 2 H), 2.01 (s, 6 H), 1.41-1.44 (m, 3 H); ESI-MS: m/z 387.9 (M+H)$^+$.

1-(4-(4-Methoxy-2,6-dimethylphenyl)thiazol-2-yl)-3-(pyridin-4-yl)urea (II-67)

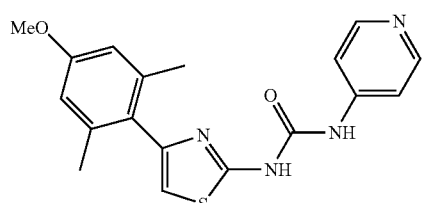

1-(4-(4-Methoxy-2,6-dimethylphenyl)thiazol-2-yl)-3-(pyridin-4-yl)urea compound II-67

1-(4-(4-Methoxy-2,6-dimethylphenyl)thiazol-2-yl)-3-(pyridin-4-yl)urea (II-67) Yield: 40%; $^1$H NMR (500 MHz, DMSO-d$_6$) δ 10.49 (s, 1 H), 8.54 (d, J=6.5 Hz, 2 H), 7.94 (s, 2 H), 6.88 (s, 1 H), 6.74 (s, 2 H), 3.76 (s, 3 H), 2.10 (s, 6 H); ESI-MS: m/z 354.8 (M+H)$^+$.

N-(3,5-Dimethyl-4-(2-(3-pyridin-4-ylureido)thiazol-4-yl)phenyl)acetamide (II-68)

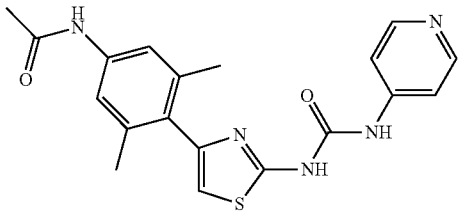 [SMILES: CC(=O)Nc1cc(C)c(-c2csc(NC(=O)Nc3ccncc3)n2)c(C)c1]

N-(3,5-Dimethyl-4-(2-(3-pyridin-4-ylureido)thiazol-4-yl)phenyl)acetamide compound II-68

N-(3,5-Dimethyl-4-(2-(3-pyridin-4-ylureido)thiazol-4-yl)phenyl)acetamide (II-68)
Yield: 73%; $^1$H NMR (500 MHz, DMSO-$d_6$) δ 9.87 (s, 1 H), 9.40 (s, 1 H), 8.39 (d, J=6.0 Hz, 2 H), 7.49 (d, J=6.5 Hz, 2 H), 7.32 (s, 2 H), 6.92 (s, 1 H), 2.06 (s, 6 H), 2.04 (s, 3 H); ESI-MS: m/z 381.8 (M+H)$^+$.

2-Fluoro-N-(4-(4-methoxy-2,6-dimethylphenyl)thiazol-2-yl)isonicotinamide (II-69)

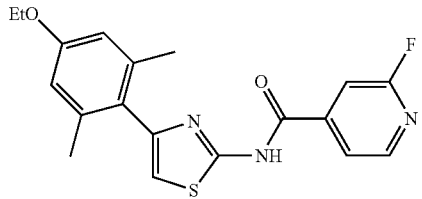 [SMILES: CCOc1cc(C)c(-c2csc(NC(=O)c3ccnc(F)c3)n2)c(C)c1]

2-Fluoro-N-(4-(4-methoxy-2,6-dimethylphenyl)thiazol-2-yl)isonicotinamide compound II-69

2-Fluoro-N-(4-(4-methoxy-2,6-dimethylphenyl)thiazol-2-yl)isonicotinamide (II-69)
Yield: 68%; $^1$H NMR (500 MHz, CDCl$_3$) δ 8.36-8.38 (m, 1 H), 7.72 (s, 1 H), 7.42 (s, 1 H), 6.84 (s, 1H), 6.48 (s, 2 H), 3.78 (s, 3 H), 2.03 (s, 6 H); ESI-MS: m/z 357.5 (M+H)$^+$.

N-(4-(4-Ethoxy-2,6-dimethylphenyl)thiazol-2-yl)-2-fluoroisonicotinamide (II-70)

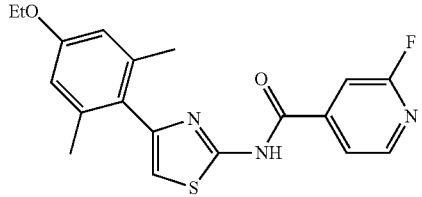 [SMILES: CCOc1cc(C)c(-c2csc(NC(=O)c3ccnc(F)c3)n2)c(C)c1]

N-(4-(4-Ethoxy-2,6-dimethylphenyl)thiazol-2-yl)-2-fluoroisonicotinamide compound II-70

N-(4-(4-Ethoxy-2,6-dimethylphenyl)thiazol-2-yl)-2-fluoroisonicotinamide (II-70)
Yield: 94%; $^1$H NMR (500 MHz, CDCl$_3$) δ 8.39-8.40 (m, 1 H), 7.78 (s, 1 H), 7.48 (s, 1 H), 6.85 (s, 1H), 6.50 (s, 2 H), 3.98-4.01 (q, 2 H), 2.05 (s, 6 H), 1.42-1.44 (t, 3 H); ESI-MS: m/z 371.8 (M+H)$^+$.

4-(Mesitylthiazol-2-ylcarbamoyl)pyridine 1-oxide (II-71)

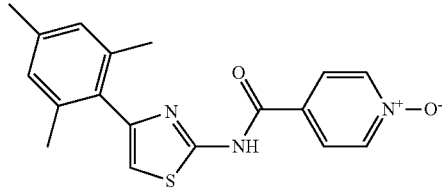 [SMILES: Cc1cc(C)c(-c2csc(NC(=O)c3cc[n+]([O-])cc3)n2)c(C)c1]

4-(4-Mesitylthiazol-2-ylcarbamoyl)pyridine 1-oxide compound II-71

4-(4-Mesitylthiazol-2-ylcarbamoyl)pyridine 1-oxide (II-71) Yield: 75%; $^1$H NMR (500 MHz, CDCl$_3$) δ 8.15-8.16 (d, 2 H), 7.78-7.79 (d, 2 H), 6.83 (s, 1 H), 6.80 (s, 2 H), 2.23 (s, 3 H), 2.01 (s, 6 H); ESI-MS: m/z 340.1 (M+H)$^+$.

4-(4-(4-Methoxy-2,6-dimethylphenyl)thiazol-2-ylcarbamoyl)pyridine 1-oxide (II-72)

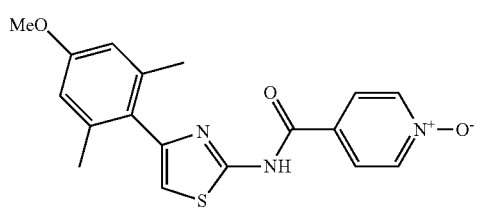 [SMILES: COc1cc(C)c(-c2csc(NC(=O)c3cc[n+]([O-])cc3)n2)c(C)c1]

4-(4-(4-Methoxy-2,6-dimethylphenyl)thiazol-2-ylcarbamoyl)pyridine 1-oxide compound II-72

4-(4-(4-Methoxy-2,6-dimethylphenyl)thiazol-2-ylcarbamoyl)pyridine 1-oxide (II-72)
Yield: 43%; $^1$H NMR (500 MHz, CDCl$_3$) δ 8.23 (s, 2 H), 8.04 (s, 2 H), 6.85 (s, 1 H), 6.60 (s, 2 H), 3.80 (s, 3 H), 2.12 (s, 6 H); ESI-MS: m/z 355.8 (M+H)$^+$.

N-(4-(2,4,6-Triisopropylphenyl)thiazol-2-yl)isonicolinamide (II-73)

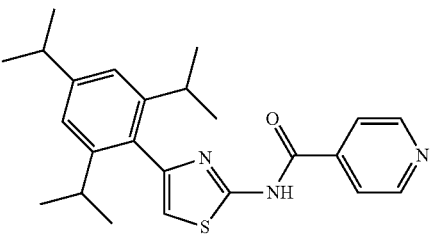

N-(4-(2,4,6-Triisopropylphenyl)thiazol-2-yl)isonicotinamide compound II-73

N-(4-(2,4,6-Triisopropylphenyl)thiazol-2-yl)isonicolinamide (II-73) Yield: 62%; $^1$H NMR (500 MHz, CDCl$_3$) δ 8.83 (d, J=5.5 Hz, 2 H), 7.83 (d, J=6.0 Hz, 2 H), 7.06 (s, 2 H), 6.82 (s, 1 H), 2.94 (m, 1 H), 2.64 (m, 2 H), 1.29 (d, J=7.0 Hz, 6 H), 1.13 (d, J=7.0 Hz, 12 H); ESI-MS: m/z 407.9 (M+H)$^+$.

N-(4-(4-Acetamido-2,6-dimethylphenyl)thiazol-2-yl)isonicotinamide (II-74)

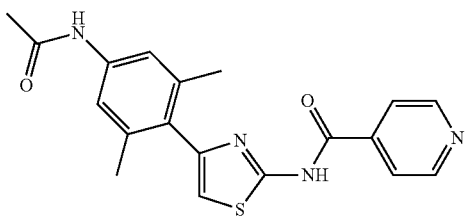 [SMILES: CC(=O)Nc1cc(C)c(-c2csc(NC(=O)c3ccncc3)n2)c(C)c1]

N-(4-(4-Acetamido-2,6-dimethylphenyl)thiazol-2-yl)isonicotinamide compound II-74

N-(4-(4-Acetamido-2,6-dimethylphenyl)thiazol-2-yl)isonicotinamide (II-74) Yield: 39%; $^1$H NMR (500 MHz, DMSO-$d_6$) δ 13.03 (s, 1 H), 9.86 (s, 1 H), 8.80 (d, J=5.5 Hz, 2 H), 7.99 (d, J=5.5 Hz, 2 H), 7.34 (s, 2 H), 7.13 (s, 1 H), 2.06 (s, 6 H); ESI-MS: m/z 385.7 (M+H)$^+$.

N-(4-(4-Methoxy-2,6-dimethylphenyl)thiazol-2-yl)thiazole-5-carboxamide (II-75)

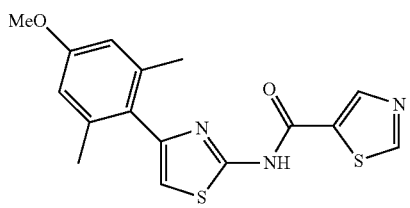 [SMILES: COc1cc(C)c(-c2csc(NC(=O)c3cncs3)n2)c(C)c1]

N-(4-(4-Methoxy-2,6-dimethylphenyl)thiazol-2-yl)thiazole-5-carboxamide compound II-75

N-(4-(4-Methoxy-2,6-dimethylphenyl)thiazol-2-yl)thiazole-5-carboxamide (II-75)
Yield: 18%; $^1$H NMR (500 MHz, CDCl$_3$) δ 9.01 (s, 1 H), 8.66 (s, 1 H), 6.82 (s, 1 H), 6.59 (s, 2 H), 3.81 (s, 3 H), 2.13 (s, 6 H); ESI-MS: m/z 345.6 (M+H)$^+$.

N-(4-(2,4,6-Trifluorophenyl)thiazol-2-yl)isonicotinamide (II-76)

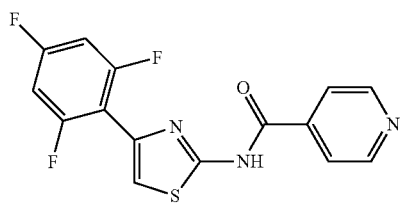 [SMILES: O=C(Nc1nc(-c2c(F)cc(F)cc2F)cs1)c1ccncc1]

N-(4-(2,4,6-Trifluorophenyl)thiazol-2-yl)isonicotinamide compound II-76

N-(4-(2,4,6-Trifluorophenyl)thiazol-2-yl)isonicotinamide (II-76) Yield: 46%; $^1$H NMR (500 MHz, CDCl$_3$) δ 8.78-8.79 (m, 2 H), 7.73-7.74 (m, 2 H), 7.26-7.28 (m, 1 H), 6.76-6.79 (m, 1 H), 6.67-6.70 (m, 2 H); ESI-MS: m/z 335.5 (M+H)$^+$.

3-Fluoro-N-(4-mesitylthiazol-2-yl)isonicotinamide (II-77)

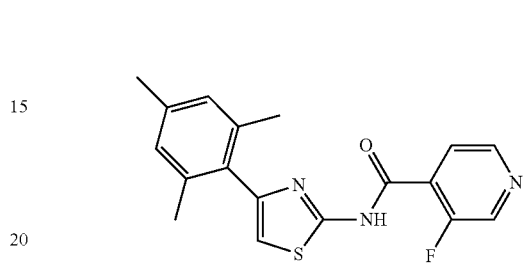

3-Fluoro-N-(4-mesitylthiazol-2-yl)isonicotinamide compound II-77

3-Fluoro-N-(4-mesitylthiazol-2-yl)isonicotinamide (II-77) Yield: 23%; $^1$H NMR (500 MHz, CDCl$_3$) δ 11.32 (s, 1 H), 8.57 (m, 2 H), 7.80 (t, J=5.5 Hz, 1 H), 6.80 (s, 1 H), 6.71 (s, 2 H), 2.23 (s, 3 H), 1.96 (s, 6 H); ESI-MS: m/z 341.9 (M+H)$^+$.

N-(4-(2,6-Difluoro-4-methoxyphenyl)thiazol-2-yl)isonicotinamide (II-78)

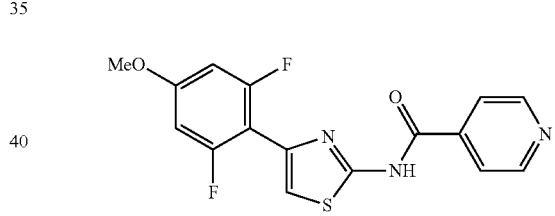

N-(4-(2,6-Difluoro-4-methoxyphenyl)thiazol-2-yl)isonicotinamide compound II-78

N-(4-(2,6-Difluoro-4-methoxyphenyl)thiazol-2-yl)isonicotinamide (II-78) Yield: 49%; $^1$H NMR (500 MHz, DMSO-$d_6$) δ 13.13 (s, 1 H), 8.81 (d, J=5.9 Hz, 2 H), 8.00 (d, J=5.9 Hz, 2 H), 7.46 (s, 1 H), 6.86-6.88 (m, 2 H), 3.83 (s, 3 H); ESI-MS: m/z 348.7 (M+H)$^+$.

N-(4-(2,6-Dimethyl-4-phenoxyphenyl)thiazol-2-yl)isonicotinamide (II-79)

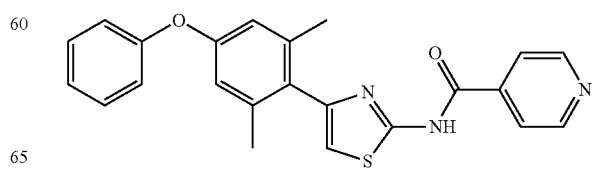

N-(4-(2,6-Dimethyl-4-phenoxyphenyl)thiazol-2-yl)isonicotinamide compound II-79

N-(4-(2,6-Dimethyl-4-phenoxyphenyl)thiazol-2-yl)isonicotinamide (II-79) Yield: 30%; $^1$H NMR (500 MHz, CDCl$_3$) δ 8.81 (d, J=5.5 Hz, 2 H), 7.99 (d, J=5.5 Hz, 2 H), 7.41 (t, J=8.0 Hz, 2 H), 7.19 (s, 1 H), 7.15 (t, J=7.5 Hz, 1 H), 7.04 (d, J=8.2 Hz, 2 H), 6.78 (s, 2 H), 2.07 (s, 6H); ESI-MS: m/z 401.8 (M+H)$^+$.

3-Chloro-N-(4-mesitylthiazol-2-yl)isonicotinamide (II-80)

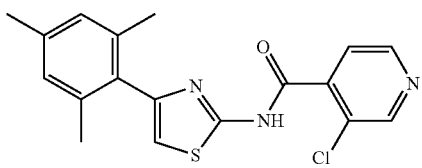 [SMILES: Cc1cc(C)c(-c2csc(NC(=O)c3ccncc3Cl)n2)c(C)c1]

3-Chloro-N-(4-mesitylthiazol-2-yl)isonicotinamide compound II-80

3-Chloro-N-(4-mesitylthiazol-2-yl)isonicotinamide (II-80) Yield: 21%; $^1$H NMR (500 MHz, CDCl$_3$) δ 8.68 (s, 1 H), 8.59-8.60 (m, 1 H), 7.54-7.55 (m, 1 H), 6.81-6.83 (m, 2 H), 2.30 (s, 3 H), 2.01 (s, 6 H); ESI-MS: m/z 357.8 (M+H)$^+$.

2-Chloro-N-(4-mesitylthiazol-2-yl)isonicotinamide (II-81)

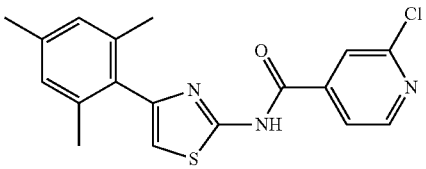 [SMILES: Cc1cc(C)c(-c2csc(NC(=O)c3ccnc(Cl)c3)n2)c(C)c1]

2-Chloro-N-(4-mesitylthiazol-2-yl)isonicotinamide compound II-81

2-Chloro-N-(4-mesitylthiazol-2-yl)isonicotinamide (II-81) Yield: 42%; $^1$H NMR (500 MHz, DMSO-d$_6$) δ 8.63-8.64 (m, 1 H), 8.11 (s, 1 H), 7.98-7.99 (m, 1 H), 7.12 (s, 1 H), 6.93 (m, 2 H), 2.50 (s, 3 H), 2.05 (s, 6 H); ESI-MS: m/z 357.9 (M+H)$^+$.

N-(4-(4-Isopropoxy-2,6-dimethylphenyl)thiazol-2-yl)isonicotinamide (II-82)

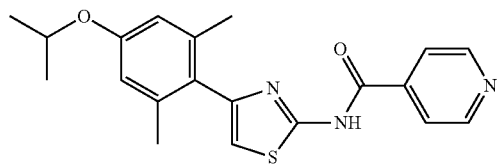 [SMILES: Cc1cc(OC(C)C)cc(C)c1-c1csc(NC(=O)c2ccncc2)n1]

N-(4-(4-Isopropoxy-2,6-dimethylphenyl)thiazol-2-yl)isonicotinamide compound II-82

N-(4-(4-Isopropoxy-2,6-dimethylphenyl)thiazol-2-yl)isonicotinamide (II-82) Yield: 80%; $^1$H NMR (500 MHz, CDCl$_3$) δ 8.67 (d, J=6.0 Hz, 2 H), 7.55 (d, J=6.0 Hz, 2 H), 6.77 (s, 1H), 6.30 (s, 2 H), 4.43 (m, 1 H), 1.89 (s, 6 H), 1.31 (d, J=6.0 Hz, 6 H); ESI-MS: m/z 368.1 (M+H)$^+$.

N-(4-(4-(Cyclopentyloxy)-2,6-dimethylphenyl)thiazol-2-yl)isonicotinamide (II-85)

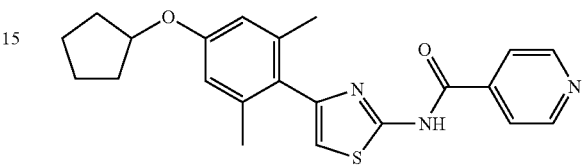

N-(4-(4-(Cyclopentyloxy)-2,6-dimethylphenyl)thiazol-2-yl)isonicotinamide compound II-85

N-(4-(4-(Cyclopentyloxy)-2,6-dimethylphenyl)thiazol-2-yl)isonicotinamide (II-85)
Yield: 62%; $^1$H NMR (500 Hz, CDCl$_3$) δ 8.71 (d, J=6.0 Hz, 2 H), 7.60 (d, J=6.0 Hz, 2 H), 6.78 (s, 1 H), 6.37 (s, 2 H), 4.68 (m, 1 H), 1.95 (s, 6 H), 1.80-1.92 (m, 6 H), 0.85 (m, 2 H); ESI-MS: m/z 394.1 (M+H)$^+$.

N-(4-Mesitylthiazol-2-yl)-2-methoxyisonicotinamide (II-86)

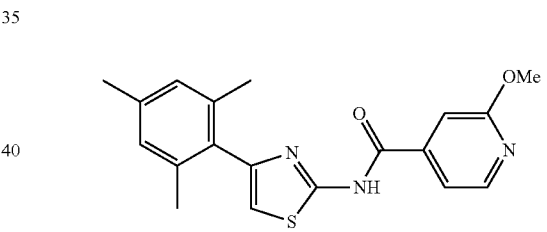

N-(4-Mesitylthiazol-2-yl)-2-methoxyisonicotinamide compound II-86

N-(4-Mesitylthiazol-2-yl)-2-methoxyisonicotinamide (II-86) Yield: 40%; $^1$H NMR (500 MHz, CDCl$_3$) δ 8.38-8.39 (m, 1 H), 7.55-7.56 (m, 1 H), 7.41 (s, 1 H), 6.91-6.93 (m, 2 H), 6.86 (s, 1 H), 5.30 (s, 1 H), 4.00 (s, 3 H), 2.32 (s, 3 H), 2.12 (s, 6 H); ESI-MS: m/z 355.0 (M+H)$^+$.

2-Chloro-N-(4-mesitylthiazol-2-yl)-6-methoxyisonicotinamide (II-87)

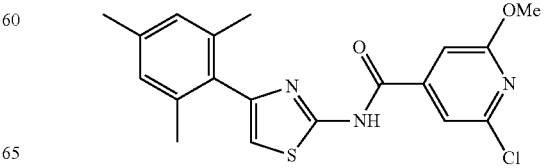

2-Chloro-N-(4-mesitylthiazol-2-yl)-6-methoxyisonicotinamide compound II-87

2-Chloro-N-(4-mesitylthiazol-2-yl)-6-methoxyisonicotinamide (II-87) Yield: 63%; $^1$H NMR (500 MHz, CDCl$_3$) δ 7.31 (s, 1 H), 7.06 (s, 1 H), 6.81 (s, 1 H), 6.76 (s, 2 H), 4.00 (s, 3 H), 2.32 (s, 3 H), 1.98 (s, 6 H); ESI-MS: m/z 387.9 (M+H)$^+$.

2,6-Dichloro-N-(4-mesitylthiazol-2-yl)isonicotinamide (II-88)

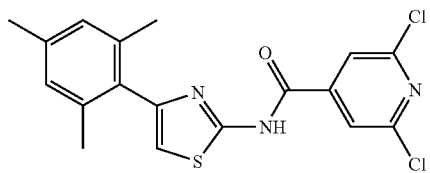 [SMILES: Cc1cc(C)c(-c2csc(NC(=O)c3cc(Cl)nc(Cl)c3)n2)c(C)c1]

2,6-Dichloro-N-(4-mesitylthiazol-2-yl)isonicotinamide compound II-88

2,6-Dichloro-N-(4-mesitylthiazol-2-yl)isonicotinamide (II-88) Yield: 70%; $^1$H NMR (500 MHz, CDCl$_3$) δ 7.61 (s, 2 H), 6.80 (s, 1 H), 6.73 (s, 2 H), 2.29 (s, 3 H), 1.94 (s, 6 H); ESI-MS: m/z 392.0 (M+H)$^+$.

2-Accetamido-N-(4-mesitylthiazol-2-yl)isonicotinamide (II-89)

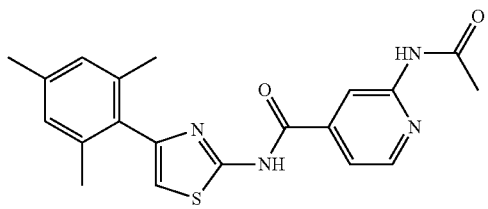 [SMILES: CC(=O)Nc1cc(C(=O)Nc2nc(-c3c(C)cc(C)cc3C)cs2)ccn1]

2-Acetamido-N-(4-mesitylthiazol-2-yl)isonicotinamide compound II-89

2-Acetamido-N-(4-mesitylthiazol-2-yl)isonicotinamide (II-89) Yield: 61%; $^1$H NMR (500 MHz, CDCl$_3$) δ 8.81 (s, 1 H), 8.37 (s, 1 H), 7.80-7.77 (m, 1 H), 6.91 (s, 2 H), 6.80 (s, 1 H), 2.30 (s, 3 H), 2.26 (s, 3 H), 2.11 (s, 6 H); ESI-MS: m/z 381.2 (M+H)$^+$.

2,6-Difluoro-N-(4-mesitylthiazol-2-yl)isonicotinamide (II-90)

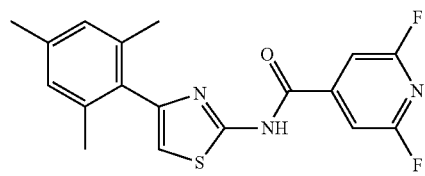 [SMILES: Cc1cc(C)c(-c2csc(NC(=O)c3cc(F)nc(F)c3)n2)c(C)c1]

2,6-Difluoro-N-(4-mesitylthiazol-2-yl)isonicotinamide compound II-90

2,6-Difluoro-N-(4-mrsitylthiazol-2-yl)isonicotinamide (II-90) Yield: 67%; $^1$H NMR (500 MHz, CDCl$_3$) δ 7.11 (s, 2 H), 6.81 (s, 1 H), 6.68 (s, 1 H), 2.30 (s, 3 H), 1.91 (s, 6 H); ESI-MS: m/z 360.0 (M+H)$^+$.

N-(4-Mesitylthiazol-2-yl)-2-(pyridin-4-yl)acetamide (II-93)

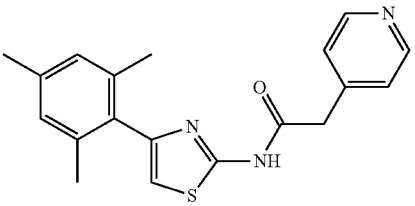 [SMILES: Cc1cc(C)c(-c2csc(NC(=O)Cc3ccncc3)n2)c(C)c1]

N-(4-Mesitylthiazol-2-yl)-2-(pyridin-4-yl)acetamide compound II-93

N-(4-Mesitylthiazol-2-yl)-2-(pyridin-4-yl)acetamide (II-93) Yield: 65%; $^1$H NMR (500 MHz, DMSO-d$_6$) δ 8.52-8.53 (m, 2 H), 7.35-7.36 (m, 2 H), 6.99 (s, 1 H), 6.91 (s, 1 H), 3.84 (s, 1 H), 2.25 (s, 3 H), 2.02 (s, 6 H); ESI-MS: m/z 338.1 (M+H)$^+$.

N-(4-(4-(2-Hydroxypropoxy)-2,6-dimethylphenyl)thiazol-2-yl)isonicotinamide (II-94)

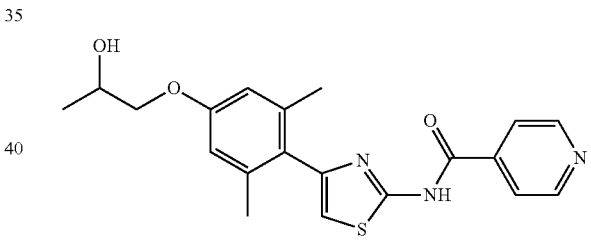

N-(4-(4-(2-Hydroxypropoxy)-2,6-dimethylphenyl)thiazol-2-yl)isonicotinamide compound II-94

N-(4-(4-(2-Hydroxypropoxy)-2,6-dimethylphenyl)thiazol-2-yl)isonicotinamide (II-94) Yield: 4.0%; $^1$H NMR (500 MHz, CDCl$_3$) δ 8.80 (d, J=5.9 Hz, 2 H), 7.69 (d, J=5.9 Hz, 2 H), 6.81 (s, 1 H), 6.55 (s, 2 H), 4.19-4.25 (s, 1 H), 4.10-4.15 (m, 1 H), 3.91-3.98 (m, 1 H), 3.78-3.82 (m, 1H), 2.05 (s, 6 H), 1.28 (s, 3 H); ESI-MS: m/z 384.7 (M+H)+.

N-(4-(4-(4-Methoxyphenoxy)-2,6-dimethylphenyl)thiazol-2-yl)isonicotinamide (II-95)

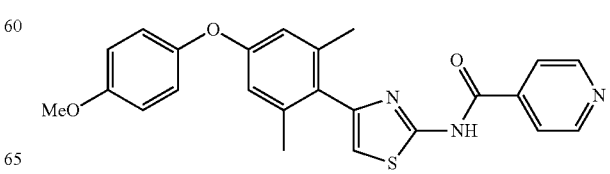

N-(4-(4-(4-Methoxyphenoxy)-2,6-dimethylphenyl)thiazol-2-yl)isonicotinamide compound II-95

N-(4-(4-(4-Methoxyphenoxy)-2,6-dimethylphenyl)thiazol-2-yl)isonicotinamide (II-95) Yield: 95%; $^1$H NMR (500 MHz, CDCl$_3$) δ 8.73 (m, 2 H), 7.62 (m, 2 H), 6.90-6.96 (m, 4 H), 6.80 (s, 1 H), 6.45 (s, 2 H), 3.83 (s, 3 H), 1.92 (s, 6 H); ESI-MS: m/z 431.7 (M+H)$^+$.

N-(4-(4-(4-Fluorophenoxy)-2,6-dimethylphenyl)thiazol-2-yl)isonicotinamide (II-96)

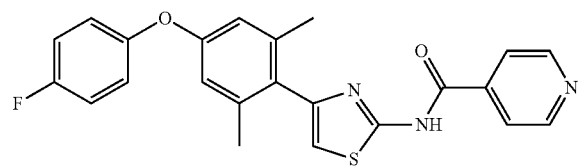 [SMILES: Cc1cc(Oc2ccc(F)cc2)cc(C)c1-c1csc(NC(=O)c2ccncc2)n1]

N-(4-(4-(4-Fluorophenoxy)-2,6-dimethylphenyl)thiazol-2-yl)isonicotinamide compound II-96

N-(4-(4-(4-Fluorophenoxy)-2,6-dimethylphenyl)thiazol-2-yl)isonicotinamide (II-96)
Yield: 17%; $^1$H NMR (500 MHz, CDCl$_3$) δ 8.72 (d, J=5.5 Hz, 2 H), 7.60 (d, J=5.5 Hz, 2 H), 7.04 (m, 2 H), 6.94 (m, 2 H), 6.81 (s, 1 H), 6.43 (s, 2 H), 1.92 (s, 6 H); ESI-MS: m/z 420.2 (M+H)$^+$.

N-(4-(4-(2,3-Dihydroxypropoxy)-2,6-dimethylphenyl)thiazol-2-yl)isonicotinamide (II-97)

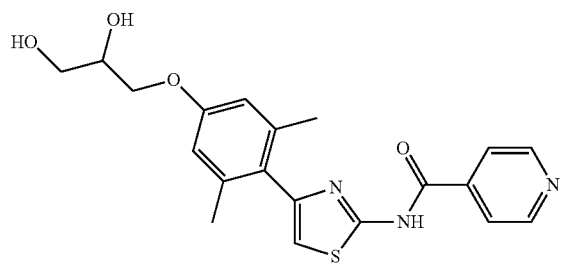 [SMILES: Cc1cc(OCC(O)CO)cc(C)c1-c1csc(NC(=O)c2ccncc2)n1]

N-(4-(4-(2,3-Dihydroxypropoxy)-2,6-dimethylphenyl)thiazol-2-yl)isonicotinamide compound II-97

N-(4-(4-(2,3-Dihydroxypropoxy)-2,6-dimethylphenyl)thiazol-2-yl)isonicotinamide (II-97) Yield: 12%; $^1$H NMR (500 MHz, DMSO-d$_6$) δ 8.78 (d, J=4.5 Hz, 2 H), 7.98 (d, J=4.5 Hz, 2 H), 7.15 (s, 1 H), 6.69 (s, 2 H), 4.95-4.96 (m, 1 H), 4.68-4.69 (m, 1 H), 3.97-3.98 (m, 1 H), 3.84-3.85 (m, 1 H), 3.78-3.79 (m, 1 H), 2.06 (s, 6 H); ESI-MS: m/z 400.7 (M+H)$^+$.

2-Fluoro-N-(4-(4-(4-methoxyphenoxy)-2,6-dimethylphenyl)thiazol-2-yl)isonicotinamide (II-98)

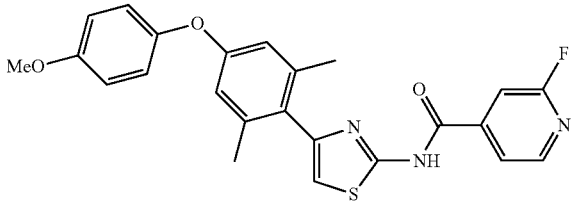

2-Fluoro-N-(4-(4-(4-methoxyphenoxy)-2,6-dimethylphenyl)thiazol-2-yl)isonicotinamide compound II-98

2-Fluoro-N-(4-(4-(4-methoxyphenoxy)-2,6-dimethylphenyl)thiazol-2-yl)isonicotinamide (II-98) Yield: 70%; $^1$H NMR (500 MHz, CDCl$_3$) δ 8.38-8.40 (m, 1 H), 7.66-7.67 (m, 2 H), 7.43 (s, 1 H), 6.98-7.00 (m, 2 H), 6.91-6.93 (m, 2 H), 6.84 (s, 1 H), 6.54 (s, 1 H), 3.83 (s, 3 H), 2.0 (s, 6 H); ESI-MS: m/z 450.0 (M+H)$^+$.

2-Fluoro-N-(4-(4-isopropoxy-2,6-dimethylphenyl)thiazol-2-yl)isonicotinamide (II-99)

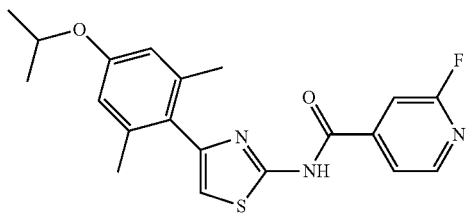 [SMILES: Cc1cc(OC(C)C)cc(C)c1-c1csc(NC(=O)c2ccnc(F)c2)n1]

2-Fluoro-N-(4-(4-isopropoxy-2,6-dimethylphenyl)thiazol-2-yl)isonicotinamide compound II-99

2-Fluoro-N-(4-(4-isopropoxy-2,6-dimethylphenyl)thiazol-2-yl)isonicotinamide (II-99)
Yield: 83%; $^1$H NMR (500 MHz, CDCl$_3$) δ 8.40 (m, 1 H), 7.78 (s, 1 H), 7.50 (s, 1 H), 6.84 (s, 1 H), 6.53 (s, 2 H), 4.52-4.56 (m, 1 H), 2.06 (s, 6 H), 1.33 (s, 6 H); ESI-MS: m/z 385.8 (M+H)$^+$.

N-(4-(4-Isobutoxy-2,6-dimethylphenyl)thiazol-2-yl)isonicotinamide (II-100)

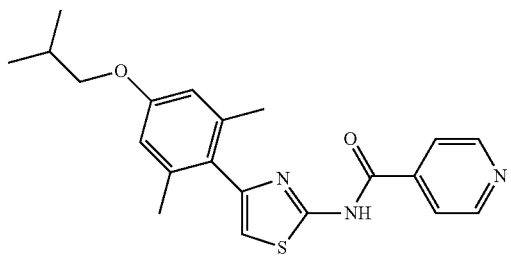 [SMILES: Cc1cc(OCC(C)C)cc(C)c1-c1csc(NC(=O)c2ccncc2)n1]

N-(4-(4-Isobutoxy-2,6-dimethylphenyl)thiazol-2-yl)isonicotinamide compound II-100

N-(4-(4-Isobutoxy-2,6-dimethylphenyl)thiazol-2-yl)isonicotinamide (II-100) Yield: 99%; $^1$H NMR (500 MHz, CDCl$_3$) δ 8.68 (d, J=6.0 Hz, 2 H), 7.56 (d, J=6.0 Hz, 2 H), 6.77 (s, 1H), 6.33 (s, 2 H), 3.62 (d, J=6.5 Hz, 2 H), 2.08 (m, 1 H), 1.91 (s, 6 H), 1.05 (d, J=6.7 Hz, 6 H); ESI-MS: m/z 381.1 (M+H)$^+$.

N-(4-(4-(Benzo(d)(1,3)dioxol-5-yloxy)-2,6-dimethylphenyl)thiazol-2-yl)isonicotinamide (II-101)

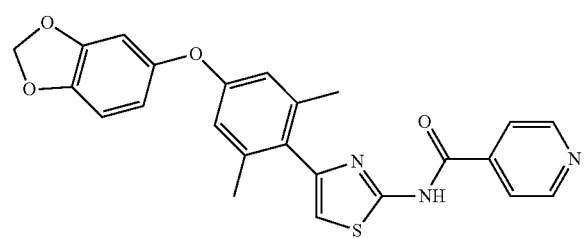 [SMILES: Cc1cc(Oc2ccc3c(c2)OCO3)cc(C)c1-c1csc(NC(=O)c2ccncc2)n1]

N-(4-(4-(Benzo[d][1,3]dioxol-5-yloxy)-2,6-dimethylphenyl)thiazol-2-yl)isonicotinamide compound II-101

N-(4-(4-(Benzo(d)(1,3)dioxol-5-yloxy)-2,6-dimethylphenyl)thiazol-2-yl)isonicotinamide (II-101) Yield: 92%; $^1$H NMR (500 MHz, CDCl$_3$) δ 8.73 (m, 2 H), 7.62 (m, 2H), 6.81 (s, 1 H), 6.78 (d, J=8.5 Hz, 1 H), 6.43-6.52 (m, 4 H), 6.00 (s, 2 H), 1.93 (s, 6 H); ESI-MS: m/z 445.9 (M+H)$^+$.

N-(4-(4-(3,5-Dimethylphenoxy)-2,6-dimethylphenyl)thiazol-2-yl)isonicotinamide (II-102)

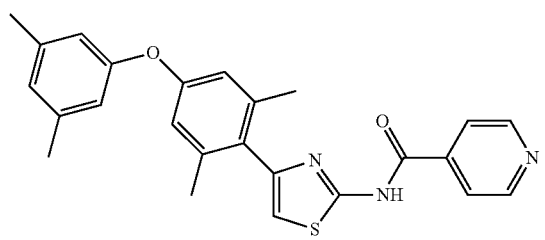 [SMILES: Cc1cc(C)cc(Oc2cc(C)c(-c3csc(NC(=O)c4ccncc4)n3)c(C)c2)c1]

N-(4-(4-(3,5-Dimethylphenoxy)-2,6-dimethylphenethyl)thiazol-2-yl)isonicoinamide compound II-102

N-(4-(4-(3,5-Dimethylphenoxy)-2,6-dimethylphenyl)thiazol-2-yl)isonicotinamide (II-102) Yield: 94%; $^1$H NMR (500 MHz, CDCl$_3$) δ 8.81 (d, J=5.1 Hz, 2 H), 7.78 (d, J=5.6 Hz, 2 H), 6.84 (s, 1 H), 6.78 (s, 1 H), 6.64 (s, 2 H), 6.61 (s, 2 H), 2.31 (s, 6 H), 2.02 (s, 6 H); ESI-MS: m/z 429.8 (M+H)$^+$.

(E)-N-(4-Mesitylthiazol-2-yl)-3-(pyridin-3-yl)acrylamide (II-103)

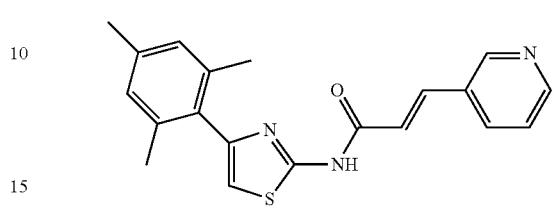

(E)-N-(4-Mesitylthiazol-z-yl-3-(pyridin-3-yl)acrylamide compound II-103

(E)-N-(4-Mesitylthiazol-2-yl)-3-(pyridin-3-yl)acrylamide (II-103) Yield: 34% yield; $^1$H NMR (500 MHz, DMSO-d$_6$) δ 12.48 (s, 1 H), 8.82-8.83 (m, 1 H), 8.60-8.61 (m, 1 H), 8.04-8.05 (m, 1 H), 7.76-7.79 (m, 1 H), 7.49-7.51 (m, 1 H), 7.00-7.03 (m, 2 H), 6.92 (s, 2 H), 2.26 (s, 3 H), 2.05 (s, 6 H); ESI-MS: m/z 350.7 (M+H)$^+$.

N-(4-Mesitylthiazol-2-yl)-1H-indazole-6-carboxamide (II-104)

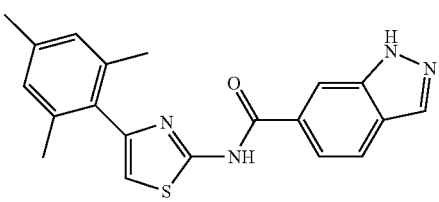 [SMILES: Cc1cc(C)c(-c2csc(NC(=O)c3ccc4cn[nH]c4c3)n2)c(C)c1]

N-(4-Mesitylthiazol-2-yl)-1H-indazole-6-carboxamide compound II-104

N-(4-Mesitylthiazol-2-yl)-1H-indazole-6-carboxamide (II-104) Yield: 25%; $^1$H NMR (500 MHz, DMSO-d$_6$) δ 13.20 (s, 1 H), 8.36 (s, 1 H), 8.19 (s, 1 H), 7.87-7.88 (m, 1 H), 7.72-7.83 (m, 1 H), 7.00 (s, 1 H), 6.93 (s, 2 H), 2.27 (s, 3 H), 2.07 (s, 6 H); ESI-MS: m/z 363.9 (M+H)$^+$.

N-(4-Mesitylthiazol-2-yl)-1H-indazole-5-carboxamide (II-105)

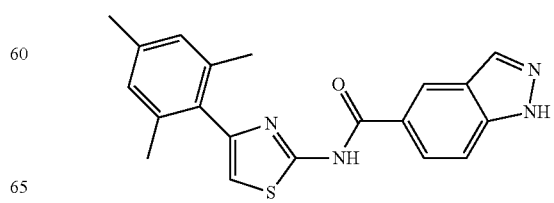

N-(4-Mesitylthiazol-2-yl)-1H-indazole-5-carboxamide compound II-105

N-(4-Mesitylthiazol-2-yl)-1H-indazole-5-carboxamide (II-105) Yield: 38%, $^1$H NMR (500 MHz, DMSO-d$_6$) δ 13.20 (s, 1 H), 8.66 (s, 1 H), 8.26 (s, 1 H), 8.08 (d, J=8.4 Hz, 1 H), 7.65 (d, J=8.4 Hz, 1 H), 7.02 (s, 1 H), 6.93 (s, 2 H), 2.36 (s, 3 H), 2.07 (s, 6 H); ESI-MS: m/z 363.9 (M+H)$^+$.

N-(4-Mesitylthiazol-2-yl)-1H-benzo(d)(1,2,3)triazole-5-carboxamide (II-106)

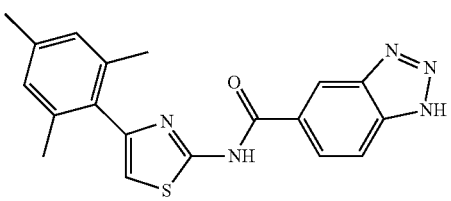 [SMILES: Cc1cc(C)c(-c2csc(NC(=O)c3ccc4[nH]nnc4c3)n2)c(C)c1]

N-(4-Mesitylthiazol-2-yl)-1H-benzo[d][1,2,3]triazole-5-carboxamide compound II-106

N-(4-Mesitylthiazol-2-yl)-1H-benzo(d)(1,2,3)triazole-5-carboxamide (II-106) Yield: 41%; $^1$H NMR (500 MHz, DMSO-d$_6$) δ 8.78 (s, 1 H), 8.11 (d, J=8.4 Hz, 1 H), 7.96 (d, J=8.4 Hz, 1H), 7.07 (s, 1 H), 6.93 (s, 2 H), 2.27 (s, 3 H), 2.07 (s, 6 H); ESI-MS: m/z 364.9 (M+H)$^+$.

N-(4-(4-(3-Methoxyphenoxy)-2,6-dimethylphenyl)thiazol-2-yl)isonicotinamide (II-107)

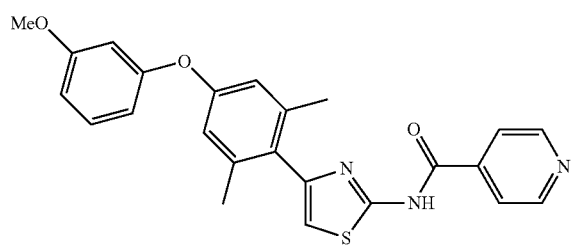 [SMILES: COc1cccc(Oc2cc(C)c(-c3csc(NC(=O)c4ccncc4)n3)c(C)c2)c1]

N-(4-(4-(3-Methoxyphenoxy)-2,6-dimethylphenyl)thiazol-2-yl)isonicotinamide compound II-107

N-(4-(4-(3-Methoxyphenoxy)-2,6-dimethylphenyl)thiazol-2-yl)isonicotinamide (II-107) Yield: 51%; $^1$H NMR (500 MHz, CDCl$_3$) δ 8.75 (m, 2 H), 7.62 (m, 2 H), 7.25 (m, 1 H), 6.82 (s, 1 H), 6.69 (m, 1 H), 6.56 (d, 1 H), 6.51 (m, 2 H), 6.47 (s, 2 H), 3.81 (s, 3 H), 1.94 (s, 6 H); ESI-MS: m/z 431.6 (M+H)$^+$.

N-(4-(2,6-Dimethyl-4-(4-(trifluoromethyl)phenoxy)phenyl)thiazol-2-yl)isonicotinamide (II-108)

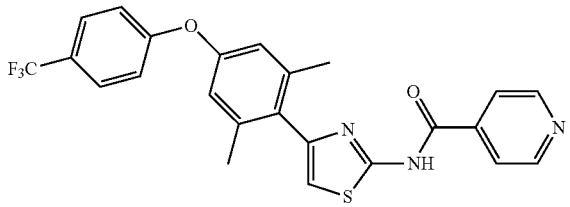 [SMILES: Cc1cc(Oc2ccc(C(F)(F)F)cc2)cc(C)c1-c1csc(NC(=O)c2ccncc2)n1]

N-(4-(2,6-Dimethyl-4-(4-(trifluoromethyl)phenoxy)phenyl)thiazol-2-yl)isonicotinamide compound II-108

N-(4-(2,6-Dimethyl-4-(4-(trifluoromethyl)phenoxy)phenyl)thiazol-2-yl)isonicotinamide (II-108) Yield: 87%; $^1$H NMR (500 MHz, CDCl$_3$) δ 8.76 (m, 2 H), 7.64 (m, 2H), 7.58 (d, J=8.5 Hz, 2 H), 7.01 (d, J=8.5 Hz, 2 H), 6.86 (s, 1 H), 6.57 (s, 2 H), 1.98 (s, 6 H); ESI-MS: m/z 469.7 (M+H)$^+$.

N-(4-(4-(2-Methoxyethoxy)-2,6-dimethylphenyl)thiazol-2-yl)isonicotinamide (II-109)

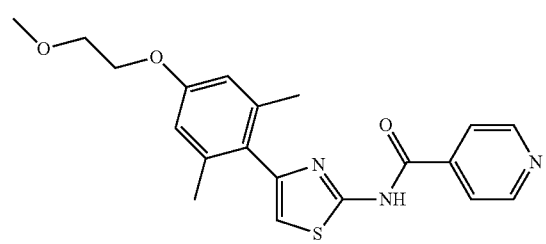 [SMILES: COCCOc1cc(C)c(-c2csc(NC(=O)c3ccncc3)n2)c(C)c1]

N-(4-(4-(2-Methoxyethoxy)-2,6-dimethylphenyl)thiazol-2-yl)isonicotinamide compound II-109

N-(4-(4-(2-Methoxyethoxy)-2,6-dimethylphenyl)thiazol-2-yl)isonicotinamide (II-109)
Yield: 19%; $^1$H NMR (500 MHz, DMSO-d$_6$) δ 8.79-8.80 (m, 12 H), 7.98-7.99 (m, 2 H), 7.08 (s, 1H), 6.70 (s, 2 H), 4.08-4.10 (m, 2 H), 3.65-3.66 (m, 2 H), 3.31 (s, 3 H), 2.06 (s, 6 H); ESI-MS: m/z 384.6 (M+H)$^+$.

N-(4-(4-(3-Methoxypropoxy)-2,6-dimethylphenyl)thiazol-2-yl)isonicotinamide (II-110)

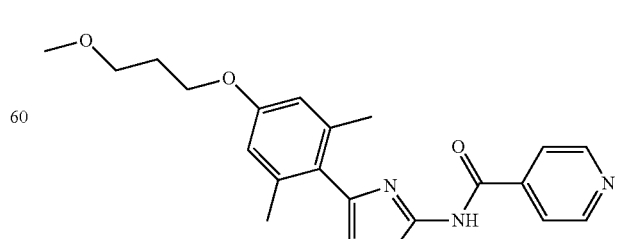

N-(4-(4-(3-Methoxypropoxy)-2,6-dimethylphenyl)thiazol-2-yl)isonicotinamide compound II-110

N-(4-(4-(3-Methoxypropoxy)-2,6-dimethylphenyl)thiazol-2-yl)isonicotinamide (II-110) Yield: 58%; $^1$H NMR (500 MHz, DMSO-$d_6$) δ 8.78-8.79 (m, 2 H), 7.98-7.99 (m, 2 H), 7.05 (s, 1 H), 6.69 (s, 2 H), 4.00-4.02 (m, 2 H), 3.46-3.48 (m, 2 H), 3.25 (s, 3 H), 2.06 (s, 6 H), 1.93-1.95 (m, 2 H); ESI-MS: m/z 398.8 (M+H)$^+$.

N-{4-(4-(2-Methoxyphenoxy)-2,6-dimethylphenyl)thiazol-2-yl)isonicotinamide (II-111)

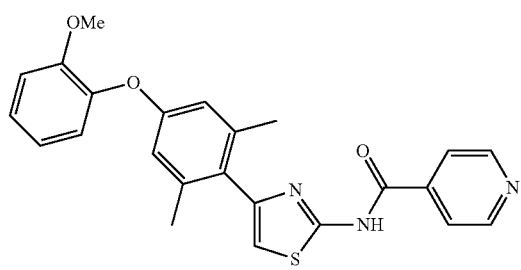 [SMILES: COc1ccccc1Oc1cc(C)c(-c2csc(NC(=O)c3ccncc3)n2)c(C)c1]

N-(4-(4-(2-Methoxyphenoxy)-2,6-dimethylphenyl)thiazol-2-yl)isonicotinamide compound II-111

N-{4-(4-(2-Methoxyphenoxy)-2,6-dimethylphenyl)thiazol-2-yl)isonicotinamide (II-111) Yield: 85%; $^1$H NMR (500 MHz, DMSO-$d_6$) δ 8.80-8.81 (m, 2 H), 7.98-7.99 (m, 2 H), 7.16-7.21 (m, 3 H), 6.99-7.06 (m, 2 H), 6.59 (s, 2 H), 3.76 (s, 3 H), 2.03 (s, 6 H); ESI-MS: m/z 431.5 (M+H)$^+$.

N-(4-(2,6-Dimethyl-4-(p-tolyloxy)phenyl)thiazol-2-yl)isonicotinamide (II-112)

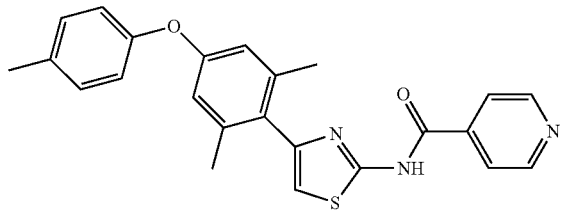

N-(4-(2,6-Dimethyl-4-(p-tolyloxy)phenyl)thiazol-2-yl)isonicotinamide compound II-112

N-(4-(2,6-Dimethyl-4-(p-tolyloxy)phenyl)thiazol-2-yl)isonicotinamide (II-112) Yield: 89%; $^1$H NMR (500 MHz, DMSO-$d_6$) δ 8.80-8.81 (m, 2 H), 7.98-7.99 (m, 2 H), 7.18-7.22 (m, 3 H), 6.94-6.95 (m, 2 H), 6.73 (s, 2 H), 2.30 (s, 3 H), 2.06 (s, 6 H); ESI-MS: m/z 414.9 (M−H)$^−$.

N-(4-(4-(4-Ethylphenoxy)-2,6-dimethylphenyl)thiazol-2-yl)isonicotinamide (II-113)

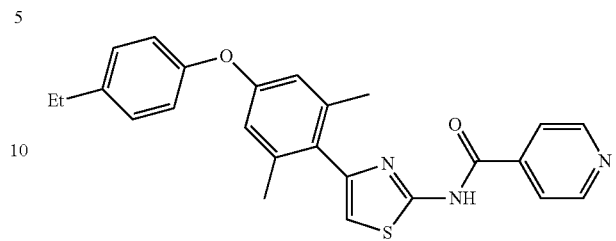

N-(4-(4-(4-Ethylphenoxy)-2,6-dimethylphenyl)thiazol-2-yl)isonicotinamide compound II-113

N-(4-(4-(4-Ethylphenoxy)-2,6-dimethylphenyl)thiazol-2-yl)isonicotinamide (II-113)

Yield: 91%; $^1$H NMR (500 MHz, CDCl$_3$) δ 8.78 (d, J=6.0 Hz, 2 H), 8.67 (m, 2 H), 7.18 (d, J=8.0 Hz, 2 H), 6.93 (d, J=8.5 Hz, 2 H), 6.83 (s, 1 H), 6.56 (s, 2 H), 2.65 (m, 2 H), 1.98 (s, 6 H), 1.26 (t, J=7.5 Hz, 3 H); ESI-MS: m/z 429.6 (M+H)$^+$.

N-(4-(4-Iodo-2,6-dimethylphenyl)thiazol-2-yl)isonicotinamide (II-114)

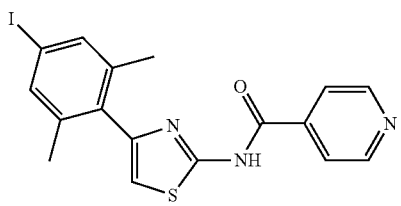

N-(4-(4-Iodo-2,6-dimethylphenyl)thiazol-2-yl)isonicotinamide compound II-114

N-(4-(4-Iodo-2,6-dimethylphenyl)thiazol-2-yl)isonicotinamide (II-114) Yield: 61%; $^1$H NMR (500 MHz, CDCl$_3$) δ 8.76 (m, 2 H), 7.52 (m, 2 H), 7.11 (s, 2 H), 6.80 (s, 1 H), 1.84 (s, 6H); ESI-MS: m/z 435.6 (M+H)$^+$.

N-(4-(2,6-Dimethyl-4-(phenylthio)phenyl)thiazol-2-yl)isonicotinamide (II-115)

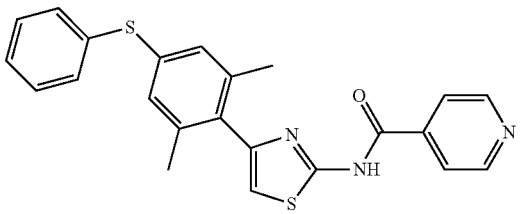 [SMILES: Cc1cc(Sc2ccccc2)cc(C)c1-c1csc(NC(=O)c2ccncc2)n1]

N-(4-(2,6-Dimethyl-4-(phenylthio)phenyl)thiazol-2-yl)isonicotinamide compound II-115

N-(4-(2,6-Dimethyl-4-(phenylthio)phenyl)thiazol-2-yl)isonicotinamide (II-115)
Yield: 63%; $^1$H NMR (500 MHz, DMSO-$d_6$) δ 8.77 (d, J=5.4 Hz, 2 H), 7.98 (d, J=5.4 Hz, 2 H), 7.38-7.40 (m, 2 H), 7.31-7.35 (m, 3 H), 7.11 (s, 3 H), 2.07 (s, 6 H); ESI-MS: m/z 418.8 (M+H)$^+$.

N-(4-(2,6-Dimethyl-4-(p-tolylthio)phenyl)thiazol-2-yl)isonicotinamide (II-116)

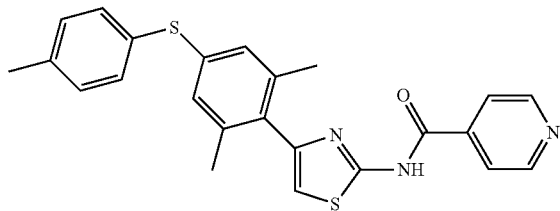

N-(4-(2,6-Dimethyl-4-(p-tolylthio)phenyl)thiazol-2-yl)isonicotinamide compound II-116

N-(4-(2,6-Dimethyl-4-(p-tolylthio)phenyl)thiazol-2-yl)isonicotinamide (II-116) Yield: 84%; $^1$H NMR (500 MHz, DMSO-$d_6$) δ 8.78 (d, J=5.2 Hz, 2 H), 7.98 (d, J=5.2 Hz, 2 H), 7.30 (d, J=8.0 Hz, 2 H), 7.23 (d, J=8.0 Hz, 2 H), 7.10 (s, 1 H), 7.02 (s, 2 H), 2.36 (s, 3 H), 2.04 (s, 6 H); ESI-MS: m/z 432.5 (M+H)$^+$.

N-(4-(4-(4-Methoxyphenylthio)-2,6-dimethylphenyl)thiazol-2-yl)isonicotinamide (II-117)

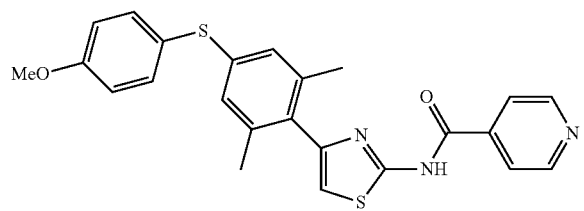

N-(4-(4-(4-Methoxyphenylthio)-2,6-dimethylphenyl)thiazol-2-yl)isonicotinamide compound II-117

N-(4-(4-(4-Methoxyphenylthio)-2,6-dimethylphenyl)thiazol-2-yl)isonicotinamide (II-117) Yield: 64%; $^1$H NMR (500 MHz, DMSO-$d_6$) δ 8.79 (d, J=5.0 Hz, 2 H), 7.98 (d, J=5.0 Hz, 2H), 7.43 (d, J=8.4 Hz, 2 H), 7.12 (s, 1 H), 7.02 (d, J=8.4 Hz, 2 H), 6.92 (s, 2 H), 3.79 (s, 3 H), 2.02 (s, 6 H); ESI-MS: m/z 448.1 (M+H)$^+$.

4-(4-(4-(4-Methoxyphenoxy)-2,6-dimethylphenyl)thiazol-2-ylcarbamoyl)pyridine 1-oxide (II-120)

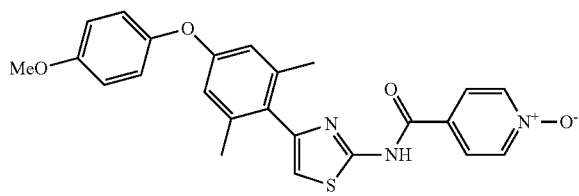 [SMILES: COc1ccc(Oc2cc(C)c(-c3csc(NC(=O)c4cc[n+]([O-])cc4)n3)c(C)c2)cc1]

4-(4-(4-(4-Methoxyphenoxy)-2,6-dimethylphenyl)thiazol-2-ylcarbamoyl)pyridine 1-oxide compound II-120

4-(4-(4-(4-Methoxyphenoxy)-2,6-dimethylphenyl)thiazol-2-ylcarbamoyl)pyridine 1-oxide (II-120) Yield: 69%; $^1$H NMR (500 MHz, CDCl$_3$) δ 8.46-8.48 (m, 1 H), 8.39-8.43 (m, 2 H), 8.32-8.33 (m, 1 H), 7.02-7.05 (m, 2 H), 6.93-6.95 (m, 3 H), 6.70 (s, 2 H), 3.84 (s, 3 H), 2.19 (s, 3 H), 2.16 (s, 3 H); ESI-MS: m/z 447.8 (M+H)$^+$.

N-(4-(4-(4-Methoxyphenoxy)-2,6-dimethylphenyl)thiazol-2-yl)-3-methylisonicotinamide (II-121)

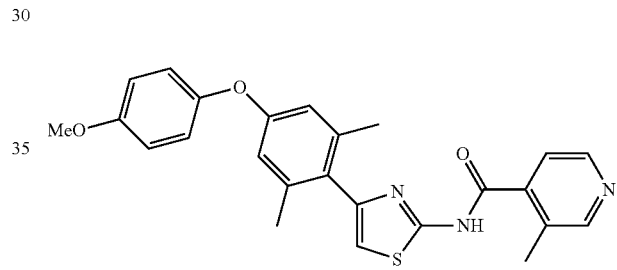

N-(4-(4-(4-Methoxyphenoxy)-2,6-dimethylphenyl)thiazol-2-yl)-3-methylisonicotinamide compound II-121

N-(4-(4-(4-Methoxyphenoxy)-2,6-dimethylphenyl)thiazol-2-yl)-3-methylisonicotinamide (II-121) Yield: 62%; $^1$H NMR (500 MHz, DMSO-$d_6$) δ 12.8 (s, 1 H), 8.54-8.58 (m, 2 H), 7.55-7.56 (m, 1 H), 7.14 (s, 1 H), 6.96-7.03 (m, 4 H), 6.67 (s, 2 H), 3.76 (s, 3 H), 2.40 (s, 3 H), 2.05 (s, 6 H); ESI-MS: m/z 445.7 (M+H)$^+$.

N-(4-(4-(4-Bromophenylamino)-2,6-dimethylphenyl)thiazol-2-yl)isonicotinamide (II-122)

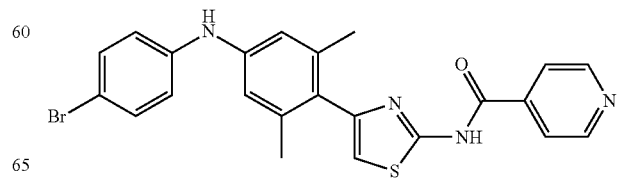

N-(4-(4-(4-Bromophenylamino)-2,6-dimethylphenyl)thiazol-2-yl)isonicotinamide compound II-122

N-(4-(4-(4-Bromophenylamino)-2,6-dimethylphenyl)thiazol-2-yl)isonicotinamide (II-122) Yield: 60%; $^1$H NMR (500 MHz, CDCl$_3$) δ 8.79 (d, J=4.5 Hz, 2 H), 7.85 (d, J=4.5 Hz, 2 H), 7.39 (d, J=8.6 Hz, 2 H), 6.97 (d, J=8.6 Hz, 2 H), 6.83 (s, 1 H), 2.05 (s, 6 H); ESI-MS: m/z 479.2 (M+H)$^+$.

N-(4-(3-Bromo-2,6-dimetbyl-4-(phenylamino)phenyl)tbiazol-2-yl)isonicotinamide (II-123)

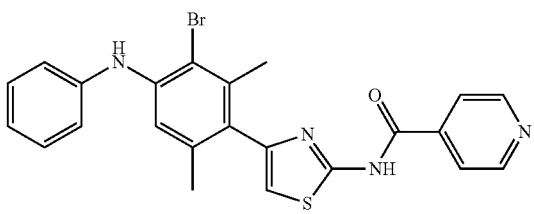 [SMILES: Cc1cc(Nc2ccccc2)c(Br)c(C)c1-c1csc(NC(=O)c2ccncc2)n1]

N-(4-(3-Bromo-2,6-dimethyl-4-(phenylamino)phenyl)thiazol-2-yl)isonicotinamide compound II-123

N-(4-(3-Bromo-2,6-dimethyl-4-(phenylamino)phenyl)tbiazol-2-yl)isonicotinamide (II-123) Yield: 58%; $^1$H NMR (500 MHz, CDCl$_3$) δ 8.87 (d, J=4.5 Hz, 2 H), 8.02 (d, J=4.5 Hz, 2H), 7.47 (d, J=8.6 Hz, 2 H), 7.08 (d, J=8.6 Hz, 2 H), 6.89 (s, 1 H), 6.85 (s, 1 H), 6.24 (s, 1 H), 2.04 (s, 6 H); ESI-MS: m/z 479.3 (M+H)$^+$.

N-(4-(4-(4-Methoxyphenoxy)-2,6-dimethylphenyl)tbiazol-2-yl)-2-nitroisonicotinamide (II-124)

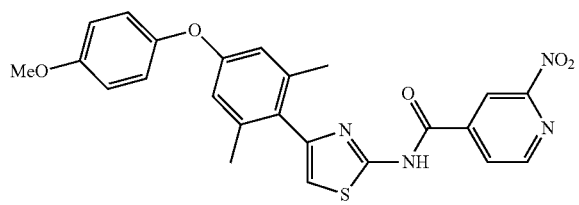 [SMILES: COc1ccc(Oc2cc(C)c(-c3csc(NC(=O)c4ccnc([N+](=O)[O-])c4)n3)c(C)c2)cc1]

N-(4-(4-(4-Methoxyphenoxy)-2,6-dimethylphenyl)thiazol-2-yl)-2-nitroisonicotinamide compound II-124

N-(4-(4-(4-Methoxyphenoxy)-2,6-dimethylphenyl)tbiazol-2-yl)-2-nitroisonicotinamide (II-124) Yield: 94%; $^1$H NMR (500 MHz, DMSO-d$_6$) δ 8.82 (s, 1 H), 8.71-8.72 (m, 1 H), 8.39-8.40 (m, 1 H), 7.01-7.03 (m, 2 H), 6.96-6.99 (m, 2 H), 6.64-6.67 (m, 3 H), 3.75 (s, 3 H), 2.03 (s, 6 H); ESI-MS: m/z 476.8 (M+H)$^+$.

N-(4-(2,6-Dimethyl-4-(methylthio)phenyl)thiazol-2-yl)isonicotinamide (II-125)

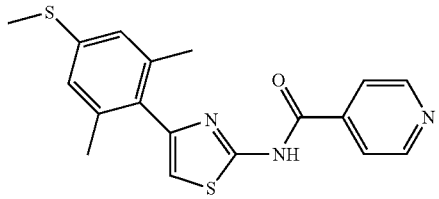 [SMILES: CSc1cc(C)c(-c2csc(NC(=O)c3ccncc3)n2)c(C)c1]

N-(4-(2,6-Dimethyl-4-(methylthio)phenyl)thiazol-2-yl)isonicotinamide compound II-125

N-(4-(2,6-Dimethyl-4-(methylthio)phenyl)thiazol-2-yl)isonicotinamide (II-125)
Yield: 94%; $^1$H NMR (500 MHz, CDCl$_3$) δ 8.66-8.68 (m, 2 H), 7.49-7.50 (m, 2 H), 6.77 (s, 1 H), 6.57 (s, 2 H), 2.42 (s, 3 H), 1.87 (s, 6 H); ESI-MS: m/z 355.6 (M+H)$^+$.

2-Fluoro-N-(4-(4-(4-methoxyphenylthio)-2,6-dimethylphenyl)thiazol-2-yl)isonicotinamide (II-126)

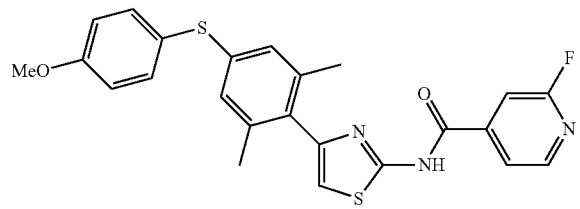

2-Fluoro-N-(4-(4-(4-methoxyphenylthio)-2,6-dimethylphenyl)thiazol-2-yl)isonicotinamide compound II-126

2-Fluoro-N-(4-(4-(4-methoxyphenylthio)-2,6-dimethylphenyl)thiazol-2-yl)isonicotinamide (II-126) Yield: 65%; $^1$H NMR (500 MHz, DMSO-d$_6$) δ 13.1 (s, 1 H), 8.46-8.47 (m, 1 H), 7.93-7.94 (m, 1 H), 7.78 (s, 1 H), 7.42-7.44 (m, 2 H), 7.19 (s, 1 H), 7.DI-7.Q3 (m, 2 H), 6.91 (s, 2 H), 3.79 (s, 3 H), 2.02 (s, 6 H); ESI-MS: m/z 465.4 (M+H)$^+$.

N-(4-(2,6-Dimethyl-4-(methylsulfonyl)phenyl)thiazol-2-yl)isonicotinamide (II-127)

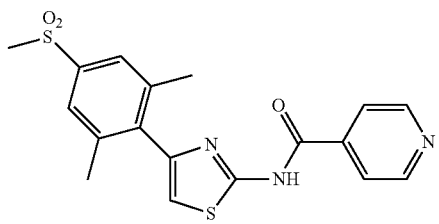 [SMILES: Cc1cc(S(C)(=O)=O)cc(C)c1-c1csc(NC(=O)c2ccncc2)n1]

N-(4-(2,6-Dimethyl-4-(methylsulfonyl)phenyl)thiazol-2-yl)isonicotinamide compound II-127

N-(4-(2,6-Dimethyl-4-(methylsulfonyl)phenyl)thiazol-2-yl)isonicotinamide (II-127)
Yield: 39%; $^1$H NMR (500 MHz, CDCl$_3$) δ 8.80-8.81 (m, 2 H), 7.98-8.00 (m, 2 H), 7.70 (s, 2 H), 7.30 (s, 1 H), 3.30 (s, 1 H), 2.20 (s, 6 H); ESI-MS: m/z 387.6 (M+H)$^+$.

N-(4-(4-(4-Methoxyphenylsulfonyl)-2,6-dimethylphenyl)thiazol-2-yl)isonicotinamide (II-129)

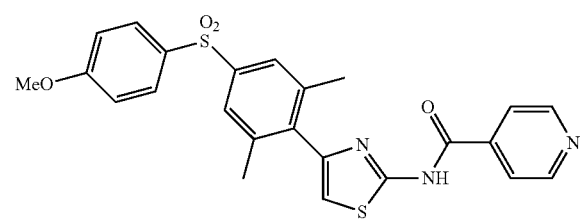 [SMILES: COc1ccc(S(=O)(=O)c2cc(C)c(-c3csc(NC(=O)c4ccncc4)n3)c(C)c2)cc1]

N-(4-(4-(4-Methoxyphenylsulfonyl)-2,6-dimethylphenyl)thiazol-2-yl)isonicotinamide compound II-129

N-(4-(4-(4-Methoxyphenylsulfonyl)-2,6-dimethylphenyl)thiazol-2-yl)isonicotinamide (II-129) Yield: 61%; $^1$H NMR (500 MHz, DMSO-d$_6$) δ 8.79 (s, 2 H), 7.97 (d, J=6.0 Hz, 2 H), 7.91 (d, J=8.9 Hz, 2 H), 7.69 (s, 2 H), 7.27 (s, 1 H), 7.15 (d, J=8.9 Hz, 2 H), 3.84 (s, 3 H), 2.16 (s, 6 H); ESI-MS: m/z 480.6 (M+H)$^+$.

N-(4-(4-(4-Methoxyphenylsulfinyl)-2,6-dimethylphenyl)thiazol-2-yl)isonicotinamide (II-130)

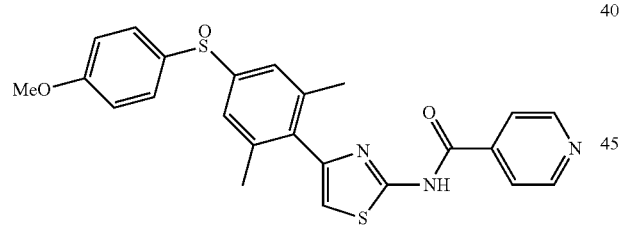

N-(4-(4-(4-Methoxyphenylsulfinyl)-2,6-dimethylphenyl)thiazol-2-yl)isonicotinamide compound II-130

N-(4-(4-(4-Methoxyphenylsulfinyl)-2,6-dimethylphenyl)thiazol-2-yl)isonicotinamide (II-130) Yield: 43%; $^1$H NMR (500 MHz, DMSO-d$_6$) δ 13.1 (s, 1 H), 8.80 (d, J=6.0 Hz, 2 H), 7.97 (d, J=6.0 Hz, 2 H), 7.66 (d, J=8.8 Hz, 2 H), 7.42 (s, 2 H), 7.23 (s, 1 H), 7.10 (d, J=8.8 Hz, 2 H), 3.80 (s, 3 H), 2.13 (s, 6 H); ESI-MS: m/z 464.7 (M+H)$^+$.

N-(4-(4-(4-methoxyphenoxy)-2,6-dimethylphenyl)thiazol-2-yl)isonicotinamide (II-131)

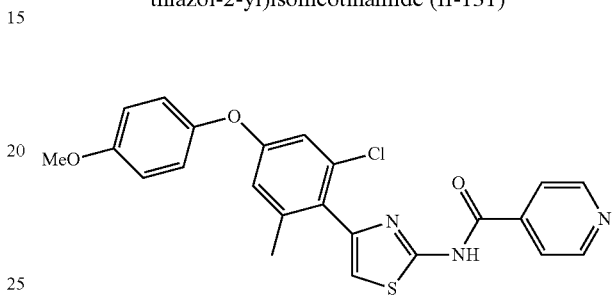

N-(4-(4-(4-methoxyphenoxy)-2,6-dimethylphenyl)thiazol-2-yl)isonicotinamide compound II-131

N-(4-(4-(4-methoxyphenoxy)-2,6-dimethylphenyl)thiazol-2-yl)isonicotinamide (II-131) Yield: 24%; $^1$H NMR (500 MHz, CDCl$_3$) δ 8.80 (s, 2 H), 7.70 (d, J=5.1 Hz, 2 H), 6.97 (m, 2H), 6.92 (m, 3 H), 6.70 (d, J=2.4 Hz, 1 H), 6.61 (d, J=2.3, 1 H), 3.83 (s, 3 H), 2.02 (s, 3 H); ESI-MS: m/z 452.4 (M+H)$^+$.

Exemplary Compounds and Inhibitory Activity

The following Table 1 lists exemplary results for selected compounds illustrating the antiproliferative activity on selected cancer cells using exposure of the cells in growth medium with the compounds as indicated. Antiproliferative effect is expressed as IC$_{50}$ values in nanomolar final concentration.

TABLE 1

| No. | Structure | Antiproliferative IC$_{50}$ (nM) | | | |
|---|---|---|---|---|---|
| | | Hela | K562 | MDA-MB-468 | MDA-MB-231 |
| 1 | 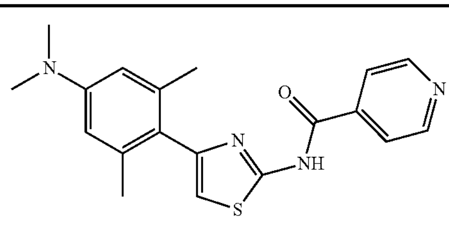 | 251.4 | 86.7 | 167.0 | 144.0 |

TABLE 1-continued

| No. | Structure | Antiproliferative IC$_{50}$ (nM) | | | |
|---|---|---|---|---|---|
| | | Hela | K562 | MDA-MB-468 | MDA-MB-231 |
| 2 | 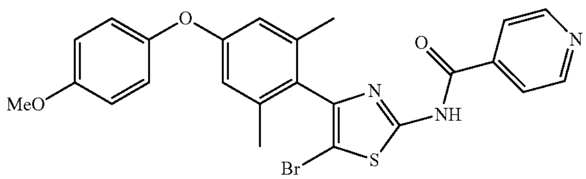 [SMILES: COc1ccc(Oc2cc(C)c(-c3nc(NC(=O)c4ccncc4)sc3Br)c(C)c2)cc1] | 659.9 | 273.2 | 594.0 | 484.0 |
| 3 | 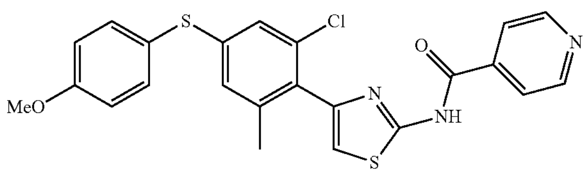 [SMILES: COc1ccc(Sc2cc(C)c(-c3csc(NC(=O)c4ccncc4)n3)c(Cl)c2)cc1] | 26.9 | 23.4 | 27.0 | 28.2 |
| 4 | 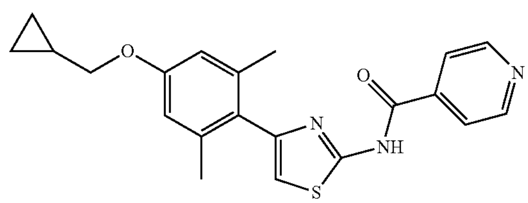 [SMILES: Cc1cc(OCC2CC2)cc(C)c1-c1csc(NC(=O)c2ccncc2)n1] | 280.7 | 206.5 | 245.0 | 157.0 |
| 5 | 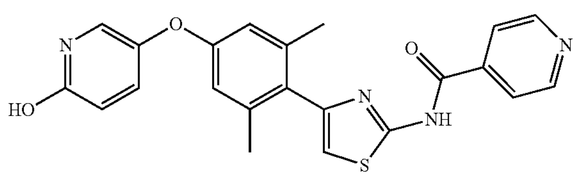 [SMILES: Cc1cc(Oc2ccc(O)nc2)cc(C)c1-c1csc(NC(=O)c2ccncc2)n1] | 903.0 | 562.6 | 1007.0 | 1242.0 |
| 6 | 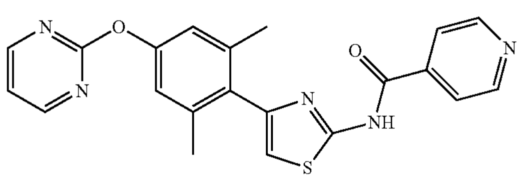 [SMILES: Cc1cc(Oc2ncccn2)cc(C)c1-c1csc(NC(=O)c2ccncc2)n1] | 1020.0 | 366.1 | 661.0 | 713.0 |
| 7 | 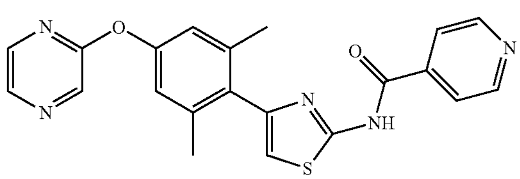 | 216.9 | 92.0 | 191.0 | 161.0 |
| 8 | 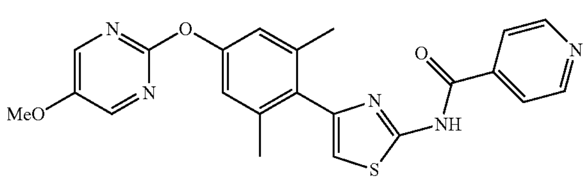 [SMILES: COc1cnc(Oc2cc(C)c(-c3csc(NC(=O)c4ccncc4)n3)c(C)c2)nc1] | 129.6 | 71.8 | 85.4 | 120.9 |
| 9 | 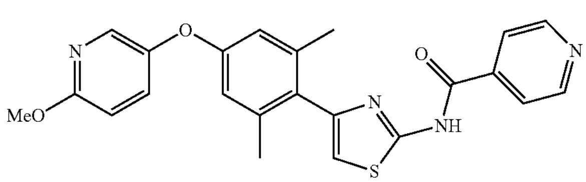 [SMILES: COc1ccc(Oc2cc(C)c(-c3csc(NC(=O)c4ccncc4)n3)c(C)c2)cn1] | 81.6 | 39.1 | 48.4 | 65.8 |

TABLE 1-continued
| No. | Structure | Antiproliferative IC$_{50}$ (nM) | | | |
| --- | --- | --- | --- | --- | --- |
| | | Hela | K562 | MDA-MB-468 | MDA-MB-231 |
| 10 | 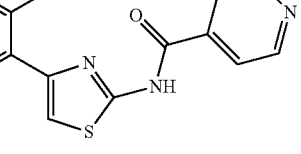 | 4427.0 | 633.2 | 6548.0 | 2332.0 |
| 11 | 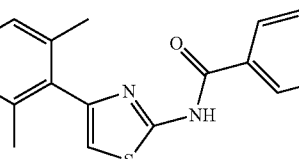 | 33.4 | 38.2 | 52.4 | 47.4 |
| 12 | 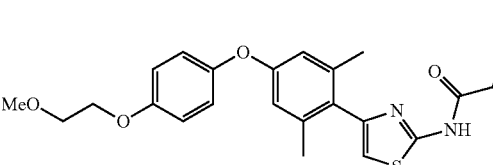 | 9.1 | 9.9 | 11.6 | 14.1 |
| 13 | 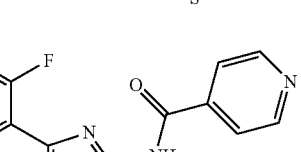 | 374.9 | 246.6 | 1024.0 | 386.3 |
| 14 | 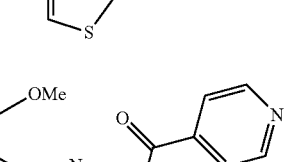 | 2986.8 | 3686.0 | 9431.0 | 6352.0 |
| 15 | 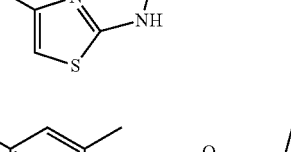 | 25.6 | 24.4 | 24.9 | 33.7 |
| 16 | 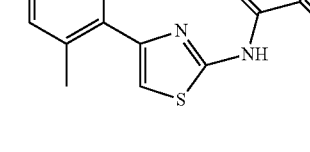 | 80.1 | 59.2 | 69.7 | 80.7 |
| 17 | 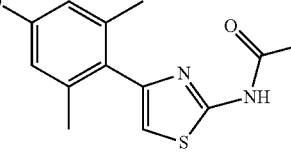 | 11.0 | 10.1 | 13.7 | 8.2 |

TABLE 1-continued

| No. | Structure | Antiproliferative IC$_{50}$ (nM) | | | |
| --- | --- | --- | --- | --- | --- |
| | | Hela | K562 | MDA-MB-468 | MDA-MB-231 |
| 18 | 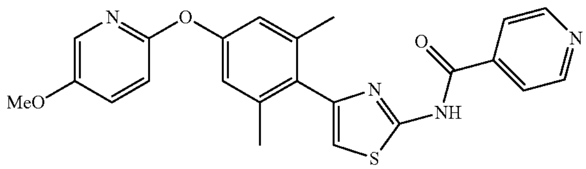 | 40.6 | 43.7 | 49.4 | 40.8 |
| 19 (110078) | 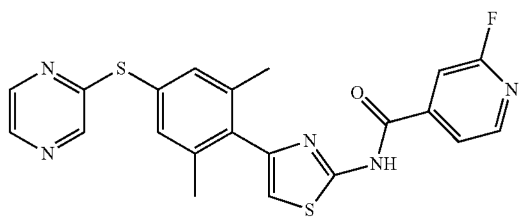 [SMILES: Cc1cc(Sc2cnccn2)cc(C)c1-c1csc(NC(=O)c2ccnc(F)c2)n1] | 35.6 | 37.6 | 60.1 | 32.0 |
| 20 (110079) | 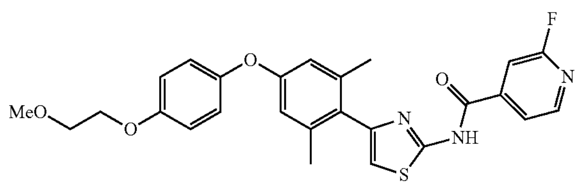 [SMILES: COCCOc1ccc(Oc2cc(C)c(-c3csc(NC(=O)c4ccnc(F)c4)n3)c(C)c2)cc1] | 10.9 | 14.1 | 10.4 | 7.5 |
| 21 | 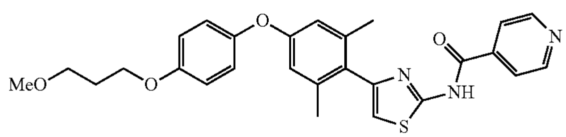 [SMILES: COCCCOc1ccc(Oc2cc(C)c(-c3csc(NC(=O)c4ccncc4)n3)c(C)c2)cc1] | 16.6 | 20.6 | 22.3 | 14.1 |
| 22 (110091) | 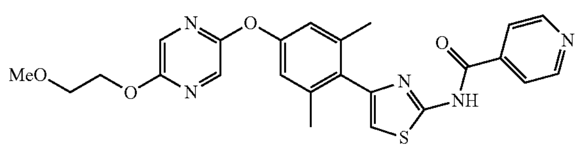 [SMILES: COCCOc1cnc(Oc2cc(C)c(-c3csc(NC(=O)c4ccncc4)n3)c(C)c2)cn1] | 15.1 | 12.0 | 20.5 | 13.4 |
| 23 | 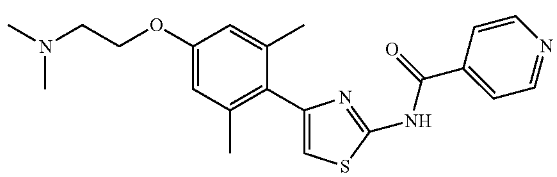 [SMILES: Cc1cc(OCCN(C)C)cc(C)c1-c1csc(NC(=O)c2ccncc2)n1] | >10,000 | >10,000 | >10,000 | >10,000 |
| 24 | 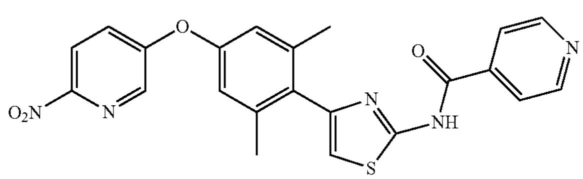 [SMILES: Cc1cc(Oc2ccc([N+](=O)[O-])nc2)cc(C)c1-c1csc(NC(=O)c2ccncc2)n1] | 73.8 | 147.8 | 157.7 | 180.8 |
| 25 (110093) | 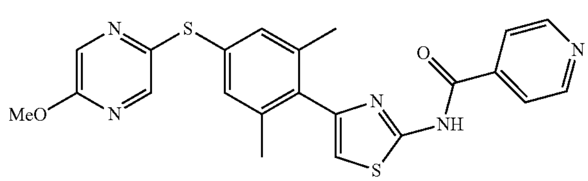 | 15.5 | 14.7 | 18.4 | 24.1 |

TABLE 1-continued

| No. | Structure | Antiproliferative IC$_{50}$ (nM) | | | |
| --- | --- | --- | --- | --- | --- |
| | | Hela | K562 | MDA-MB-468 | MDA-MB-231 |
| 26 | 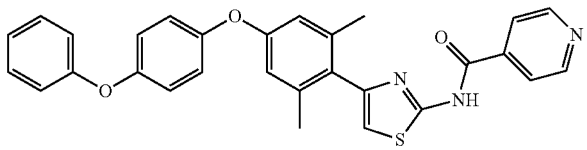 [SMILES: Cc1cc(Oc2ccc(Oc3ccccc3)cc2)cc(C)c1-c1csc(NC(=O)c2ccncc2)n1] | 84.8 | 64.4 | 132.1 | 99.4 |
| 27 (110095) | 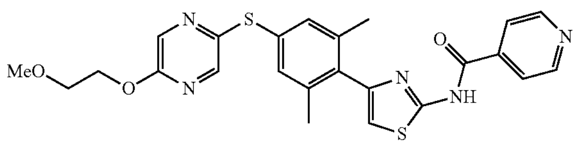 | 21.1 | 18.0 | 19.1 | 35.1 |
| 28 | 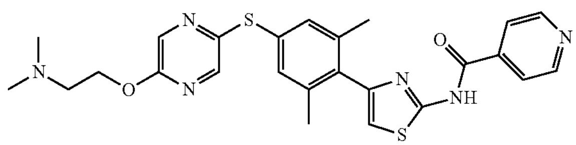 [SMILES: Cc1cc(Sc2cnc(OCCN(C)C)cn2)cc(C)c1-c1csc(NC(=O)c2ccncc2)n1] | 32.8 | 59.2 | 74.5 | 123.7 |
| 29 | 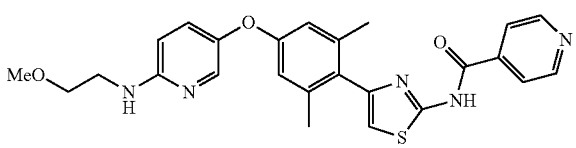 [SMILES: COCCNc1ccc(Oc2cc(C)c(-c3csc(NC(=O)c4ccncc4)n3)c(C)c2)cn1] | 8.3 | 11.7 | 16.6 | 21.9 |
| 30 | 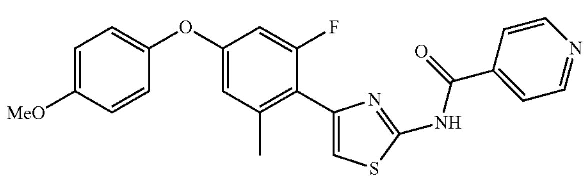 [SMILES: COc1ccc(Oc2cc(C)c(-c3csc(NC(=O)c4ccncc4)n3)c(F)c2)cc1] | 108.2 | 106.6 | 142.9 | 269.6 |
| 31 | 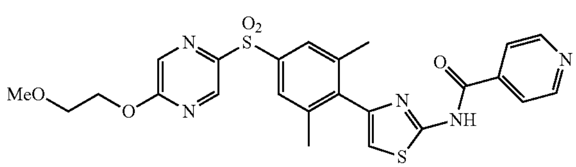 [SMILES: COCCOc1cnc(S(=O)(=O)c2cc(C)c(-c3csc(NC(=O)c4ccncc4)n3)c(C)c2)cn1] | 957.4 | 634.8 | 1001.5 | 1115.5 |
| 32 | 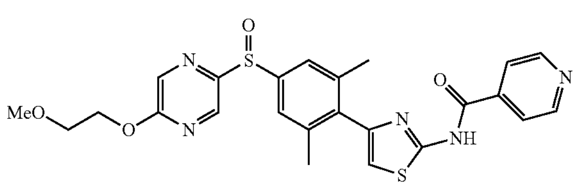 [SMILES: COCCOc1cnc(S(=O)c2cc(C)c(-c3csc(NC(=O)c4ccncc4)n3)c(C)c2)cn1] | 1118.5 | 733.9 | 1284.0 | 1700.5 |
| 33 | 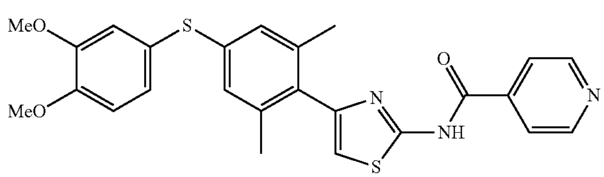 [SMILES: COc1ccc(Sc2cc(C)c(-c3csc(NC(=O)c4ccncc4)n3)c(C)c2)cc1OC] | 57.1 | 28.3 | 73.0 | 49.4 |
| 34 | 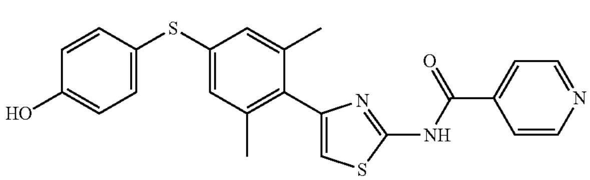 [SMILES: Cc1cc(Sc2ccc(O)cc2)cc(C)c1-c1csc(NC(=O)c2ccncc2)n1] | 301.5 | 89.4 | 279.4 | 183.5 |

TABLE 1-continued

| No. | Structure | Antiproliferative IC$_{50}$ (nM) | | | |
|---|---|---|---|---|---|
| | | Hela | K562 | MDA-MB-468 | MDA-MB-231 |
| 35 | 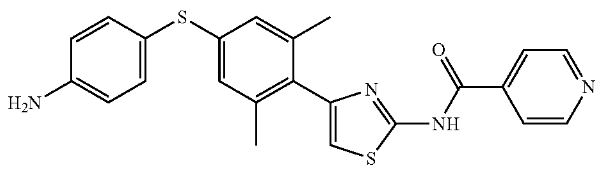 [SMILES: Cc1cc(Sc2ccc(N)cc2)cc(C)c1-c1csc(NC(=O)c2ccncc2)n1] | 43.8 | 26.1 | 95.8 | 46.9 |
| 36 | 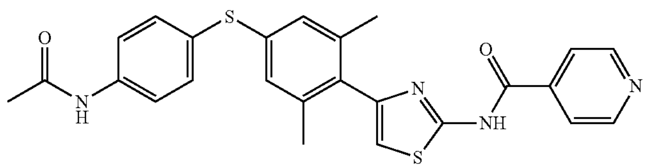 [SMILES: CC(=O)Nc1ccc(Sc2cc(C)c(-c3csc(NC(=O)c4ccncc4)n3)c(C)c2)cc1] | 24.5 | 18.9 | 62.4 | 44.3 |
| 37 | 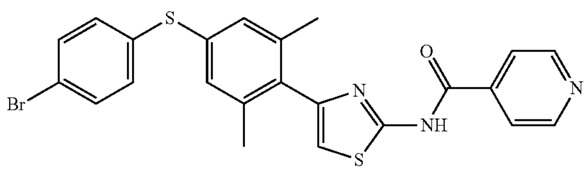 | 243.4 | 62.5 | 226.5 | 147.8 |
| 38 | 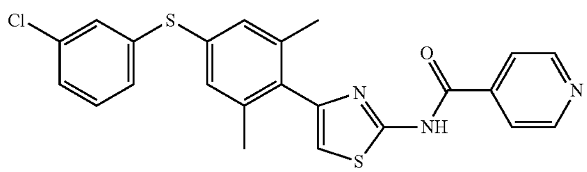 [SMILES: Cc1cc(Sc2cccc(Cl)c2)cc(C)c1-c1csc(NC(=O)c2ccncc2)n1] | 500.5 | 128.4 | 352.4 | 196.6 |
| 39 | 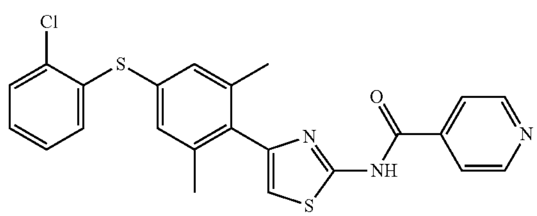 [SMILES: Cc1cc(Sc2ccccc2Cl)cc(C)c1-c1csc(NC(=O)c2ccncc2)n1] | 211.0 | 36.2 | 73.9 | 55.9 |
| 40 | 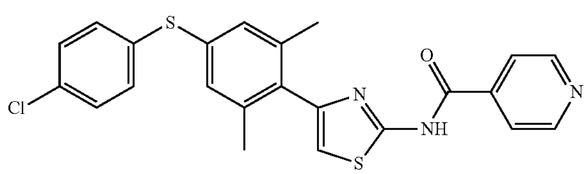 [SMILES: Cc1cc(Sc2ccc(Cl)cc2)cc(C)c1-c1csc(NC(=O)c2ccncc2)n1] | 585.4 | 93.5 | 123.5 | 199.8 |
| 41 | 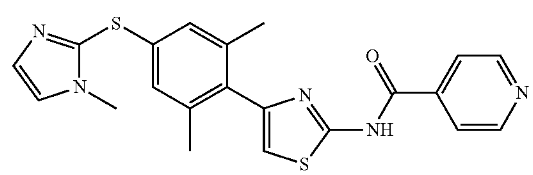 [SMILES: Cc1cc(Sc2nccn2C)cc(C)c1-c1csc(NC(=O)c2ccncc2)n1] | 61.5 | 31.1 | 62.9 | 86.1 |
| 42 | 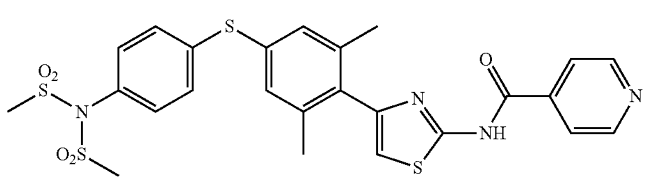 [SMILES: Cc1cc(Sc2ccc(N(S(C)(=O)=O)S(C)(=O)=O)cc2)cc(C)c1-c1csc(NC(=O)c2ccncc2)n1] | 166.6 | 59.3 | 120.7 | 76.6 |

TABLE 1-continued

| No. | Structure | Antiproliferative IC$_{50}$ (nM) | | | |
|---|---|---|---|---|---|
| | | Hela | K562 | MDA-MB-468 | MDA-MB-231 |
| 43 | 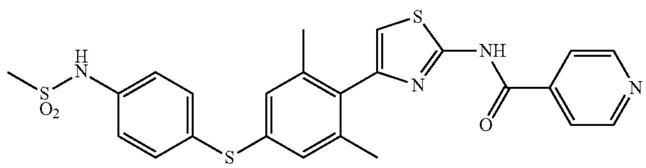 [SMILES: Cc1cc(Sc2ccc(NS(C)(=O)=O)cc2)cc(C)c1-c1csc(NC(=O)c2ccncc2)n1] | 66.4 | 26.6 | 49.4 | 53.1 |
| 44 | 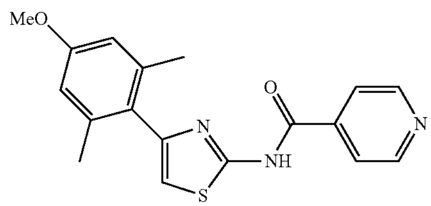 [SMILES: COc1cc(C)c(-c2csc(NC(=O)c3ccncc3)n2)c(C)c1] | 99.5 | 171.6 | 150.0 | 160.0 |
| 45 | 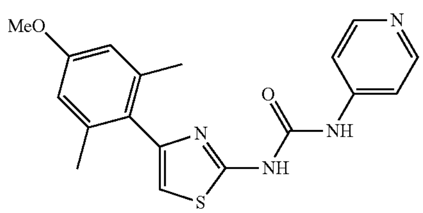 [SMILES: COc1cc(C)c(-c2csc(NC(=O)Nc3ccncc3)n2)c(C)c1] | >10,000 | 486.5 | 614.6 | 628.1 |
| 46 | 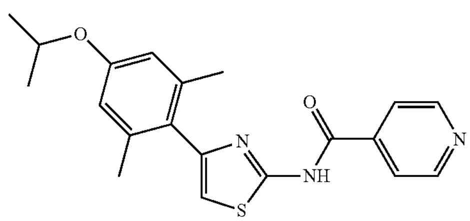 [SMILES: Cc1cc(OC(C)C)cc(C)c1-c1csc(NC(=O)c2ccncc2)n1] | 162.0 | 52.0 | 120.0 | 96.0 |
| 47 | 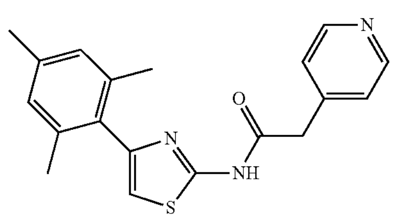 [SMILES: Cc1cc(C)c(-c2csc(NC(=O)Cc3ccncc3)n2)c(C)c1] | 619.0 | 382.0 | 304.0 | 312.0 |
| 48 | 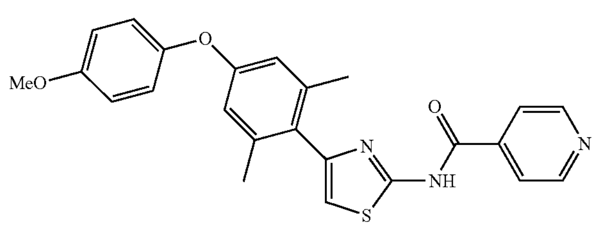 [SMILES: COc1ccc(Oc2cc(C)c(-c3csc(NC(=O)c4ccncc4)n3)c(C)c2)cc1] | 48.6 | 34.9 | 37.0 | 32.0 |
| 49 | 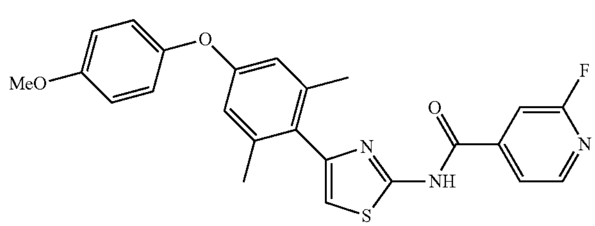 | 42.7 | 16.3 | 40.0 | 20.0 |

TABLE 1-continued

| No. | Structure | Antiproliferative IC$_{50}$ (nM) | | | |
| --- | --- | --- | --- | --- | --- |
| | | Hela | K562 | MDA-MB-468 | MDA-MB-231 |
| 50 | 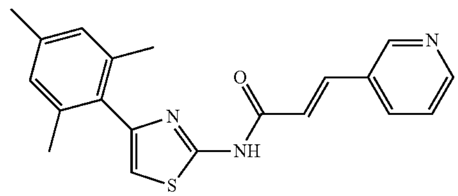 [SMILES: Cc1cc(C)c(-c2csc(NC(=O)/C=C/c3cccnc3)n2)c(C)c1] | >10,000 | 2,480 | 2,169 | 1,113 |
| 51 | 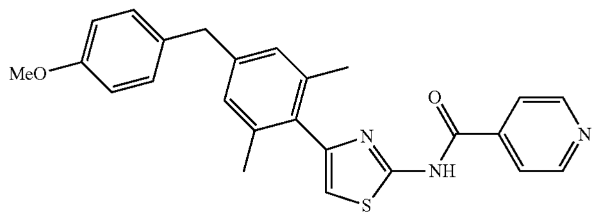 | 72.0 | 33.0 | 66.0 | 49.0 |
| 52 | 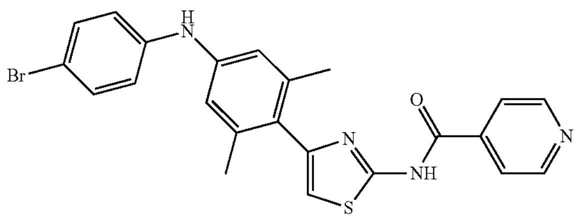 | 2,131 | 362.0 | 1,220.0 | 717.0 |
| 53 | 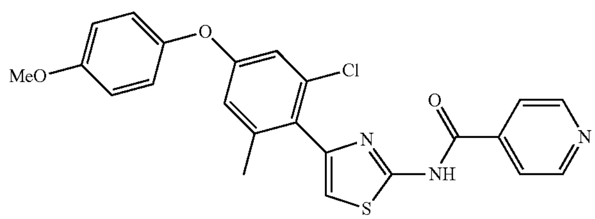 [SMILES: COc1ccc(Oc2cc(C)c(-c3csc(NC(=O)c4ccncc4)n3)c(Cl)c2)cc1] | 64.8 | 42.4 | 53.0 | 39.0 |

The following Table 2 lists exemplary results for further selected compounds illustrating the antiproliferative activity on selected cancer cells using exposure of the cells in growth medium with the compounds as indicated. Antiproliferative effect is expressed as IC$_{50}$ values in micromolar final concentration.

TABLE 2

| Compound | Structure | Antiproliferative IC$_{50}$ (nM) | | | |
| --- | --- | --- | --- | --- | --- |
| | | Hela | K562 | MDA-MB-468 | MDA-MB-231 |
| II-1 | 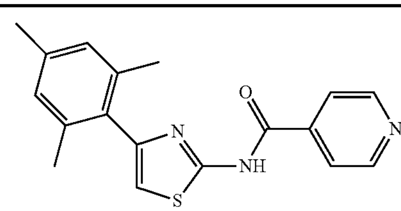 | 0.67 | 0.43 | 0.35 | 0.30 |
| II-2 | 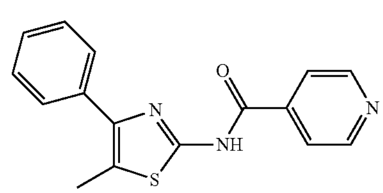 [SMILES: Cc1sc(NC(=O)c2ccncc2)nc1-c1ccccc1] | >10 | >10 | 8.15 | >10 |

TABLE 2-continued

| Compound | Structure | Antiproliferative IC$_{50}$ (nM) | | | |
| --- | --- | --- | --- | --- | --- |
| | | Hela | K562 | MDA-MB-468 | MDA-MB-231 |
| II-3 | 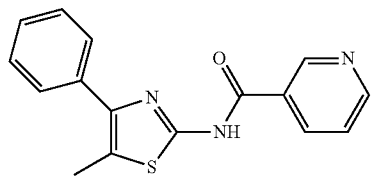 [SMILES: Cc1sc(NC(=O)c2cccnc2)nc1-c1ccccc1] | >10 | >10 | >10 | >10 |
| II-4 | 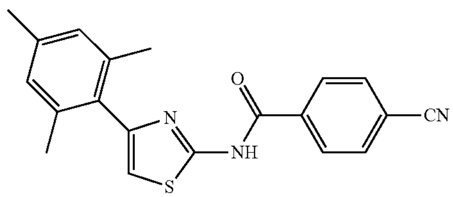 [SMILES: Cc1cc(C)c(-c2csc(NC(=O)c3ccc(C#N)cc3)n2)c(C)c1] | >10 | 2.07 | 0.79 | 0.61 |
| II-5 | 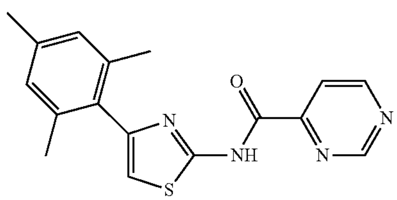 [SMILES: Cc1cc(C)c(-c2csc(NC(=O)c3ccncn3)n2)c(C)c1] | >10 | 5.74 | 4.57 | 7.37 |
| II-6 | 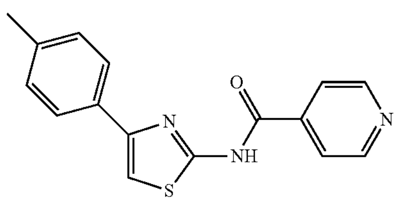 [SMILES: Cc1ccc(-c2csc(NC(=O)c3ccncc3)n2)cc1] | 1.05 | 1.48 | 1.14 | 0.67 |
| II-7 | 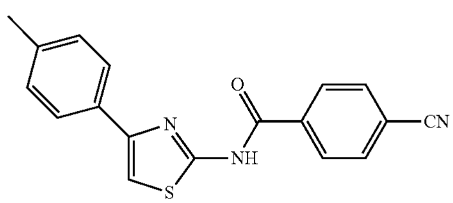 [SMILES: Cc1ccc(-c2csc(NC(=O)c3ccc(C#N)cc3)n2)cc1] | >10 | >10 | >10 | >10 |
| II-8 | 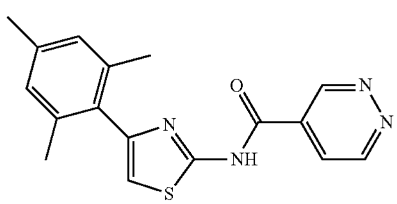 [SMILES: Cc1cc(C)c(-c2csc(NC(=O)c3ccnnc3)n2)c(C)c1] | 8.75 | 5.60 | 6.18 | 3.12 |
| II-9 | 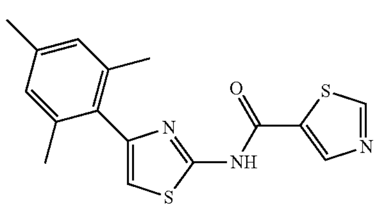 [SMILES: Cc1cc(C)c(-c2csc(NC(=O)c3cncs3)n2)c(C)c1] | 1.51 | 2.68 | 1.83 | 1.24 |

TABLE 2-continued

| Compound | Structure | Antiproliferative IC$_{50}$ (nM) | | | |
| --- | --- | --- | --- | --- | --- |
| | | Hela | K562 | MDA-MB-468 | MDA-MB-231 |
| II-10 | 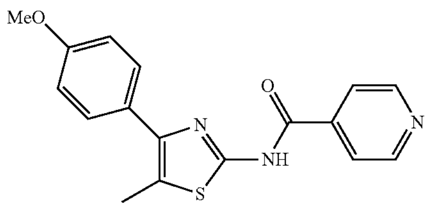 [SMILES: COc1ccc(-c2nc(NC(=O)c3ccncc3)sc2C)cc1] | >10 | >10 | 8.89 | 8.03 |
| II-11 | 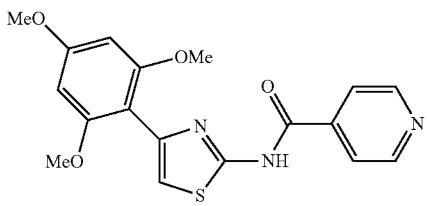 [SMILES: COc1cc(OC)c(-c2csc(NC(=O)c3ccncc3)n2)c(OC)c1] | >10 | >10 | >10 | >10 |
| II-12 | 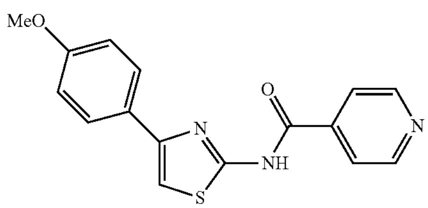 [SMILES: COc1ccc(-c2csc(NC(=O)c3ccncc3)n2)cc1] | >10 | 3.91 | 2.88 | 1.41 |
| II-13 | 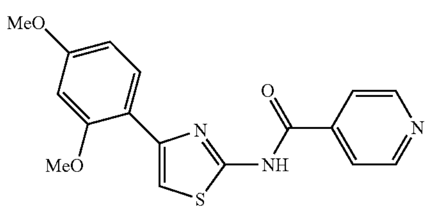 [SMILES: COc1ccc(-c2csc(NC(=O)c3ccncc3)n2)c(OC)c1] | >10 | >10 | >10 | >10 |
| II-14 | 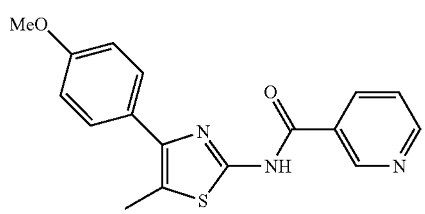 [SMILES: COc1ccc(-c2nc(NC(=O)c3cccnc3)sc2C)cc1] | >10 | >10 | >10 | >10 |
| II-15 | 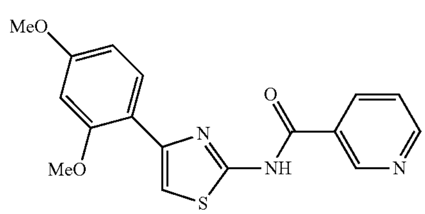 [SMILES: COc1ccc(-c2csc(NC(=O)c3cccnc3)n2)c(OC)c1] | >10 | >10 | >10 | >10 |
| II-16 | 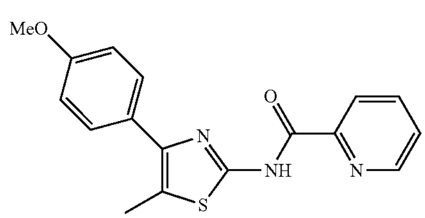 [SMILES: COc1ccc(-c2nc(NC(=O)c3ccccn3)sc2C)cc1] | >10 | >10 | >10 | >10 |

TABLE 2-continued

| Compound | Structure | Antiproliferative IC$_{50}$ (nM) | | | |
| --- | --- | --- | --- | --- | --- |
| | | Hela | K562 | MDA-MB-468 | MDA-MB-231 |
| II-17 | 4-MeO-phenyl-thiazole-NH-C(O)-2-pyridyl | >10 | >10 | >10 | >10 |
| II-18 | 2,4-diMeO-phenyl-thiazole-NH-C(O)-2-pyridyl | >10 | >10 | >10 | >10 |
| II-19 | phenyl-(5-methyl)thiazole-NH-C(O)-2-pyridyl | >10 | >10 | 6.85 | 6.75 |
| II-20 | 3,4,5-triMeO-phenyl-thiazole-NH-C(O)-3-pyridyl | >10 | >10 | >10 | >10 |
| II-21 | 4-MeO-2-F-phenyl-thiazole-NH-C(O)-3-pyridyl | >10 | >10 | >10 | >10 |
| II-22 | 4-MeO-2-F-phenyl-thiazole-NH-C(O)CH$_2$CH$_2$-4-MeO-phenyl | >10 | >10 | 4.19 | >10 |
| II-23 | 4-MeO-2-F-phenyl-thiazole-NH-C(O)CH$_2$CH$_2$-phenyl | >10 | >10 | 7.12 | >10 |

TABLE 2-continued
| Compound | Structure | Antiproliferative IC$_{50}$ (nM) | | | |
|---|---|---|---|---|---|
| | | Hela | K562 | MDA-MB-468 | MDA-MB-231 |
| II-24 | 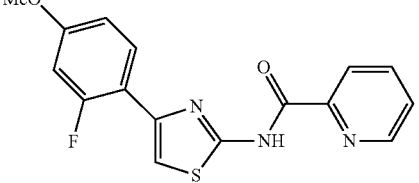 | >10 | >10 | >10 | >10 |
| II-25 | 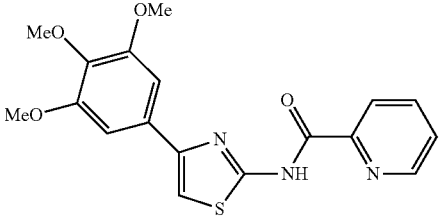 [SMILES: COc1cc(-c2csc(NC(=O)c3ccccn3)n2)cc(OC)c1OC] | >10 | >10 | >10 | >10 |
| II-26 | 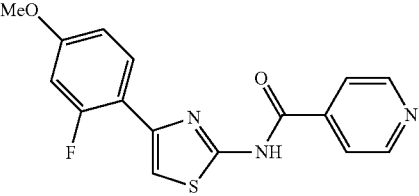 [SMILES: COc1ccc(-c2csc(NC(=O)c3ccncc3)n2)c(F)c1] | >10 | 2.43 | 2.25 | 6.85 |
| II-27 | 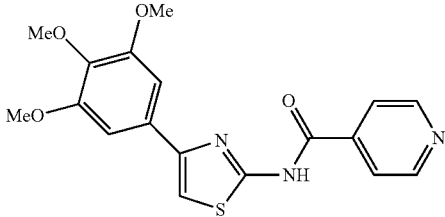 [SMILES: COc1cc(-c2csc(NC(=O)c3ccncc3)n2)cc(OC)c1OC] | >10 | >10 | >10 | >10 |
| II-28 | 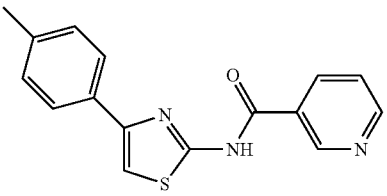 [SMILES: Cc1ccc(-c2csc(NC(=O)c3cccnc3)n2)cc1] | >10 | >10 | >10 | >10 |
| II-29 | 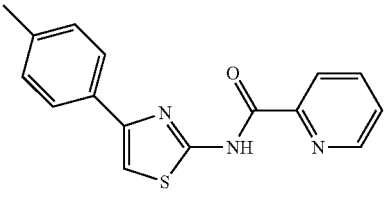 [SMILES: Cc1ccc(-c2csc(NC(=O)c3ccccn3)n2)cc1] | >10 | >10 | >10 | >10 |
| II-30 | 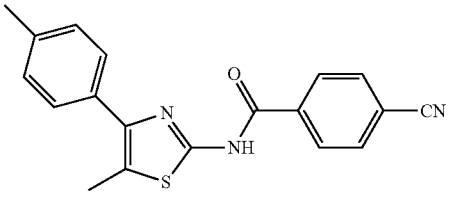 [SMILES: Cc1ccc(-c2nc(NC(=O)c3ccc(C#N)cc3)sc2C)cc1] | >10 | >10 | >10 | >10 |

TABLE 2-continued

| Compound | Structure | Antiproliferative IC$_{50}$ (nM) | | | |
|---|---|---|---|---|---|
| | | Hela | K562 | MDA-MB-468 | MDA-MB-231 |
| II-31 | 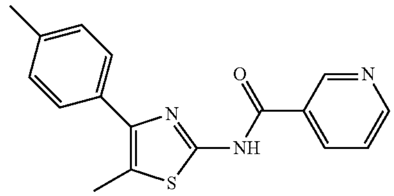 [SMILES: Cc1ccc(-c2nc(NC(=O)c3cccnc3)sc2C)cc1] | >10 | >10 | >10 | >10 |
| II-32 | 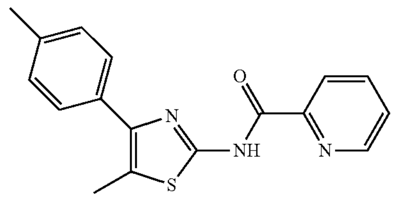 [SMILES: Cc1ccc(-c2nc(NC(=O)c3ccccn3)sc2C)cc1] | >10 | >10 | >10 | >10 |
| II-33 | 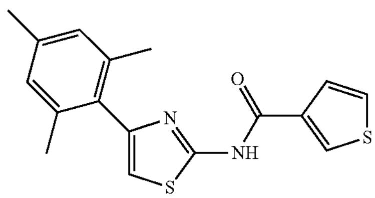 [SMILES: Cc1cc(C)c(-c2csc(NC(=O)c3ccsc3)n2)c(C)c1] | >10 | >10 | 0.79 | >10 |
| II-34 | 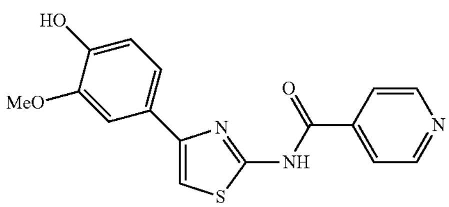 [SMILES: COc1cc(-c2csc(NC(=O)c3ccncc3)n2)ccc1O] | >10 | >10 | >10 | >10 |
| II-35 | 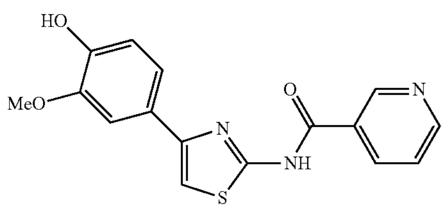 [SMILES: COc1cc(-c2csc(NC(=O)c3cccnc3)n2)ccc1O] | >10 | >10 | >10 | >10 |
| II-36 | 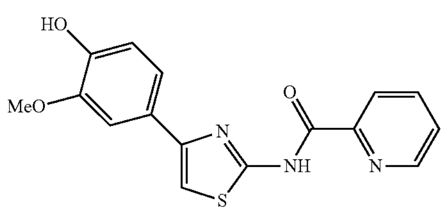 | >10 | >10 | >10 | >10 |
| II-37 | 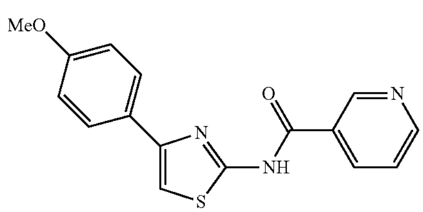 [SMILES: COc1ccc(-c2csc(NC(=O)c3cccnc3)n2)cc1] | >10 | >10 | >10 | >10 |

TABLE 2-continued

| Compound | Structure | Antiproliferative IC$_{50}$ (nM) | | | |
|---|---|---|---|---|---|
| | | Hela | K562 | MDA-MB-468 | MDA-MB-231 |
| II-38 | 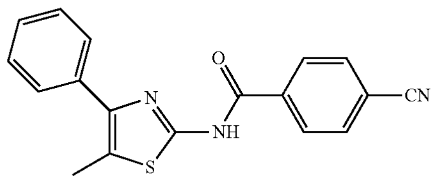 [SMILES: Cc1sc(NC(=O)c2ccc(C#N)cc2)nc1-c1ccccc1] | >10 | >10 | 3.40 | 5.68 |
| II-39 | 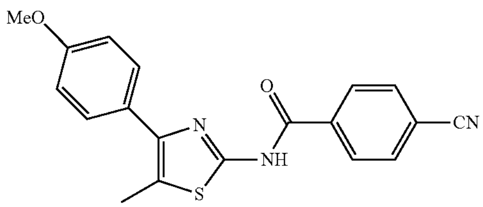 [SMILES: COc1ccc(-c2nc(NC(=O)c3ccc(C#N)cc3)sc2C)cc1] | >10 | >10 | >10 | >10 |
| II-40 | 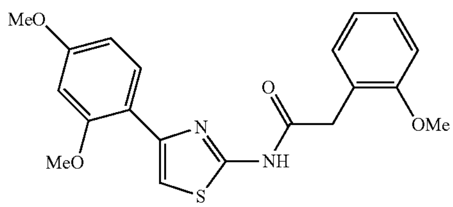 [SMILES: COc1ccc(-c2csc(NC(=O)Cc3ccccc3OC)n2)c(OC)c1] | >10 | >10 | >10 | >10 |
| II-41 | 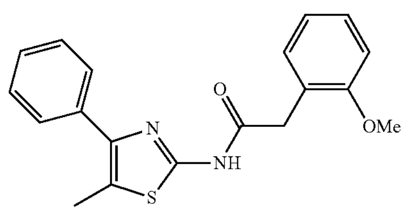 [SMILES: COc1ccccc1CC(=O)Nc1nc(-c2ccccc2)c(C)s1] | >10 | >10 | >10 | >10 |
| II-42 | 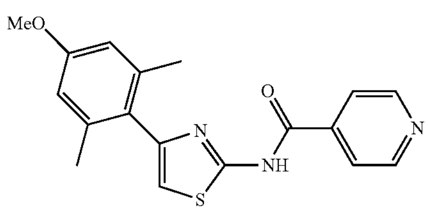 | 0.10 | 0.17 | 0.15 | 0.16 |
| II-43 | 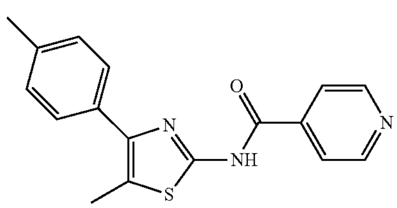 [SMILES: Cc1ccc(-c2nc(NC(=O)c3ccncc3)sc2C)cc1] | >10 | >10 | >10 | >10 |
| II-44 | 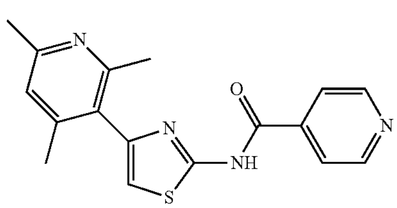 | >10 | 1.96 | 1.01 | 1.24 |

TABLE 2-continued

| Compound | Structure | Antiproliferative IC$_{50}$ (nM) | | | |
| --- | --- | --- | --- | --- | --- |
| | | Hela | K562 | MDA-MB-468 | MDA-MB-231 |
| II-45 | 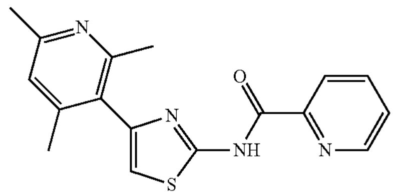 | >10 | >10 | 7.68 | >10 |
| II-46 | 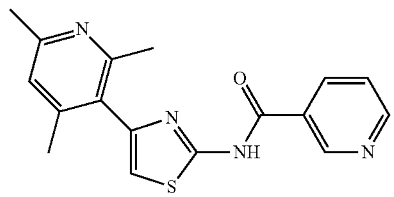 [SMILES: Cc1cc(C)c(-c2csc(NC(=O)c3cccnc3)n2)c(C)n1] | >10 | >10 | 7.19 | 7.41 |
| II-47 | 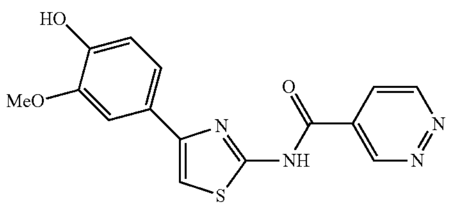 [SMILES: COc1cc(-c2csc(NC(=O)c3ccnnc3)n2)ccc1O] | >10 | >10 | >10 | >10 |
| II-48 | 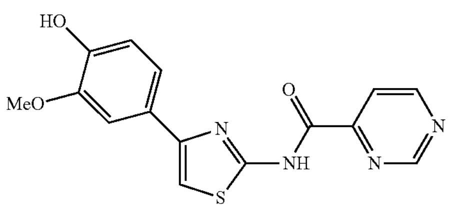 [SMILES: COc1cc(-c2csc(NC(=O)c3ccncn3)n2)ccc1O] | >10 | >10 | >10 | >10 |
| II-49 | 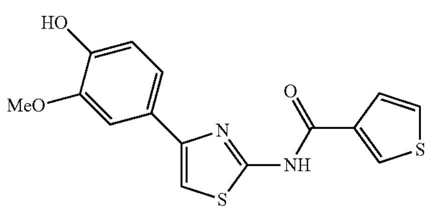 [SMILES: COc1cc(-c2csc(NC(=O)c3ccsc3)n2)ccc1O] | >10 | >10 | >10 | >10 |
| II-50 | 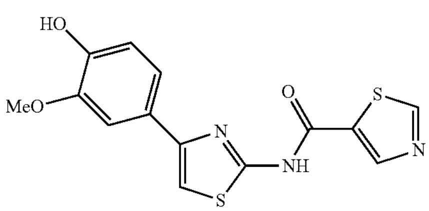 [SMILES: COc1cc(-c2csc(NC(=O)c3cncs3)n2)ccc1O] | >10 | >10 | >10 | >10 |
| II-51 | 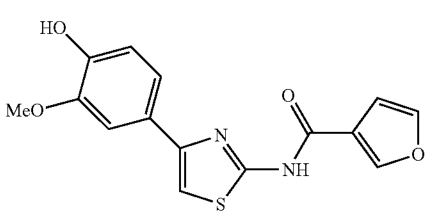 [SMILES: COc1cc(-c2csc(NC(=O)c3ccoc3)n2)ccc1O] | >10 | >10 | >10 | >10 |

TABLE 2-continued

| Compound | Structure | Antiproliferative IC$_{50}$ (nM) | | | |
|---|---|---|---|---|---|
| | | Hela | K562 | MDA-MB-468 | MDA-MB-231 |
| II-52 | 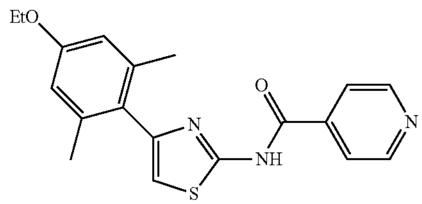 [SMILES: CCOc1cc(C)c(-c2csc(NC(=O)c3ccncc3)n2)c(C)c1] | 0.04 | 0.21 | 0.17 | 0.17 |
| II-53 | 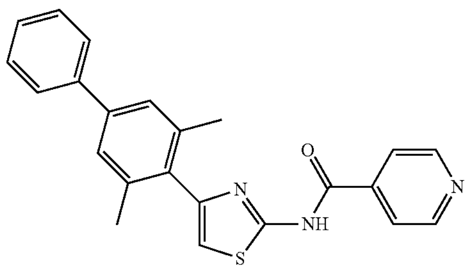 [SMILES: Cc1cc(-c2ccccc2)cc(C)c1-c1csc(NC(=O)c2ccncc2)n1] | 0.48 | 0.62 | 0.48 | 0.43 |
| II-54 | 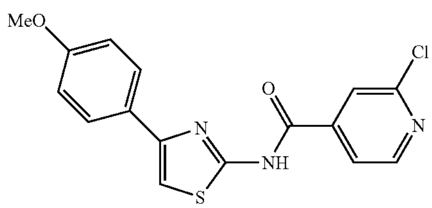 [SMILES: COc1ccc(-c2csc(NC(=O)c3ccnc(Cl)c3)n2)cc1] | 5.92 | 6.65 | 6.95 | 4.56 |
| II-55 | 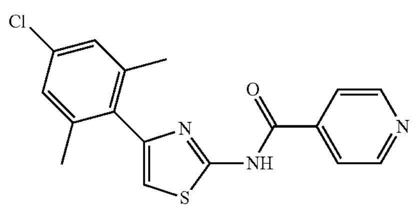 [SMILES: Cc1cc(Cl)cc(C)c1-c1csc(NC(=O)c2ccncc2)n1] | 0.73 | 0.76 | 0.89 | 0.59 |
| II-56 | 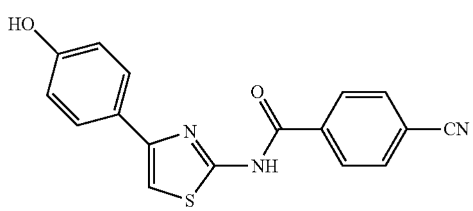 [SMILES: N#Cc1ccc(C(=O)Nc2nc(-c3ccc(O)cc3)cs2)cc1] | >10 | >10 | >10 | >10 |
| II-57 | 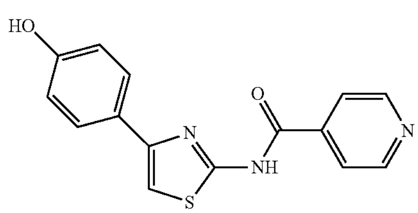 [SMILES: O=C(Nc1nc(-c2ccc(O)cc2)cs1)c1ccncc1] | >10 | >10 | >10 | >10 |
| II-58 | 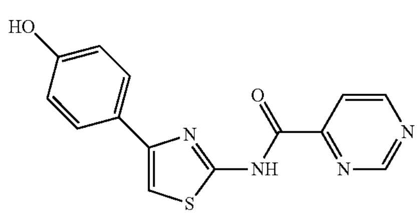 [SMILES: O=C(Nc1nc(-c2ccc(O)cc2)cs1)c1ccncn1] | >10 | >10 | >10 | >10 |

TABLE 2-continued
| Compound | Structure | Antiproliferative IC$_{50}$ (nM) | | | |
|---|---|---|---|---|---|
| | | Hela | K562 | MDA-MB-468 | MDA-MB-231 |
| II-59 | 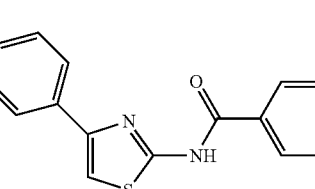 | >10 | >10 | >10 | >10 |
| II-60 | 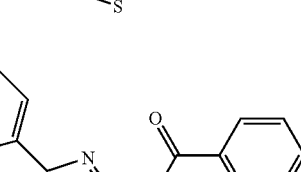 | >10 | >10 | >10 | >10 |
| II-61 | 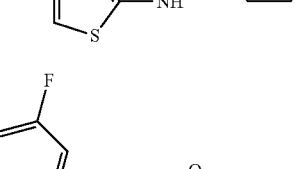 | >10 | >10 | >10 | >10 |
| II-62 | 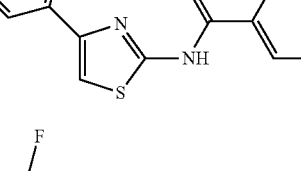 | >10 | 7.16 | 5.45 | 4.00 |
| II-63 | 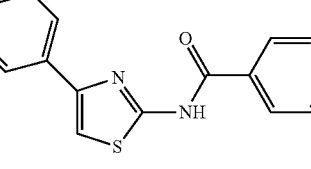 | >10 | >10 | >10 | >10 |
| II-64 | 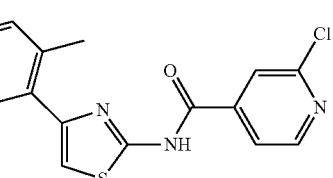 | 0.84 | 0.93 | 0.98 | 0.62 |
| II-65 | 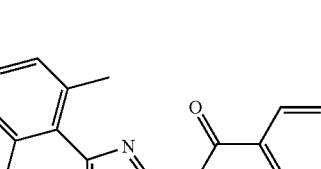 | 0.20 | 0.24 | 0.28 | 0.16 |

TABLE 2-continued

| Compound | Structure | Antiproliferative IC$_{50}$ (nM) | | | |
|---|---|---|---|---|---|
| | | Hela | K562 | MDA-MB-468 | MDA-MB-231 |
| II-66 | 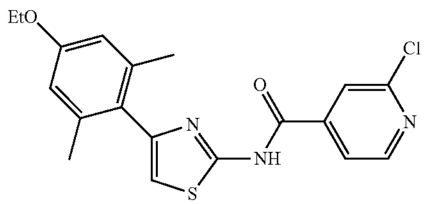 [SMILES: CCOc1cc(C)c(-c2csc(NC(=O)c3ccnc(Cl)c3)n2)c(C)c1] | 0.20 | 0.21 | 0.24 | 0.11 |
| II-67 | 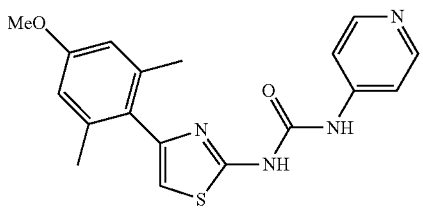 [SMILES: COc1cc(C)c(-c2csc(NC(=O)Nc3ccncc3)n2)c(C)c1] | >10 | 0.82 | 0.78 | 0.57 |
| II-68 | 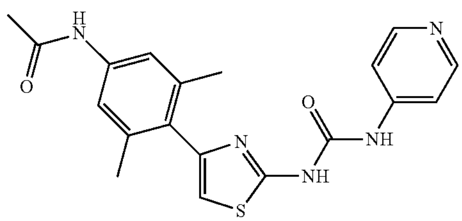 [SMILES: CC(=O)Nc1cc(C)c(-c2csc(NC(=O)Nc3ccncc3)n2)c(C)c1] | 5.13 | 4.96 | 3.61 | 4.24 |
| II-69 | 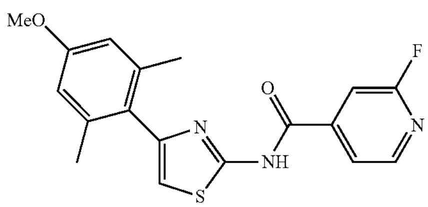 [SMILES: COc1cc(C)c(-c2csc(NC(=O)c3ccnc(F)c3)n2)c(C)c1] | 0.08 | 0.20 | 0.22 | 0.13 |
| II-70 | 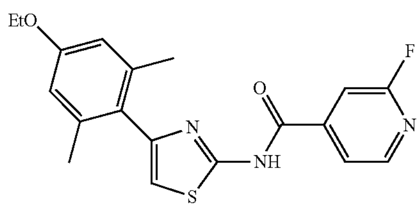 [SMILES: CCOc1cc(C)c(-c2csc(NC(=O)c3ccnc(F)c3)n2)c(C)c1] | 0.03 | 0.16 | 0.21 | 0.11 |
| II-71 | 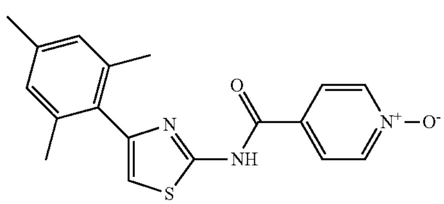 [SMILES: Cc1cc(C)c(-c2csc(NC(=O)c3cc[n+]([O-])cc3)n2)c(C)c1] | 2.29 | 4.58 | 4.18 | 3.57 |
| II-72 | 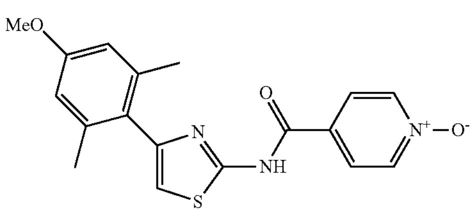 [SMILES: COc1cc(C)c(-c2csc(NC(=O)c3cc[n+]([O-])cc3)n2)c(C)c1] | 2.70 | 5.40 | 4.81 | 4.28 |

TABLE 2-continued

| Compound | Structure | Antiproliferative IC$_{50}$ (nM) | | | |
| --- | --- | --- | --- | --- | --- |
| | | Hela | K562 | MDA-MB-468 | MDA-MB-231 |
| II-73 | 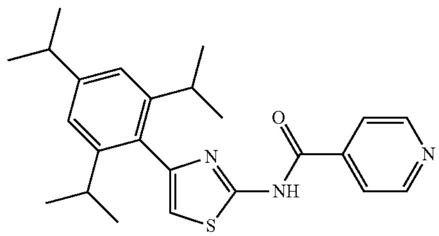 [SMILES: CC(C)c1cc(C(C)C)c(-c2csc(NC(=O)c3ccncc3)n2)c(C(C)C)c1] | >10 | >10 | >10 | >10 |
| II-74 | 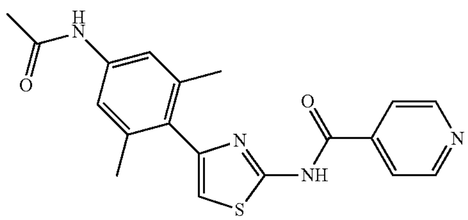 [SMILES: CC(=O)Nc1cc(C)c(-c2csc(NC(=O)c3ccncc3)n2)c(C)c1] | 1.59 | 2.13 | 1.27 | 1.46 |
| II-75 | 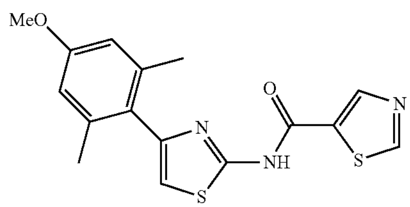 [SMILES: COc1cc(C)c(-c2csc(NC(=O)c3cncs3)n2)c(C)c1] | 2.93 | 3.70 | 4.34 | 2.37 |
| II-76 | 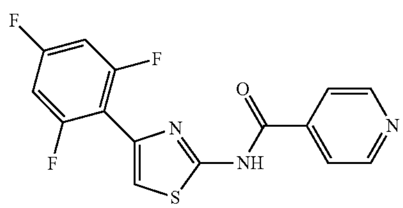 [SMILES: O=C(Nc1nc(-c2c(F)cc(F)cc2F)cs1)c1ccncc1] | 1.12 | 0.94 | 1.25 | 0.54 |
| II-77 | 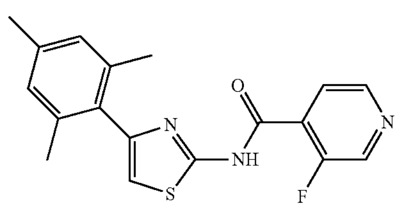 [SMILES: Cc1cc(C)c(-c2csc(NC(=O)c3ccncc3F)n2)c(C)c1] | 2.29 | 2.82 | 2.78 | 1.22 |
| II-78 | 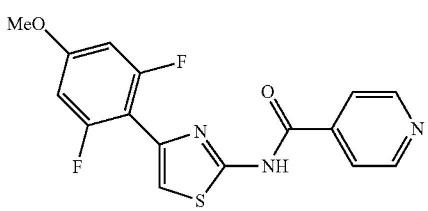 [SMILES: COc1cc(F)c(-c2csc(NC(=O)c3ccncc3)n2)c(F)c1] | 0.31 | 0.22 | 0.45 | 0.17 |
| II-79 | 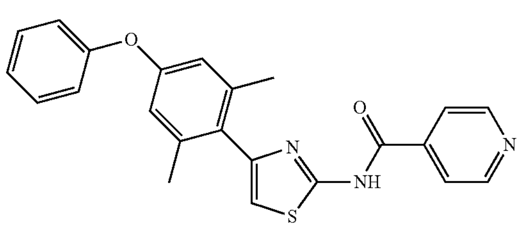 | 0.24 | 0.09 | 0.15 | 0.17 |

TABLE 2-continued

| Compound | Structure | Antiproliferative IC$_{50}$ (nM) | | | |
| --- | --- | --- | --- | --- | --- |
| | | Hela | K562 | MDA-MB-468 | MDA-MB-231 |
| II-80 | 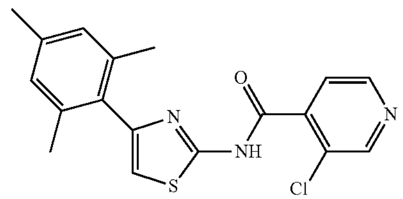 | 7.16 | 6.07 | 5.20 | 6.79 |
| II-81 | 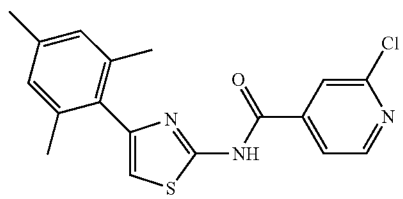 [SMILES: Cc1cc(C)c(-c2csc(NC(=O)c3ccnc(Cl)c3)n2)c(C)c1] | 0.86 | 0.79 | 0.82 | 0.72 |
| II-82 | 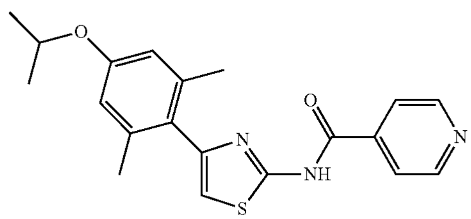 [SMILES: Cc1cc(OC(C)C)cc(C)c1-c1csc(NC(=O)c2ccncc2)n1] | 0.16 | 0.05 | 0.12 | 0.10 |
| II-83 | 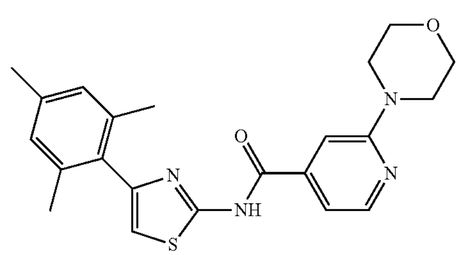 [SMILES: Cc1cc(C)c(-c2csc(NC(=O)c3ccnc(N4CCOCC4)c3)n2)c(C)c1] | 2.37 | 2.23 | 4.17 | 3.51 |
| II-84 | 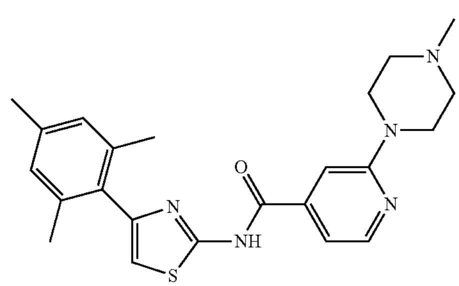 | >10 | >10 | 28.8 | >10 |
| II-85 | 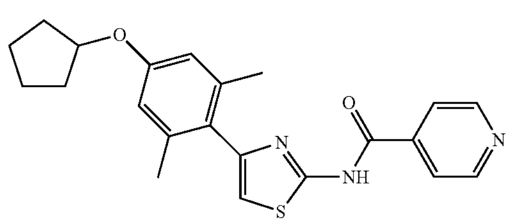 [SMILES: Cc1cc(OC2CCCC2)cc(C)c1-c1csc(NC(=O)c2ccncc2)n1] | 0.22 | 0.12 | 0.13 | 0.10 |

TABLE 2-continued

| Compound | Structure | Antiproliferative IC$_{50}$ (nM) | | | |
|---|---|---|---|---|---|
| | | Hela | K562 | MDA-MB-468 | MDA-MB-231 |
| II-86 | 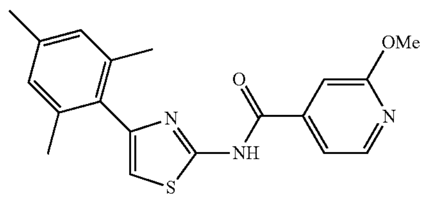 [SMILES: COc1cc(C(=O)Nc2nc(-c3c(C)cc(C)cc3C)cs2)ccn1] | 1.72 | 0.69 | 2.51 | 0.77 |
| II-87 | 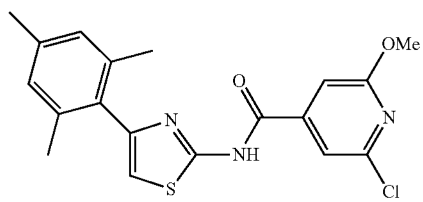 [SMILES: COc1cc(C(=O)Nc2nc(-c3c(C)cc(C)cc3C)cs2)cc(Cl)n1] | >10 | >10 | >10 | >10 |
| II-88 | 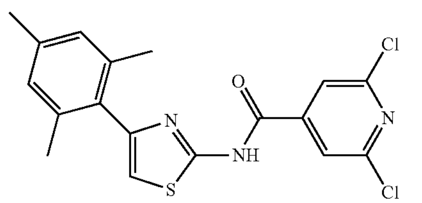 [SMILES: Cc1cc(C)c(-c2csc(NC(=O)c3cc(Cl)nc(Cl)c3)n2)c(C)c1] | >10 | 8.30 | 15.47 | 7.98 |
| II-89 | 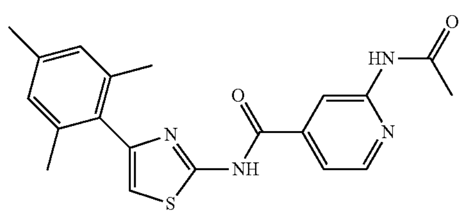 [SMILES: CC(=O)Nc1cc(C(=O)Nc2nc(-c3c(C)cc(C)cc3C)cs2)ccn1] | >10 | >10 | 8.20 | >10 |
| II-90 | 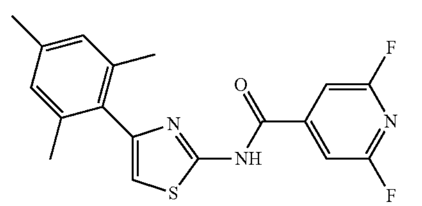 [SMILES: Cc1cc(C)c(-c2csc(NC(=O)c3cc(F)nc(F)c3)n2)c(C)c1] | 1.15 | 0.99 | 1.22 | 0.80 |
| II-91 | 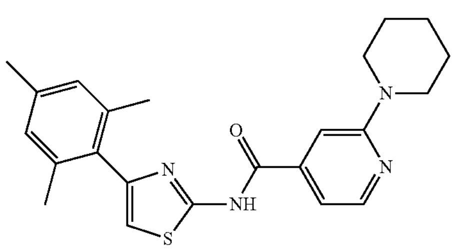 [SMILES: Cc1cc(C)c(-c2csc(NC(=O)c3ccnc(N4CCCCC4)c3)n2)c(C)c1] | >10 | 1.40 | 4.66 | 6.06 |
| II-92 | 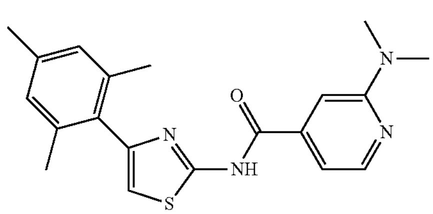 | >10 | 0.45 | 3.29 | 2.21 |

TABLE 2-continued
| Compound | Structure | Antiproliferative IC$_{50}$ (nM) | | | |
| --- | --- | --- | --- | --- | --- |
| | | Hela | K562 | MDA-MB-468 | MDA-MB-231 |
| II-93 | 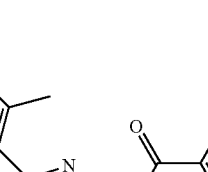 | 0.62 | 0.38 | 0.30 | 0.31 |
| II-94 | 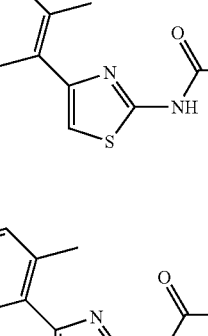 | 0.23 | 0.23 | 0.39 | 0.30 |
| II-95 (Hec1001, 101001) | 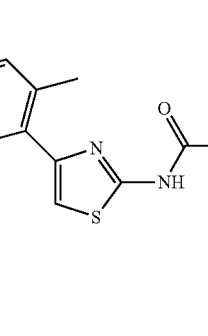 | 0.05 | 0.03 | 0.04 | 0.03 |
| II-96 | 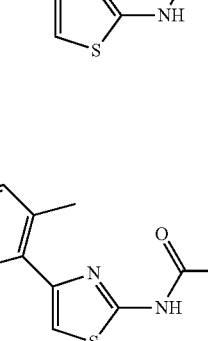 | 0.26 | 0.28 | 0.25 | 0.24 |
| II-97 | 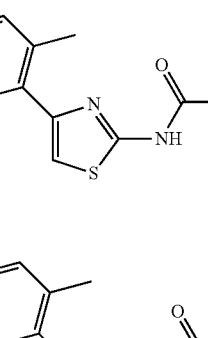 | 3.26 | 9.11 | 3.11 | 8.30 |
| II-98 (Hec1015, 101015) | 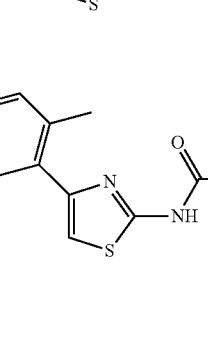 | 0.04 | 0.02 | 0.04 | 0.02 |

TABLE 2-continued
| Compound | Structure | Antiproliferative IC$_{50}$ (nM) | | | |
| --- | --- | --- | --- | --- | --- |
| | | Hela | K562 | MDA-MB-468 | MDA-MB-231 |
| II-99 | 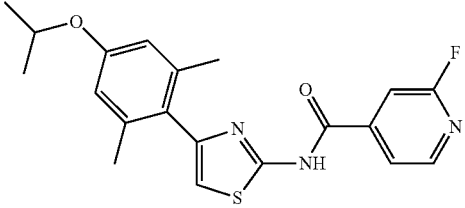 [SMILES: Cc1cc(OC(C)C)cc(C)c1-c1csc(NC(=O)c2ccnc(F)c2)n1] | 0.17 | 0.04 | 0.11 | 0.06 |
| II-100 | 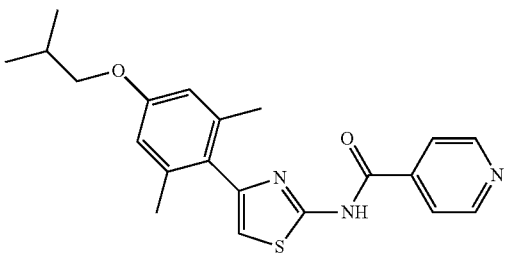 [SMILES: Cc1cc(OCC(C)C)cc(C)c1-c1csc(NC(=O)c2ccncc2)n1] | 0.28 | 0.11 | 0.39 | 0.28 |
| II-101 | 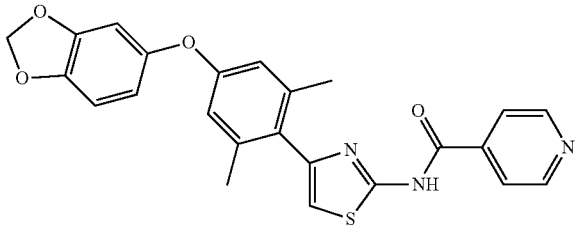 [SMILES: Cc1cc(Oc2ccc3c(c2)OCO3)cc(C)c1-c1csc(NC(=O)c2ccncc2)n1] | 0.11 | 0.05 | 0.13 | 0.07 |
| II-102 | 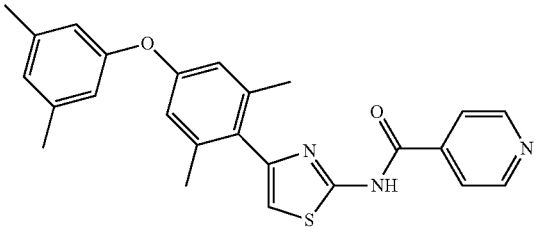 [SMILES: Cc1cc(C)cc(Oc2cc(C)c(-c3csc(NC(=O)c4ccncc4)n3)c(C)c2)c1] | 1.62 | 0.73 | 1.48 | 0.93 |
| II-103 | 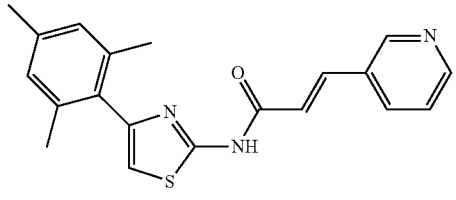 | >10 | 2.48 | 2.17 | 1.11 |
| II-104 | 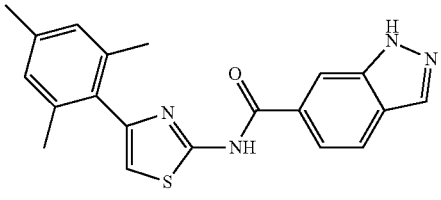 [SMILES: Cc1cc(C)c(-c2csc(NC(=O)c3ccc4cn[nH]c4c3)n2)c(C)c1] | >10 | 2.44 | 7.64 | 1.10 |

TABLE 2-continued

| Compound | Structure | Antiproliferative IC$_{50}$ (nM) | | | |
|---|---|---|---|---|---|
| | | Hela | K562 | MDA-MB-468 | MDA-MB-231 |
| II-105 | 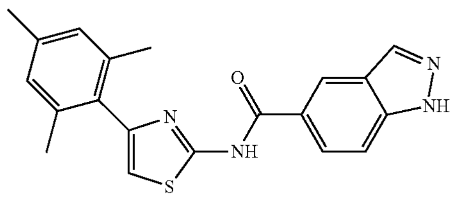 [SMILES: Cc1cc(C)c(-c2csc(NC(=O)c3ccc4[nH]ncc4c3)n2)c(C)c1] | >10 | >10 | 8.02 | >10 |
| II-106 | 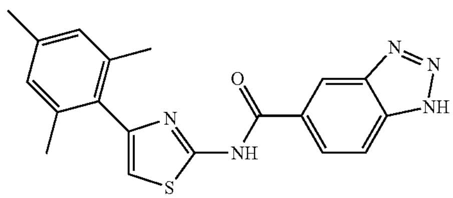 | >10 | >10 | >10 | 4.95 |
| II-107 | 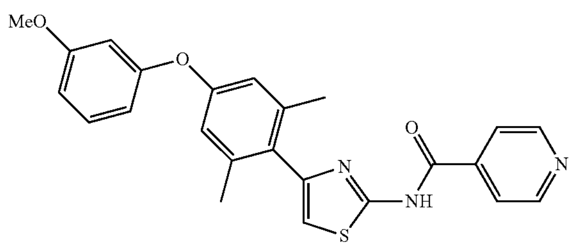 [SMILES: COc1cccc(Oc2cc(C)c(-c3csc(NC(=O)c4ccncc4)n3)c(C)c2)c1] | 0.25 | 0.10 | 0.20 | 0.20 |
| II-108 | 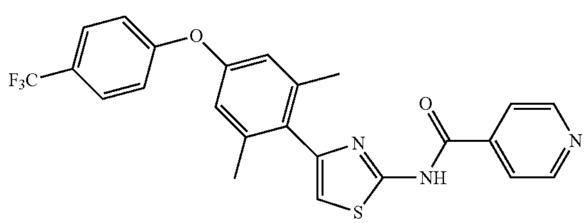 [SMILES: Cc1cc(Oc2ccc(C(F)(F)F)cc2)cc(C)c1-c1csc(NC(=O)c2ccncc2)n1] | 0.13 | 0.06 | 0.11 | 0.11 |
| II-109 | 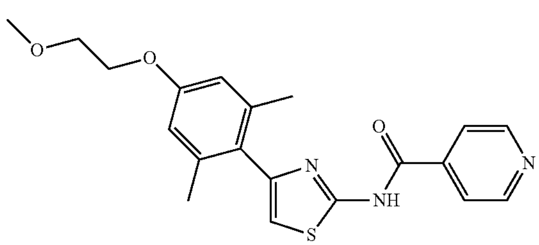 [SMILES: COCCOc1cc(C)c(-c2csc(NC(=O)c3ccncc3)n2)c(C)c1] | 0.31 | 0.24 | 0.28 | 0.26 |
| II-110 | 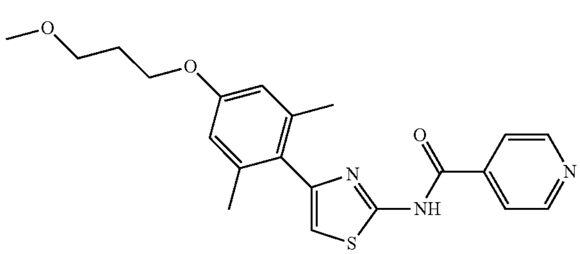 [SMILES: COCCCOc1cc(C)c(-c2csc(NC(=O)c3ccncc3)n2)c(C)c1] | 0.11 | 0.10 | 0.13 | 0.09 |

TABLE 2-continued

| Compound | Structure | Antiproliferative IC$_{50}$ (nM) | | | |
|---|---|---|---|---|---|
| | | Hela | K562 | MDA-MB-468 | MDA-MB-231 |
| II-111 | 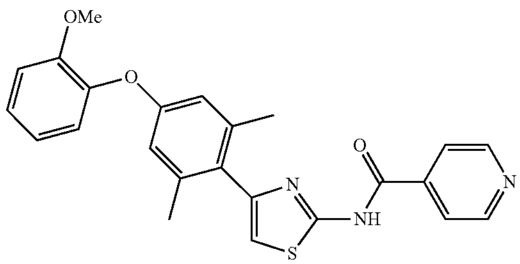 [SMILES: COc1ccccc1Oc1cc(C)c(-c2csc(NC(=O)c3ccncc3)n2)c(C)c1] | 0.33 | 0.18 | 0.33 | 0.25 |
| II-112 | 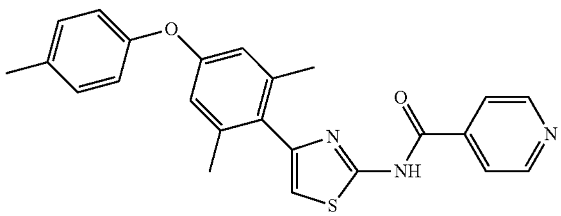 [SMILES: Cc1ccc(Oc2cc(C)c(-c3csc(NC(=O)c4ccncc4)n3)c(C)c2)cc1] | 0.24 | 0.13 | 0.22 | 0.14 |
| II-113 | 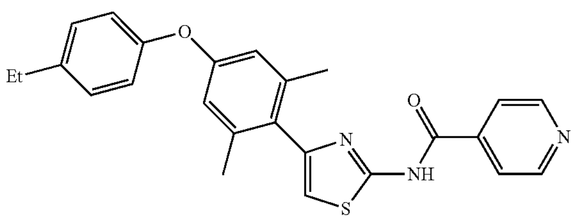 [SMILES: CCc1ccc(Oc2cc(C)c(-c3csc(NC(=O)c4ccncc4)n3)c(C)c2)cc1] | 0.18 | 0.17 | 0.17 | 0.17 |
| II-114 | 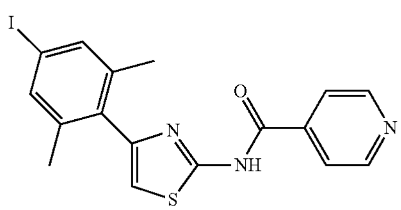 [SMILES: Cc1cc(I)cc(C)c1-c1csc(NC(=O)c2ccncc2)n1] | 0.40 | 0.23 | 0.55 | 0.30 |
| II-115 | 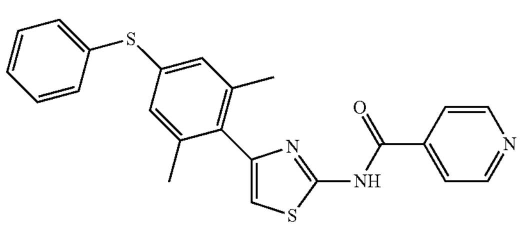 | 0.23 | 0.14 | 0.22 | 0.17 |
| II-116 | 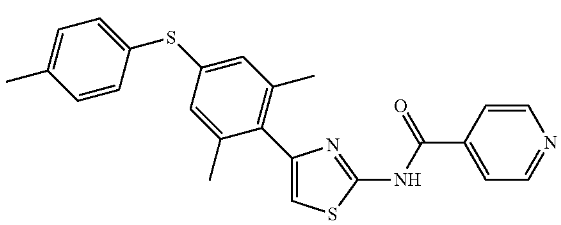 [SMILES: Cc1ccc(Sc2cc(C)c(-c3csc(NC(=O)c4ccncc4)n3)c(C)c2)cc1] | 0.15 | 0.11 | 0.13 | 0.12 |

TABLE 2-continued
| Compound | Structure | Hela | K562 | MDA-MB-468 | MDA-MB-231 |
|---|---|---|---|---|---|
| II-117 | 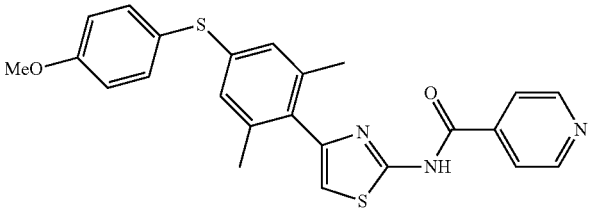 | 0.03 | 0.02 | 0.04 | 0.03 |
| II-118 | 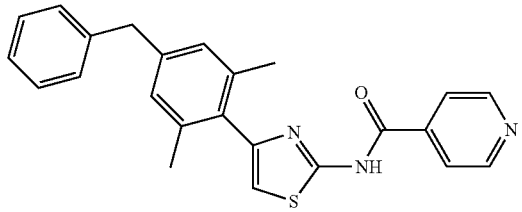 | 0.27 | 0.15 | 0.22 | 0.24 |
| II-119 | 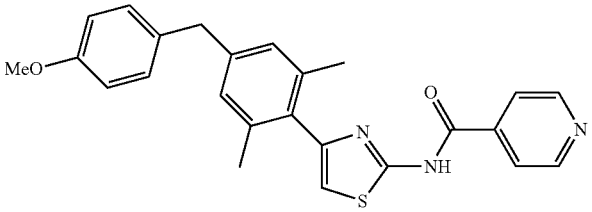 [SMILES: COc1ccc(Cc2cc(C)c(-c3csc(NC(=O)c4ccncc4)n3)c(C)c2)cc1] | 0.06 | 0.03 | 0.06 | 0.05 |
| II-120 | 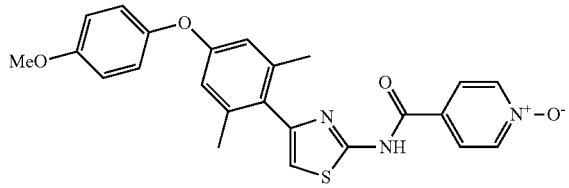 [SMILES: COc1ccc(Oc2cc(C)c(-c3csc(NC(=O)c4cc[n+]([O-])cc4)n3)c(C)c2)cc1] | 0.16 | 0.18 | 0.25 | 0.22 |
| II-121 | 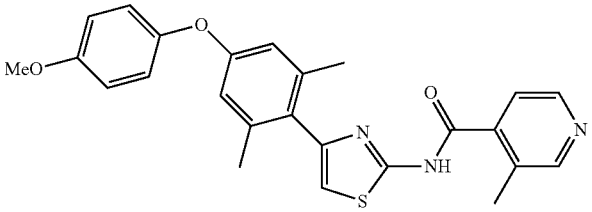 [SMILES: COc1ccc(Oc2cc(C)c(-c3csc(NC(=O)c4ccncc4C)n3)c(C)c2)cc1] | 0.90 | 0.32 | 0.81 | 0.44 |
| II-122 | 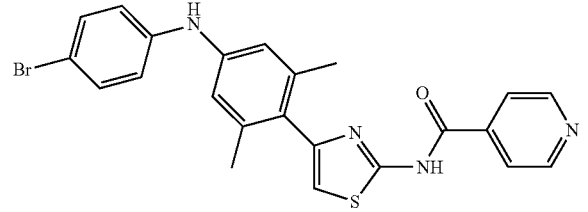 [SMILES: Cc1cc(Nc2ccc(Br)cc2)cc(C)c1-c1csc(NC(=O)c2ccncc2)n1] | 2.13 | 0.36 | 1.22 | 0.72 |
| II-123 | 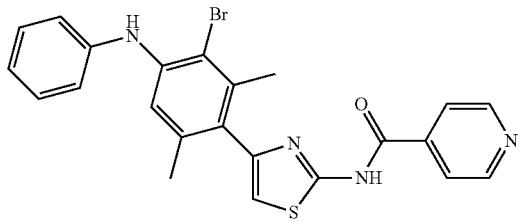 [SMILES: Cc1cc(Nc2ccccc2)c(Br)c(C)c1-c1csc(NC(=O)c2ccncc2)n1] | 0.87 | 0.33 | 0.88 | 0.61 |

TABLE 2-continued

| Compound | Structure | Antiproliferative IC$_{50}$ (nM) | | | |
| --- | --- | --- | --- | --- | --- |
| | | Hela | K562 | MDA-MB-468 | MDA-MB-231 |
| II-124 | 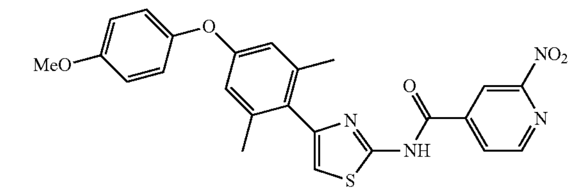 [SMILES: COc1ccc(Oc2cc(C)c(-c3csc(NC(=O)c4ccnc([N+](=O)[O-])c4)n3)c(C)c2)cc1] | 0.33 | 0.12 | 0.53 | 0.22 |
| II-125 | 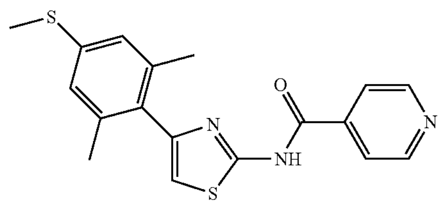 [SMILES: CSc1cc(C)c(-c2csc(NC(=O)c3ccncc3)n2)c(C)c1] | 0.27 | 0.18 | 0.25 | 0.16 |
| II-126 | 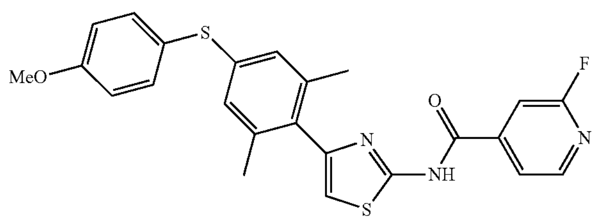 | 0.04 | 0.02 | 0.05 | 0.03 |
| II-127 | 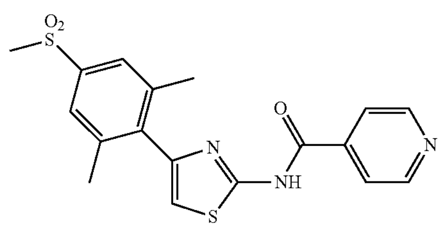 [SMILES: Cc1cc(S(C)(=O)=O)cc(C)c1-c1csc(NC(=O)c2ccncc2)n1] | 0.84 | 0.53 | 0.46 | 0.45 |
| II-128 | 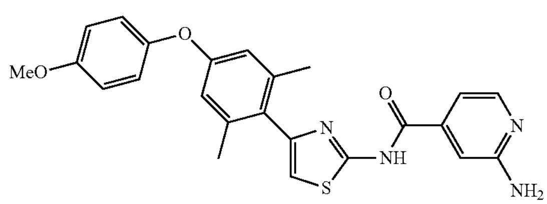 [SMILES: COc1ccc(Oc2cc(C)c(-c3csc(NC(=O)c4ccnc(N)c4)n3)c(C)c2)cc1] | 0.24 | 0.19 | 0.16 | 0.16 |
| II-129 | 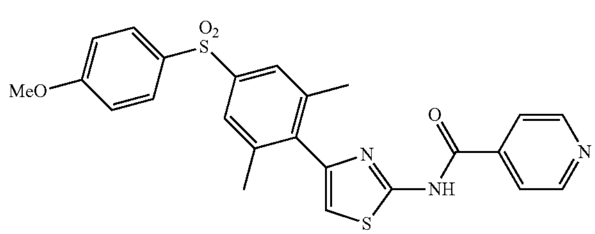 [SMILES: COc1ccc(S(=O)(=O)c2cc(C)c(-c3csc(NC(=O)c4ccncc4)n3)c(C)c2)cc1] | 0.27 | 0.19 | 0.27 | 0.20 |
| II-130 | 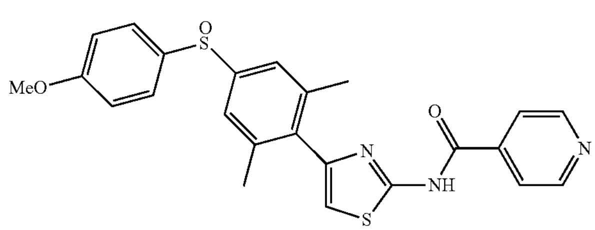 | 0.18 | 0.08 | 0.14 | 0.09 |

TABLE 2-continued

| Compound | Structure | Antiproliferative IC$_{50}$ (nM) | | | |
| --- | --- | --- | --- | --- | --- |
| | | Hela | K562 | MDA-MB-468 | MDA-MB-231 |
| II-131 | 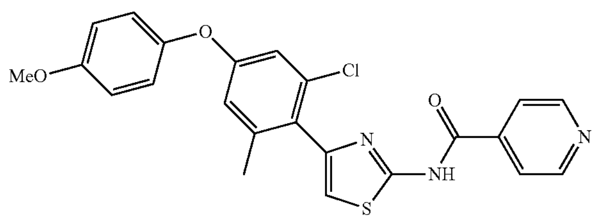 [SMILES: COc1ccc(Oc2cc(C)c(-c3csc(NC(=O)c4ccncc4)n3)c(Cl)c2)cc1] | 0.06 | 0.04 | 0.05 | 0.04 |

Metabolism Studies:

Compound 27 of the above Table 1 was treated with human microsomes in the presence of NADPH for metabolite identification. After the sample was analyzed by LC/MS, molecular ion peaks with m/z values of 510.1, 480.2, 495.1, 383.5, and other peaks were observed (positive mode). The peaks may correspond to the oxidation, demethylation, oxidation, demethylation, etc. of compound 27. Possible metabolic sites of compound 27 are represented in the following structure:

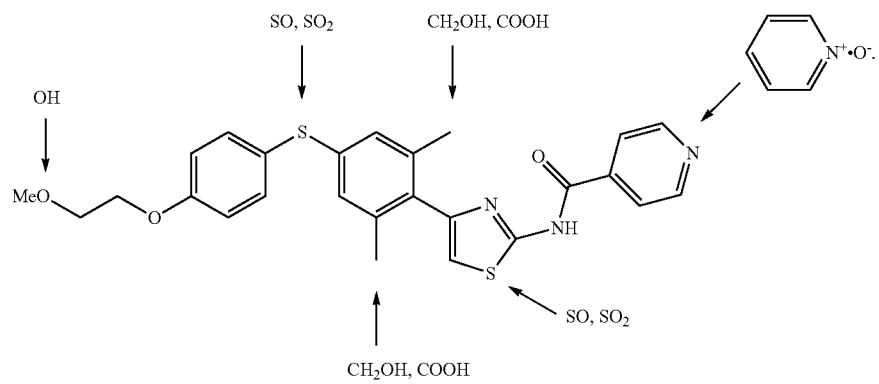

Reactions of the metabolite formation from compound 27 may occur at a single site or at a combination of sites.

Exemplary Biological Activities of Selected Compounds

The following data provide exemplary guidance with respect to the biological activity of certain compounds in vitro and in vivo. Where compounds are referenced by number, the number is with regard to the compounds listed in the tables above.

The following data provide exemplary guidance with respect to the biological activity of certain compounds (and especially compound II-95 of Table 2 and compounds 22, 25, and 27 of Table 1) in vitro and in vivo. Selected compounds of the invention, prepared as described in the Examples, were subject to the following series of biological and immunochemical assays. Descriptions of different assays are as follows:

Cell Culture: MDA-MB-231, MDA-MB-468, HeLa, and K562 cell lines were cultured in 10% FBS (Hyclone, Logan Utah 84321 USA) in DMEM medium (P/N D5523, Sigma Aldrich, St. Louis Mo. USA). Cells were grown at 37° C. in a humidified atmosphere consisting of 5% $CO_2$ and 95% air.

Antiproliferation Assays: Cells were plated in a 96-well culture plate with 2000-8000 cells per well. The compounds were prepared in DMSO and used to treat cells in a final concentration of less than 1% DMSO. Compound treatment started after overnight incubation of cells (T0). Compound was prepared in an eight point 3× dilution from 10 μM to 4.6 nM. Compound was added to the plate in triplicate wells, and the plates were then incubated for 96 hours. DMSO (compound diluent) was also included and added to the plate in control wells. Cell viability was then determined by MTS assay using the CellTiter 96® aqueous non-radioactive cell proliferation assay system (Promega, Madison, Wis. 53711 USA). A plate reader (Vmax, Molecular Devices, Sunnyvale Calif. 94089 USA) was used to determine the optical densities, and the results were used to deduce concentration-response curves. All data were determined in triplicate, with the mean of three separate determinations having variations of less than ±20%. The results were analyzed using linear regression software (GraphPad Prism 5; GraphPad Software Inc. La Jolla Calif. 92037 USA). The IC$_{50}$ value refers to a concentration that results in 50% growth inhibition. The % inhibition of test drugs were calculated using the formula: $(1-(T-T0)/(C-T0))\times 100$ (T is treatment; C is control); these value were used to plot the concentration-response curves and analyzed with linear regression software (GraphPad Prism 5; GraphPad Software Inc. La Jolla Calif. 92037 USA).

Co-Immunoprecipitation Analysis: Co-immunoprecipitation (Co-IP)/Western blotting assays were performed to assess the effects of Hec1 inhibitory compounds on Hec1-Nek2 interaction. K562 cells were treated with Hec1 inhibitory compounds as indicated. After harvesting and washing once with cold PBS, cells were lysed on ice in lysis buffer (50 mM Tris (pH 7.5), 250 mM NaCl, 5 mM EDTA (pH 8.0), 0.1% NP-40, 1 mM PMSF, 50 mM NaF, and protease inhibitor cocktail (P/N P8340 Sigma Aldrich, St. Louis Mo. USA) for 30 min. Lysates were then centrifuged at 12,000 rpm at 4° C. for 20 minutes. Input supernatant was incubated in the presence of anti Nek2 antibody (rabbit anti-Nek2, Rockland Immunochemicals, Gilbertsville, Pa. 19525 USA) or IgG control antibody for 2 h at 4° C., followed by the addition protein G coupled to agarose beads (GE Healthcare, Anaheim Calif. 92805 USA). After mixing for 1 h at 4° C., the agarose beads were centrifuged at 12,000 rpm at 4° C. for 20 seconds. The beads were then washed 5 times with cold Co-IP buffer, boiled in SDS-PAGE sample buffer followed by SDS-PAGE. The presence of Hec1 and Nek2 was detected by Western blotting with mouse monoclonal antibodies directed to Hec1 (GeneTex, Inc., Irvine Calif. 92606 USA) and Nek2 (BD Biosciences, San Jose Calif. 95131 USA).

FIG. 1 depicts an exemplary result of such an experiment where it is readily apparent that the Hec1 inhibitory compound 110095 (compound 27 of Table 1) significantly disrupted Hec1/Nek2 interaction. K562 cells were treated with 110095 or control (DMSO) for 8 or 16 hours, lysed, and lysates immunoprecipitated by Nek2 antibody to see co-immunoprecipitated Hec1. Control IgG was used as control antibody for immunoprecipitation. Results show decreased Hec1 level in the Nek2 immunoprecipitates of 110095-treated cells, indicating that 110095 exposure leads to a decreased interaction between Hec1 and Nek2.

Immunoblot Analysis: For immunoblotting experiments, cells were plated in a 6-well culture plate and cultured overnight. Cells were incubated with the test compounds for the indicated time and whole cell lysate was harvested by adding 1×SDS-PAGE Sample Buffer (62.5 mM Tris-HCl (pH 6.8 at 25° C.), 2% w/v SDS, 10% glycerol, 50 mM DTT, and 0.01% w/v bromophenol blue or phenol red). Proteins were separated by SDS-PAGE electrophoresis and transferred to PVDF membrane. Protein expression was immunoblotted using various primary antibodies and detected using Immobilon Western Chemiluminescent HRP Substrate (Millipore, Billerica Mass. 01821 USA). Antibodies used include anti-Cleaved Caspase3, (Rabbit, Cell Signaling Technology, Danvers Mass. 01923 USA); anti-PARP (Rabbit, Cell Signaling Technology, Danvers Mass. 01923 USA); anti-MCL-1 (mouse, BD Biosciences, San Jose Calif. 95131 USA); anti-XIAP (rabbit, Cell Signaling Technology, Danvers Mass. 01923 USA); anti-Bcl-2 (mouse, Santa Cruz Biotechnology, Santa Cruz Calif. 95060); anti-Cyclin BI (mouse, BD Biosciences, San Jose Calif. 95131 USA); anti-Cyclin D1 (mouse, Santa Cruz Biotechnology, Santa Cruz Calif. 95060); Anti-Nek2 (mouse, BD Biosciences, San Jose Calif. 95131 USA); Anti-HEC1, (rabbit, GeneTex, Inc., Irvine Calif. 92606 USA); and anti-actin (mouse, Millipore, Billerica Mass. 01821 USA).

FIG. 2 shows reduction of Nek2 protein in 110095 (compound 27 of Table 1)-treated cancer cells. Control (DMSO) and 110095-treated cells were immunoblotted for their levels of Nek2 protein expression level. K562 cells were incubated for various time points up to 24 hrs with 1 µM of tested compounds. Results show that Nek2 content of K562 cells is unstable over time after treatment with Hec1 inhibitor. 110095 induced a reduction of Nek2 protein levels. Compound 101015 (compound II-98 in Table 2) was used as a control.

Immunostaining and Microscopy: Cells were grown on polylysine-coated coverslips. Cells were gently washed with BRB80 buffer (80 mM piperazine-N,N'-bis(2-ethanesulfonic acid) (PIPES) pH 6.8, 5 mM EGTA, 1 mM $MgCl_2$) before fixation with cold 100% methanol or 4% paraformaldehyde in BRB80 or phosphate-buffered saline (PBS). Following permeabilization with 0.4% Triton X-100, cells were blocked with 2% bovine serum albumin (BSA) in PBS and then incubated with anti-α-Tubulin antibodies (mouse, FITC Conjugate; Sigma Aldrich, St. Louis Mo. USA) diluted in 2% BSA in PBS. DAPI (4',6'-diamidino-2-phenylindole) staining was applied after secondary antibody incubation, and cells were mounted on cover slides with Prolong gold antifade reagent (Life Technologies, Carlsbad Calif. USA 92008). Images were captured with a Zeiss Axioplan 2 microscope equipped with a deconvolution module or with a Zeiss LSM-510 META laser scanning confocal microscope (Carl Zeiss Microscopy, Thornwood N.Y. 10594 USA).

FIG. 3 shows images of chromosomal misalignment in 110095-treated cancer cells and the effect of select Hec1 inhibitors on cell populations. In order to image chromosome misalignment HeLa cell were grown on polylysine-coated coverslips and treated with 110095 (compound 27 of Table 1) or control (DMSO). After fixation, cells are stained with anti-tubulin antibody and DAPI to stain for microtubules and DNA, respectively, and imaged. Similar studies were performed with select Hec1 inhibitory compounds in order to determine the phenotypic arrangements of the cellular DNA in cell cycle phases. Fluorescent images were taken of the cells and the percentage of cells with metaphase misalignment were counted and recorded. Results show that the Hec1 inhibitory compounds 110091 (compound 22 of Table 1), 110093 (compound 25 of Table 1), and 110095 caused a time-dependent increase in the number of cells with metaphase misalignment compared to control cells. This suggests that these compounds target the Hec1 pathway and lead to chromosomal aberrations.

DNA Content Analysis: Cells were plated in a 10-cm culture plate and cultured overnight. Cells were incubated with the compound for the indicated time and collected at the indicated time points. Cells were fixed with 70% ethanol overnight, stained with propidium iodide solution (1.25 mg/ml propidium iodide (Sigma) and 20 µl/ml Mase A in PBS) and subjected to fluorescence activated cell sorting (FACS). The results were analyzed by Cell Quest software (BD Biosciences, San Jose Calif. 95131 USA).

FIG. 4 shows induction of apoptosis by Hec1 inhibitory compounds in cancer cells by cell cycle analysis. Cells treated with compounds 101015 (compound II-98 of Table 2) and 110095 (compound 27 of Table 1) or control (DMSO) were analyzed for their DNA content by staining with propidium iodide followed by analysis of the cellular population with FACS. The table shows the percentage of cells in $G_1$ (M1: non cycling cells), S (M2: DNA replication) and sub-$G_1$ stages (M4: apoptotic cells). Results show an increase in the sub-G1 population. This is indicative of DNA fragmentation during apoptosis, suggesting the induction of apoptosis by 101015 and 110095, which leads to drug-induced cell death.

Figure 5:
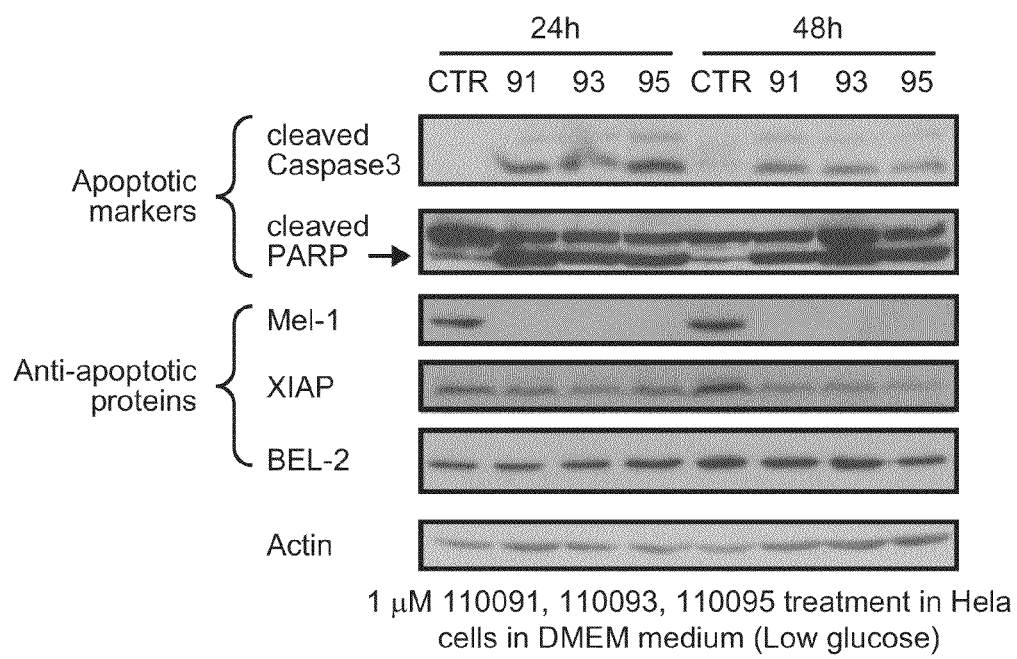
FIG. 5 shows induction of apoptosis in cancer cells by immunoblotting of apoptotic pathway proteins after treatment with exemplary compounds according to the inventive subject matter.
Figure 5:
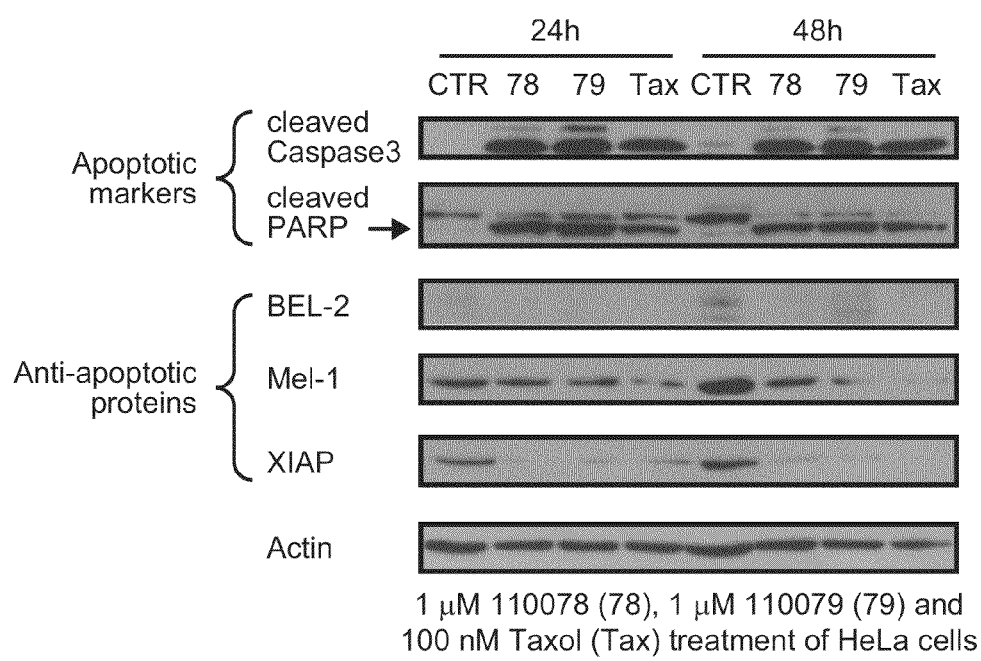

FIG. 5 shows induction of apoptosis by 110095 (compound 27 of Table 1) in cancer cells by immunoblotting of apoptotic pathway proteins. Lysates from cancer cells treated with Control (DMSO) or 1 µM of select Hec1 inhibitory compounds, including 110091 (compound 22 of Table 1), 110093 (compound 25 of Table 1), 110078 (compound 19 of Table 1), 110079 (compound of Table 1), and 110095 (compound 27 of Table 1), were immunoblotted to characterize levels of apoptotic proteins (caspase-3 and PARP) and anti-apoptotic proteins (Mcl-1 and XIAP) at time points 24 or 48 hours. 100 nM Taxol was used as a positive control drug for apoptosis. Results show cleavage of the apoptotic proteins accompanied by down-regulation of the anti-apoptotic proteins, indicative of the activation of apoptotic pathway, suggesting that these Heci compounds causes cell death through apoptosis.

FIG. 6 shows cyclin B1 and cyclin D degradation in 110095-treated cancer cells. Control (DMSO) or 1 μM 110095 (95, compound 27 of Table 1) treated cells were immunoblotted for their cyclin B1 (protein levels peak in G2/M phase) and cyclin D1 (protein levels peak in G1 phase) to see their relative change during the cell cycle. Results show that control cells progress through G2/M to G1 phase during the experimental time period while the 110095-treated cells shows cyclin levels that are unexpected and difficult to interpret. Hec1 inhibitors such as 110095 may induce cell cycle arrest in the S phase, which will induce an increase in cyclin A levels, however this remains to be elucidated.

Mouse Xenograft Studies: Xenograft studies adapted from a previous published protocol (Wu et al, Cancer Res. 2008 Oct. 15; 68(20):8393-9). Female BALB/c nude (nu/nu) mice (5-8 weeks) were obtained from Lasco (Industrial Park, Tai-Ping Area, Taichung City, Taiwan). The animals were maintained under specific pathogen-free conditions, and food and water were supplied ad libitum. Housing and all procedures involving animals were performed according to protocols approved by the IACUC in DCB. Nude mice were inoculated with 17-β-estradiol pellets 72 to 96 h before implantation of BT-474 cells. For subcutaneous implantation of BT-474 cells, cells ($1\times10^7$ in matrix gel/animal) were injected subcutaneously into the right subaxillary region. Treatment started when average tumor volume reached about 200 mm$^3$; mice were treated (p.o., QD/28 cycles in total) with vehicle A (0.5% methylcellulose), or candidate compounds formulated in vehicle A (10-50 mg/kg body weight). Perpendicular diameter measurement of each tumor were made with digital calipers and the volume of the tumor calculated using formula (L×W×W)/2, in which L and W represent the length and the width, respectively. Body weights were measured three times weekly. Mean tumor growth inhibition of each treated group was compared with vehicle control and a Tumor growth inhibition value calculated using the formula: (1-(T/C)×100%).

FIG. 7A to FIG. 7D show inhibition of xenograft tumor outgrowth by compound 27 (110095, of Table 1) and compound II-95 (Hec1001; 101001, of Table 2) in MDA-MB-231 (FIG. 7A and FIG. 7B) and BT474 (FIG. 7C) on xenografted breast cancer models and a Huh-7 liver cancer (FIG. 7D) model in nude mice. The in vivo effectiveness of contemplated compounds in the reduction of tumor volume in nude mice is readily apparent. Surprisingly despite the tumor reduction body weight remained constant in all cases, suggesting that overall toxicity of Hec1 inhibitory compounds is low.

Figure 7A:
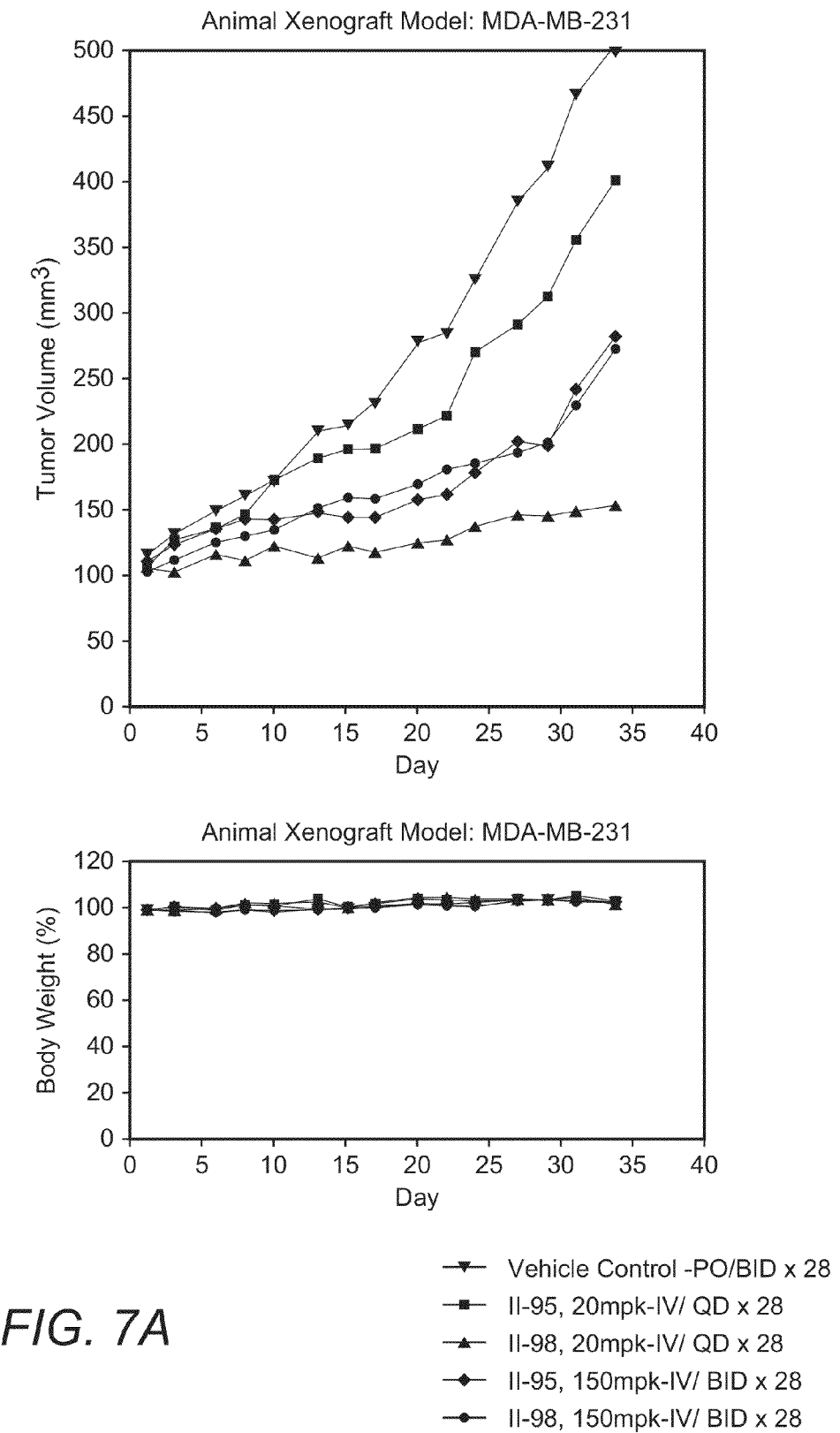
FIG. 7A and FIG. 7B show the effects of select compounds on MDA-MB-231 breast cancer xenografts.
Figure 7B:
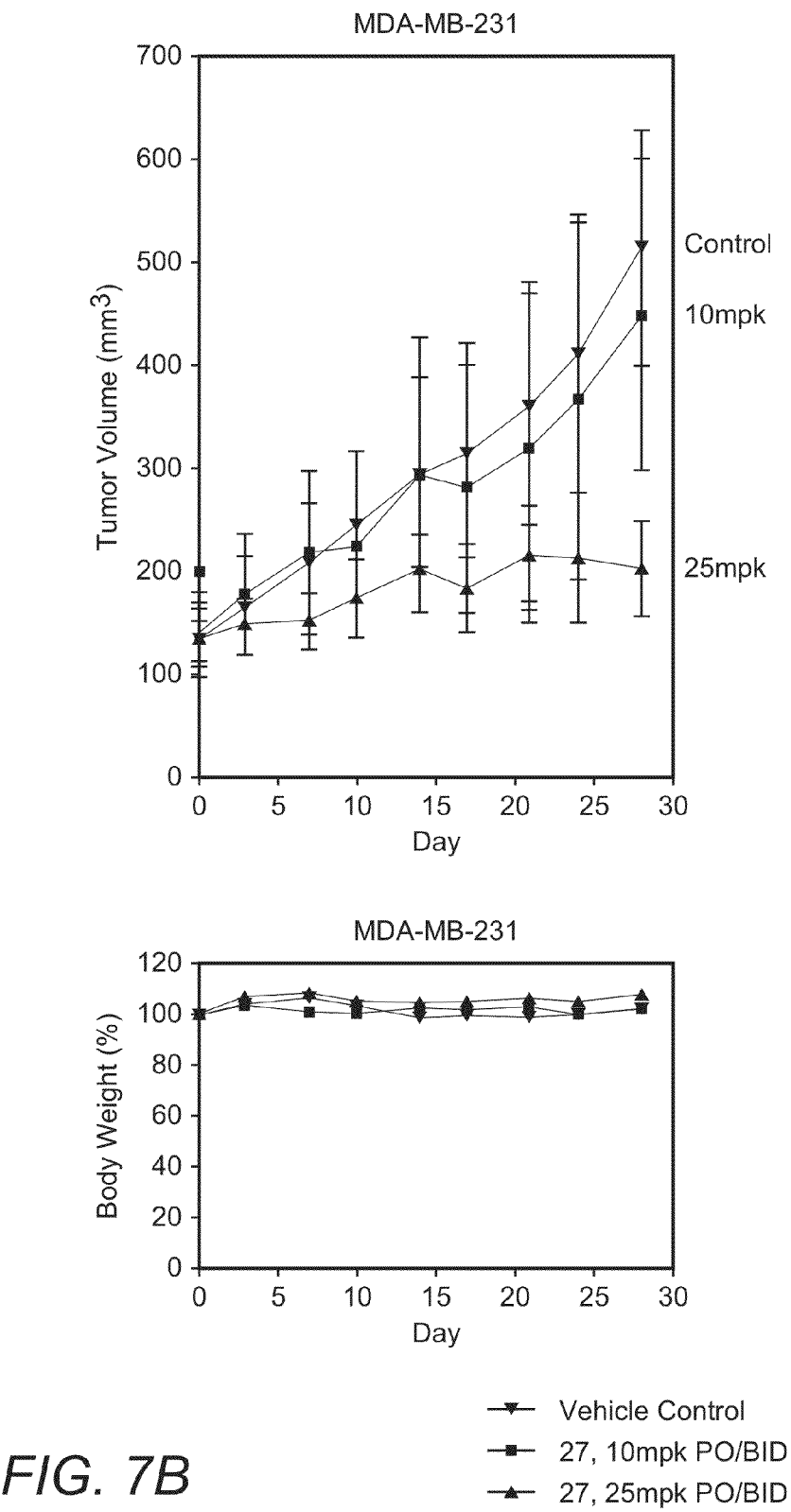
Figure 7C:
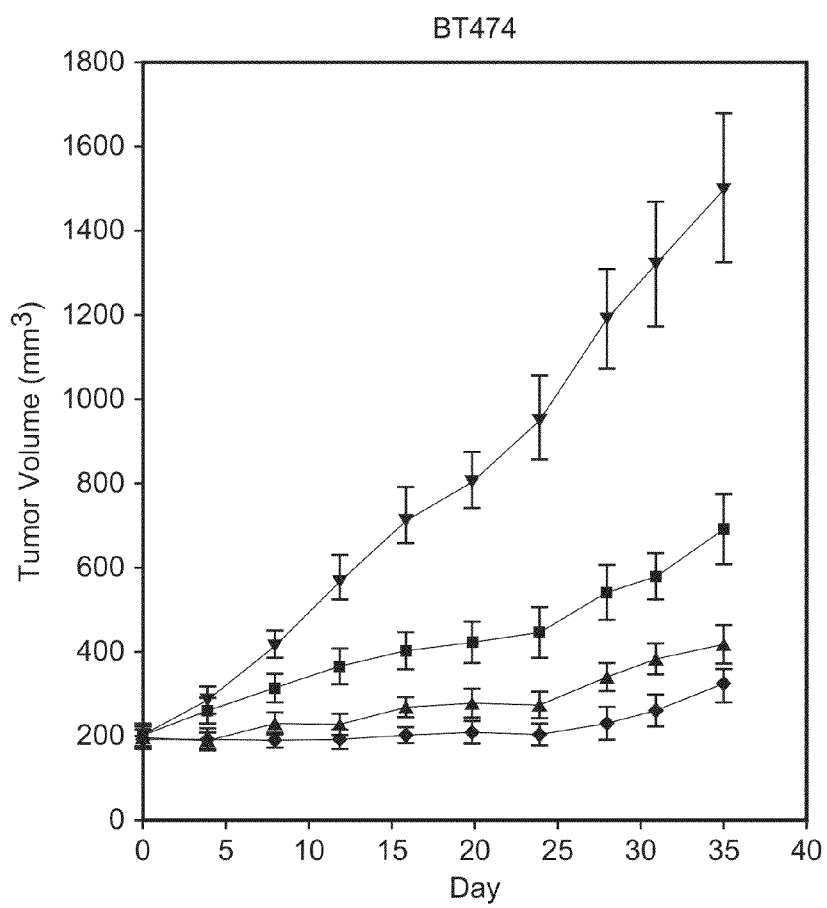
FIG. 7C shows the effects of select compound on BT474 breast cancer xenografts.
Figure 7C:
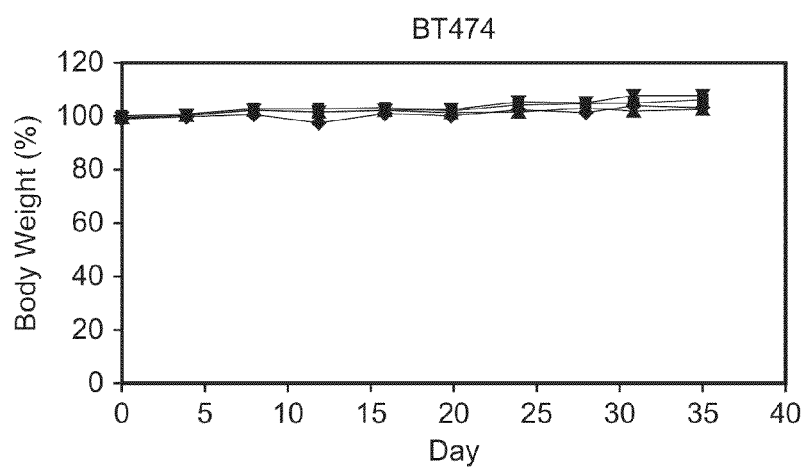
Figure 7D:
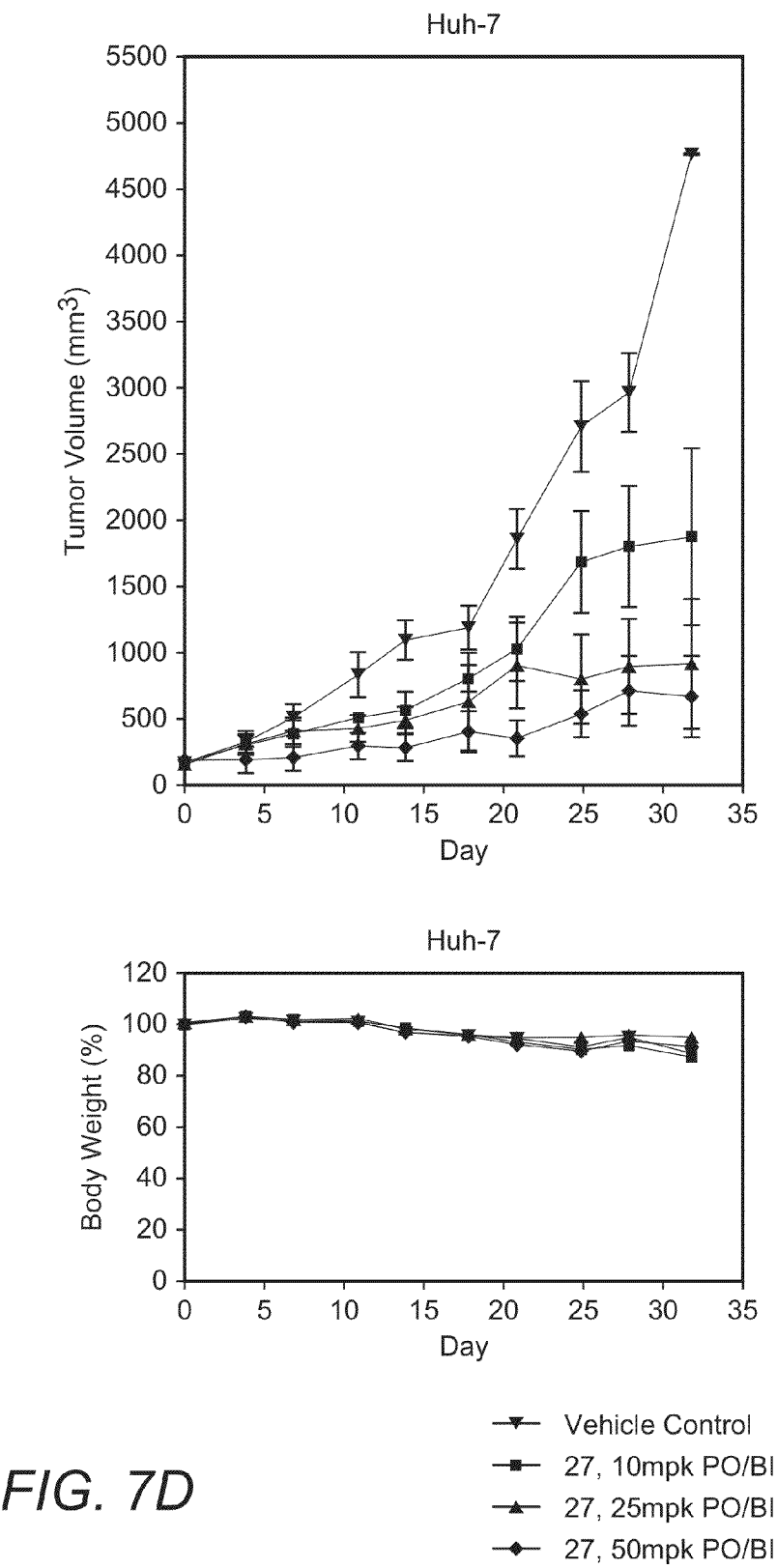
FIG. 7D shows the effects of select compound on Huh7 liver cancer xenografts.
Figure 7E:
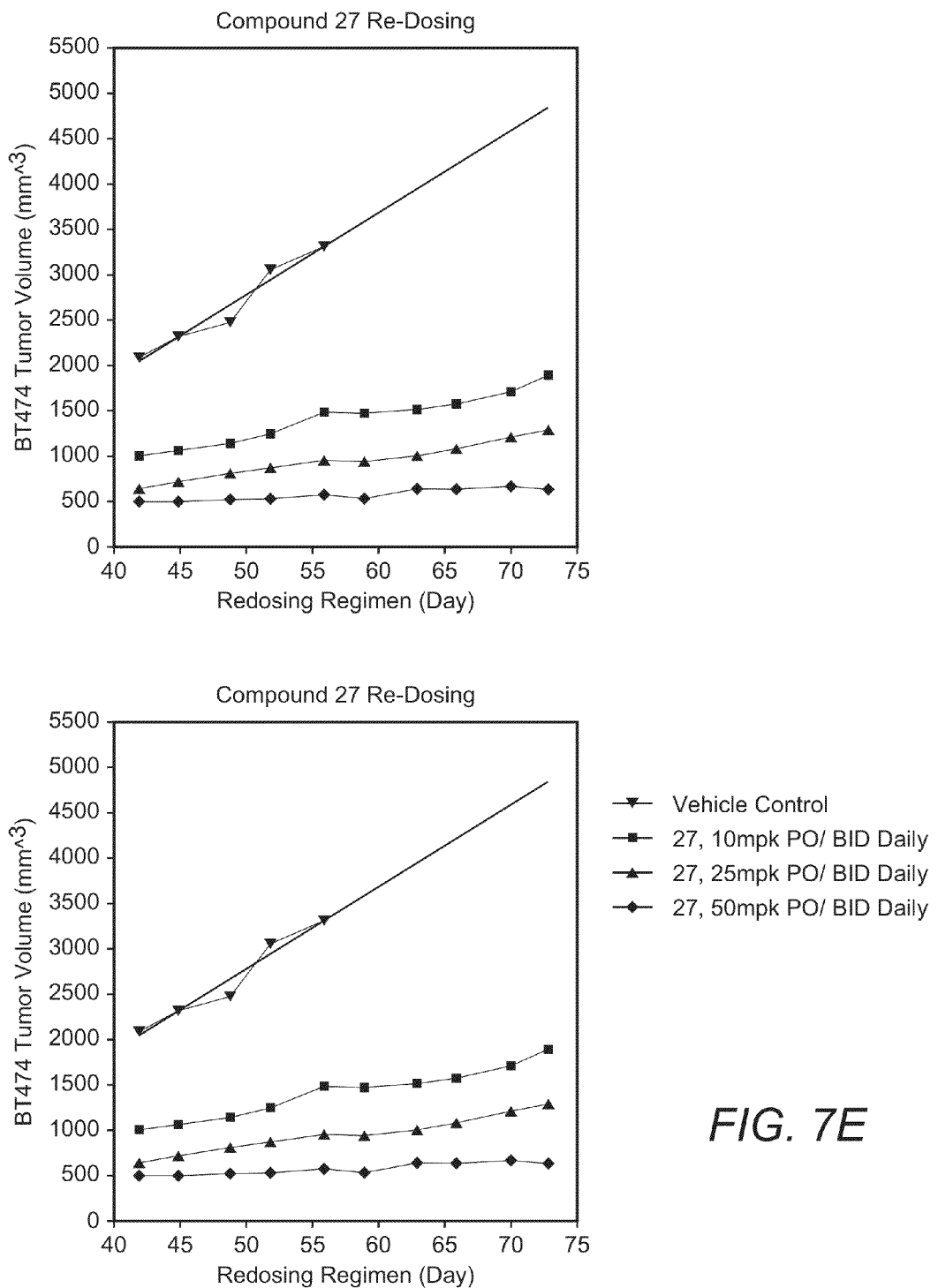
FIG. 7E shows the effects of re-treatment of previously treated, late stage MDA-MB-231 xenografts with select compound. In all instances tumor growth is inhibited.

Development of resistance to treatment in advanced stage tumors is a well known phenomenon. Activity of select Hec1 inhibitor in such late stage tumors was determined by re-dosing of BT474 xenografted animals that had previously subjected to 35 days of treatment with 110095 (compound 27 of Table 1). Re-treatment with 110095 was starting on day 42 and continued for 21 days. Results are shown in FIG. 7E, which demonstrates that the Hec1 inhibitor remained effective with late stage tumors. This suggests that such compounds may have a reduced tendency to induce resistance in tumors and other proliferative diseases. Similar to early stage treatment studies described above, body weight remained constant.

Cell Permeability: FIG. 8 shows moderate Caco-2 permeability of compound 110095 (compound 27 of Table 1) and 110091 (compound 22 of Table 1) in both directions, with no indication of significant active efflux. Here, Caco-2 cell line (cat. HTB-37TM) was purchased from the ATCC. Cells were cultivated in T-75 flasks in a cell culture incubator set at 37° C., 5% CO2, 95% relative humidity. Cells were allowed to grow to reach 80-90% confluence before seeding. Caco-2 cells were seeded onto filter membranes at a density of 1.25× 10$^4$ cells/mL for 12 well Caco-2 cell plates. The cells were grown in culture medium consisting of Dulbecco's modified Eagle's medium supplemented with 10% fetal bovine serum, 100 U/mL penicillin and 100 μg/mL streptomycin. The culture medium was replaced every 2 days and the cells were maintained at 37° C., 95% relative humidity and 5% $CO_2$. Permeability studies were conducted with the monolayers cultured for approximately 21 days with the cell passage numbers between 58 and 78. Rhodamine 123 was used as a model substrate for in vitro Caco-2 assay.

For a quality integrity control of the monolayers of seeded cells, the Lucifer yellow (LY) transport experiment was performed to evaluate monolayer integrity. As for a quality control of each filter, the transepithelial electrical resistance (TEER) was measured before the start of and at the end of transport experiments. Physiologically and morphologically well developed Caco-2 cell monolayers with TEER values greater than 400 Ωcm$^2$ were used for the studies.

Test and reference control compounds (Rhodamine 123) were added to either the apical or basolateral chambers of the transwell plate assembly at a concentration of 10 μM. The solution volumes in apical and basolateral chambers were set to 0.4 and 0.6 ml respectively. Samples were taken from both the apical and basolateral compartment at the end of the 2 hour incubation at 37° C. Lucifer Yellow and Rhodamine 123 were detected by Fusion™ (Packard BioSceince Company). The excitation and emission wavelengths were 490 nm and 530 nm, respectively. Concentrations of TAI-1 in the samples were measured by LC-MS/MS.

Hec1 Inhibitory Compound binding to hERG: FIG. 9 shows hERG binding of compounds 110095 (compound 27 of Table 1), 110093 (compound 25 of Table 1), and 110091 (compound 22 of Table 1) with IC$_{50}$ of >10~100 μM. Here, [3H] Astemizole competitive binding assays were performed to determine the ability of compounds to displace the known radioligand [3H]-astemizole from the hERG potassium channels, following standard protocol with minor modifications. In brief, assays were performed in 200 μl of binding buffer (50 mM HEPES, pH 7.4, 60 mM KCl, and 0.1% BSA) containing 1.5 nM of [3H]astemizole, 3 μg/well of hERG membrane protein (PerkinElmer), and TAI-1 (in 1% DMSO final concentration) at 27° C. for 60 min. Nonspecific binding (NSB) was determined in the presence of 10 μM astemizole. IC50 assay for TAI-1 contained 8 concentration points with 10-fold serial dilution in triplicate. Binding was terminated by rapid filtration onto polyethyleneimine-presoaked, buffer-washed UniFilter-96, GF/C (Perkin Elmer) using a vacuum manifold (Porvair Sciences). Captured radiolabel signal was detected using TopCount NXT (Perkin Elmer). The data were analyzed with nonlinear curve fitting software (PRISM, Graphpad) and IC50 value (defined as the concentration at which 50% of [3H]-astemizole binding is inhibited) was calculated. All results are derived from two independent experiments.

Pharmacokinetics of Hec1 Inhibitor Salts: Pharmacokinetic comparison of different salt forms (HCl, tosylate, mesylate salt) was studied for the compounds as shown in Table 3 below:

TABLE 3

| Compound | Structures | MW |
|---|---|---|
| 110095-HCl-1007 | (structure) | 530.06 |
| 110095-03-03 | (structure) | 665.80 |
| 110095-02-02 | (structure) | 589.71 |

Formulations for both PO (oral) and IV (intravenous) doses were prepared in saline with 2% Tween 80 and 10% DMSO. Concentrations were adjusted based on the molecular weights of the freebase and salts.

PO studies: A single dose of 10 mg/kg of each of the three test compounds was orally administered to 21 healthy male CD-1 mice (weight ranged from 18-27 g). The dosing volume was mL/kg. Animals were fasted approximately 16 hours prior to dosing until 4 hours post dosing. Water was available to all animals during the experiment period.

IV studies: A single dose of 1 mg/kg of each of the three test articles was IV administered to 21 healthy male CD-1 mice (weight ranged from 18-27 g). The dosing volume was 5 mL/kg. Food and water were available to all animals during the experiment period.

Three mice were bled (ca. 1 mL) at each timepoint (0.5, 1, 1.5, 2, 4, 6, and 24 hours post-dose for PO study and 0.083, 0.5, 1, 2, 4, 6, and 24 hours post-dose for IV study) by cardiac puncture and blood was collected into $K_3$EDTA blood collection tubes. Blood samples were centrifuged immediately at 4° C. at 3000 rpm for 10 min. Plasma samples were transferred and stored at −20° C. prior to analysis.

No adverse events were observed for all CD-1 mice after a single oral dose of 10 mg/kg or a single IV dose of 1 mg/kg of each of the test articles. The plasma concentrations of 110095 (compound 27 of Table 1, the free base of all three test articles) were determined by LC MS/MS in the positive MRM mode; all doses were normalized to the freebase (110095) concentration. Results are presented in Table 4 and Table 5. The mean plasma concentration from each time point (n=3) were used to calculate the PK parameters using a non-compartmental model. Pharmacokinetic parameters (Cmax, Tmax, t½, AUC, etc.) were calculated using WinNonlin Software (version 5.3, Pharsight, Sunnyvale Calif. 94086 USA), the results and absolute bioavailability results are presented in Table 6. Table 4 lists mean concentrations (ng/mL) of 110095 in mouse plasma following a single oral dose of 10 mg/kg of 110095-HCl-1007, 110095-03-03 or 110095-02-02 to CD-1 mice, and Table 5 lists mean concentrations (ng/mL) of 110095 in mouse plasma following a single IV dose of 1 mg/kg of 110095-HCl-1007, 110095-03-03 or 110095-02-02 to CD-1 mice. Table 6 lists PK parameters and absolute bioavailability result of 110095-HCl-1007, 110095-03-03 or 110095-02-02 in CD-1 mice.

Surprisingly, the toyslate salt unexpectedly provided the best AUC with a desirable absorption fraction (F %) as compared to the other two compounds.

TABLE 4

| | Time (h) | | | | | | |
|---|---|---|---|---|---|---|---|
| Compound | 0.5 | 1 | 1.5 | 2 | 4 | 6 | 24 |
| 110095-HCl-1007 | 1801 | 4063 | 3660 | 3563 | 2173 | 1137 | 14.8 |
| 110095-03-03 | 3117 | 4013 | 3797 | 3887 | 2210 | 1590 | 16.9 |
| 110095-02-02 | 2870 | 3740 | 4167 | 3833 | 1074 | 1080 | 21.2 |

TABLE 5

| | Time (h) | | | | | | |
|---|---|---|---|---|---|---|---|
| Compound | 0.083 | 0.5 | 1 | 2 | 4 | 6 | 24 |
| 110095-HCl-1007 | 870 | 684 | 549 | 422 | 202 | 93.2 | 3.68 |
| 110095-03-03 | 1100 | 624 | 643 | 568 | 307 | 139 | 2.87 |
| 110095-02-02 | 1348 | 772 | 659 | 365 | 182 | 175 | 8.65 |

TABLE 6

| | | Compound | | |
|---|---|---|---|---|
| Route | PK Parameters | 110095-HCl-1007 | 110095-03-03 | 110095-02-02 |
| IV | dose (mg/kg) | 1.00 | 1.00 | 1.00 |
| | $t_{1/2}$ (h) | 3.61 | 2.96 | 4.38 |
| | MRT(h) | 3.30 | 3.46 | 3.92 |
| | $AUC_{0-t}$ (ng·h/mL) | 2983 | 3976 | 3987 |
| | $AUC_{0-\infty}$ (ng·h/mL) | 3002 | 3988 | 4043 |
| PO | dose (mg/kg) | 10.0 | 10.0 | 10.0 |
| | $T_{max}$ | 1.00 | 1.00 | 1.50 |
| | $C_{max}$ | 4063 | 4013 | 4167 |
| | $t_{1/2}$ (h) | 2.81 | 2.81 | 3.38 |

TABLE 6-continued

| | | Compound | | |
|---|---|---|---|---|
| Route | PK Parameters | 110095-HCl-1007 | 110095-03-03 | 110095-02-02 |
| | MRT(h) | 4.11 | 4.29 | 4.00 |
| | AUC $_{0-t}$ (ng · h/mL) | 25065 | 30794 | 23319 |
| | AUC $_{0-\infty}$ (ng · h/mL) | 25125 | 30863 | 23424 |
| | F %[a] | 84.0 | 77.4 | 58.5 |

[a] $\% \ F = \dfrac{AUC_{PO} \times Dose_{IV}}{AUC_{IV} \times Dose_{PO}} \times 100$ It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

-continued
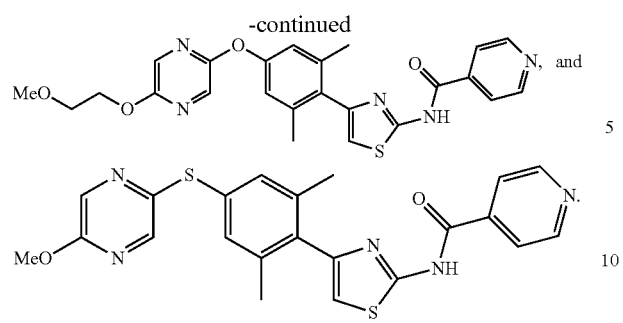

What is claimed is:

1. A compound having a structure according to Formula I

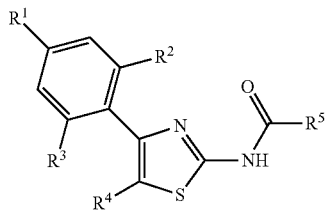

Formula I or a pharmaceutically acceptable salt thereof, wherein:

$R^1$ is $OR_a$ or $SR_a$;

$R_a$ of $OR_a$ or $SR_a$ is pyrazine, wherein $R_a$ of $OR_a$ or $SR_a$ is optionally substituted with alkoxy or methoxyalkoxy;

$R^2$ and $R^3$ are independently hydrogen, $C_1$-$C_6$ alkyl, or halogen;

$R^4$ is hydrogen or halogen;

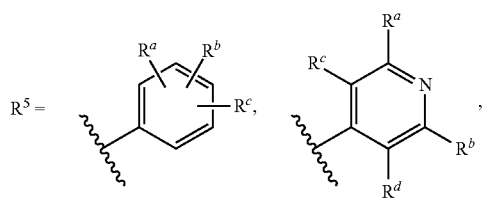

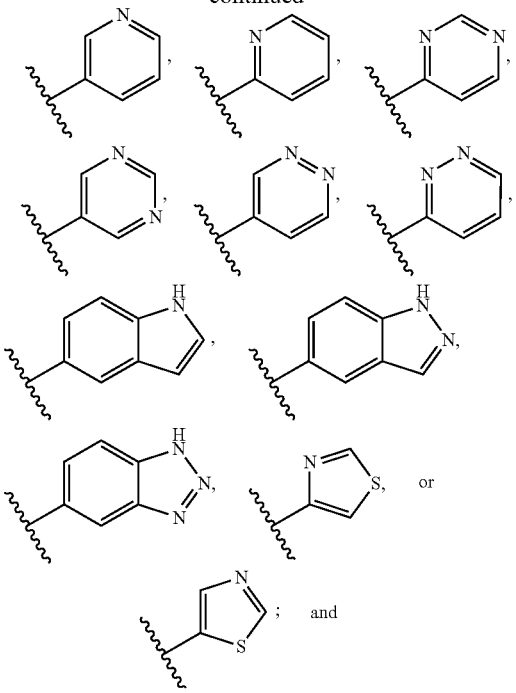

wherein $R^a$, $R^b$, $R^c$, and $R^d$ in $R^5$ are independently hydrogen, halogen, $C_1$-$C_6$ alkyl, or amino.

2. The compound of claim 1 having a structure according to Formula II

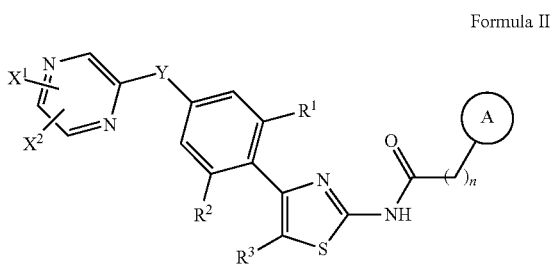

Formula II wherein $X^1$ is alkoxy or methoxyalkoxy and $X^2$ is hydrogen;

Y is O or S;

$R^1$ and $R^2$ are independently $CH_3$; and $R^3$ is hydrogen; n is 0;

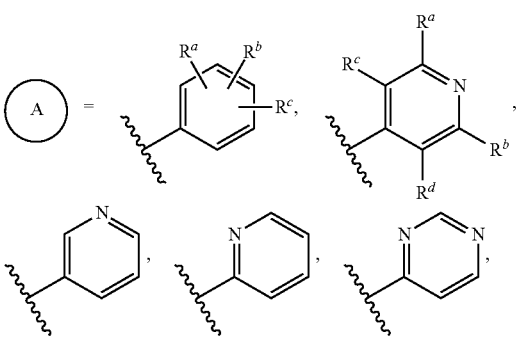

-continued

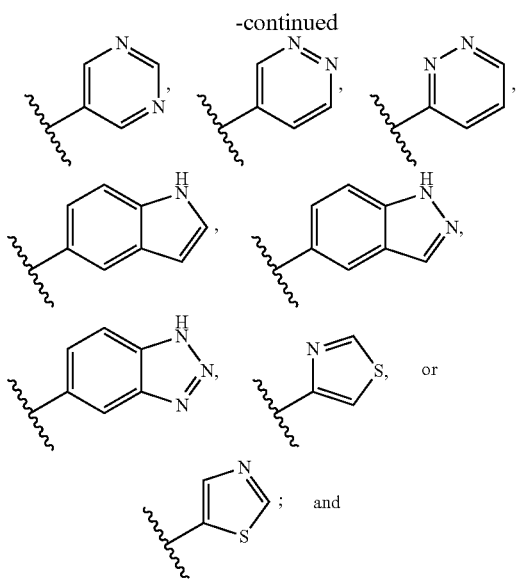

wherein $R^a$, $R^b$, $R^c$, and $R^d$ in

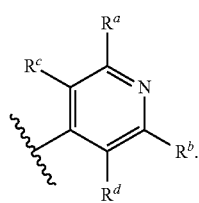

are independently hydrogen, halogen, $C_1$-$C_6$-alkyl, or amino.

3. The compound of claim 2 wherein

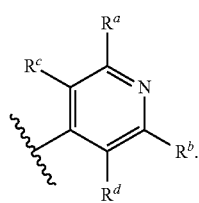

is

4. The compound of claim 1 having a structure selected from the group consisting of

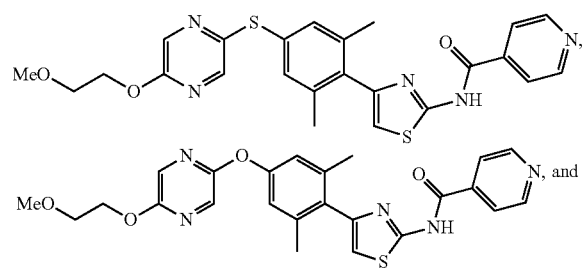

-continued

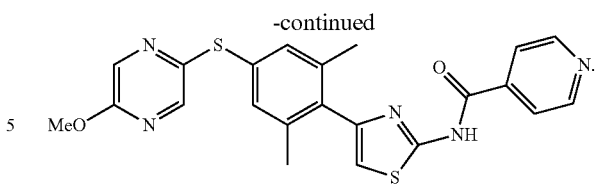

5. The compound of any one of claim 1, claim 2, or claim 4, in combination with an ion to thereby form a pharmaceutically acceptable salt.

6. A metabolite of the compound of any one of claim 1, claim 2, or claim 4.

7. The metabolite of claim 6, wherein $R^1$ is $SR_a$, and wherein the S in $SR_a$ is a sulfone or a sulphoxide.

8. A pharmaceutical composition comprising a pharmaceutically acceptable carrier and a compound, optionally present as a pharmaceutically acceptable salt, according to claim 1 in a concentration effective to disrupt Hec1/Nek2 binding in a mammal when the composition is administered to the mammal.

9. The pharmaceutical composition of claim 8, further comprising a drug that interferes with microtubule formation or degradation.

10. The pharmaceutical composition of claim 8 wherein the compound is a compound according to claim 4.

11. The pharmaceutical composition of claim 8 formulated as an orally administerable drug or an injectable drug.

12. A method of improving a pharmacokinetic parameter for a compound having a structure selected from the group consisting of

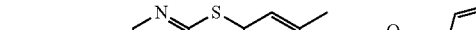

and

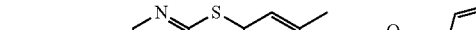

comprising a step of forming a tosylate salt of the compound;

wherein the pharmacokinetic parameter comprises an area under the curve (AUC); and wherein the improvement is increasing AUC in oral administration of the compound.

13. A pharmaceutical composition comprising a carrier and a tosylate salt of a compound having a structure selected from the group consisting of